US006566325B2

(12) United States Patent
Moore et al.

(10) Patent No.: US 6,566,325 B2
(45) Date of Patent: May 20, 2003

(54) 49 HUMAN SECRETED PROTEINS

(75) Inventors: Paul A. Moore, Germantown, MD (US); Steven M. Ruben, Olney, MD (US); Henrik S. Olsen, Gaithersburg, MD (US); Yanggu Shi, Gaithersburg, MD (US); Craig A. Rosen, Laytonsville, MD (US); Kimberly A. Florence, Rockville, MD (US); Daniel R. Soppet, Centreville, VA (US); David W. LaFleur, Washington, DC (US); Gregory A. Endress, Potomac, MD (US); Reinhard Ebner, Gaithersburg, MD (US); George Komatsoulis, Silver Spring, MD (US); Roxanne D. Duan, Bethesda, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/904,615

(22) Filed: Jul. 16, 2001

(65) Prior Publication Data

US 2002/0026040 A1 Feb. 28, 2002

Related U.S. Application Data

(63) Continuation of application No. 09/739,254, filed on Dec. 19, 2000, now abandoned, which is a continuation of application No. 09/511,554, filed on Feb. 23, 2000, now abandoned, which is a continuation-in-part of application No. PCT/US99/19330, filed on Aug. 24, 1999.
(60) Provisional application No. 60/097,917, filed on Aug. 25, 1998, and provisional application No. 60/098,634, filed on Aug. 31, 1998.

(51) Int. Cl.⁷ .............................................. C07K 14/00
(52) U.S. Cl. ........................... 514/2; 530/350; 530/300
(58) Field of Search ............................... 530/350, 300; 514/2

(56) References Cited

FOREIGN PATENT DOCUMENTS

| WO | WO 00/11014 | 3/2000 |
|---|---|---|
| WO | WO00/70049 | 11/2000 |
| WO | WO01/40466 | 6/2001 |

OTHER PUBLICATIONS

Genbank Accession No. AI796127 (Dec. 20, 1999).
Hillier et al., Genbank Accession No. AA455585 (Jun. 6, 1997).
Genbank Accession No. AI554899 (Apr. 13, 1999).
Hillier et al., Genbank Accession No. AA456082 (Jun. 6, 1997).
Genbank Accession No. AI273705 (Nov. 18, 1998).
Genbank Accession No. AI095506 (Oct. 23, 1998).
Genbank Accession No. AA420823 (Oct. 16, 1997).
Genbank Accession No. AA689489 (Dec. 24, 1997).
Genbank Accession No. AI658624 (May 10, 1999).
Genbank Accession No. AA420683 (Oct. 16, 1997).
Genbank Accession No. AI223791 (Oct. 28, 1998).
Hillier et al., Genbank Accession No. AT75260 (Mar. 3, 1995).
Genbank Accession No. AI631711 (Dec. 17, 1999).
Genbank Accession No. AI990874 (Sep. 8, 1999).
Auffray et al., Genbank Accession No. F12884 (Mar. 14, 1995).
Genbank Accession No. AI082100 (Oct. 1, 1998).
Auffray et al., Genbank Accession No. Z45663 (Nov. 14, 1994).
Auffray et al., Genbank Accession No. F05387 (Feb. 19, 1995).
Genbank Accession No. AI093661 (Aug. 18, 1998).
Supplementary Partial European Search Report Feb. 2, 2002.

*Primary Examiner*—Karen Cochrane Carlson
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating diseases, disorders, and/or conditions related to these novel human secreted proteins.

52 Claims, No Drawings

SEQUENCE LISTING

```
<160> NUMBER OF SEQ ID NOS: 170

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg      60
aattcgaggg tgcaccgtca gtcttcctct tcccccaaa acccaaggac accctcatga     120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agcccctcca accccatcg     360 agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                        733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring
      L-amino acids

<400> SEQUENCE: 2

Trp Ser Xaa Trp Ser
  1               5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc      60
cccgaaatat ctgccatctc aattag                                           86

<210> SEQ ID NO 4
<211> LENGTH: 27
<212> TYPE: DNA
```

```
<213> ORGANISM: Homo sapiens

<400> SEQUENCE: 4
gcggcaagct ttttgcaaag cctaggc                                              27

<210> SEQ ID NO 5
<211> LENGTH: 271
<212> TYPE: DNA
<213> ORGANISM: Homo sapiens

<400> SEQUENCE: 5
ctcgagattt ccccgaaatc tagatttccc cgaaatgatt tccccgaaat gatttccccg          60
aaatatctgc catctcaatt agtcagcaac catagtcccg cccctaactc cgcccatccc         120
gcccctaact ccgcccagtt ccgcccattc tccgcccat ggctgactaa ttttttttat          180
ttatgcagag gccgaggccg cctcggcctc tgagctattc cagaagtagt gaggaggctt         240
ttttggaggc ctaggctttt gcaaaaagct t                                        271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg                                        32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c                                         31

<210> SEQ ID NO 8
<211> LENGTH: 12
<212> TYPE: DNA
<213> ORGANISM: Homo sapiens

<400> SEQUENCE: 8
ggggactttc cc                                                              12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccgggact tccgggact ttccatcctg            60 ccatctcaat tag                                                             73

<210> SEQ ID NO 10
<211> LENGTH: 256
<212> TYPE: DNA
<213> ORGANISM: Homo sapiens

<400> SEQUENCE: 10 ctcgaggga ctttcccggg gactttccgg ggactttccg ggactttcca tctgccatct           60
caattagtca gcaaccatag tccgcccct aactccgccc atcccgcccc taactccgcc          120
cagttccgcc cattctccgc ccatggctg actaattttt tttatttatg cagaggccga          180
```

```
ggccgcctcg gcctctgagc tattccagaa gtagtgagga ggcttttttg gaggcctagg    240
cttttgcaaa aagctt                                                   256

<210> SEQ ID NO 11
<211> LENGTH: 3289
<212> TYPE: DNA
<213> ORGANISM: Homo sapiens

<400> SEQUENCE: 11
cccgggtcga cccacgcgtc cggcgaggac cgcgtccggc gcagtcttca atgagcagcg     60
cggaaactgc accccagacc cgagcctgct gcgcgccccc tcccagagct cacctggtgc    120
caggtaacag gcctggcctc gccctgtgga tgatgatggc cttgccccg tgagctacaa     180 cctggccttc agcacccgcc cacctccaac cagcaggatg cggctgtgga aggcggtggt    240
ggtgactttg gccttcatga gtgtggacat ctgcgtgacc acggccatct atgtcttcag    300
ccacctggac cgcagcctcc tggaggacat ccgccacttc aacatctttg actcggtgct    360
ggatctctgg gcagcctgcc tgtaccgcag ctgcctgctc ctgggagcc accattggtg     420 tggccaagaa cagtgcgctg ggccccggc ggctgcgggc ctcgtggctg gtcatcaccc     480
tcgtgtgcct cttcgtgggc atctatgcca tggtgaagct gctgctcttc tcagaggtgc    540
gcaggcccat ccgggacccc tggttttggg ccctgttcgt gtggacgtac atttcactcg    600
gcgcatcctt cctgctctgg tggctgctgt ccaccgtgcg gccaggcacc caggccctgg    660
agccaggggc ggccaccgag gctgaaggct cccctgggag cggccggcca ccgcccgaac    720
aagcgtctgg ggccacgctg cagaagctgc tctcctacac caagcccgac gtggccttcc    780
tcgtggccgc ctccttcttc ctcatcgtgg cagctctggg agagaccttc ctgccctact    840
acacgggccg cgccattgat ggcatcgtca tccagaaaag catggatcag ttcagcacgg    900
ctgtcgtcat cgtgtgcctg ctggccattg gcagctcatt tgccgcaggt attcggggcg    960 gcattttac cctcatatt tgccagactga acattcgcct tcgaaactgt ctcttccgct   1020
cactggtgtc ccaggagaca agcttctttg atgagaaccg cacagggga ctcatctccc    1080 gcctgacctc ggacaccacc atggtcagcg acctggtctc cagaacatca atgtcttcct    1140
gcggaacaca gtcaaggtca cgggcgtggt ggtcttcatg ttcagcctct catggcagct    1200
ctccttggtc accttcatgg gcttcccat catcatgatg gtgtccaaca tctacggcaa    1260
gtactacaag aggctctcca agaggtcca gaatgccctg ccagagcga gcaacacggc    1320 ggaggagacc atcagtgcca tgaagactgt ccggagcttc gccaatgagg aggaggaggc    1380
agaggtgtac ctgcggaagc tgcagcaggt gtacaagcta acaggaagg aggcagctgc    1440 ctacatgtac tacgtctggg gcagcgggct cacactgctg gtggtccagg tcagcatcct    1500
ctactacggg ggccaccttg tcatctcagg ccagatgacc agcggcaacc tcatcgcctt    1560
catcatctac gagtttgtcc tgggagattg tatggagaat gtctccttca gcctgtcccc    1620
cggcaaggtg acgccctgg tggggccctc gggcagtggg aagagctcct gtgtcaacat    1680
cctggagaac ttctaccccc tggagggggg ccgggtgctg ctggacggca gcccatcag    1740 cgcctacgac cacaagtact tgcaccgtgt gatctccctg gtgagccagg agcccgtgct    1800
gttcgcccgc tccatcacgg ataacatctc ctacggcctg cccactgtgc ctttcgagat    1860
ggtggtggag gccgcacaga aggccaatgc ccacggcttc atcatggaac tccaggacgg    1920
ctacagcaca gagacagggg agaagggcgc ccagctgtca ggtggccaga agcagcgggt    1980
```

```
ggcatggccc gggctctggt gcggaacccc ccagtcctca tcctggatga agccaccagc   2040
gctttggatg ccgagagcga gtatctgatc cagcaggcca tccatggcaa cctgcagaag   2100
cacacggtac tcatcatcgc gcaccggctg agcaccgtgg agcacgcgca cctcattgtg   2160
gtgctggaca agggccgcgt agtgcagcag ggcacccacc agcagctgct ggcccagggc   2220
ggcctctacg ccaagctggt gcagcggcag atgctgggc ttcagcccgc cgcagacttc   2280
acagctggcc acaacgagcc tgtagccaac ggcagtcaca aggcctgatg ggggcccct   2340 gcttctcccg gtggggcaga ggacccggtg cctgcctggc agatgtgccc acggaggccc   2400
ccagctgccc tccgagccca ggcctgcagc actgaaagac gacctgccat gtcccatgga   2460
tcaccgcttc ctgcatcttg ccctggtcc ctgccccatt cccagggcac tccttacccc   2520
tgctgccctg agccaacgcc ttcacggacc tccctagcct cctaagcaaa ggtagagctg   2580 ccttttaaa cctaggtctt accagggttt ttactgtttg gtttgaggca ccccagtcaa   2640
ctcctagatt tcaaaaacct ttttctaatt gggagtaatg gcgggcactt tcaccaagat   2700
gttctagaaa cttctgagcc aggagtgaat ggcccttcct tagtagcctg ggggatgtcc   2760
agagactagg cctctcccct ttaccctcc agagaagggg cttccctgtc ccggaggag    2820 acacggggaa cggggttttc cgtctctccc tcttgccagc tctgtgagtc tggccagggc   2880 gggtaggag cgtggagggc atctgtctgc catcgcccgc tgccaatcta agccagtctc    2940
actgtgaacc acacgaaacc tcaactgggg gagtgagggg ctggccaggt ctggaggggc   3000 ctcagggtg cccccagccc ggcacccagc gctttcgccc ctcgtccacc cacccctggc    3060
tggcagcctc cctccccaca cccgcccctg tgctctgctg tctggaggcc acgtggatgt   3120
tcatgagatg cattctcttc tgtctttggt ggatgggatg gtggcaaagc ccaggatctg   3180
gctttgccag aggttgcaac atgttgagag aacccggtca ataaagtgta ctacctctta   3240
cccctaaaaa aaaaaaaaa aaaaaaaaaa aaagggcggc cgctctaga                3289
```

<210> SEQ ID NO 12
<211> LENGTH: 2342
<212> TYPE: DNA
<213> ORGANISM: Homo sapiens

<400> SEQUENCE: 12

```
ggcacgagct cagatctctc ctggtacccc ttccccacgc ccttagataa tccatctcaa    60
ttcctcatgc taattgagga gctatggctg caaggcacct tccaggattt cacacctaca   120
caaatctcct tttctcctt ttgccttctc tgcttatggg atattctgag tccccacccc   180
caatcactga cagctgggcc cccttcatca gcctcacaca ccacgtatta agtcagtcac   240
aatckcccct ctcmtctaac tgctggattt gtctttctac acacacccaa tgattcacgg   300
ctcttccggc tgamctactt acatggacac agtccaacgt gagcttacac atttcttact   360
tggctatacc attcttggct gattcattcc tgaaamcggt tcataacctg gaaactcagc   420
taaacacctt tccttcaaac tcagctctct cagcatggtt tcaggtaggg ctgttgccct   480
ccttcaccta atagcttctg gactaacatc catacaaacc aacacagcat catctaaacc   540
accaatatgg gggtaccatt tctactcaaa cttccttcat atcccacccc ccttatgtc    600 tcagccgaac ctaccctaat ccagcccacg ccacaatggt gggacaggtt ccccagtccc   660
tatgtggtct tattttacc cttgcactcc ctgtagacca tcaattctac accctaatta   720
caaaatcata tccacctctg cctggcagaa ggtgttatgc ttttctggct cgcctaccat   780
ccacacatcc ctacacctca ccaccggatc ctcttttctt ccttccatc caattcctgg    840
```

-continued

```
cttccccgct gccaactctg ctctctatgt ctccagttta aaggtgcccc ctggaaaaaa      900
tgtaacaatt ccctcacctg tgactggtac ctgacagcca ccacaccggg gcagcaatgg      960
ctaacggttg acaaagacaa tttctttctc tctccaaaac caaacagcct tcatcaactc     1020
cctagccaag actccctatc aggcccttac aggtgccgct ctggctggca gttacccaat     1080
ttgggaaaac gaaaataccc tatcatgta cctaccttca cctacaactt tgctgtcacc      1140
cccagttctc ttttgtgtga tacaactgat atttkgccta ccagccaact ggtcaggaac     1200
ttgcaccctg gtctttcagg ctccaaccat caacatccta cccctaacc aaactattct      1260
aatttctgta gaagcctcta tctcctcttc acccataaga aataaatggg ctctacatct     1320
catcaccctg ctaacaggat taggcatcac tgctgcactt ggcactggaa tagcaggcat     1380
aaccacctca atcacctcat accaaacact attcacaacc ctttctaaca ccgtagaaga     1440
tatgcacact tccattacca gtctccaacg acaattagac ttcctcgtgg gagtcatcct     1500
tcaaaactgg agtcctgg acctcctaac cactgagaaa gggggtacct gcatatacct       1560
ccaggaagaa tgctgtttct gtgttaatga atctggcatt gttcatatcg cagttcgtag     1620
gcttcatgac agggctgcag agctttgaca tcaagtcgct gactcctggt ggcaaggatc     1680
atccttcta agatggatac cctggggttgc ccccttccta ggacccctga tcttcctctt     1740
cctgttacta atgattgggc catgcatatt taaccttgta tcccgcttca tttcccaaag     1800
gctgaattgt tttatccagg caagcatgca aaaacacatt gataatatat ttcacctttg     1860
ccacgtctaa taccagagcc tacgaggaaa ccattcggaa gctccagaac ccaggcccta     1920
atcacaacgc ccctatccag caggaagcag ccagatgatc aacgacgccc ttttttcttt     1980
ttatactaaa gtaagaaata agaatgttag cccaaactgc actattttgc agacccctac     2040
cattttacaa actggtcaga gtggaaaatt ccaccagggc ctgagctgtg agaaacatcc     2100
tgtcaggcag gtcccaggcc taaccctgg ctgcactaaa ttccttcatt atcagcagcc      2160
aaacacaccg ccccaccc attttcacaa caatcccaga cctctcctgc ccgggactgt       2220
aactggtcca gcctgtaagc gggaagggg ctctggcact agctggtacc ccctctccgc      2280
aggtctttct cccaataaat ctgtgttgcc attgaaaaaa aaaaaaaaaa aaaaaaactc     2340
ga                                                                   2342
```

<210> SEQ ID NO 13
<211> LENGTH: 1666
<212> TYPE: DNA
<213> ORGANISM: Homo sapiens

<400> SEQUENCE: 13

```
ggtggagttc gcacctccag ctcgggccga tgtggaagct ttggagagct gaagagggcg       60
cggcggcgct cggcggcgcg ctcttcctgc tgctcttcgc gctaggggtc cgccagctgc      120
tgaagcagag gcggccgatg ggcttccccc cggggccgcc ggggctgcca tttatcggca      180
acatctattc cctggcagcc tcatccgagc ttccccatgt ctacatgaga aagcagagcc      240
aggtgtacgg agagatcttc agtttagatc ttggaggcat atcaactgtg gttctaaatg      300
gctatgatgt agtaaaggaa tgccttgttc atcaaagcga aatttttgca gacagaccat      360
gccttccttt attcatgaag atgacaaaaa tgggaggctt actcaattcc agatatggcc      420
gaggatgggt tgatcacaga cgattagctg taaacagttt tcgatatttt ggatatggcc      480
aaaagtcttt tgaatctaaa atcttggaag aaaccaaatt tttcaatgat gctattgaaa      540
```

| | |
|---|---|
| catacaaagg tagacctttt gactttaaac agttaataac gaatgctgtt tcaaacataa | 600 |
| ccaatctgat cattttttgga gaacgattca cttatgaaga caccgatttt cagcacatga | 660 |
| ttgagttatt tagtgaaaat gtggaactag ctgccagtgc ctcagtcttc ttgtataatg | 720 |
| cctttccatg gattggcatc ctgccttttg gaaaacatca acagctgttt agaaatgcag | 780 |
| ctgtagtcta tgattttctc tccagactca ttgaaaaagc ttcagtcaac agaaagcctc | 840 |
| agctacctca gcattttgtt gatgcttatt tagatgagat ggatcaaggt aaaaatgacc | 900 |
| catcatctac tttctccaaa gaaaacctaa ttttctcagt gggtgaactc atcattgctg | 960 |
| gaactgaaac tacaaccaat gtgctacggt gggcgattct tttcatggcc ctttatccta | 1020 |
| atattcaagg acaagttcag aaagagattg atttaattat gggccctaat gggaagcctt | 1080 |
| cttgggacga caaatgcaaa atgccttata ctgaggcagt tttgcatgaa gttttaagat | 1140 |
| tctgtaatat agttccatta gggatttttcc atgcaacctc tgaagatgca gttgtacgtg | 1200 |
| gttattccat tcctaaaggc acaacagtaa ttacaaatct ttattctgta cactttgatg | 1260 |
| aaaagtactg gagagaccca gaagtgttcc atcctgagcg atttctggac agcagtggat | 1320 |
| attttgccaa gaaggaagct ttggttcctt tttccctagg aagaagacat tgtcttggag | 1380 |
| aacacttggc tcggatggaa atgttcttgt tttttacagc attgcttcag aggtttcatt | 1440 |
| tgcattttcc acatgaacta gttccagatc tgaagcccag gttaggcatg acattgcagc | 1500 |
| cccaacccta cctcatctgt gctgaaagac gctgaaactg cctgggatgt tttcgggaac | 1560 |
| aagaatgtat atttgcctta tccctgaact tggtttaatc aaatcaatgt gtgtattaga | 1620 |
| ataaaagtca cagcatcaaa aagmcaaaaa aaaaaaaaaa aaaaaa | 1666 |

```
<210> SEQ ID NO 14
<211> LENGTH: 2027
<212> TYPE: DNA
<213> ORGANISM: Homo sapiens
<220> FEATURE:
<221> NAME/KEY: SITE
<222> LOCATION: (294)
<223> OTHER INFORMATION: n equals a,t,g, or c
<221> NAME/KEY: SITE
<222> LOCATION: (1976)
<223> OTHER INFORMATION: n equals a,t,g, or c
<221> NAME/KEY: SITE
<222> LOCATION: (1981)
<223> OTHER INFORMATION: n equals a,t,g, or c
<221> NAME/KEY: SITE
<222> LOCATION: (1985)
<223> OTHER INFORMATION: n equals a,t,g, or c
<221> NAME/KEY: SITE
<222> LOCATION: (2021)
<223> OTHER INFORMATION: n equals a,t,g, or c

<400> SEQUENCE: 14
```

| | |
|---|---|
| ggcacgagtt gggagcagct ctgcgtgcgg ggcctcagag aatgaggccg gcgttcgccc | 60 |
| tgtgcctcct ctggcaggcg ctctggcccg ggccgggcgg cggcgaacac cccactgccg | 120 |
| accgtgctgg ctgctcggcc tcggggcct gctacagcct gcaccacgct accatgaagc | 180 |
| ggcaggcggc cgaggaggcc tgcatcctgc gaggtggggc gctcagcacc gtgcgtgcgg | 240 |
| gcgccgagct gcgcgctgtg ctcgcgctcc tgcgggcagg cccagggccc ggangggggct | 300 |
| ccaaagacct gctgttctgg gtcgcactgg agcgcaggcg ttcccactgc amcctggaga | 360 |
| acgagccttt gcgggttttc tcctggctgt cctccgaccc cggcggtctc gaaagcgaca | 420 |
| cgctgcagtg ggtggaggag ccccaacgct cctgcaccgc gcggagatgg gtacttccag | 480 |
| gccaccggtg gggtcgagcc cgcagctgga aggagatgcg atgccacctg ygcgccaacg | 540 |

-continued

```
ctacctgtgc aagtaccagt ttgaggtctt gtgtcctgcg ccgcgccccg gggccgcctc        600
taacttgagc tatcgcgcgc ccttccagct gcacagcgcc gctctggact tcagtccacc        660
tgggaccgag gtgagtgcgc tctgccgggg acagctcccg atctcagtta cttgcatcgc        720
ggacgaaatc ggcgctcgyt gggacaaact ytcgggcgat gtgttgtgtc cctgccccgg        780
gaggtacctc cgtgctggca aatgcgcaga gctccctaac tgcctagacg acttgggagg        840 cttttgcctgc gaatgtgcta cgggcttcga gctggggaag gacggccgct cttgtgtgac       900
cagtggggaa ggacagccga cccttggggg gaccggggtg cccaccaggc gcccgccggc        960
cactgcaacc agccccgtgc cgcagagaac atggccaatc agggtcgacg agaagctggg       1020
agagacacca cttgtccctg aacaagacaa ttcagtaaca tctattcctg agattcctcg       1080
atggggatca cagagcacga tgtctaccct tcaaatgtcc cttcaagccg agtcaaaggc       1140
cactatcacc ccatcaggga gcgtgatttc caagtttaat tctacgactt cctctgccac      1200
tcctcaggct ttcgactcct cctctgccgt ggtcttcata tttgtgagca cagcagtagt      1260
agtgttggtg atcttgacca tgacagtact ggggcttgtc aagctctgct ttcacgaaag      1320
cccctcttcc cagccaagga aggagtctat gggcccgccg ggctggagag tgatcctgaa      1380
gcccgctgct ttgggctcca gttctgcaca ttgcacaaac aatggggtga agtcggggga      1440
ctgtgatctg cgggacagag cagagggtgc cttgctggcg gagtcccctc ttggctctag      1500
tgatgcatag ggaaacaggg gacatgggca ctcctgtgaa cagttttca cttttgatga      1560 aacgggggaac caagaggaac ttacttgtgt aactgacaat ttctgcagaa atccccttc      1620 ctctaaattc cctttactcc actgaggagc taaatcagaa ctgcacactc cttccctgat      1680
gatagaggaa gtggaagtgc ctttaggatg gtgatactgg gggaccgggt agtgctgggg      1740
agagatattt tcttatgttt attcggagaa tttggagaag tgattgaact tttcaagaca      1800
ttggaaacaa atagaacaca atataattta cattaaaaaa taatttctac caaaatggaa      1860
aggaaatgtt ctatgttgtt caggctagga gtatattggt tcgaaatccc agggaaaaaa      1920
ataaaaataa aaaattaaag gattgttgat aaaaaaaaaa aaaagggcg gccgcnctag       1980 ngggnccaag ctttacgtac gcgggcatgc gacgtcaagc ncttcca                    2027
```

<210> SEQ ID NO 15
<211> LENGTH: 2334
<212> TYPE: DNA
<213> ORGANISM: Homo sapiens
<220> FEATURE:
<221> NAME/KEY: SITE
<222> LOCATION: (2278)
<223> OTHER INFORMATION: n equals a,t,g, or c
<221> NAME/KEY: SITE
<222> LOCATION: (2290)
<223> OTHER INFORMATION: n equals a,t,g, or c

<400> SEQUENCE: 15

```
gggagtgtgg ctgcagaacc caggtggcag ggctttcctc aggcccctta ctcctgacct        60
ggacgaggcc gggcttcct caaggaggct ctctgactgc caccctgcc tgcctgcccg        120 gccctgcaca acatgcagcc ctccggcctg gagggtcccg gcacgtttgg tcggtggcct       180
ctgctgagtc tgctgctcct gctgctgctg ctccagcctg taacctgtgc ctacaccacg       240
ccaggccccc ccagagccct caccacgctg gcgcccccca gagcccacac catgccgggc       300
acctacgctc cctcgaccac actcagtagt cccagcaccc agggcctgca agagcaggca       360
cgggccctga tgcgggactt cccgctcgtg gacggccaca acgacctgcc cctggtccta       420
```

```
aggcaggttt accagaaagg gctacaggat gttaacctgc gcaatttcag ctacggccag      480
accagcctgg acaggcttag agatggcctc gtgggcgccc agttctggtc agcctatgtg      540
ccatgccaga cccaggaccg ggatgccctg cgcctcaccc tggagcagat tgacctcata      600
cgccgcatgt gtgcctccta ttctgagctg gagcttgtga cctcggctaa agctctgaac      660
gacactcaga aattggcctg cctcatcggt gtagagggtg gccactcgct ggacaatagc      720
ctctccatct tacgtacctt ctacatgctg ggagtgcgct acctgacgct cacccacacc      780
tgcaacacac cctgggcaga gagctccgct aagggcgtcc actccttcta caacaacatc      840
agcgggctga ctgactttgg tgagaaggtg gtggcagaaa tgaaccgcct gggcatgatg      900
gtagacttat cccatgtctc agatgctgtg gcacggcggg ccctggaagt gtcacaggca      960
cctgtgatct tctcccactc ggctgcccgg ggtgtgtgca acagtgctcg gaatgttcct     1020
gatgacatcc tgcagcttct gaagaagaac ggtggcgtcg tgatggtgtc tttgtccatg     1080
ggagtaatac agtgcaaccc atcagccaat gtgtccactg tggcagatca cttcgaccac     1140
atcaaggctc tcattggatc caagttcatc gggattggtg agattatga tggggccggc     1200 aaattccctc aggggctgga agacgtgtcc acatacccag tcctgataga ggagttgctg     1260
agtcgtggct ggagtgagga agagcttcag ggtgtccttc gtggaaacct gctgcgggtc     1320
ttcagacaag tggaaaaggt acaggaagaa acaaatggc aaagcccctt ggaggacaag     1380
tccccggatg agcagctgag cagttcctgc cactccgacc tctcacgtct gcgtcagaga     1440
cagagtctga cttcaggcca ggaactcact gagattccca tacactggac agccaagtta     1500
ccagccaagt ggtcagtctc agagtcctcc ccccacatgg ccccagtcct tgcagttgtg     1560
gccaccttcc cagtccttat tctgtggctc tgatgaccca gttagtcctg ccagatgtca     1620
ctgtagcaag ccagagacac cccacaaagt tcccctgttt gcaggcacaa atatttcctg     1680
aaataaatgt tttggacata gaaaaaaaaa aaaaaaaaag ggcggccgct ctagaggatc     1740
cctcgagggg cccaagctta cgcgtgcatg cgacgtcata gctctctccc tatagtgagt     1800
cgtattataa gctaggcact ggccgtcgtt ttacaacgtc gtgactggga gatctgctag     1860
cttgggatct ttgtgaagga accttacttc tgtggtgtga cataattgga caaactacct     1920
acagagattt aaagctctaa ggtaaatata aaattttta gtgtataatg tgttaaacta     1980
gctgcatatg cttgctgctt gagagttttg cttactgagt atgatttatg aaaatattat     2040
acacaggagc tagtgattct aattgtttgt gtattttaga ttcacagtcc caaggctcat     2100
ttcaggcccc tcagtcctca cagtctgttc atgatcataa tcagccatac cacatttgta     2160
gaggttttac ttgctttaaa aaacctycca cacctccccc tgaacctgaa acataaaatg     2220
aatgcaattg gtggtggtaa cttggttaat ggagcttata atggtaccaa taaagcantg     2280
catcacaaan ttcccaaata aagcattttt tcctggaatt taaatggggg ttgg           2334
```

<210> SEQ ID NO 16
<211> LENGTH: 2608
<212> TYPE: DNA
<213> ORGANISM: Homo sapiens

<400> SEQUENCE: 16

```
ccacgcgtcc gcacagggct caggctgggc tcagaggcca ctgagatgcc agctccttga       60
gagcagtggg ggtgtcccag gccagagcag cctcttcctc tcctggtccc agaaaaaccc      120
ttgcagtaaa tggtggcctc tgggtggtta cttctagcgc aggcttcctt ccttcctcta      180
```

-continued

| | |
|---|---|
| gctcctcccg gtgccctggg tgctgggtgc tggatggatg ggcgtcctct agctcctccc | 240 |
| ggtgccctgg gtgctgggtg ctggatgggt gggcgtcctc tagctcctcc cggtgccctg | 300 |
| ggtgctgggt gctggatggg tgggcgccac ggtgcaccct tgttgggctg cctgtgcccg | 360 |
| agtggcctct gcagctctta tgtctgcctc taatgggatg tgcgccctga ctgcctcgtt | 420 |
| cttaagggca tagtgggtcg gctaagatct gatcgccagg actgcgttct gggcaggtgc | 480 |
| tgggaaggcg gaaccaagcc gtccgtgccg ctagggagcc gagactgccg gaaagaagag | 540 |
| cggcaggagg gggcgtggtt gtgcagcccc accccgggga ggggctttag gcactgggaa | 600 |
| ggaaagtcct gttggaggaa ttcggtggct gttcacaccc gcctcgctgt cttggagtct | 660 |
| tgatctgtcg tcggcgggtc gctggcacag gactaaacat ggctgaggct gggctccagc | 720 |
| cagatctggc tggggacagc accgcgtggg cccaggatcc acccagagca ggcaggcctt | 780 |
| gctggggccc cagtcaagtc cacttccagt gaggagagcc agccgggagg tcagtgccag | 840 |
| agctctggtg gagcccagac cctgccttcc ctgagggccg ccctgtcgc cgccctgggg | 900 |
| tccctgtcct cctatcctga ctcctgcccc agggccacca cccctgaact gtgccctggg | 960 |
| gccccacccc tccacctggc cgactccatc tctgggcctg tcagtccacc tgggtcctct | 1020 |
| ctgggccctg atgcctggac cctctgtgcc aagcaccacc aagcaaaggg gatgaccttg | 1080 |
| ggcaccccca aggtgctgag actacagcca gtgagcccct gctgggggcc aaagtcatgg | 1140 |
| agggtgcctg ggcccttcca acctggaagg aggaggggag agagcaggca gcagggcagg | 1200 |
| gggaagagga ggagtgcccg atctgcacag agccctacgg gcccagagag cgccgcctgg | 1260 |
| ccctgctgaa ctgtagccac ggcctgtgtg tgggctgcct gcacaggctg ctgggctcgg | 1320 |
| cctccagtgc cgacctgggc cgggtgcgct gcccgctgtg ccgcagaaga cgcccgtgct | 1380 |
| ggagtgggag atctgccggc tacaggagga gctgctacag gccgacgggc cctcacgcca | 1440 |
| gccccgccga gaggcccctg catcctatca ccgcaaccct gggccctggg gctccctgga | 1500 |
| gcaccgctac cagctgcgct tcctggcagg gcccgtgggc ggccggggct gcctgccctt | 1560 |
| cctgccctgt ccaccctgcc tgggtgcccg gctctggacc ctgcgggagc ggggacccig | 1620 |
| tgcccgccgc ctggcgctgc tgagcctgct ggcccttgag cttctggggc tgctgctggt | 1680 |
| cttcacgccg ctcctgctgc tgggactgct cttcgtgctc ctggaccgct ctggccgctg | 1740 |
| agcagagccc aggacagccc cgccgcaaca ggccaggggg cccagactgg cccacgtccc | 1800 |
| catgcctggg tgctgtgagg cctgatgacc aggctggaaa acccaaggt tgggtccagg | 1860 |
| gcagtggcct tcaatcaaga cctcccattg ctgaacccac aaccagggct acccagaggc | 1920 |
| ctgaccctgc agagtccatg gctgcactgc tgcccagaca ctagctgaac caaggacac | 1980 |
| cagcgcccaa ggacagctcc tggaggaggc cagcccagca ggaaagtctg tgagcaggac | 2040 |
| cccattcacc ctgcggcaga cgggcaccgt actggccacg gctgacgcc ggccacactt | 2100 |
| cccctccgag ggccagctga gcacagcagg catgaaagca aacagagata cagcagtgag | 2160 |
| tcagttcctt ggagagggca gggactccgc ccaccctgtg ttcagataag gccagtgtg | 2220 |
| tgtccctgaa ggtcaggcca gccggggag gggtccatgc tgcgaaaatt cagcctgcaa | 2280 |
| aggctcctct ccccacttga tcaggcccag accaggtggg ggttggcgct ggcctgtgtt | 2340 |
| gcagggggaca agggcccacc caggccttgg aacataagct ctgcccctgc acaccctcat | 2400 |
| gtcaccacac ctgggatgga gacatccagg ggcccagcga gagatggagg actgatcctg | 2460 |
| gaacgtgaag cagctttcaa taaaccagct cctgggaaa aaaaaaaaa aaaaaaaaa | 2520 |
| aaaaaaaaa aaaaaaaaa aaaaaaaaa aaaaaaaaa aaaaaaaaa aaaaaaaaa | 2580 |

-continued

|  |  |
|---|---|
| aaaaaaaaaa aaaaaaaaa aaaaaaaa | 2608 |

<210> SEQ ID NO 17
<211> LENGTH: 1291
<212> TYPE: DNA
<213> ORGANISM: Homo sapiens
<220> FEATURE:
<221> NAME/KEY: SITE
<222> LOCATION: (1279)
<223> OTHER INFORMATION: n equals a,t,g, or c
<221> NAME/KEY: SITE
<222> LOCATION: (1286)
<223> OTHER INFORMATION: n equals a,t,g, or c
<221> NAME/KEY: SITE
<222> LOCATION: (1290)
<223> OTHER INFORMATION: n equals a,t,g, or c

<400> SEQUENCE: 17

| | |
|---|---|
| aaacctcttc tataggtaaa gctggwacgc ctgcaggtac cggtccggaa ttcccgggtc | 60 |
| gcccacgcgt ccggaaagag gaaacataga ggtgccaaag gaacaaagac ataatgatgt | 120 |
| catccaagcc aacaagccat gctgaagtaa atgaaaccat acccaaccct tacccaccaa | 180 |
| gcagctttat ggctcctgga tttcaacagc ctctgggttc aatcaactta gaaaaccaag | 240 |
| ctcagggtgc tcagcgtgct cagccctacg gcatcacatc tccgggaatc tttgctagca | 300 |
| gtcaaccggg tcaaggaaat atacaaatga taaatccaag tgtgggaaca gcagtaatga | 360 |
| actttaaaga gaagcaaag gcactagggg tgatccagat catggttgga ttgatgcaca | 420 |
| ttggttttgg aattgttttg tgtttaatat ccttctcttt tagagaagta ttaggttttg | 480 |
| cctctactgc tgttattggt ggatacccat tctggggtgg cctttctttt attatctctg | 540 |
| gctctctctc tgtgtcagca tccaaggagc tttcccgttg tctggtgaaa ggcagcctgg | 600 |
| gaatgaacat tgktagttct atcttggcct tcattggagt gattctgctg ctggtggata | 660 |
| tgtgcatcaa tggggtagct ggccaagact actgggccgt gctttctgga aaaggcattt | 720 |
| cagccacgct gatgatcttc tccctcttgg agttcttcgt agcttgtgcc acagcccatt | 780 |
| ttgccaacca agcaaacacc acaaccaata tgtctgtcct ggttattcca aatatgtatg | 840 |
| aaagcaaccc tgtgacacca gcgtcttctt cagctcctcc cagatgcaac aactactcag | 900 |
| ctaatgcccc taaaagaaaa aggggtatca gtctaatctc atggagaaaa actacttgca | 960 |
| aaacttcttt aagaagatgt ctttttattgt ctacaatgat ttctagtctt taaaaactgt | 1020 |
| gtttgagatt tgttttttagg ttggtcgcta atgatggctg tatctccctt cactgtctct | 1080 |
| tcctacatta ccactactac atgctggcaa aggtgaagga tcagaggact gaaaaatgat | 1140 |
| tctgcaactc tcttaaagtt agaaatgttt ctgttcatat tactttttcc ttaataaaat | 1200 |
| gtcattagaa acaaaaaaaa aaaaaaaaa aaaaaaaaa aaaagggcg gccgctctag | 1260 |
| aggatccaag cttacgtang cgtgcntgcn a | 1291 |

<210> SEQ ID NO 18
<211> LENGTH: 3129
<212> TYPE: DNA
<213> ORGANISM: Homo sapiens

<400> SEQUENCE: 18

| | |
|---|---|
| cggcacgagg ggagaccgaa tggcggggtg aggggagcta ctgcgtccgg ctttgcaggc | 60 |
| cgttcctttc agggttgccg cagcaatggc acttcatcct ggcagcagcc atttgctggt | 120 |
| tgcagtgcca gtttcttggt ttctttttttg cattcctgga atcagtttca tcactctctc | 180 |

```
ttggagttac caagagtcgc cagtcagttt cctctccgtg gaaggctgag tcccaattcc    240 ataggctct gtgccagact tttagtctct gataactccg aaatccttcc ttctgtttcc    300
taagctctac aggtattcta gttttctcg caatttttca ttactaggct acatcagtgt    360 ccttttctt tctttctttt tctcactttt tatttgtacc tttagtcctc caacaattaa    420
caattcccca tgttaaattc tctctgttta aacaactaac gggctctctg tattccaact    480
agatctcggc tgatgcaaat gccgtagaca atcaatcgat caatcaatca gcaaatccaa    540
tttccctcta gccactaaag ggacttaata taattgaatg attataaaat tctgatccca    600
tttatctcaa gccattgaaa atatttttcg tgtgattata agatacgtaa ttttaaaaaa    660
tgattttcta aatcaggatt cttaccagat tatttcacag cttattcact cattgattgc    720
tttcctccca cccttgttag cttttgtatg cctgtcctgc attttaaacc aaggtatgag    780
gaggataaag taaatagtaa atggtatgat agtggccaaa actttgaatc ttttttcccta    840 ttcatcatct ttgtgcaagt tggtagggag gtccactaat tcagcctccc cattccctgt    900
cccttcaaag taaatcagaa gcttcaggta aaaagcagag aagctaccca agttcttttc    960
atttatttta tcatcatact aataatttg ctttctgaaa tgattactct tacaagcagc   1020
aaatatattt tttaggaagt tagaattatt gatgtcacgt tttcatattc agtatcccaa   1080
gtaaatatca ggtaaattca ggaaaataaa tacaaccatt ttcttggtta attgttttta   1140
aatttaatat atgttcattt attcttttaa atatatattt cataaatggt gactatgtat   1200
tccatgacat aaaaactaag tattttagt gggaaattct ttgtggaatc actgaaatga   1260
taactagtgt tagcaatact tctgtttcat gagacgagtc actttatgaa gattgcaaat   1320 tatttttgt cccctctaga gttcatttca tgggaaattt aaattttatt gtcttaactt   1380
taatgttaaa catttccttc acatatggta tggccagaca tgttttcttc tttgctgcta   1440
ttttacattt tagatgtagt ccattcagga tctttttttt ttttttttag gagtcagagc   1500
ttgaagtgat gcaacacttt cactctttat ctctgattta catgctaata aagacaactg   1560
atagacaata tgatatactt tggccctaga agatccttaa tgaggaaatt ctgtggcctg   1620
ttttctcttc tgtgctattt tttgtcttct aaggcaggca tttttatcag ttcagtttgt   1680
tgctgtgact agttcaaact tgttcagggc tttatgcctg aaataagtaa tcaattagcc   1740
tatatatata aatatataac caaccattac aattatctaa gaatgtcagg gagttgtgaa   1800
gtggaaacaa attaaagagt tgcaaaatta aagagctcg tcttccaaca gaagtgtgct   1860
gacatatatt aaagaataaa tgaattaaag tcaccaaaga ggaacaggag ttaaaaagaa   1920
gaccattgtt tagatggagt caggctggtg cactgccaag gaaagcaaac aggatttctg   1980
aaggcttggt atgaatttca gcttgcatca ttccgctgga gggggtgatt tccccaatat   2040
catgttagat ccatagcttg ttcttgacag agtggcagta cctttcctcc actgcactct   2100
caccactagc atagatgtaa aacacagtaa gtactcagaa actacttgaa gagtgcagtt   2160
atcagtagag atgatcgaaa catttgtttt tctagggaat atttttgcct ttcttcttcc   2220
agaatcctct ggttataatg tgctcactgc taggtcacca gtcataaaac attatgtaga   2280
ggttactggt cattatccta atatatttat caaaaaatct ggagtatatg aaactgcctt   2340
tcattgtaac attagacaaa acatttatt ctatcaaata cagacttaaa actgccacca   2400
aattggaaga atatgatctt aaatttaaaa aaaccccata tacttaaaca caataatcta   2460
tctttatcta ccttcctaaa cattaatgca tgagacttct cttaatatca tgaatatgca   2520
ctatgatttt tatgttacat ctttttcttg tttccattta tgctagtgaa atttattagt   2580
```

```
atccttcatt gaaacactat tattttccat ggaggaaaat attttatttc ctttatgaaa    2640
agggtgcttt acttctgaaa tacagaattc attttgtttc ggattctgtt tgtttgtttt    2700
cacatcaact tcattctaaa tgttcattca aaattatttt tcagacttga gttcaggtga    2760
aaatgttaat ggaattaaaa agtagttagt caaatgaaat ttcaatatat aagtcaaatt    2820
tgaagaaaac tgaattaata aaggattcta agtttataaa gaaatcaaaa ttatgctttc    2880
aaaaatatta tgtaactgga gaaagtaatt ttattttgag atctctcatg attctttaat    2940 atatatttt  tcttattagt atgcaacctt ttggtaacat ataggaga cagttaattt      3000 tggtaagact acataattca tacattcttc atcttgacat acatgatcaa atactttata    3060
acgtccacta gccttgctct tgtccactgc aatggaaaaa aaaaaaaaa aactcgaggg     3120 ggggcccgg                                                            3129
```

<210> SEQ ID NO 19
<211> LENGTH: 3629
<212> TYPE: DNA
<213> ORGANISM: Homo sapiens

<400> SEQUENCE: 19

```
ccacgcgtcc gccagaggct gggaaggaaa aattattccc atcttaaaat atcttaaaaa      60
tatgtacaga tttattgtaa atcaaaattt tcctcataac tacagcccct tcccacacat     120
aaaattcccc ctaaatcagg aacataatgt acagcctgtt tttaacttgt attttttccat    180 tcacactatg tcacaaaaaa attctcatgg tgatccatga tttcacaggt cctgtccatg     240
tgtttcctga aagacagtc  ctggaatgga attactaatt caaaaggcat ttttaaggct     300
gttacacata ctgccaaatc ggccttcagg aggatgacac aaattccacc tatgtcatct     360
gagcgtgcca ctatctgctg ctattgcccc atgtttgagg ttttgtcctt tctcctcatt     420
ctcatgggca actgtcaaca tcaccaccac tgtgatcctg aaaagaaagg ctcagaagac     480
atagacagtc tgggattttt tttttttccct acctttcttt gcactgtagg gaaggagtga    540
gatgtggctg caggattggg gaatagctaa gtcagaaatg agcagcagtg caactgtggc     600
aatcttggag ggggggtctca gccatgaaag aaaacagggg gtgccttgcc agctggaggc    660
tgcagaatct tagcttgggt gttttgcctt ctccgtggaa ctgacagatg acaggaatga    720
cgtggagtat tctcatcaag cgtctcagca tagtcagtct ctgagatggc aaactttagg    780
caaagacacc tgggctgaaa ggtcccacat ttaaaacttg tcagtcagat aactgcccac    840
caccaccctc tgtaagatac ctagatatgg gaaccccaca ctcttcccca ataagactct    900
tgtatgactg aaagactttg tggttaaaaa catatcttaa tctaacctgt attttccctg    960
ctgcaatttc agccttttcc tatcttttca tggtgaatga acaccacaca ggctttcaga   1020
tcagacaact tctggctccg tcatttacta gctgtatcag ttaacaccag ctgctgactt   1080
cacttctgca tatgcattcc aaaattagtg tcttaaaata caactactt  attactttc    1140 acaagcctaa aagttggctg aatggttctg ctgatctgac ttggttaatc ttggctggac   1200
actgtctgat tcagcatagg ttgactgtcc tctgcctcat gtctcttatc atccataaat   1260
tgcccaggct tgcttgcctg aaggcagaag agttcccact agcaggagag ggcaagcact   1320
tttcaatgca caagcacctt tcaagcctct atttgcatca agtttgctaa tgtcccgctg   1380
accaaagcaa atcatgtggc ttacttcgga gtcagtgtgg gtaggcatta cccaaagaaa   1440
gtggctatag ggaagcatga agatctagag ccattagtac aatcaatcta ccacattaac   1500
```

-continued

```
tttgtgacct tgggcaattc ccttagcctc tctgagcttt aactctataa tctataaaag    1560
tgcagaattt ttttgggatt ctttgctata atgtatgtaa aatgtctgct acacaataaa    1620
catgccatat ttattaattt tcttttctcc tccttttcat catttgaatt ttttcttaaa    1680
tgcatatata tatgtgcata tatatatgtc catctcgata tatatatatg tatatatata    1740
tatatatatg acttactctg tcatccaggt gagagtgcag tggcatgatc acagctcact    1800
gcggcctcga cctcccaggc tcgagtgatc gtcccacctc agcctccag gtagctggaa     1860 ctacagatgt gtgccaccac acccagctaa attttttttgt atattttata gagaagggtt   1920
tcattatgtt gctgaggctg gtctttaact cctgggttca agcaatccac ccaccttgac    1980
ctcgcaaagt attgggatta caggcatgag ccaccatgcc tggcccttaa atgcatcatt    2040
cttatacatt cctttataca tacaaagctc gaagataata ataataaaca ttattcccac    2100
ggcttctgtt gaatccccaa ctcctagcct gtgcctaatc aagtgtgccc tcaattcatt    2160
ccaatggtct ggaatttgaa gactaaagga atcaaagggt atctcttccc tttgttcctg    2220
ggaccatcaa gttgtgaaat gacctcttgg ctttctgatc tgggtccact accacaaatg    2280
aaatagaaag gagttaacac atttgcatta actgatgatt cttaatagag gcaataaaat    2340
gagaaacccc catttcctaa tttaaatgtg gctttgggga taggataagt atcctggccg    2400
ctccttagct aatcaggctc cagaagggac attaattgca gccagcgcat cctgctgggg   2460
agacccaagg ctgccagctc ccttgctgag aatggaatag aatttttaatt ggctgtgaaa   2520 gcatcatggt aggaggtaca gggaagagtt ggtctgctcc cccaaagcag gttagggaag    2580
ctccaaggga aaggactcaa acaggtgcat ggcagcaaga acctcccatg ctcaggggcc   2640
ttcccagctg caacaccaca gttccaattc cagggctgga ctccagccta ggtgaaggac    2700
cttctcacac ttgggcgatt agtactggag cacggagcct gtgaatcttc tcatctctgt    2760
gcttccccca acttccatga gagaagcacc acatagttac tgtcacttgt attgtcaatc    2820
ttcgacttca gagaggtctc caaatataag ctcaactccc cagtgtactg tgtgtgtgcc    2880
attagtccat gtgtatggtc tgaagcaatg gcacagcatt cctgtactgt tgtttcagag    2940
caatgtgaat ttatttcact cacaataaat taatctaact atgcttaggg caaagttgtt    3000
ctcatggtaa tgagtatgtc ctttctgcca tggcaatttc tggaacacac atatagacaa    3060
gaatgacatg tgaaggtcaa tagatgagac tatgaaaaac aagacaatat agcttttag    3120 cataaatgta caatgatgca tgtggttttt ggagattgtt ggacaaatta cttaacctct    3180
tggtgcctta gttttctaat tattaaaatg agggcaacag tattgctgat ctaataaggc    3240
ttttggaaag aataatgaga tgtaaagagc ttagaatagt gcagagtctt aataaacatg    3300
tcttcgtgat tccttctagt gaagtgacat agagaagtgg gaccagtcat tgacccaccc    3360
aagctctgtc aacctagtgg tatagtaaat ctgttggcaa aaagcaaagc agaacaacaa    3420
aaaaacgcaa gcaaaatcat tgctttcagg aaactatttt gtgagacaga agcttgataa    3480
aaattcaaaa tttgcagtaa actctacttc attaatactt taaaactcac agcaataaac    3540
cattacttag aacaagtaag cagttttgtt tttattgtgc attttgatat ttattttcaa    3600
aaaaaaaaaa aaaaaaaaa aaaaaaaa                                        3629
```

<210> SEQ ID NO 20
<211> LENGTH: 1144
<212> TYPE: DNA
<213> ORGANISM: Homo sapiens

<400> SEQUENCE: 20

```
tcgacccacg cgtccgcgct tgacttgctt ccagacaaag gttgtctcaa gtttgttgct     60
caaaccgagt tctggagaac gccatcagct cgctgcttaa aattaaacca caggttccat    120
tatgggtcga cttgatggga agtcatcat  cctgacggcc gctgctcagg ggattggcca    180
agcagctgcc ttagcttttg caagagaagg tgccaaagtc atagccacag acattaatga    240
gtccaaactt caggaactgg aaaagtaccc gggtattcaa actcgtgtcc ttgatgtcac    300
aaagaagaaa caaattgatc agtttgccaa tgaagttgag agacttgatg ttctctttaa    360
tgttgctggt tttgtccatc atggaactgt cctggattgt gaggagaaag actgggactt    420
ctcgatgaat ctcaatgtgc gcaatgtacc tgatgatcaa ggcattcctt cctaaaatgc    480
ttgctcagaa atctggcaat attatcaaca tgtcttctgt ggcttccagc gtcaaaggag    540
ttgtgaacag atgtgtgtac agcacaacca aggcagccgt gattggcctc acaaaatctg    600
tggctgcaga tttcatccag cagggcatca ggtgcaactg tgtgtgccca ggaacagttg    660
atacgccatc tctacaagaa agaatacaag ccagaggaaa tcctgaagag gcacggaatg    720
atttcctgaa gagacaaaag acgggaagat tcgcaactgc agaagaaata gccatgctct    780
gcgtgtattt ggcttctgat gaatctgctt atgtaactgg taaccctgtc atcattgatg    840
gaggctggag cttgtgattt taggatctcc atggtgggaa ggaaggcagg ccttcctat    900 ccacagtgaa cctggttacg aagaaaactc accaatcatc tccttcctgt aatcacatg    960 ttaatgaaaa taagctcttt ttaatgatgt cactgttttg caagagtctga ttctttaagt   1020 atattaatct ctttgtaatc tcttctgaaa tcattgtaaa gaaataaaaa tattgaactc   1080
atagcaggaa aaaaaaaaaa aaaaaaaaaa aaaaaaaaaa aaaaaaaaaa aaaaaaact    1140 cgag                                                               1144

<210> SEQ ID NO 21
<211> LENGTH: 1443
<212> TYPE: DNA
<213> ORGANISM: Homo sapiens

<400> SEQUENCE: 21
ggaaccattg gcctatattg ggttggatct attattatga gtgttgttgt ttttgtgcca     60
ggaaacattg tagggaagta tggaacacga atttgccctg ctttttttctt aagcatacca    120 tatacttgtc ttcctgtctg ggctggtttc agaatctata atcagccatc agaaaaattat   180 aattacccct caaaggttat tcaagaagcc caagcgaaag acctgctgag aagaccattt    240
gatttaatgt tggttgtgtg tctcctcctg gcaactggat tttgcctgtt cagaggtttg    300
attgctttgg attgcccatc tgagctctgc cgattatata cgcaatttca agagccctat    360
ctaaaggatc ctgctgctta tcctaaaatt cagatgctgg catatatgtt ctattctgtt    420
ccttactttg tgactgcact gtatggctta gtggttcctg gatgttcctg gatgcctgac    480
atcacattga tacatgctgg aggtctggct caggctcagt tttctcacat tggtgcatct    540
cttcatgcta gaactgctta tgtctacaga gtccctgaag aagcaaaaat cctttttttta    600 gcattaaaca tagcatatgg agttcttcct cagctcttgg cctatcgttg tatctacaaa    660
ccagagttct tcataaaaac aaaggcagaa gaaaagtgg aataaaaata ttacttcatg    720
ttcctccttt ctaaattact aacttttgtt atactggtac tgatattttg tcccatttca    780
ctctcttctc atacgtgagt acttaagaat atgtacattc ttgctctgca ctgtatgtgt    840
gagctatatg gtattgtgta aatttttttt gaaggaaaat ggaaattctt gagaaacagt    900
```

```
ttgtttaaag aaatatattc aaaatcattt gtgaataaac ttgatcatcc atctcaatat    960
tgtttgacat ataaataat tataagtgta aaaaattaca atttagtgcc aacagtagtg   1020
agcatgaaat gaaactattc aaaagagaat atggcctgtg catattaaaa aattcaaaac   1080
agtgaatgca gactggagga gtaacttttg caaataagat gaatatgctt cattattaaa   1140
ctcaatataa aaggcaaatc atcagaatat ttttaaatgt tgtttgaaaa atgtttttccc   1200
aaggaaagtt tattatttgc tgctgtttca agaaaattac ttttactaaa ttttttttgtg   1260
tgaatttaaa cagctaaata gggatcagta actttatctc tatccttaat gaacatttgt   1320
tttattggtg gctgaaaata tttctattgt atttctgtgt atattttaa taaaattatt   1380
tttggcctct taaaaaaaaa aaaaaaaaaa aaaaaaaaaa aaaaaaaaaa aaaaaaactc   1440
gag                                                                1443

<210> SEQ ID NO 22
<211> LENGTH: 1053
<212> TYPE: DNA
<213> ORGANISM: Homo sapiens

<400> SEQUENCE: 22
cttcgctggt gggaagaagc cgagatggcg gcagccagcg ctggggcaac ccggctgctc     60
ctgctcttgc tgatggcggt agcagcgccc agtcgagccc ggggcagcgg ctgccgggcc    120
gggactggtg cgcgaggggc tggggcggaa ggtcgagagg gcgagkcccc tgtgtcctca    180
gccatcccaa gaagggtttg ctggtccctc ctttcccccc gtcccacgag gccacctggg    240
ccagcccctt gtcctctgcc ttctgctggc agaggagcag ctggactggg gcctttggca    300
cagcagccgg tgtctcctgc gcccgcctcc cccatggccc catgcagccc caggggcttc    360
cccctgccc atggagtaga gcccgagatc ctggccacta tgccagttct gacctcgcat    420
cccctaccc cgagcccatg cagtctggga acatgccgcc ttctctccag cctctgtgcc    480
tttgttccag gtggtctcac cctcctgtcc ctggctgggc taggtggtcc tgtccaggct    540
cctgcagcgc cccctcact ttgacactgg actaggatgc agcctccctt ctgtgtcccc    600
ttgagggtac cctgggtccc ctcatcaggg gcagaggcat gaaagagtcg ggctggatg    660
gccagggct tctgggcccg acgcctagtg cagcccctgg ggtcgtggtt tgacatttgt    720
ctgcctggtg caaacaagga atccttgcct ttaaggtgac aggccctcca caggcttcca    780
gacttgaagg aaaaggttta agaaagaaaa caaaaccaac agttagtggc cggtgagggc    840
ccaggctggt cagcgtcccg tcttgcacac ccaggggcct cccttctgc tggagtcccc    900
tgtgtcctcc accacccccc gccgccagc atcctacctg gactgcggtg ctacgagggc    960
ctgcgggcct ttgctgtgtg ccaccctccc tgtaagtcta tttaaaaaca tcgacgatac   1020
attgaaaaaa aaaaaaaaaa aaagggcggc cac                                1053

<210> SEQ ID NO 23
<211> LENGTH: 741
<212> TYPE: DNA
<213> ORGANISM: Homo sapiens

<400> SEQUENCE: 23
gtagacttct ggaccttgra tgtcactgag tttaagagaa aggtagtccc aggactctgg     60
tctagcagct gagtaaggct caggccttag aatggcttag cttgctccat tgcaatgcat    120
catcctggat gttaaaatcc agctgtctct ctgaaamcta aatatgaaag actgagattt    180
agtcaacttt gctgagattt aatttacata taataaaatg aatcatttta actgtgcagt    240
```

```
tcagtaagtt ttgaaaaatg tctatacaga ttcatgtaac tgccaccaaa attgagaaag      300
gacacttcca ccatctcaaa agattctgtg tgttcctttg tagtaagtct cttctacccc      360
atccctagac aacagctgat gtgctgtcat tgtacacata tattagcttt gcctgtccta      420
gaacttcatg ttaatgggaa gcatcctgta tgtactgttt tgtgtctggc ttcttcagtg      480
tatttttgaa atttatccac attgttgtgt gtatccaaag tgtgttcttt ttcattgcca      540
aataatgttc tgctatatga atatattaca aaatatttgt ctgtttatct attggtggat      600
ttttgcattc gttccagttt ggggctatta tgaataaagc ttctgtgaaa attcaaaaaa      660
aaaaaaaaaa aaaatgaccc tcgagggggg gcccggwacc caaaacggag tatttccctt      720 tttcccccc cccgccccccc g                                                 741

<210> SEQ ID NO 24
<211> LENGTH: 946
<212> TYPE: DNA
<213> ORGANISM: Homo sapiens

<400> SEQUENCE: 24
ggcacgagcg aaagcctctc tcttaacaac ggtgccgcac agctttgccc ttgaaagcat       60
ctctactgga ccggaacaca ctcatgtgcc ccgctccctg acccagccaa ggctgccctt      120
tcatctccaa ggctgagatg ttgccggtgg tcccatgaga gcctgcccat gggctcaggt      180 gccccttttac cttctgctgg atggacatct ggctgtgagc caggctgggg tcatggccgg      240
ggtgagcgga ggcaggggtg gacggaggct tcagggccc atcactagta gggtcattac       300
ctcttgccaa cagccggggg tgggagtctg ggtctcgctc aggccagagc ttctcaacct      360
ggagtccctg ggggtggctg ccaaaggtgt gtatgacaag cacgtatccc tggacatttc      420
cggggagagg tctggggctt tggtcacatt tccaagggc tgctgggctt cggagcagtc       480
cccccccatg tctcagccac tacagggtcc ctctctctcc ttgcacccca gaccctccgc      540
tgccctggta atgagcagaa ggaaagtctt ggggtgtgct caaagtcagg agagcaaaat      600
atgccaggca aaagctcccg ggaaaagccg gaggagtctg gggtggccac cgggatgtgg      660
agcagcgagg gcaaagacgg tgaacacagc cctccagctg tctgagcctc agttttctaa      720
tctgtagaat ggggatgatc atacctgcct cacaagaatg ttgagacaat tcacagagac      780
gttctggagc ccctttcccc cgagaccggc attcatgagt ctgctgggac cagaaaaccc      840
atctcagggg cccagcgggg cacccaggag agtctggcgc tgcaagcgct gtataaacca      900
caagcgttct ccaaaaaaaa aaaaaaaaa aaaaaaaaa aaaaa                         946

<210> SEQ ID NO 25
<211> LENGTH: 831
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (10)
<223> OTHER INFORMATION: n equals a,t,g, or c
<221> NAME/KEY: SITE
<222> LOCATION: (11)
<223> OTHER INFORMATION: n equals a,t,g, or c
<221> NAME/KEY: SITE
<222> LOCATION: (15)
<223> OTHER INFORMATION: n equals a,t,g, or c
<221> NAME/KEY: SITE
<222> LOCATION: (27)
```

<223> OTHER INFORMATION: n equals a,t,g, or c

<400> SEQUENCE: 25

| | | | | | |
|---|---|---|---|---|---|
| catcnacggn | naccnctact | ataggtnaag | ctggtacgcc | tgcaggtacc | ggtccggaat | 60 |
| tcccgggtcg | acccacgcgt | ccgggggaaw | tcccagtcga | tttttccaag | cagtactccg | 120 |
| cttcctggat | gtgtttgtct | ctcttggctg | cactggcctg | ctctgctgga | gacacatggg | 180 |
| cttcagaagt | tggcccagtt | ctgagtaaaa | gttctccaag | actgataaca | acctgggaga | 240 |
| aagttccagt | tggtaccaat | ggaggagtta | cagtggtggg | ccttgtctcc | agtctccttg | 300 |
| gtggtacctt | tgtgggcatt | gcatacttcc | tcacacagct | gattttgtg | aatgatttag | 360 |
| acatttctgc | cccgcagtgg | ccaattattg | catttggtgg | tttagctgga | ttactaggat | 420 |
| caattgtgga | ctcatactta | ggggctacaa | tgcagtatac | tgggttggat | gaaagcactg | 480 |
| gcatggtggt | caacagccca | acaaataakg | caaggcacat | agcagggaaa | cccattcttg | 540 |
| ataacaacgc | agtgaatctg | ttttcttctg | ttcttattgc | cctcttgctc | ccaactgctg | 600 |
| cttgggggttt | ttgcccagg | gggtgaactt | tatttcattt | ccmcaggttg | aaactgaatg | 660 |
| ggcagttcat | gktaaaatcm | cttttcatgg | aaagagctct | atgtaacagc | ataataaaac | 720 |
| tgsctaccta | gcagcaaaaa | aaaaaaaaa | aaaaaaaaa | aaaaaaaaaa | aaaaagggcg | 780 |
| gccgctctag | aggatccaag | cttacgtacg | cgtgcatgcg | acatcatagc | t | 831 |

<210> SEQ ID NO 26
<211> LENGTH: 1294
<212> TYPE: DNA
<213> ORGANISM: Homo sapiens

<400> SEQUENCE: 26

| | | | | | |
|---|---|---|---|---|---|
| ctgcagaatt | cggcacgagg | ttatttcacc | tctcttggcc | tcagtttctc | tgtgaaatca | 60 |
| ggaattaaca | tggtctctga | gacccccttc | tgatggtgaa | tgtgtggttt | ggtgattttg | 120 |
| tggccctgca | tcatgacctt | atttagttct | ctttcaacag | gggatgtttt | actgccttgt | 180 |
| aaaatcctcg | tgggactgcg | tgtctttata | ggagccaggt | tgtaaatgaa | cagaattcag | 240 |
| attggttcta | atatatttta | cctctaaaag | aaagggcatg | gggaggccat | gaccttaaag | 300 |
| caggtttttt | ctgttgtctg | tgaagcctgt | gatgattgag | agtggctggg | actggcggga | 360 |
| cgatgtttgg | gtggaagagg | gaggccatct | cgatgcgccc | cgtcccgggg | aggcacccag | 420 |
| cctgtaagga | ggtgatgtct | atctacactg | agcgcaagga | ccctgaaccg | ggggaggctg | 480 |
| aggcggggcc | tcttgattcc | caccctgtcc | cccagtggct | aggctagtgt | ggcccgggaa | 540 |
| atgacttcca | tctctccctc | caggcatatt | taataagagg | ccagtatttt | cagattctgc | 600 |
| cgcttctgga | cgaatgtctc | agagagctgg | gaggcgccct | ggaggatgga | accttccttt | 660 |
| gagcgttgtt | gaggtgtgtc | ggggtgccg | tggcacaggc | ccctcccct | gggggcatc | 720 |
| actgttccct | tgctctgcat | ccccgctgtt | tcccctgccc | ctgaacaggc | gtggagatgt | 780 |
| gcacgggaca | ctcggaggcc | ggatgctcaa | cagagtggag | tgccgcgacg | gtgtggccgc | 840 |
| agcctggctg | tgccttcacg | acgcagctgc | aatcagagga | gctgtgggac | gctgtcccat | 900 |
| gtggacacag | cccactcact | gggtgctgct | cctgtgctgg | gcgctgcact | tttattgtcg | 960 |
| ttaaaaattt | atattaagat | gcggccgggc | atggtggctc | atgcttgtaa | tcccagcacc | 1020 |
| ttgggaggcc | gagacgggcg | gatcacgagg | tcaggagatc | gagaccatcc | tggcttacat | 1080 |
| ggtgaaaccc | cgtctctact | aaaaatacaa | aaaattagc | cgggtgtagt | ggtgagtgcc | 1140 |
| tgtagtccca | gctactcggg | aggctgaggc | aggagaatgg | cgtgaacccg | ggaggcggag | 1200 |

```
cttgcagtga gccgagatcg tgccactgct ctccagcctg ggcgactgag cgaaactccg    1260
tctcaaaaaa aaaaaaaaaa aaaaaaaact cgag                                1294
```

<210> SEQ ID NO 27
<211> LENGTH: 1656
<212> TYPE: DNA
<213> ORGANISM: Homo sapiens

<400> SEQUENCE: 27

```
ggcacgaggt tcacagcacc tgatttgcaa ggcagctata caagttcctg gactcttgta     60
gttccggagt gtttcacctg accttaagcc caccccatcc atctttaatc aagaaaccat    120
gtgctttccc gcatgcctgt gttccccccct cacgtgtctg ctgtctgtgt ggaagcctgg   180
cctggcgcat gctgtggtgc actgcatgct ggaacccgtg gagtttgcac gcgtggtaca    240
gtatgaggcg ggtcacgttt tgtagtgtgt gccgtgggct cccgagaaac aagttaaagt    300
gtgtgctgaa atagatttta ttgacataaa ataagcctta ttgctaaatt taagagaatg    360
tgttacaaat gttttttgct aaacatcagt attgattatt ctacatgatg tacttattga    420
cataacaacc tgaaattctt gattttagac aatttctcct caagttgatt cagctgcatg    480
actctcagaa atcagtcatt ttttattgta gattgctggt tttcttcctc tagttttgtat   540 cgtgtatttt cctcctgtgg agaaaatgtg gttggcaaga aatgccatat tttaaagctg    600
tatcgtggct gttaatgcag aaaacaccag tgtactgcag gctgtttggc agtggggctg    660
gggctgagtg tcctgccctc agtggcctgt gtctgtgctc ttgttcgctg acatgcagat    720
acaggggcag atctgagggt ttgatggagt gcagaaggcc acacgtgtgg ctttctgtaa    780
atgcagaaac atggaatcct tgagcagaca cttgtcttct ggagcacctt gcatggattt    840
cgcctcctga tgcttcattg ccgttaatag agtggtggtg gttgtgttat gagaaatttt    900
gtctaacctg gcttctgaaa tttctcaaac taaatattca tgctgttttg tgttttcctt    960
aatgactgag gctagtgata ttactcagaa aagtaacagt aacttgggtc ttctgagcgt   1020
caggatgttc accatttaac ttgtttctcg ttagtgtcta gtacgtcggc tttcggtagt   1080
gtaggtgtgt gttctgtgtc ctttcccgtg tgtgcctgca ctagtggcag cctctgcttc   1140
caggtcagtt tagagtagac tggctctggt attgctagca agtagttgct gttacccagt   1200
gtagccatga agcccagctc cttggatctt gacatatatg ttccaggcaa agtacgtaat   1260
ccagacgttt ctaactcttt ctagatgatt gcaattgttc tccatgttgt ctgttaggcg   1320
ttatgttaat tctcgatcta acagtgtgcc tgtaacatat atggtagtga agagacatca   1380
catgcagaga ccgttttcct tttatcaact acaggtccgc tatcgacgag agcacctttc   1440
tgctaggcag tcaccctact tcccgttgtt ggaggatttg atgagagacg gcagtgatgg   1500
tgctgctctc ttagctgtga ttcactatta ttgcccagag cagatgaaac tggatggtga   1560
gtggagaatg cttcctgaaa cagatccgaa aaggcttaaa ggaaaattat agtgtacatt   1620
gatccacata tatattaaaa aaaaaaaaa aaaaaa                              1656
```

<210> SEQ ID NO 28
<211> LENGTH: 1350
<212> TYPE: DNA
<213> ORGANISM: Homo sapiens

<400> SEQUENCE: 28

```
gtgacttcta tattcaatag attttttgtaa atgttaaaac atctatattt aaatgttaaa    60
```

```
acactaaata tagagagggg ctttatttca atcatagagc aacaacaaaa ataatgctta      120
tagctaaact gcctgttcta gaaagcatct gcttttttcat gttattccta aatcctcttg     180
tcatactttt gtcattgaac aatgctctcc ctctcgtctt ccatcctcat tcagaattt     240 tagaagacca caatcgtgga gatacactac ccagtattgt ttgatacatt tttatttgat     300
aaacattcag tgcaggaaac tgtgatttgc tatatgttta tgtatataat cttattctgt     360
agtcatcaga atgttaatgt aaggtacatt tgatttttat ttttttacatg tgtagttttc     420 tttcttcaca gtcaaagcat ttatattatt ggggtgggg gcagggaatt aagttggtgg      480
gctcgaaaat ccattcatat gtatctgtct acaaatgtct ggggataatt taaatttgaa     540
acctaagtta tatatagttt ggcaatgctc ttcttcaata tttacaataa taggatgatc      600
tacaagaaaa taagtttctt tttgcaaatt tttatcatac taaagttgtt cttttaattt      660
agcatatcta aaataggatt tagttcagtt tagctcacac aggtgtttgc tgacattcat      720
tggccattta atacagtgtt gagtggttct ccgtaaaagt ataagtgcta acactacgaa      780
gaaatgcaca cgatcattct tgctcacttc tataacaaac ttacataaaa tggatttaaa      840
aattcctact cacagcctaa aacttctgga gttcactacc ttttttttcaa attcatagta     900 agatcacctg tgtatttat attttagtaa agccaattat gaagtacaag tatcatacac      960
gtacttttga gctactatta tttgaaaaaa atctgccaaa tagcatcttt aggatatatt     1020
tacattttca ctcatctaaa aagtatacaa aaataaaaag tggaaaaagg tatcttctga    1080
atgttcaaga gcatcctata gtgccaaata taaagcacc attttttct tcataaccag      1140 gattaaaatt catatatact gcagggcaga catacatatg atagcttgtg ctgattaatt    1200 taacccccatt tgtaaacaga tgaaaattt attttcttat tcatttata agatggctca     1260 atgtattggg aggcttcttt tttattacag aaagtgtata ttggtatata ataaatgaac    1320
ttttcaaatg aaaaaaaaaaa aaaaaaaaa                                     1350
```

<210> SEQ ID NO 29
<211> LENGTH: 1766
<212> TYPE: DNA
<213> ORGANISM: Homo sapiens
<220> FEATURE:
<221> NAME/KEY: SITE
<222> LOCATION: (1743)
<223> OTHER INFORMATION: n equals a,t,g, or c
<221> NAME/KEY: SITE
<222> LOCATION: (1748)
<223> OTHER INFORMATION: n equals a,t,g, or c
<221> NAME/KEY: SITE
<222> LOCATION: (1749)
<223> OTHER INFORMATION: n equals a,t,g, or c

<400> SEQUENCE: 29

```
gctcagcgcg ctgcccggct ggggacccgc gcacctgcag cgcccgctgc tcggccctgc       60
atcctgcctg ggcatcctgc gcccggccat gacggcgcac tcattcgccc tcccggtcat     120
catcttcacc acgttctggg gcctcgtcgg catcgcgggc cctggttcgt gccgaaggga     180
cccaaccgcg gagtgatcat caccatgctg gtcgccaccg ccgtctgctg ttacctcttc     240
tggctcatcg ccatcctggc gcagctgaac ccctgttcg ggcccagct gaagaatgag      300 accatctggt acgtgcgctt cctgtgggag tgacccgccg ccccgaccc aggtgcccag      360 ctctcggaat gactgtggct ccactgtccc tgacaacccc ttcgtccgga ccctcccca      420 cacaactatg tctggtcacc agctccctcc tgctggcacc cagagacccg gacccgcagg     480
cctgcctggt tcctggaagt cttcccagtc ttcccagcca gcccgggccc tggggagccc    540
```

| | |
|---|---|
| tgggcacagc agcggccgag gggatgtcct gctccaatac ccgcactgct ctggagtttg | 600 |
| ccctctttcc caaggagatg ctgctgggga gctggtatgg gtgggtctt tcccctttaca | 660 |
| gacgggcag atgccaggac tcagcccatc ctgaggagga cacgtgtcct catggagagg | 720 |
| gtgctccggc ccaggcgggg gagtcggtgc ccagtcagca gctctgccac catcctgctg | 780 |
| ggaactgggg gggcctctat tgggttatag gcaaggcctt ttctctggca tggaattgtt | 840 |
| aattttctga cacgtctaga tgtgaaattt ctgaaaatgt tgaagcagag aaacattcac | 900 |
| acacaaaaag caacatagtc atgtgggtcc agatggcctc agtcctagat gttggcaccc | 960 |
| tttgctgtgt ctcctcagag tatcctgttc cgcctcctgc cacctggacc tccctcagtg | 1020 |
| gatgtcttcc ctcccccgac cccagcctgt cagtccgagc acagtgcagg tttggctctg | 1080 |
| acttgggcct ttggctgcag tgggggtgga tttcagagcc tctcatggca gcatctaagt | 1140 |
| gaccagagct gggatgagag agggaaggg gcaatgtgag tggcgctatg ggacgggcca | 1200 |
| gccctgctcc tgagccagcc ccgccctctg cccctggcc ctgggctctg tgctagggat | 1260 |
| ggtgaagaat gggggcgtgc carcctgcag gagtgggaag caacacgcag gggtcccgga | 1320 |
| cctctcmagc cttgccctya cgcttatccg agctcccagt gtggttagca cagagctcac | 1380 |
| ccaccttgcc tggctcccag ctggggcctg tcctcactgg tgctccaggg gaagaaacga | 1440 |
| cagcctcact tctgtatgga ctgctgatgt ggcctgccat cctgttcagc gggcattgtc | 1500 |
| tttggagcag caggagacta ggatgcctct cactcacatg ccagttcctg gctggccagc | 1560 |
| tgctcagggc tcaggctggg gcctcccatt gacatcctcc ccctacactc cctctctgag | 1620 |
| cctccgtcgc ccctcctgtt gggtaagggt gttgagtgtg acttgtgctg aaaacctggt | 1680 |
| tcatatataa taaataatgg tgatgaaaaa aaaaaaaaa aaaaaaaaa aaaaaaaaa | 1740 |
| aanaaaanna aaaaaaaaaa aaaaaa | 1766 |

<210> SEQ ID NO 30
<211> LENGTH: 2790
<212> TYPE: DNA
<213> ORGANISM: Homo sapiens

<400> SEQUENCE: 30

| | |
|---|---|
| ccgtcttggg ctactggcag ctcctctcct tgggctcctg gctgccaggc gttggtgcca | 60 |
| cttcttaaag gcctggaacc agggaggaga ggaaatgcta ttgttgtggg cttctccgg | 120 |
| ggtctgtgct gtgcctgcta gagcaacccc tgtacccagc tccttttgtc ccagggccc | 180 |
| ctccctctgc cccaagcagc cagccagtct tgcctaggcc aaatgcacaa gctcagaata | 240 |
| gatctgatgg tgagctggga agctgtactc agagcagagc aaatgaggga ggggcgctc | 300 |
| aggacccagg ccctccatgg gctaatgtga gtggcagcca tgcctcatgc cacaccttct | 360 |
| tcgcaaactg atggaccggg tgggcctggc ctgagctggg gccacaaatc aaatcaaggg | 420 |
| ctccagcatc cagcctgtgt gttctgtaat ggaactgacc ccctcccctg aaaacgaaag | 480 |
| ggccccgggg ctgcaatca gggaaagctc acggtgcgc ggctgtggca caacttctg | 540 |
| gaaggctggc tgactggaat gcagggaaaa cggcagtacc tgggaaagga cccacccatc | 600 |
| ttcctgctgc tgtaactgct gagccactcg cagtcccagg atccgctgcc accacgtctg | 660 |
| ccaggcccat ctcaggtgcc actccctgag cttgggac agttggcaga gaaggcctct | 720 |
| tgtgctcacg ctcccccgca gtcccagcc cttctgcctt tctcccccga cactgctgca | 780 |
| ccagagtgaa agggctatgg caagggggtg tcatctgagg agtattaaga atgcagattc | 840 |

-continued

```
ctgggcctgt cccccaaggt tttggagtca gtaggtccaa gggccatact tttgagaggg     900
gtttgggtta agtatgaggt gaaatgggag atggtcagtg tggagagggg tgcacccact     960
caccagggtc cgcaccagct gctctgcccc ttgggcatcc acccagtgct gccatgccac    1020
tgccaggcac ctggcctgct gggaacccg cagcccgtga agcagtgcct cgaggcaccg    1080
gcgctgcagg tacttcctcc tgatggccaa gagcatcgtg acccttcagg ccagaaggga    1140 ggcagagcc atgggcctgg gcctgctttt ccaggatcct gcaggaacga gcactggcca    1200
gagagggccc agctgtagcc atggctcagg caagcccctc agcccttgcc cccatccctc    1260
ggacccacca aactgcacac acagctcctc ttaccgtagc ctccgtttat gggccttgct    1320
ttgggctttg caggctctgg gctcagggct ggagtgcgct cttggtccct ggtccctcgt    1380
ccacaggggc aggcctggga cccagctact ctgtccaggc cactgtggcc agagctggaa    1440
ggcagggcag agggaatgtt ccctgcaccc tggaaagggg agttgagtca caagaggtta    1500
aggtgggtcc aggaaggcag ctgctcttag tgcccgccta ggagttgagt acagtgagga    1560
gggtggagga agtgctgag cttagccttg tgccctgccc ccatctcccc aggcctccag    1620
cctctcccgg ctgcctgcca cccaaagaga aatcacaggg gcggggcagg aatgcaaagt    1680
gttttctcag aacagctgaa acattccgaa gagggaatgg atgggagaa tggtcaatac    1740 acataagacc gtgtcccaag gagctgattt ccaggcccct gaggactgga gaccgcttca    1800
cccctgcact tcagacaccg tttgtccccc ggggcaaggt ctccttactc tgagcccagg    1860
ccgttcccct tggcttcctc cgtccaccca ggctgcactg cagtgatggc gcgggaggca    1920
ccagctctgt ggcctgtgtc cagcagctgc gggtctgaag gaatagccag agaggagcac    1980
ctgaacccca tgggcttgga cttcctgggg ccccgctggg atttcttcgc tgctctagct    2040
ggcaggacac atcccggcct cttcttccac ccattccccc atgtggctga agacattcca    2100
acaatggggt gggcccataa tagttagccc tcagtcagtt cccggagcac agccctggga    2160
gggggctatt tctctcccca ctgaaaacat ttcaaagctg agttacttgt ctgaggcctc    2220
atccctcgga agccgtctga ctccagagtc tgagcccccg gctagtaccc tatagagagg    2280
gggctctcca aaggggctgc tggggcatgt gtgcctgtgg cagaaaagag gagaccctgg    2340
aattcagcac cctgggtgcc attcccagcg tttagtttct agaggcctca gtttctccat    2400
cagcttatgg gatccttgtc tttactgaca agaatggaat agaaatgtaa aagtactctg    2460
aaaagcaatt gccctgtaac ttatctagaa agaaaagacc ctgagactcc agaatctgct    2520
gttgccatag ccccatatgt gtgaattctg caactagcca aggctagttc ctttcaattc    2580
catttaaaaa acaaaaacca gcaggtgtgg tggctcatgg cgtaatgggc ctgcccaatg    2640
ctttgggagg ccaaggcagg tagatcgctt gagcccagga gtttgagaca agccctggca    2700
acatagtgag atcccatttc tacaaaaaaa aaaaaaaaag gaattcgata tcaagcttat    2760
cgataccgtc gacctcgagg gggggcccgg                                    2790
```

<210> SEQ ID NO 31
<211> LENGTH: 1417
<212> TYPE: DNA
<213> ORGANISM: Homo sapiens

<400> SEQUENCE: 31

```
ttttttttg attaaaaaaa tttaaaaaat tataaaatga tgtcctatat gagtttaata      60
catgacgttg gaggagcata gagatagacc tagactaggc atgtgtatgt gtgtgtgtgc    120
atgtgtgtat gcatgcatgc ttatgcatgt gtgtgtgcat gcatgcttgt gtgtgtgtgt    180
```

```
gtgtgtgtgt gtagagcctt ggtcatcccg acagagcaaa gacacaggag ggtggcacat      240
ggaagaacaa gtgactccac cctcccttgc acagttaaaa tctggccaag tgagagggga      300
gatgggagag gggagagggg agaaaggaga agaggcactg actggagggg ctgaagcttt      360
gtccctcctg ggcaggcgtt ctccatccac acccctcttc ttggatagag aggataagca      420
ggccaaagat gcacgaaacc tgagttccac tgtagctcca gacttctaga aaagtcaaca      480
gcccctgtat ctctagctga tcctctgttg ttcaatgtct gcattaccgc actgggagac      540
acttgacaga ttgggcctgc cgcaggccat agcagacatt gggcagccct agaacgaagc      600
tgactgtcct tggaatgtgc cacagggtg tgacgccccg ccaactcca gtgctgccta       660 aaatggcctc ttgcaacatt ccctctctt catcttaaat cagggacttg aagccacaaa       720
atggcaaata cacagttctg gcagtcgttt tgagtattgg agaaatcgct ctggccatct      780
gttttgtctc cagcatgttt ctcacggaat atccacggat atatccatgg ataacagaa       840 catcctgcca aggcagagct tggctcttga gaactcggca agctcagtgc ttgcctggat      900
tcctgcctca tgtcccatcc agtgtttgga gaaaagctct gagagaaaga tgaatgtctg      960
aggccacaca gcctagaagt agtcaagagc acaggctcta gaactagccc cacgtgggct     1020
gaaatcccag caccagcgcc tgccggctgt gtgatgtagg agagcttctt accagctctg     1080
tgcctcactt gtctcacttg taaaatgaga ataagaattg gccgggctcg gtggctcacg     1140
cttgtaattc cagcacttcg ggaggctgag gtgggcggat cacttgaagt caggagttca     1200
agaccagtct ggccaacgtg gtggaaaccc cgtctctgcc aaaaatacaa aaattagcca     1260
ggcgtggtgg cgggcacctg cagtctcagc tactcaaaag gctgaagcag gagaatcgct     1320
tgaacctggg aggtggaggc tgtcagtgag ccaagatcac accactgcac tgcagcctgg     1380
gtgacagagc aagactctgt ctcaaaaaaa aaaaagg                              1417

<210> SEQ ID NO 32
<211> LENGTH: 1906
<212> TYPE: DNA
<213> ORGANISM: Homo sapiens
<220> FEATURE:
<221> NAME/KEY: SITE
<222> LOCATION: (617)
<223> OTHER INFORMATION: n equals a,t,g, or c
<221> NAME/KEY: SITE
<222> LOCATION: (940)
<223> OTHER INFORMATION: n equals a,t,g, or c
<221> NAME/KEY: SITE
<222> LOCATION: (1461)
<223> OTHER INFORMATION: n equals a,t,g, or c
<221> NAME/KEY: SITE
<222> LOCATION: (1901)
<223> OTHER INFORMATION: n equals a,t,g, or c

<400> SEQUENCE: 32
tctggagctc caccgcggtg gcggccgctc tagaactagt ggatccccg ggctgcagga        60 attcggcacg agcccagctt ctggtggttg ctggcaatct ttggtgttcc ttggcttgta      120
gatgcatcat cccaatctct gccttcattt tcatgctgca ttctccctgt gtgtgcatgg      180
ctgtctctgt gtccaatttt tcccttttta taggacacc artcatattg gattagagcc       240
caccctaatg acctcatctt aacttgataa tctgaaagca ccctatttcc aaatagggtg      300
acattcarag ggtgttagga cttcaatatc ttttgagggg acacagttca acccataaca      360
cctaccaacg gtttctggaa tcatctctca aaataaacta tctaaactct aatctttgwt      420
tcagggtcag cttctagcag aactcaatgt aagacaccct tttaaagatg gtacctcaga      480
```

-continued

```
ggtacagaca gattgtgaac cttccctagc acagtgtaac aagtcccttg caaaaatcct    540
gatttgagtc aacattgtaa tttcttgctt aaatctaaga atatgcctyc cagcttcttc    600
caagactatc tgggggnagt tgkttctagg gtggctcaat ttattcgttt tgaacgctga    660
tggccgtgca ccacaccgtg gctcaatggg tgttgaggac acgttcacat gcaataaatg    720
cacagggctt tgccattagg tggcattagg ggaaggacac ttycagcata ctgcagaggc    780
attctcttcc agcctggttg cctgtcaagc acctgctgag atgactggcc cagacggaga    840
ttgtggggtt gctgagccag ccctgtcccc tccttatctc cggaagatgg aataaatgcg    900
tgtcagaagg gagggtgcct cccatctcgg grgcaccggn gttgcccttc agaaaaacat    960
tgcctgcaca ttttgtagtc ttgaaatgaa tctgagtggc aattcaagcg ggcagagctt   1020
gttttggatt ttagacagtt ctacctgcgt gctcctcttc tctgctccag ctctgacatc   1080
tcggctccac atacagtggt ctgaagtggc atacggaccc tgagaagagg agaggcaaag   1140
gwrgcagctg tggctggccc ctcctgccyt ctggtctcct tggctggtga gggaagaaca   1200
aacacagttg tgtttccagg tcacagctgc cagggctcca cctgtggggt gggtggctcc   1260
agttctgttc tgagttaaga aatgctgcaa atacgttctc cttraaagag mcctaggaat   1320
tgccatttct ttctgcagct ttctgtagcc aataagcatt tgaggaactg ragaagggtt   1380
cagccctgaa ttgcaaggga aaactgtgtg agtgtgtttt agttaagaaa aagttaatt    1440
ctagtgagac ctgcttgttt ncaaaacaga tgtataggcc agacagatgt acagggatga   1500
ccttgacttt cttttgtcat tgcaggaagg tggggtatgt atgacccctg gttaagacca   1560
ataggaggcc gggcgcagtg gcttacgcct gtggtcccag cactttggga ggccggggcg   1620
ggtggatcgc ccgaggtcgg gagtttgaga tcagcctggc caacatggag aaaccccgtc   1680
tctactgaaa aaaaaaaata cagaattggc cgggtgtggt ggcatgcctg tggtcccggc   1740
tgctcgggag gctggggcag gagaatggct tgaacccggg aggcggaggt tgtggtgagc   1800
cgaggtcgcg ccattgcact ccagcctggg caacaggtgc ggaactcggt caaaaaaaaa   1860
aaaaaaaaaa raactcgggg gggmaccga acccgggtcg nacatt                  1906
```

<210> SEQ ID NO 33
<211> LENGTH: 543
<212> TYPE: DNA
<213> ORGANISM: Homo sapiens
<220> FEATURE:
<221> NAME/KEY: SITE
<222> LOCATION: (367)
<223> OTHER INFORMATION: n equals a,t,g, or c
<221> NAME/KEY: SITE
<222> LOCATION: (376)
<223> OTHER INFORMATION: n equals a,t,g, or c

<400> SEQUENCE: 33

```
ggcacgagaa aatattgact cctatctggc cttcatcaac tgacctcgaa aagcctcatg     60
agatgctttt tcttaatgtg attttgttca gcctcactgt ttttacctta atttcaactg    120
cccacacact tgaccgtgca gtcaggagtg actggcttct ccttgtcctc atttatgcat    180
gtttggagga gctgattcct gaactcatat ttaatctcta ctgccaggga aatgctacat    240
tatttttcta attggaagta taattagagt gatgttggta gggtagaaaa agagggagtc    300
acttgatgct ttcaggttaa tcagagctat gggtgctaca ggcttgtctt tctaagtgac    360
atattcntat ctaatnctca gatcaggttt tgaaagcttt ggggtctttt ttagatttta   420
atccctactt tctttatggt acaaatatgt acaaagaaa aagtcttat attctttttac    480
```

| acaaatttat aaataaattt tgaactcctt ctgtttaaaa aaaaaaaaaa aaaaaaaaaa | 540 |
| aaa | 543 |

<210> SEQ ID NO 34
<211> LENGTH: 1452
<212> TYPE: DNA
<213> ORGANISM: Homo sapiens
<220> FEATURE:
<221> NAME/KEY: SITE
<222> LOCATION: (283)
<223> OTHER INFORMATION: n equals a,t,g, or c
<221> NAME/KEY: SITE
<222> LOCATION: (596)
<223> OTHER INFORMATION: n equals a,t,g, or c
<221> NAME/KEY: SITE
<222> LOCATION: (607)
<223> OTHER INFORMATION: n equals a,t,g, or c
<221> NAME/KEY: SITE
<222> LOCATION: (1275)
<223> OTHER INFORMATION: n equals a,t,g, or c
<221> NAME/KEY: SITE
<222> LOCATION: (1284)
<223> OTHER INFORMATION: n equals a,t,g, or c

<400> SEQUENCE: 34

| gaattcggca cgagattaag ttgtgcactt taattgggtg aattgtacat gtragttata | 60 |
| tatctractg tagttgtwat taaaaaacaa caggaggcca tgtgggctgc taggagtagc | 120 |
| aatgtctgty cccagccagc aggtagagac cagggctgga cagagkagta tgggctgtgc | 180 |
| tgcagattat ttgtggtacc caactgttgc ataaaacagg gtgtgatctc ttgcattgct | 240 |
| atgcatgagt ggattcccag taaattgtgc caggctgcct gantgatgtg tggcttgtgc | 300 |
| tttggatcgt aatgcttacc tatgctactt aagttacata ccctgtggcc tttgtggcca | 360 |
| ggactgtggg ctactacctg kagtgattcg ttaggggaaa ggacccacag cctgtgcagg | 420 |
| aggaaaaaag catctctgag tacagggtgg atgagctgga tgagctgccg ggcaagagcc | 480 |
| acgcacaccc aggtggtgag tcttaaggat aaggtggaat ttgccccata gctgtcctgg | 540 |
| acagaaactg cccagagaag aatgaatgga ggacataggg ctctgtggtc ccaccnttt | 600 |
| ttgggancc tgtgactggt cctgttacca tgtcaactta gccccaaacc catctctgat | 660 |
| tgacttggtt gcttattttg gcacattctt gctccacaca gccacataca tactggctgc | 720 |
| tcctcsaagg ccaggcagat gcagcagctg ttgggccagc aaagaggaar gtcctggaag | 780 |
| gttctggcct gaacgctgca tctgttgtgt gacagccaca actgctcagg cttccttgtc | 840 |
| tgtgggtgca ctgtggggag gagtgttatg ataagaacat tggctctcag tctccctggg | 900 |
| gagaagtttg gcctcacgtg ggatttgggc gttgccttta ggaaggctct ctgcatgtct | 960 |
| agttccagtt tgtactggga agaattaaaa aagtctgcca gcttctttag tttgtcctgt | 1020 |
| cttttgtgat gattctttct gagatcccct cctatcagct caggagtggg attttctgga | 1080 |
| gaaggaaagt gttttctgt tcctcactgc tcaccttggg gcattcagga acatgggcct | 1140 |
| gatgaatttg cttgaaggca gtctgtaatc ccatcacttt gggagccaaa gargcggatc | 1200 |
| atttgagctc aggagtttga gaccagcctg agcaacgtga caaaccctg tctccaccaa | 1260 |
| acaacaacaa caacnacaac aacnacaaca acaactacaa caaactgggc tggatggcac | 1320 |
| gctcctgtaa tcccagctac ttgggaggct gagatgggag gattgcttga gcccaggagg | 1380 |
| tcaaggctgc agtgagccat gattgcacca ctgcattcca gcctgggtga cagagggaga | 1440 |
| ctgtttcaaa aa | 1452 |

```
<210> SEQ ID NO 35
<211> LENGTH: 2908
<212> TYPE: DNA
<213> ORGANISM: Homo sapiens
<220> FEATURE:
<221> NAME/KEY: SITE
<222> LOCATION: (1653)
<223> OTHER INFORMATION: n equals a,t,g, or c
<221> NAME/KEY: SITE
<222> LOCATION: (1655)
<223> OTHER INFORMATION: n equals a,t,g, or c
<221> NAME/KEY: SITE
<222> LOCATION: (2850)
<223> OTHER INFORMATION: n equals a,t,g, or c

<400> SEQUENCE: 35
```

| | | | | | |
|---|---|---|---|---|---|
| gagctctaga | ctgatcgtag | taagttttgt | gacttaacaa | tgaaagaaag | tagaaagatg | 60 |
| ctttgggttt | tcaaaatgtt | gttttttaaa | attgttcttt | gggtgaattt | actcagtgct | 120 |
| gctttgagtt | gtatacagaa | acaaatgttg | ggaattgctc | ctcagaaatg | tgttcctaag | 180 |
| ttgtgttttc | aactttacat | catgaggtga | agcattaggg | aaagagattc | tttcgatttg | 240 |
| tttaataatc | taattataca | gaccaaagtg | ctttacgttt | ctgctctatg | ttaatgtttt | 300 |
| agaatggtga | ttttgctgat | taatttagac | ctggcaattg | aaataatgtg | ctcagaataa | 360 |
| taacatggtt | atagttcttg | tatgataaag | tattcaattt | cagaatagtg | ttggaatcct | 420 |
| gagtttgaat | aatgtgttgt | atttagaaac | atagccctat | ctgttttaaa | caaataattt | 480 |
| gttggccgat | tgtccatggt | tgagcatgac | aaaaatacct | cgtcgaaagg | caagcttagg | 540 |
| taactgctgg | caaaacactg | ggtgcactat | ttttctggat | aaaatttata | gttattttct | 600 |
| atattaccct | tcaaaaggga | tctcttcagg | ttaaaaatca | cgcttatgct | gaagtcttta | 660 |
| tctggtgtta | actaaaaatc | tcatatgggt | tcataaccga | ggtcactaat | aattcatttt | 720 |
| tatcacttgt | aaaaatttgc | tcaaaattcc | aaaaaaatat | tgatttgttt | tttagtgatt | 780 |
| ttgcaggctg | accccaacct | aagttttgat | aacatctggt | aagtcagtat | agttctgtga | 840 |
| cttcatgttt | taactaagaa | ggaaaattca | tagatattcc | tattagattt | tataaacctt | 900 |
| caaaagtctg | aaacttaatt | ttgagtctaa | attttctgac | actggcccct | tttaatattg | 960 |
| taagttttg | ttcactttct | taagtaaaaa | aaacatttaa | ttactagtta | gcccttaact | 1020 |
| gggaaactca | ggtaatgaac | tgctgacttt | tctaaagttc | tttaactgat | caattctgta | 1080 |
| tagagggata | tttatctaac | cactttccgt | attttacaag | tgctctttct | aaaaaggaat | 1140 |
| aactattata | gctctatttc | cccaatctct | ataggactca | tgagagattg | cttgtgtaaa | 1200 |
| tataaaagca | ccatatgtgt | tcttaactcc | tatggctgct | tgaagctcat | gatgaaaaag | 1260 |
| tcttttttgtc | agttttaatt | gttaagtaca | gaacaaacaa | ttgtttggtg | atggcctggt | 1320 |
| tgaaagagag | catataaata | tatcccagtg | gaactcacca | agaagaccca | cacctcagaa | 1380 |
| attattgcat | tttctcatta | tgtgttgggt | ttgatttgct | tttgttttta | atgcagctct | 1440 |
| tttaatataa | agattcttga | tacagtgaaa | tctcttattt | caagtgtaag | ttattcttca | 1500 |
| cccaccccctt | cccctgccat | tgtatttccc | atctgtttca | aggagtttca | acaatttaca | 1560 |
| ttgcatcgta | tgcagtaggt | actgcttttt | cagaaagacc | tggaaaacat | acctgctatg | 1620 |
| aatattttgt | tcagatgtag | ccatttacct | ggntntcaag | gttgccttct | gtggagagga | 1680 |
| tcttagacaa | aaatcttcct | tgtatttact | tgggttaagt | gaagtccaaa | ttcttacagt | 1740 |
| atgctatttc | aggattctg | atattaaaaa | agaaaaaaca | aaatctttat | atctcttatt | 1800 |
| aacacttccc | ccaagaaggg | ttgtgctgtt | atttattttc | tattataaga | aaagttcatt | 1860 |

-continued

```
ctttaagtag tttcttttac ctctaatcta atttcatacc aaatacctga tcaatagaaa    1920
tgatatattt aagcagcaaa gattcctaat ccatcattat gaaaagtgtc agcatactta    1980
gtagtgaaca gataaagtca atttgaatat aattccactt tgttttagaa gactaaatta    2040
agattcaatt aacattatcc tatgaattct gaatgtgata atgtgattca aacagtcaaa    2100
ttttattaag ctcttagtaa ctcaggatag cattccatac taacctcaag ttagcaaaac    2160
aaattagtta aacagcttgg ttcttagcag actgcttaaa agatcaagaa aattttctca    2220
tcttttcttt ctacttagaa acattgcaag aaaccttgga cagtcttcac cagacctgcc    2280
atgattttat aagatttagg cctcagtgac atgctcctga aagtttcctg ccagccatcc    2340
aaactaagca tccactcatt ccatcttccc aaagtcactc accgataaag gtagcatcct    2400
taagttcatt tttgaaaggt ggaggaggat ctcccctgc ccaaaggaat tttttatca     2460 gaataccttg aaagggggt atataaattt ggaaaactta atttcttggc tgtgtttgat    2520
aacagttcct atgcatggtt tttaatgtga ggtaaatttg tttctttctt cagaatacct    2580
ctctccaccc cccaccttat tcttcctctt taatgaatat ttttattgga gctcaaactc    2640
catgacttac gtgctcacta agttttcttt tttccccttg tttactctgt ctgtatgtat    2700
gtcaaaagct ggcaaaacct ctaaaactgt caagaaaatg cttgaaagtt gatttgtcat    2760
agtgcaaatt catgataaaa tgtcttaatg ttatttggat atgtagtaca tagaaacaga    2820
aaaataaagt cattttata acttaaaatn aaaaaaaaaa aaaaaaaaaa aaaaaaaaaa    2880
aaaaaaaaaa aaaaaaaaa aaaaaaa                                       2908
```

<210> SEQ ID NO 36
<211> LENGTH: 953
<212> TYPE: DNA
<213> ORGANISM: Homo sapiens

<400> SEQUENCE: 36

```
aattcggcac gagaaccaag gtactttcag ctgcagactg accataccc tgtccacctg      60 gcgttgctgg atgagatcag cacctgccac cagctcctgc accccaggt cctgcagctg     120 cttgttaagc ttttgagac tgagcactcc cagctggacg tgatggagca gcttgagttg     180
aagaagacac tgctggacag gatggttcac ctgctgagtc gaggttatgt acttcctgtt     240
gtcagttaca tccgaaagtg tctggagaag ctggacactg acatttcact cattcgctat     300
tttgtcactg aggtgctgga cgtcattgct cctccttata cctctgactt cgtgcaactt     360
ttcctcccca tcctggagaa tgacagcatc gcaggtacca tcaaaacgga aggcgagcat     420
gaccctgtga cggagtttat agctcactgc aaatctaact tcatcatggt gaactaattt     480
agagcatcct ccagagctga agcagaacat tccagaaccc gttgtggaaa aaccctttca     540
agaagctgtt ttaagaggct cgggcagcgt cttgaaaatg ggcaccgctg ggaggaggtg     600
gatgacttct ttacaaagga aaatggtagc agcttcagtg agaaactgcc cttacaaaca     660
gtcccttctc tgctgtcaat ccaatactgc tcccaaatcc tgttttcagt gttcatttcc     720
ctcaaggcag gcgctgggct cccacgaccc ctcaggacag atctggccgt cagccgcggg     780
ccgctgggaa ctccactcgg ggaactcctt tccaaagctg acctcagttt tcttacaaga     840
acccagttag ctgatgtttt attgtaattg tcttaatttg ctaagaacaa ggtaataagt     900 aaattttaa aaagcctttc tgctgggttg gattaaaaa aaaaaaaaaa aaa              953
```

<210> SEQ ID NO 37

<211> LENGTH: 3864
<212> TYPE: DNA
<213> ORGANISM: Homo sapiens

<400> SEQUENCE: 37

```
acccacgcgt ccgtttctga agcaatgtta atcctactag ccaagcatat cacttagtcc      60
ccactgtgag atgagggata tgtgcttaaa ttgtgaaaca atatatgag tcaggtattt      120
ttcctttgag tccaagtggt ttatgacttt cttttcctgtg ttctttgtat atgtgggagt     180
tttataattt tttatcaaga atgaaaggtt ggcctgtgtt cttactggtg caggctgtca     240
catttctctc tgttgcccag tcaggtgcta tggcatgtgc tgcttctggc gtagtgtact     300
ctgtggatgt accagcatgt tcttcaaggt catgactgat tttccagacc tttggaattg     360
agataaatgt taaatttgta gctatctctg aatttcttcc agatactttt cttcatttgt     420
ttgtttgtag ggtaaacata cctgatagca gcaatttaag cataccctta gaatgaccat     480
gtatggccag tgcacctgaa tgtgtgttcc aaggtaggga atccaggaat ggccaactcg     540
gagattcatt ccttactatg ataaatatct gagcccctg ctcatcctgt ggaacatggg      600
cttattgggg attaaggccc tgagttttag gttaaatgaa ggttaccaga tggaggtcat     660
taggggggagg gtgttaaatg aaaatgctttt ataaactgca tgctgttttgc aagcagttgc    720
agttttcctg cccagcccgc agccactggc catgcagtca tgttgtccag cctgccgcca     780
ctggaccatt tctgtacata aggcagttct cctgtccgcc tgccaccagt tctccactct     840
ctccccatat gtaagcccct agtaaacccc atgtctcatt tgctgcctct gggtcttttc     900
ttcagcctct tgaacctagt gccttccctg ctgaggttaa taggggtaca gcacaacagt     960
gttgtaacac agaaagtgat atttacaggg atatctctct cacaatatct cttaggaaag    1020
gtaaataaaa tgttcacaac ttgtaggtga gtaattcctt agataagttg tttcttaact    1080
tgggaggagt ttgggaagga acctaagcag gctgcagagg ctgggcatgg gagcttgtca    1140
tggctggaag ttgaaatggt caactccagg cagatctcct ggggcaaagc agcctccacc    1200
accagtagcc cttcctttct gtctttcata ccccactgct ccatctgaag cctgaacccc    1260
ttccagaaaa ttgatggata gattttttt ttcggctata tatagttta gaggttagaa      1320
ctagatataa ttcagtctag aagatttctc cttccccaga aatgattgtt tttgtgcaaa    1380
gccccgccaa aatagtacgg agacttagac tgagttcact catcactaac aattaacttt    1440
ataaacattc aacaagtagg acaactatta ttactgttac tcagacccct tcgctctgta    1500
tatacagttt gatttaagat gccacattta catggcattt tcaaccttca aactctagca    1560
gattttaaaa ctaggtggat gaaaataaaa tcattctaat aaatgtagtg tgtcagattt    1620
gaaaaatcat ttggtgagca ggatctctgt aaagttatat gggccacgta tacaagacgt    1680
aactgaagaa aattaattca acagagcatg ccgtacttga acgacataga gatttactcg    1740
aactgaacta actcaagctg cagaactccg agcaagcctg gattgtaaaa gtctgggtga    1800
aaatagatgg agtatgccct gactgaacct ctgtactgcc ccacatgctt atacaggtgg    1860
gggattggat ggctgttagg tgatcattgc attctctttt ggatccctat tgagaagaaa    1920
tgataagaga gggaaaggat atggggcaag aacagtctga aaagaaagg ataaagttct      1980
cagactctct tcacactcta agaagaactt tctgaaaagc ttggattagg tctggcaatg    2040
gatataataa gcaaaggact cttggaatgt gttcttggct cttagcccca cctctgactt    2100
tgagcaaatc agctgatttc tctgcctgta aaataatagt ccctctgata ttaatactta    2160
cctcatgagg ttatttagag gatagtgttg gtaataatgc cttgtgttta catcattcct    2220
```

```
ttcacagaga gctcaaagca ctttacatgc attgagagag aagcttctcg tgaagagtaa      2280
atagaagtgt tcactttttg gaaatgaact taggccataa gagcctgaat ttaatgcatt      2340
gcaggaagaa atatggtaca tagtgaacca gtgggtcaac tgaattttt gttccactaa       2400 gagtcccctc ctggctcctt gttttgtgaa ttgaggaata tggtgagtcc ctacacctgg      2460
atgggaaatc ccacatatgc aattggaatg gtctctcacg acacatgcag agattgaaga      2520
acagtctgga catttttga taacgttctt tgggccttgg tagtagctga aagacacctg       2580
agaaatctta gctcagagct acagaatgac actaatggat cccagaaata gaatgtaga      2640 tgtggagtgt tttatctgtt tatttcacct caattcaacc aatactcctt gagtgccttt      2700
tatatacatg attttgagtg atgtggagaa ttaaaagagc cccacatgct caggaaagtt      2760
aaccctggtt ttagcaagga aaagaagtag gatttccaaa tagataagtg caccgggtat      2820
gtggaagttc agaaaagctt cccagtattt cagcccatct acttggccat tctcaaccat      2880
gtattactca tgtaccaagc agtatgctgt tcacagagag atccaatctc tgccttaggg      2940
atccttgggg aaaacatgta caagagata gttttagcac attctagtaa aggcagtgat      3000
caagggcacc tagccttacg tggcaattta gggaaggtac cttggaggat gagacttctc      3060
ctaaagtctt aagaattgaa agaacatgg aagggaatt ccaggctggg agagtagtat       3120
gttcatacgc cctcagtgtt taaccttctt tgaacaaaaa aatggccaac tacagaaagt      3180
ttggtcttat tgtagcctaa attgtactta ggggtacgag tgagaaacag ggattaagat      3240
aaaggacctg ttttgctgtc ttgtttactg ttgaatagta gtatgaagta ggtcctgaaa      3300
aactatgttt tgggaaaaa aaaaaaaag actgaatgat atgttgggtt taagtccttg        3360
caggcaggct atccaggtaa ataaacatgg aaggtgatgg gaggtaatct gggctggaaa      3420
tacagatttg gaagtcaccc catatcagtg gtgtttaaaa tcaagagcaa atgaaattgc      3480
acaaggagaa tatatagaat gaacaaatta ccatgggtga agccttgagt aatacagaca      3540
tttaagaagc aaacaaaaga caaggaaccc atgagggaga ctggaaagga aaaacagag      3600 aaataagaaa aaatgagagg agagaattga tacattttcc tcaggtgtgg cattatggag      3660
ttcactggtg tctcatcaga gaagtttcag tccagtggcc agggcagaat gacattgtgt      3720
cttgttttaa agtaaatggg tagggtaaga aagttgagaa gggttagcac aaacctctct      3780
ttcaagtcac ttgccttaga agagaaggaa gggtatggtt tctggggtgc aacccaggtt      3840
caagaagcaa aaaaaaaaaa aaaa                                              3864
```

<210> SEQ ID NO 38
<211> LENGTH: 1411
<212> TYPE: DNA
<213> ORGANISM: Homo sapiens
<220> FEATURE:
<221> NAME/KEY: SITE
<222> LOCATION: (1395)
<223> OTHER INFORMATION: n equals a,t,g, or c
<221> NAME/KEY: SITE
<222> LOCATION: (1397)
<223> OTHER INFORMATION: n equals a,t,g, or c
<221> NAME/KEY: SITE
<222> LOCATION: (1401)
<223> OTHER INFORMATION: n equals a,t,g, or c
<221> NAME/KEY: SITE
<222> LOCATION: (1408)
<223> OTHER INFORMATION: n equals a,t,g, or c

<400> SEQUENCE: 38

```
ccggtccgga attcccgggt cgacccacgc gtccggcgtg aaccaccgtg cctggccgga       60
```

```
agtctttaaa aaataaagtg attctactct tctaagctta cagagaccag accaggtgaa    120
tgtaactggg gaaaatcaag atggtacctc tctgcattat cccgccagac actgtatttt    180
atgcattcat gtctaggata cagtgtgaaa attaaaaagt ttagagggca gatgcaattg    240
tggcaagtga cctgccaata aagcaggtgc agctatagaa gctggcatag gtatatcctt    300
aatggtgctt tctccctggg cttgtctttt tgttgttttt ttccctata ttcagagctc     360 cttgagaagt gataaacacc tccagctttc taacatcctc cccacaccat ctcaccatat    420
ccatctccca gcatccatct gcattcagct aagggcggga aactgaccta gtgcctgtgt    480
tgcagaccat ttctgaggtc tccaccatcc aaggaggcac agccgtcatt actgtcctcc    540
atgccttcag cagcccccct cacagctaag gtacatacca cccttctgc cgcgcctcca    600 cccctggcac caaggtcttc tgctgcttat gtctaaaggg atcacctata tttaactgcc    660
tcagtgacct aacctctttc ttctcatgtg ccagatgtta agatgaagga ggaatacmac    720
acatactcaa gcctcagcct gtttagttgt tttcactggg gctcgctttt ctgggacggt    780
atttattatc agactggcaa gcctaactcc ataggtttac aggaagtagg gtatttttta    840
taaaacaatt gtgtcctccc cacattttgc tatgttaata tttgcttcta acaatttgca    900
gctgtttcac ttttttcctca tttgtctcta agttgaaggc tttgttggag gggacagagc    960
acaggaacag ccttgacagt ctgtaattat tgtacagata ttttaatagc atataaataa   1020
gtatattcct tttattttga acaaaaatg atcagacact gccttttgtg tgtttgctgc    1080
ctgtggcatc ctttttttaaa aagactgtta catattaaaa tagtgtacat atataaatat   1140
tacctctttt gctgtacagt tgtgatagag actgaagatt ttatttttg tgtgcttttt    1200 ataagaaaaa aattaataca ctaaagaatc ttgctgatgt gattgtaatg tacctatgta   1260
acttatttac ttttgaatgt tcttctgtat ctttaaacct tttattaaat aaggttttaa    1320
aaattcaaaa aaaaaaaaaa aaaaaaaag ggsggccsct ytaraggatc caascttgcg    1380
tacgcgtgca acganancag ngtcgagngg t                                   1411
```

<210> SEQ ID NO 39
<211> LENGTH: 1182
<212> TYPE: DNA
<213> ORGANISM: Homo sapiens
<220> FEATURE:
<221> NAME/KEY: SITE
<222> LOCATION: (496)
<223> OTHER INFORMATION: n equals a,t,g, or c
<221> NAME/KEY: SITE
<222> LOCATION: (1162)
<223> OTHER INFORMATION: n equals a,t,g, or c

<400> SEQUENCE: 39

```
ctaagctggt tcgcctgcag gtaccggtcc ggaattcccg ggtcgaccca cgcgtccgat     60
aagcacccat gtctttgaat atgaatgtat ttgtaaaata ccacgtttca tgtgtgaata   120
tgtgctttta ctgtacatag tgctattgtg caataggtct tatgctgttt tcactcaatg   180
tgtgctaaga tctagcccca ttgactcttc tagaaatgca gtattgcttt gacctgccat   240
gtggcactcc acaatgtcaa ttgcagttta cacacattgc ctaaagtggg gacacctgg   300 gtgcccctga ccccttggca ccggatacag gccacgataa acatcctttc gtgtgttccc   360
ttctgtgctt gtgtggcatg tgtacccagg atgggcctat aggtcacaga ggtcagtttc   420
tctttggttt tccagatttt ctttagaacg gtgactgacc ctcctacttg aggccgcctt    480
ttctccttat ccttgncagc acttgtattg ccagactacc taattttgc cagtctcatg    540
```

-continued

```
ggtagatagt ggtscagtgc tttamcatac attcatctga tcagcattaa tttggggaat      600
tttttcactt agcctttctg gtttcccttc ctgtgcattg cccatttcct catggagttt      660
cttatctttt ttggtttatt ctcaggagtt gcttgtacat tcttgggcaa ttgcagataa      720
ttccaagaat gcatatttgg gctgggtatg gaggttcact ggtaatccca gcactttggg      780
aggsccaggc agaaggatcg ctgcagccca ggagttcgag actagcctgg caacatagc      840 gagacctcgt ctctacaaaa aaaaattaaa aaggggcttt tgggaggcca aggcgggcag      900
atcatgaggg caggagattg agaccctcct ggccaacatg gtgaaacccc gtctctacta      960
aaatacaaaa aattagctgg gcatggtggc gcacacctgt agtcccagct actctggagg     1020
ctgaggcagg ggaatcgctt aaacccagga ggcggagatt gcagtgagcc aaggttccac     1080
cactgcactc cagcctggcg acagagcaag gctccactca aamaaaaaaa aaaaagggcg     1140
gccgctctag aggatccaag cntacgtacg cgtgcatgcg ac                       1182
```

<210> SEQ ID NO 40
<211> LENGTH: 2457
<212> TYPE: DNA
<213> ORGANISM: Homo sapiens
<220> FEATURE:
<221> NAME/KEY: SITE
<222> LOCATION: (1622)
<223> OTHER INFORMATION: n equals a,t,g, or c
<221> NAME/KEY: SITE
<222> LOCATION: (1713)
<223> OTHER INFORMATION: n equals a,t,g, or c

<400> SEQUENCE: 40

```
gtcgacccac gcgtccgccc acgcgtccga ttataataaa aagtattatt aggacaggta       60
aactcatcca tctactgtga gctgctggct tggagaacga cttttgagga gccagtttcc      120
tgaggagaaa tgctttttata aagcactcat gctttgtaa aaggagacaa aactgatcct      180
aaatgaccac tccagggttg ctgattttgt ttctggctca tgtctgccta gtaaaccacc      240
agcaagctgc tgaaccaggc tggaaacaac attgttgcaa ctgggaggga catagagtac      300
tgtgaaagca gcgttccaac acatcttcac ttttacaaag ggataggcag agacttccaa      360
catagaggtt cttaaacttc gaggggttac aatcccttg caaatatttt tatagctatg      420
gaccctctcc tcagatctac agccaacatt tcagtgcac cttaggaggt cattttagtc      480
cacgcctctg aaaaagctgc actccaacgg ctgaagagca agccatacgg ccgagaatgg      540
ggctcccttt gccttcatga aagctacttc ccccaacact aagactcagc tgtacgtttg      600
cttagctcag tcacatttac attcttctgg gtgaactgta ccttttgagt acctgccttc      660
attttctaga atcagaccta acaaggtcag tagaagcctg ggcagcagcg ggcctggaaa      720
gacgaggcag ccagcatgaa ctgctgttct ctccctgacc acaaggcgtc gtcttcctcc      780
agggtcaagt aattgttctt gttccgcctc acaggaatgt ggggaggaag gacgttaaca      840
ctataaaatg ctgcgtccta ccttaaactt gtactgtgag aaagctggaa acttccacct      900
gtacagtggg tctggtttgc atgtttagtt tcatttgtgg gaactgcttg tccaagagtg      960
agctcaggtc aggcagttt gtgcctatga gaattagctc agctatcagg caggttttta     1020 gacaccttt taaaatgtgc tcgtgtttgg tttgttttgc ttactgtcag tcctgggtca     1080
atcaaaggtt tgtaagggtg agaatttta tgcactgcta tatcgcaagt gcttaaaaca     1140
gagactggcc cagatgaggc attcttcaaa tgttgttga aatgaatgga caaactctta     1200
ggataaatcc taatttgttg gcaactgtta tttgattta gaaggcaaac tgatttatt      1260
```

```
ttagagaggg aaggggagg ggaggctcat tagcctcttg gtagaaagag gactatttct   1320
gcaaatgaat aggtttccac cttaagtagt gacagtcctt aacttcttat tatggagtga   1380
gtcttgaccg ctttccaagt tcaatagaag ttcaagattg cctctcagtg attagggaaa   1440
ttgaagcttt taaagctcct ggtctcagta attcctcaga ataaacctct ttaaaaggga   1500
tattgatgga aatgtacaat taccagtaat tgaggtttta tctgagggga tggagatgat   1560
gaaatggttc cttcttggaa gttgttggca ttttggcttt attttttcaca aataaagtga   1620 anccatttaa aacgattgac aacgattata tagtgccatg tggaatacaa tagatattaa   1680
tttgtggttg gttttctgc ctgctttaaa tgnaatgtat tatgtttctg ggttccttt   1740 ttagctgtaa aaatacttcg tcactaaagc atgaaattta atcagcagtt gttcttcaag   1800
ttcctgaaag ctatarragt ttctcatgac ttgagtggtt ttttccctgc ccaccagagg   1860
agaaagccct tgtagaattc tgcagtgtta caagtgttcc ctacaaaaac tgaaaccatc   1920
agctcctctt taacaagttg gcttttttaaa agcacgtaat tacaatttaa tggtattctg   1980
taaagtggtg ctctaggcat aatttaaatt cttttaatg actatatttc ttcaaaactt   2040
tgaaagaaaa atgtgttctt tttgctgcat cctttgtaag aagactgcca acagaggaaa   2100
aaggacttta caaattaaga ccatcttggt ttcatttcca caaagatgag aacaaatcat   2160
ggtgttagga aaggatcctt agaagaacac aagaatttga aagcccttgg tggttatcac   2220
tactatattt catatttcca cagaagtgac ttagccaagc tctgcatttt gagcctgctg   2280
actttcattt aaaaggaatg aaaggctgaa aatccaggct gctgtgtctg tagataaagg   2340
tcaaaccatg tttgagttct tcactgttgt gtccacctaa ataaaactga gtaagtaatg   2400
aaaaaaaaaa aaaaaaaact cgaggtcgac ggtatcgata agcttgatat cgaaatt      2457
```

<210> SEQ ID NO 41
<211> LENGTH: 1847
<212> TYPE: DNA
<213> ORGANISM: Homo sapiens
<220> FEATURE:
<221> NAME/KEY: SITE
<222> LOCATION: (1279)
<223> OTHER INFORMATION: n equals a,t,g, or c

<400> SEQUENCE: 41

```
gactccttag ctaagcatac aaggtaactg gccctgcctt gctgttttgc ctcacctgct     60
aacgtgcaca tgctctgcca cgtgtacctg ctgctagtgg gacatgctga mttctcagtg   120
ggcctcatgg gccagaggaa gttgcgttgt tccataaact cagctctcag aagtgctgtt   180
tcctctgcct ggaattcgtc tatctgcttc aatagctgaa tgctgcttat ccctcaagac   240
tcaattctgg tggcacctca gttctgaccc ttccccagtc tctctttccc ttctccccac   300
aggctgtctc cccttgatat tttgcctgct tgctacccat gtccttttct cctggtgaca   360
gtgctacagc ctttccttgg ggaatcaacc ttgtctgaga gtggacagaa attatccacc   420
cctccatcca gggatgaacc aatgacctgg ccaatcacag tcgctgtgat tggtcctggg   480
acaggcagga gactcaagct aggccacaga gcatcagtgc tgagactgaa actactggga   540
aaacaatatg ctctttctgc ctgaggcgcc tagtggatac aatggaagcc ttgaggcagc   600
tgatcatctt tgccttgaga gaggtggctg cctaagaagg aagccaattg agaaaaagca   660
ggcagagaaa aaaacagga acagatacaa caggcaagac tcagctgatt tctcatgtca   720
gcaaatacaa gagaaggaga ctggtcaaga tagagatgtc tgatgatact gagctcccga   780
```

-continued

| | |
|---|---|
| ctccagccac tcctgaagtc attcctaagc ctctcgttac acaagccaat acatgatctt | 840 |
| gktagattaa aaatagtttg actttggtgt tgccacttgc cgtagaaagc atycacgatg | 900 |
| atacactcty ccgtgtgcty ccacacccta atttaaccty ctycatagca ctgactcgga | 960 |
| ggccctatga gactgkgaac tctytgaggg caggaaatgt atcttattcg tctccaaggc | 1020 |
| cacgagactt ggtgtatgat agatattcaa tacaggtttg tgaaataaaa aatgaaggaa | 1080 |
| tgtttatcta gaaattaatg aagcttttca tttacttttt tacttcaggg cctttctgcc | 1140 |
| aagaactctt aagatgcctt aggatcttgg ttgcagccag gtggctgtcc tcccagagc | 1200 |
| ccttgttgtc agtcctctga agtcattggw cctggagata cagggaggg caggtcccga | 1260 |
| ctgctgagaa agtccaggnc cccggatcct accattacca tgctacctgt tcacttgggc | 1320 |
| ttcacccaag gccacactca tctccgtacc ccttcccaac agtggtgagg ggcaggagca | 1380 |
| cctggacatc aagaatcgag tgcatgcctg aacctgtcca ttacccatgc ttctgcagct | 1440 |
| ttgctcatgc tttcccctcc ctgaaacgct cttcccttgt ctacttaatt attcaaagct | 1500 |
| cagaggaaaa aaaatcacct gctccaaaac gtcttcccg aaccctgcag ggaaccaaat | 1560 |
| tcaaaagcca tcagaaggcc gaggcgggcg gatcacttga ggttaggagt tcgagatcgg | 1620 |
| cctggccaac atggtgaaac cctgtctcta ctaaaaatac aaaaattagc caggcatggt | 1680 |
| ggcaggtgcc tgtaatccta gcaactctgg aggtgacgca ggagaactgt ttgaacccag | 1740 |
| gaggcagagg ttgcagtgaa ctcagattgc accactgcac tctagcctgg gaaacagagc | 1800 |
| aagactaggt taaaaaaaaa aaaaaaaaaa aaaaaaaaa actcgag | 1847 |

<210> SEQ ID NO 42
<211> LENGTH: 2597
<212> TYPE: DNA
<213> ORGANISM: Homo sapiens

<400> SEQUENCE: 42

| | |
|---|---|
| ggcacgaggt tacacctcac cccctacttt cgctgactcc agaccccaga ggctgaggga | 60 |
| cagtagatat gctgcctgcc attgcctctt tccttgtgca tgtctgagtg gtgccagcct | 120 |
| gatcagattc tgttgcagtt ccccgtgctt gccacaatgt cggtcgcgtt tcttatccaa | 180 |
| cgctgtttct gcttctggtg gtttgtgcta aatgcatttt caatcccaag tggtacagag | 240 |
| aagaaaagga ttgtctttaa aaagtggctt tgaatgtgtc gaaagcaagg ttgcctgctg | 300 |
| tgtgtttttg acaattgcct ccccagagga gcctttgaaa acctcacttt tcaagacgct | 360 |
| tcaactccta ttagaaagtg acttaaataa aattgctctt ctgaccatcg cggctctgga | 420 |
| tgccaggcta gtgattattt gtctaatctg agtctccagg gctagaactt cacaccgtgt | 480 |
| cttttcacta ccctcccaga ggaggtgaga ggaggtgaat agacacttgt cagattcttc | 540 |
| tgcctggtgt cactgtgggg ggatgcacac acactggagt ataggcttgc taaagagaga | 600 |
| ctgcattgct atttcaacta gacacgttta cttttcccgc aaatgattac tgagcaccta | 660 |
| tggtgtgccc ggtaccatgt tagggcaaga gatctacctc atccttgcat tgtaaacctg | 720 |
| tagcatccgt ggcaatgttt tacaccactg ccctcccagg gttcctgcaa gctgactcct | 780 |
| tttatttttcc ttgtgcatgc tgatgtgttc aaggtatttc agtgggctac tgtgagacta | 840 |
| tctccccatc aggatctctc aaccttggca ctaggaacat gttgggaaaa gtaggtctct | 900 |
| gttaagggag gaagagggc tttcctgtgc gtgataggat gcttggcagc atccctgtcc | 960 |
| agtagcacca catctacctc agttgtgaca accaaaaatg tctgcagaca ttgtcaaatg | 1020 |
| tctcctccct attttacatt taccaaagtg ctctttatgt cctttacagt taaggaaact | 1080 |

```
taggaccagg aagaaacttg ctcaagtcaa acagtgagtt ggcggtagag ctttagctac   1140
aatttaagtc ttgtcttccc aacccagtgt ccatcttatg gatccattca gtggtttgct   1200
cctaaatgct taataaccaa ttatctggga taaacgaaag ccaaacaaac ttgctgggag   1260
cgtgggacaa tttccatggt gtaaatactt ccaccatggc tggtttcaag ctacttccat   1320
ggcgtcactg aatgtgaagt tgggaaggga tctgtacagt tggatctggt gagctggtgc   1380
cagccagctc agaatgcccc caagtccatg tgtgctgctg atcacatatt agtcttgctc   1440
tcctctggac cttgttctgc cacccccag acacatgccc ttatcactgt gatgtgctgt   1500
ggggaaagca gtcacctggt aagagttttt gataacttct ctggataaac ataaagcagt   1560
tagagtggag ttatccccct cttctgttaa atgaaagttt cttttcacag tctttccatt   1620
gaaggaatta gaaagtcat gggatacctc tggtcttaga gcagaaatga agttccccag   1680
aagggggtcc tggacagaat ggtctcttgg gcagggacta gatgctgtta cttaccatca   1740
gatgtgtcta ctgtaagatg cttgggaggc atcaaagtgg tgacagtggg gggctgttgg   1800
attttaccat tctggaatat aagagaaggg gtgtggctgg tgttttagtc cagatagcag   1860
ctgtgaccac tgggagcctc attttccaca cctgcaaaag gagaaatagt gatccccttc   1920
ctagtgttgg tgtaaagagt agatgaacct ctgcctgagt ctcagatgcc tgctgcccac   1980
ttggttgctt agtggatcgg ctggctgtca acagtgtaag cttatcaagc ctaaatactt   2040
agttggtctt gacttttca cctcgaccat gactcagtgt catgtgctcc tagtcattct   2100
gtctgtggtc caacgttagc ctgggaagca cctgggactg agggaagaac cctcagctag   2160
ttattcagcg atccaggttc tcctcctgcc tttgatatca cctcattata taaccttggg   2220
aaacactttg gtgtgactgg aatgtggata ctcccagggg aagggtagga gcatggtagg   2280
gcatttggac tttatcatga aggtggtagg aaatacttga agggttttaa gcagggatga   2340
cacatcatca aatgtgtgtt ttgaaaactt ttttctgcag aggacagggc cacagcccaa   2400
gcaggatcaa accagttagg agattgatgt aacagtcccg tcagaaagtg atgaggtagc   2460
tgggtgcggt ggctcatgcc tgtaatccca gtcaccgtgg gaggctgaga ctggcagata   2520
gtttgagacc agcccttggc aacatggtga accccttct ctacagaaaa aaaaaaaaaa   2580 aaaaaaaaa aaaaaa                                                   2597

<210> SEQ ID NO 43
<211> LENGTH: 3116
<212> TYPE: DNA
<213> ORGANISM: Homo sapiens

<400> SEQUENCE: 43
ggtgataatg aaagtggtgg tggtgatggt ggtaatactg gtggtggtga cattggtggt     60
ggtggtgatg gtggtgatac tggtgatggt ggtgatggtg gtggcgctgg tgaccctgac    120
atggggtcca gtagcagtga cagtggatgc aggctcctgg tgactgagga gcatctcagg    180
ctgrggaggc acctctgatc cccgccactg ctccttaccc cctacagtct ctcagcaaac    240
ctgctgggcg acagcggact cagatgcctt ctggaatgtc tgccgcagtg cccatctccg    300
gtttgcttga tctgagtcac aacagcattt ctcaggaaag tgccctgtac ctgctggaga    360
cactgccctc ctgcccacgt gtccgggagg cctcagtgaa cctgggctct gagcagagct    420
tccggattca cttctccaga gaggaccagg ctgggaagac actcaggcta agtgagtgca    480
gcttccggcc agagcacgtg tccaggctgg ccaccggctt gagcaagtcc ctgcagctga    540
```

```
cggagctcac gctgacccag tgctgcctgg gccagaagca gctggccatc ctcctgagct      600
tggtggggcg acccgcaggg ctgttcagcc tcagggtgca ggagccgtgg gcggacagag      660
ccagggttct ctccctgtta gaagtctgcg cccaggcctc aggcagtgtc actgaaatca      720
gcatctccga gacccagcag cagctctgtg tccagctgga atttcctcgc caggaagaga      780
atccagaagc tgtggcactc aggttggctc actgtgacct ggagcccac cacagccttc      840 ttgycgggca gctgatggag acatgtgcca ggctgcrgca gctcagcttg tctcaggtta      900
acctctgtga ggacgatgat gccagttccc tgctgctgca gagcctcctg ctgtccctct      960
ctgagctgaa gacatttcgg ctgacctcca gctgtgtgag caccgagggc ctcgcccacc     1020
tggcatctgg tctgggccac tgccaccact tggaggagct ggacttgtct aacaatcaat     1080
ttgatgagga gggcaccaag gcgctgatga gggcccttga ggggaaatgg atgctaaaga     1140
ggctggacct cagtcacctt ctgctgaaca gctccacctt ggccttgctt actcacagac     1200
taagccagat gacctgcctg cagagcctca gactgaacag gaacagtatc ggtgatgtcg     1260
gttgctgcca cctttctgag gctctcaggg ctgccaccag cctagaggag ctggacttga     1320
gccacaacca gattggagac gctggtgtcc agcacttagc taccatcctg cctgggctgc     1380
cagagctcag gaagatagac ctctcaggga atagcatcag ctcagccggg ggagtgcagt     1440
tggcagagtc tctcgttctt tgcaggcgcc tggaggagtt gatgcttggc tgcaatgccc     1500
tgggggatcc cacagccctg ggctggctc aggagctgcc ccagcacctg agggtcctac     1560
acctaccatt cagccatctg ggcccaggtg gggccctgag cctggccagg ccctggatgg     1620 atcccccat ttggaagaga tcagcttggc ggaaaacaac ctggctggag gggtcctgcg     1680
tttctgtatg gagctcccgc tgctcagaca gatagacctg gtttcctgta agattgacaa     1740
ccagactgcc aagctcctca cctccagctt cacgagctgc cctgccctgg aagtaatctt     1800
gctgtcctga aatctcctcg gggatgaggc agctgccgag ctggcccagg tgctgccgca     1860
gatgggccgg ctgaagagag tggacctgga gaagaatcag atcacagctt tgggggcctg     1920
gctcctggct gaaggactgg cccaggggtc tagcatccaa gtcatccgcc tctggaataa     1980
ccccattccc tgcgacatgg cccagcacct gaagagccag gagcccaggc tggactttgc     2040
cttctttgac aaccagcccc aggcccttg gggtacttga tggcccctc aagacctttg     2100 gaatccagcc aagtgatgca cccaaatgat ccacctttcg cccactggga taattgactc     2160
aggaaagaag agcctcggca gggcgctctg cactccaccc aggaggaagg atacgtgtgt     2220
cctgctgcag tcctcaggga gactttttt gggaaccagg agctgggtct ggacaaagga     2280
gtaccctgca ttcgtggga tatgtgtgat caattgggga catgcgacac acaatgaggg     2340
tgtcatgaca atgcatgaca cgtacggtta tatgtggcag tgtgaccct tgacatgtgg     2400 cgttacatga aagtcagtgt ggcacgtgtt ctgtggcatg ggtgctggca tcccaagtag     2460
caggatacat gattgttggt ctatatatga cacatgacaa atgtccatgt cacaggactc     2520
atggctggcc agatgacctc aggctggccc aagatctaat ttattaatt ttaaagcaaa     2580 tacatattta tagattgtgt gtatggagca gctaagtcag gaaaagtctt ccgcccgagc     2640
tgggagggga gagtgtccat gcactgacca gtccagggc tcaagggcca gggtctgga     2700 acaagccagg gactcagcca ttaagtcccc tcctgcctca atcctcagcc tacccatcta     2760
taaacttgat gactcctccc ttacttacat actagcttcc aaggacaggt ggaggtaggg     2820
ccagcctggc gggagtggag aagcccagtc tgtcctatgt aagggacaaa gccaggtcta     2880
atggtactgg gtagggggca ctgccaagac aataagctag gctactgggt ccagctacta     2940
```

| | |
|---|---|
| ctttggtggg attcaggtga gtctccatgc acttcacatg ttacccagtg ttcttgttac | 3000 |
| ttccaaggag aaccaagaat ggctctgtca cactcgaagc caggcttgat caataaacac | 3060 |
| aatggtattc caaaaaaaaa aaaaaaaaaa aaaaaaaaaa aaaaaaaaaa ctcgag | 3116 |

<210> SEQ ID NO 44
<211> LENGTH: 3460
<212> TYPE: DNA
<213> ORGANISM: Homo sapiens

<400> SEQUENCE: 44

| | |
|---|---|
| acgcgtccga tgaacttgac cggctaaatg ccccactttc tcagatggct tctaacgact | 60 |
| tcaggatta gggccagctg tgggtctact ccttgttgga gcccatctca cctgggatgc | 120 |
| ctgcagccag ccctccctcg tgatttgtct caccttgagt aggagacatg cttctcccct | 180 |
| aaccttttcc tttctgccat aattaacata tgtccttttc agtaagtcca tgcctctggc | 240 |
| agggatgaa gaagtactca ctggtaatta gctaccatct ttgcagcagc cctggtaact | 300 |
| tgaaaattt gggtctggtg ctgttcatga gtctttgtgt aactgcaaaa gcaggaaagg | 360 |
| aagtcaagac tcctgttgcc tcgtgcttag caaagcagtc cttatccttt atactctgtt | 420 |
| cttgggtttt gtttttgtct tgttttatac caggcaaatt gcttagtagc aaagggacca | 480 |
| aactgaaaag gtgacaatct ctaacttcta aaagcagaca ccaatcggat gctcattaga | 540 |
| ggttaatgaa gatgccattc ttggtggcct ctgcacccaa attgcatctg aaagaacta | 600 |
| gggtctcatt cagaatgtcc aaaaggaaat tcttaagagc ttaaattcag atttgtgtct | 660 |
| cattaatgca gtgaacaatt caaaaccaca cagattcctt ggcaggaagg ataatggaat | 720 |
| aacagtgttg atgagacctt tttagcttca aggtttcgga gtctaaacaa atggatgatt | 780 |
| catttggaat gaaactcaca atgcaagtag aaggacctct ccaaatcagg ccagttgggt | 840 |
| tatcctggct tggaatctgg tgtgaaacca taggtcttaa cactctggag cagcacattg | 900 |
| ctgtggatat gtccaggaga ccttagatat ggcttaaagg cttcaagat gaggacagaa | 960 |
| attgcttaca attgctcagt ttctcaacag aaagactcat aagagtgcca gcatgggta | 1020 |
| catggagtga agctgggtgg gaagcatcat ctgcacagtc cctgtcctag tgcaggactt | 1080 |
| ttctctgtat gttttcatac catgggattt ttggatatca gtgtattttg gttcttgaaa | 1140 |
| tagcctaata gctgctcaca cattgggtag gaatattata ccaatgtcat ccccaaagga | 1200 |
| agggtgagct gaatggaaat taagcccagt catttatt gatctattag ctctgttatc | 1260 |
| agtgcatgat cacccagatc accctcctca gcccacacag tgctgaacca tcttccctcc | 1320 |
| tgttctccat ggctattaat agtatagcta aatttagagt gcagagccag atataagtat | 1380 |
| tttggaatta tctcccagtt tgtggtagaa gctgactgga atacaggttg agtatctctt | 1440 |
| atccaaaatg ctagggacca gaaaggtttc agattttttc agattttgga atacttaaca | 1500 |
| gttgagcacc ccaaatctga aaggcttctg aacgtcatgt cagcactcaa aaaagtggat | 1560 |
| tttggagcac ttcaaatttc ggattttggg atttgggatg ctcatcctgt gtaggagagg | 1620 |
| ctactcgatt ccatttaatg actgtcctag tcataatcat ccaaagataa aagccaggta | 1680 |
| gatgttgaaa gctcttttcca gggctgaaaa agtgttctta cgttctctgc atgtgactag | 1740 |
| catcactgtg gaaattaatg ctctgttctt cactagaatg tagtaagtgg ttaaactgag | 1800 |
| ctatccccca cctgatgact attggcatcc atttgcaagg ccaatggcct ggattaaggg | 1860 |
| ttaggattat ttgtagctag aaggtaattt tatttctgtg aaactaattg gctcatattt | 1920 |

```
gaggttaggt gtggccttga ccttaccagt acatttatac ccactaccag ttgactagcc   1980
cagataattg ttaaatggtg cttctttttct gcttctcagt agacttccat gccattacaa   2040
aggaaatttg aattacctag tgtttgtata ttccatgata actatgtata acttctgtta   2100
cacagcttat gtattgttaa catttaagtg taaaccatgc cacagctaac acttaaaaat   2160
gaaaactaat tagttcttgc ttagggaaaa tgccaggtat gaagtatggc atatacttga   2220
cactgtcctg tgtaacccct tactttgctc aggctttcaa gattgagtct ttttcccc    2280 aaattaggtt aacatgcatt tgaccccaac ctgtggggtt tgagtaagct ggaaatctgt   2340
gacggtaggc tttctagtgt cacgaggtgg tggtgactga aggaaaagct gggatcacag   2400
gttccttctg atggagagga aggtttattt ctatgcccct cccaccaccc tccacctaga   2460
gctcacccaa gcctgctcca gtcccagggg caggccattc tgcaaaagca ggacctcaca   2520
gaaacaaggg ctgggttgag gtcacccct tcagagttgg ttcctggcca gatgggtaag   2580
aggcatttgt aattttaaaa atgtgaaact tgggtttggt gttttcttct aagtgcctaa   2640
ataagcaagc caggctgttg atattttagc cagagaaatc ggcaagccaa gattaacccg   2700
aatctgaagt ttagaatctt gagtttgcat ctgcatcata tcatgctgtt ttgatgagga   2760
aacatttgcc actgaggagt tggagggagg gcaagacgac agtgttaagt cagatcattt   2820
aatggtttcc cctaagccct ggaaaaatat ttgaaagaat ggcagcaaaa aggttaagaa   2880
agcaagccag atttactgca caatatgcag tacccagtac tactttaaat cccaagagaa   2940
cagtgtgatg tctaatatat acaggtctat gaaaatactg tggaataagc ccaggaaggt   3000
tagatgtgtt tgcaaataag ttgcccaaag ggtcccctc taagtaaaac aaatattcag   3060
accacaggct ttaatgtaaa ctgtcaaaaa gtgggatgtg gaggattttt gttaagtgtc   3120
aatcgaagtt aaaaagcaag ggtttttggc caggcgtggt gctcacgcct gtaatcccag   3180
cactttggga ggccgaggcc ggcaaatcac ctaaggtcag gagttcgaga ccagcctggc   3240
caacatggtg aaaccccgtc tctactaaaa atacaaaaaa attagccggg tgtggtggca   3300
agtgcctgta gtcccagcta cttgggaggc tgaggcagga gaactgcttg aacccgggag   3360
gtagaggttg cagtgagcca cgatcatgcc actgcactcc agcctgggca acagagcaag   3420
actccatctc aaaaaaaaaa aaaaaaaggg cggccgctct                         3460

<210> SEQ ID NO 45
<211> LENGTH: 2622
<212> TYPE: DNA
<213> ORGANISM: Homo sapiens

<400> SEQUENCE: 45
aggttccctc ctttggatat ttggcagttg tactttatgc agttcagcca agaactaaac    60
acaggccttc agtgtgtggtc agagtacagt gggccagagg tcctttcttt tcttcatgtg   120
gtcatacacc tctgttaatt caacttaagt ttatattact tttgggggtg ggagtgggga   180
agaggatcac attgttgact tgctggaagc attatgtcaa ctaaaatcct tcagttctta   240
ttttcatcat gctgttgggt tccccctatg ttgtttcttt ttaaaaacac caaatgcaga   300
acttcccttt tatactgctt ctatttcatc ttgttgactt gtagcctatc agagtatgat   360
tctttattgt catctaaggt attctgatat aatcactgca tgtctaaatt ctagttattg   420
actaaatgct acttgagacc attctcttgg ttgtcacatt attttacagt tgaagaaact   480
gaaccttaga gaggttaagt accttgttaa aggccacctg gctggaacat aacatcctgg   540
tcattttaac tactaatgct gtcatgaaag ggagttagcc agggcaggtg tgaatagagc   600
```

```
attctagcat aagcagccaa caattagagc aactgtgtat ttttagtgtg tggatagcaa    660
atctttgctg tcttggaagt tactatctta gaagcatggt attaagctct ctattcaatg    720
tggtgttcac atcagtagca ttggtttcat ttgggagctt tttagaaatg cagagctcag    780
gccccactcc aggcctaagg attcaatctg cattttaaga agtgacccat atacacatta    840
aaggtttaag aagcattgct gtagtatcct attttccaca ctttagtcat ttgcatatca    900
cttgtgcaac tttggcttta tctgcatact tcctgaaggg ggcctgcccc tccacacctg    960
tgggtatttc tcgtcaggtg gagatgaaag aatgagaaaa gaaataagac acaaagtata   1020
gagaaagaac agtgggccca ggggaccggc acactcagca tgcgaggacc tgcaccagtg   1080
ccggtctctg agttccttca gtatttattg atcattattt ttactgtctt ggcgaggcga   1140
gtgtagcagg gcaacaggtg gcgagaaggt cagcagggaa acgtgagcaa aggaatctgt   1200
atcatgaata agttcaagga aagtactgt gcctggatgt gcataggc tagatttatg   1260 tttcactta cacaaatatc taactagcag agagcaacaa agcagtattg ctgccagcat   1320
atctcgcctc cagccacagg gcggttttct cctatctcag aatagaacga atgggaatgg   1380
tcgactttac actaagacat tccattccca gggacgagca ggagacagaa gccttcatct   1440
tatctcaact gcaagaggc ctccctcttt cactactcct cctcagcaca gaccctttac   1500
atgtgtcggg ctgggggatg taaggtcttt cctttcccac gaggccatat ctcaggctgt   1560
ctcagttggg ggaaacctgg acaataccca ggcttttctg ggcaggggtc cctgcggcct   1620
tccgcagtgc attgtgtctc tggttaatcg agaatggaga atggcgatgg cttttaccaa   1680
gcatactgcc tgcaaacata ttgttaccaa ggcacatcct gcacagccct aaatccatta   1740
aaccttgatt caatatagca catgtttctg ggggcacaga gttgggcta aatttacaga   1800 ttaacagcat ctcaaagcag aacaattttt cttagtacag atcaaaatgg agtttcttat   1860
gtcttccttt tctacgtaga cacaggaaca atctgatctc ttttcccac acttcctata   1920 tgttaatgta ttttaattgt ctgttagctt ttatgtcttt ccaacttgaa ataatttcac   1980
ttacaaaata gctggaaaaa tagtaaagat aattcctgta ttttcttcac ccacgtattc   2040
ccaaatgtgt aacacctaca atcagcaaaa atcagcacat taatattatt acctaatcta   2100
cagacctcat tcacattttg ccagttgttc tgctggtgtg ctgtatgtag tgcaggatcc   2160
agtctaggcc cgtatgttgc attttgctgt catgtcttct tagtctcctt tcatctcagt   2220
ggtcttttct tttccatgac tatgacagaa atgatttgta tccttcatat atctgcagtc   2280
acatgaagtc tatttgtccc actactggtg acgtaaattt tggtaacttg gttgagggtg   2340
gtaccgtcta ggtttctcca tattaagttg ctattttttcc ttgtgtattt aataagtatc   2400
ttatagggaa atcctttgag actatgtaaa tatcatatta catgtatttt gcctatttta   2460
gcatcttttg aagataattg cctgaaacat tttttactgt gatgattttc taattctatc   2520
attctgcatt tattagtttg gaattcgatt gtaaggaagt atattccctt gtttcctatt   2580
attttattaa agaatttac atccaaaaaa aaaaaaaaa aa                        2622

<210> SEQ ID NO 46
<211> LENGTH: 1984
<212> TYPE: DNA
<213> ORGANISM: Homo sapiens
<220> FEATURE:
<221> NAME/KEY: SITE
<222> LOCATION: (106)
<223> OTHER INFORMATION: n equals a,t,g, or c
```

-continued

```
<400> SEQUENCE: 46
agttgttgct atgaatgatt ttaagccttt ttttttaagc ttggcaaaca tcccagctaa      60
tcaaaatagt catattcctg agaagtagga aactaaaact tctttncata taattgttag     120
aaggtttgtt tcccaaacta ccatagttac aaaggtgaat agccaaattt taggaacaga     180
atcaaaagaa taaaaatctg tgaagagatc ctactactct tccttctatg ttttggtttt     240
ggtttctatt gtccctatca tttcagcaag tggaacagca gcaagttttt cagtgcatat     300
gctgcacaag aacaaaatat aaatctgtat ggcaccaaaa atcaaagtga aaaccaaacc     360
aaaaacccaa acaccctatg taactatcgg aggcatatac gtggtataaa tgactgtagc     420
tgtgatacac acatggctac ttgtcacatc actttccata attatttact gcaaaatgat     480
tgagaggctt ttggtgcagg cagccgttaa cctcctgctt cctttgttac ctctggatta     540
ctttgcagta aattgcaggt cttttaagag atttaagctt cagttttctc aaaccaaacc     600
aattatcctg tcttatctga agatgcaggg ttgtgggcaa aagaggctgg ttataataat     660
gccctcatat tgagtggtct gtaaacggct gcacacttca ggcactgtag ttgctgaaga     720
tgctttgtta aatgtgacct tgactggctt tacaggggtg tagaatgtaa tctacacaag     780
gtgactttgc atctatcttg ctcttgaggt ggatgaaatt gagaagctgg agtgtgtaag     840
ccatgcacat aagtattctt cactgtaaat tttgttttca tttttaaccc aattatggta     900
ctttatccaa tgcacaactg atctctcagt agatattcat ttgaaaatag tgtggccttg     960
atcagtgaga aagggaagga gaaaagtgac ttttttgctt atgtagaaat gactcatttg    1020
ctgagagttt gtctttctgc agcactcttg gtataatgtt agtgatcggt ctccttttttg    1080
attggggaaa gttaatgttt ttgaccctgg agttaattca gttgagttat cttatatttt    1140
taggaagtat cagaattgct ctgatgaata acaagttga ctgttttgat gtccaatctc     1200
aggttttaga atatagtggt gtaaagtccc actattttta attcttaaaa caactttaat    1260
ttcgtacacc ctaaaagtca catgcataag gcctgttcag agagcagagc ctccatcttt    1320
ttgctccttt tctactttgt acttcacttg raaaaatatc aagtgacttt acatkgtata    1380
tttccattgt aaccctgaca tttctcaaag ataaagcact ttttgatcat gaaatacatg    1440
aaatctttgt gtgatgtgga tcatagtttc tcaggctccc ttagataatt gcttatgaat    1500
attgttctaa ctctgtgtaa gaagagtaga atctttgct aatgttagaa ggtttgtatt     1560
attgatccag aatgcatttt gctagtttcc aatggatggg agagtaaata atgctgcatt    1620
cacaatttaa taagttactt tcccttgagc cttaaggtaa cttttttcttt tctgtcaact    1680
acagcactga agttatagta agtgaatgag attatcagtt ttcagggttg gttttagagt    1740
actgtaaatc aattagctgt cttcctaaag agttacaact cccattcagt atactggata    1800
atgggtgtgt gggtggggct ggggagggcg ggagatagtt tgtagaaaag aaaaaagaaa    1860
aaaaaaaaaa acacatttac cttaagaaaa tacagacaaa aaaaaaaaaa aagggcggcc    1920
gctctagagg atccaagctt acgtacgcgt gcatgcgacg tcatagctct tctataggat    1980
cacc                                                                 1984
```

```
<210> SEQ ID NO 47
<211> LENGTH: 1987
<212> TYPE: DNA
<213> ORGANISM: Homo sapiens
<220> FEATURE:
<221> NAME/KEY: SITE
<222> LOCATION: (442)
<223> OTHER INFORMATION: n equals a,t,g, or c
```

-continued

```
<221> NAME/KEY: SITE
<222> LOCATION: (444)
<223> OTHER INFORMATION: n equals a,t,g, or c
<221> NAME/KEY: SITE
<222> LOCATION: (473)
<223> OTHER INFORMATION: n equals a,t,g, or c
<221> NAME/KEY: SITE
<222> LOCATION: (493)
<223> OTHER INFORMATION: n equals a,t,g, or c
<221> NAME/KEY: SITE
<222> LOCATION: (1011)
<223> OTHER INFORMATION: n equals a,t,g, or c
<221> NAME/KEY: SITE
<222> LOCATION: (1025)
<223> OTHER INFORMATION: n equals a,t,g, or c
<221> NAME/KEY: SITE
<222> LOCATION: (1111)
<223> OTHER INFORMATION: n equals a,t,g, or c
<221> NAME/KEY: SITE
<222> LOCATION: (1119)
<223> OTHER INFORMATION: n equals a,t,g, or c
<221> NAME/KEY: SITE
<222> LOCATION: (1169)
<223> OTHER INFORMATION: n equals a,t,g, or c
<221> NAME/KEY: SITE
<222> LOCATION: (1234)
<223> OTHER INFORMATION: n equals a,t,g, or c
```

<400> SEQUENCE: 47

| | | | | | |
|---|---|---|---|---|---|
| ggcacgagac | cggcgctagt | cttgcgtcgc | acagcaggat | tgcgctgctt | tctgatgacc | 60 |
| ttcgacatgg | atggcgatgg | taatgaacgc | ttttcccgta | acgccccacc | cgcaaccgac | 120 |
| ccaggccgga | atgaccctga | tcgaggtcct | ggtatctgtg | ctgatcctcg | ctgtcggcct | 180 |
| gctaagggcg | gcagtcattc | agctcaatgc | attgaaatac | accgacagtt | ccaggatgac | 240 |
| cagtcaggcc | agtttcattg | cctacgacat | gctcgaccgg | atccgcgcca | attcgggtgc | 300 |
| tgattactcc | tggggccagg | gtgaacgcgc | gccctccacc | acctcggtcg | cgagtgtgcg | 360 |
| tgatctggac | ctgcacgact | tgaagcgaa | tatcgtcggg | ttcgccgggg | aaagcgccaa | 420 |
| ggggtccgtt | gcggtcaatc | ancnagaagt | gaccatcagc | atcagttggg | acnactcccg | 480 |
| tggagcgaat | gcncaaggca | cccgggaaac | attcaccctg | accagccggg | ttgcagtcga | 540 |
| tccgagggtg | ttgccatgag | aggtccagtg | tgcggtttca | gcctggtgga | gatgctgctg | 600 |
| gcattggccc | tcggcctgat | gttgatcctg | ggggtgaccc | aaattgcact | cagctcccga | 660 |
| accacttatg | ccagccagag | tgcggcttcg | ctgttgcagg | atgatgcacg | gttcgccctt | 720 |
| ggcaagctga | ttcaggaaat | acgccaggcg | ggcatgtttg | gctgcttgtc | cgctgcatca | 780 |
| atcagcaacg | ctcccgcagg | ttttgatcgt | cccattggat | ggagtaccac | cggcagttcc | 840 |
| cggtccctga | cgctggtgac | cgccgacgtc | ggggagggtg | gcagcaagcc | ggactggacg | 900 |
| gtgctttccg | attgcaccgg | ctctgcccac | gcctatgttg | aagcccgcc | ggcagcgaac | 960 |
| gcccgggcaa | atccacttcc | cacttgcgca | aagctgacct | aacacctttg | nagggcgggc | 1020 |
| aagcnggaag | ttaagtaacg | ctggcggccc | ccgagcaaag | cggtggttgg | tggataacgt | 1080 |
| ggggcattcg | atatcagttt | tcggcgtggc | ngacaagcnt | ggctcaacgg | ttgtcagccg | 1140 |
| atatgacccc | accccggcg | atgagtcgnt | catccgcagc | gtgcggattc | tgctgacact | 1200 |
| tcaggatcca | aatgggttgg | tgaaagacca | ggcntacagc | gtggtcgcgg | cactacgtaa | 1260 |
| tcgcctggag | tagcgtgccc | atgggttatt | acctctcccg | ttcgaggcag | gcaggcatgg | 1320 |
| ttttgctgat | cagcctggta | ttcctgctgc | tgttggcact | cctcggagtg | tcttcgatgc | 1380 |
| agggagcaat | ctcgcaagaa | aaaattaccg | gcagccttcg | gcagcgcaac | cagtcgtttc | 1440 |
| agcaggccga | aagcggcctc | aggcttggcg | agtctttggt | gcaggcgtca | ggtttcgccc | 1500 |

```
tgcgcccttg ccactcgacg gctgcgtgcg cgccacctgc cgaatcggtt tcggtagtgg    1560
ggccggggac gaaccccgta tcgactgtga cctggatagg gatgaaagat ggcgtctacg    1620
gtattcaaaa cctggggccg ggaacggggtt tggtcaactc ccggcagagg cccaggccac    1680
ggtctatcgc gtgacatcag tgggcgtcag tgggcactcg cgttcggtcc tggagtctgt    1740
gtatgcccgt gtgggcagcg ggcccggcga gcgtttccga cgaatcatgt ggcgacaact    1800
tcaataggtg agcagcacga tgggcaagga ttgcacaggc ttcaccctga tcgaattact    1860
gatcgccgtg gcctcgtgcc gaattcggca cgagattaat tcccctaaaa atctttgaaa    1920
tagggcccgt atttacccta tagcacccc tctacccct ctagagccaa aaaaaaaaa    1980 aaaaaaa                                                                1987

<210> SEQ ID NO 48
<211> LENGTH: 2113
<212> TYPE: DNA
<213> ORGANISM: Homo sapiens

<400> SEQUENCE: 48
ggggaatatg gatggctttc ttctttgccc tctttgttat tttctttgtt attgttgttc      60
agatggagtc tcactccggc ctgggcaaga gagcaaaat tctgtctggg gggcaggggg     120
aagaggtata ttttttggat taaaatggaa tgctttcctc aaactgttaa aattaggtag     180
tgttacaagt ttaaagaata ggtttagcca gtgtgattat tgcagtgtaa taaaaaggat     240
cccaggtggc acacatgcta gtgtggtgcc cagatgctca actgaagtga aggataacat     300
gcgtttcaac attttctata tactaggcag ttttttcttaa gtcttggttt attgtgtatat    360 aatacagtaa aatttactct ttatacgtat gattccatta atattaacaa atttaaacag     420
tcttacagct aaatacaatc aagatacaga acatttccat cactacagga agttgttttt     480
tgctaattta actaaacttc ttaccatgct caaccccca ccccacccct gagaaccact      540
gctttgtttt tctgatcata tagttttggcc ttttcaaawa tgtcatacag ttggaatcat    600
atagtatgca tgaatcatgt agctgaagtt ttcattttcac ttaggtaaac cctaggaat    660 aggagtgctg ggttatactc taagtgttaa acttcataag aagctgctaa actgttttcc   720
aaagcatctg taccattttc ctttcccacc agcaataaag cattcattag tctacgtact    780
caccagtgct agtgtggtca gaatgtatag tttaattat acacattata atagatgtag     840
agtggtatct catcgtgatt tgccttttc ctaatgaata tctttcctta catatttgtc     900
attagtgtgt cttctttagt aaatggtcct attgttttgc ccattttaa aagttgagtt     960 ttcatattgk tcaatttcga gagttcttca tatattctgg acacaagtcc tttgtcagac    1020
atgtgatttg caaatatttt ccccccagagt ttttcctgtc ttgtcagtcc cttaatagtg    1080
tttttaggaa ggagaacagc tgcttttaat tttgataaag cttgcaattg tttttctttt    1140
atggatcatg cttttggtgt agtatctgag aactctttct taaaccagtc acacatgtct   1200
tctgttttct ttgaagcttt acaggttgag gtacattttg gtccatgatc acttttgagc    1260
tactttttat atataggtag tataagatat ggtttgaggt ttttgtttgg ggttttttttt    1320 cttcctgcat atgaatgttc agttgttcca gcaccatttg ttgaaaaaac actatccttt    1380
ctctagtaat ttgctttttt acttttgtca gttgactatt tgtgggtctg tttttaaact    1440
ccattttata ttatgtctac attatgaact ttatagttag tcttgaaatt mggtaatgtg    1500
ggtcttctca cttgtgcttt tcaaaattgt tttggctctt ctaattcttt cacttttttcc   1560
```

```
atataaattt tagaaamagc ttattgattt ctaccacttt cccccaaaaa gccacttggg    1620
aatttgacta agtttacatc gaatctaata aatgattttg gagagaagtg gtatcttagc    1680
aatacagtct tttctgataa cacttcctgt tttagttctt tttctcattt aataattttc    1740
caacattaaa accttggaca aatttagatg tgtatctgaa taattccagt tttgttgcca    1800
tttaaaatgg tacataatcc ttattttata gatgagaaaa ttaagtaact tgcccaagtc    1860
acacagttac taaatgacaa agctagattg aaatctatga gcttataaac taatgtcctg    1920
ttttgagcta cagtactagt tttattaaat tgttgtggtt aaactgaggt gggaggatag    1980
tttgagcacg gaagattgag gctgcagtga tctttgatcc tgccattgta ctccagcctg    2040
gcaacagagt gagaccctgt ctccggaaaa aaaaaaaaa caccatggaa gcaagcaaaa    2100
aaaaaaaaaa aag                                                      2113

<210> SEQ ID NO 49
<211> LENGTH: 3465
<212> TYPE: DNA
<213> ORGANISM: Homo sapiens

<400> SEQUENCE: 49
agaaaatgaa agcaccaaag agccttcttt gctacaatat ctttgtgtgc agtctcctgc      60
aggattaaat ggtttcaatg tactttatc tggcagtcaa accccccta ctgtgggccc     120 gtcctcaggt cagctgccgt ctttcagtgt cccttgcatg gtcttaccat ctccacctct     180
gggccctttt cctgttctct attctcctgc aatgccgggc ccggtttctt ctactcttgg     240
tgctctccca aacacaggac ctgtgaattt cagcttgcct ggccttggat caatagccca     300
gcttctcgtc ggccccacag ctgtggttaa tccaaagtcg tccacactcc cttctgcaga     360
ccctcagctt cagagtcagc cctcactaaa cctaagtcca gtgatgtcaa ggtcacacag     420
tgtcgtccaa caacctgagt cccccgttta cgtgggacat ccagtctcag tagtaaaatt     480
acatcagtca ccagttccag tgaccccaa gagcatccaa cgcacacatc gtgagacgtt     540
tttcaagaca cccggcagcc ttggagaccc tgtcctgaag agaagagaaa ggaacaatca     600
cgaaacacca gctcggccca gaggagacta gaaatcccca gcggcggcgc tgactaacct     660
gccgctttgc caggtggggg tgggatcaaa cgccctgaga gtcccggatg tccgaggcgg     720
gatgcaaacc atcccgtcct gagcacgggt ccttcctctc tctttcatcc acacttctgt     780
taacttccca ccaccatcaa tcatctgatt tcctgaaagt aattaattgt gcatttaata     840
ccagttagag ttccgactct gcatggtgtc acagtgaaag cgccgactga cttatggttt     900
tgattcaaga atcgtcttat tgctggaagt agatctgaat aggataccgg agccttgttt     960
ttctaaaggg gggcgctgtc tagcacttaa ctagggtaag cattcttaac atgtatttcc    1020
acttgccctg agtaaatctg tggtgagaga agcttccttt ctgcagttta aaaaagctac    1080
tgcttcctta ggcttcatca ggaagccatc ttcagttgtg aatcctatgg tgttatttat    1140
tttgttcctg aaatgggatt tagtgcaaaa agtttacaac tacagtcttt aacacatttt    1200
tttcagggta tgacgacttg aatgtttata cttttattct ataatttgcc ctgcacttat    1260
tttacaacct agtaataatg tggataaatg tatctacatg acacatgtca agaccaaaat    1320
aactgtgaat gacacacctt gctgtaaatg aactgtgcta accctgactg tgggcttgag    1380
aacaaagatg aactctagaa ctctagcagc ctaactgctg cttctcaaat aactgtgtga    1440
acagtgagat attactgttt gtttctaaaa atcctactgt gcccagtttc cttcactaca    1500
tgccctgcat tttttatttta aatatttagc tgtagcgcca tcagatatgg atgccttcta    1560
```

-continued

```
acaattgctg tttgtaaaat aaatcaggat ggtagaaagt gattttatgg aaaattggaa    1620
cctggatgag acctttcgt tgaattctga agagtaatga tgcgaaaatt gatacagggc    1680
```


```
acaattgctg tttgtaaaat aaatcaggat ggtagaaagt gattttatgg aaaattggaa    1620
cctggatgag acctttcgt tgaattctga agagtaatga tgcgaaaatt gatacagggc    1680
aagagatgat tcttttgttt ttcttctact tcatgtccag aagagtaaga gggaaaatgg    1740
acatatgttt catatccaag ggtattcaaa ctgtagttag ttggtacctc tgaaaaatga    1800
gaatggtgag cgcacgggtt ggttgttcta gcatgaatac aattctggaa actgttatgc    1860
aatttccctt ttttaaccca cattacttta ggggtgcatt aagtcgccaa actatactag    1920
ttctttgtat tcctagactt gctgatattt acctctctct tgtctcttca gagtaaatgg    1980
ttcccttctt tccttcctac tttccttcat tctctcttcc ttccctcctt cctacttctt    2040
ttcttccttc ctcttcctct cttaaaacta tcttagatgt agaatcctgg tgtagggttt    2100
tattttattt ttattttttg acccaataaa atgttatatg aaagaatgaa atatattaatt    2160
taagagactc tgggagtctg aataaagtag ctttatatta actacaggat aatattagcc    2220
ttattacccc cacaagattt tttaaaactt gaggtaggta gctacattaa ataaatttgc    2280
tacttatata aaaatttta tcaacactaa acttttaaag tttacaagtt ttttttttct    2340
tttttacagt cttctataga gttaggttaa aaatgtggtt ctaaccatca acaattgcat    2400
ggttaaatga ccctgaacta aaactgatgg gttccctatc aaaacaaata aaatatacc    2460
tttttcaggt ttcaatctgt gcagggtata tgcatgttaa ttctaccatg cttaagaact    2520
tccacaaaat atttcatgga gaggtctgca tttagacgga aacagaaatt gcttttcccc    2580
tcactgttcc tgaatgctct atacttgttt taacattttt gctatctttt tttattattc    2640
tgatcatgat atgaccattt aacctcagaa ttcataattc ctgaggggtg ttaagaagca    2700
gtcccattgg tgaggatatt atgacttggt gaccattctt aggagtagaa aaccaaggac    2760
aattgcttct gtattcagta tccacttctt aatgtggctt tatatgtaaa aataataatg    2820
cagtggttgt ttctgtcagg aaaataaatc ttacagaaca actggtggaa ttgaagctgc    2880
tgcgctagac ttggatattt tgggtagtga agaagcaatg gcaatcttga gtctattatt    2940
gtataattta gtaaaagaaa aaaataatcg ttggtggtcc tactaagaga atgcagcttt    3000
tttgagttgt cacagaggct gtgtgtgccc tacactgacc agggtttgta aaacccttc    3060
attctggtac aagagtcggg ggtataactt ttatacttga atctacctac caagtttaca    3120
tttctcaatt ccttttgta aggtgctatt tctgtattta aataactttc ttttaacgta    3180
aagctgcttt ctgcttatct tattgcactg ctagttgtat gtaggtatta attttattgc    3240
tgcttactgc ttttgttttc ttattattta gctctgctct ttttcctaat ggctatatta    3300
tctatagcta tttacttgta actgtactac atgtaaactg attttttgtt ctgatttttt    3360
ttctaatatt tttaggaaaa tattaagctt tataaaatag caataaaaaa taattcattt    3420
aaaaaaaaaa aaaaaaaact cgtagggggg gcccgtaccc aattc                   3465
```

<210> SEQ ID NO 50
<211> LENGTH: 1237
<212> TYPE: DNA
<213> ORGANISM: Homo sapiens

<400> SEQUENCE: 50

```
atgggccagg aatggggtcc ccgggcatgg tgctgggcct cctggtgcag atctgggccc      60
tgcaagaagc ctcaagcctg agcgtgcagc aggggcccaa cttgctgcag gtgaggcagg     120
gcagtcaggc gaccctggtc tgccaggtgg accaggccac agcctgggaa cggctccgtg     180
```

```
ttaagtggac aaaggatggg gccatcctgt gtcaaccgta catcaccaac ggcagcctca      240 gcctggggt  ctgcgggccc caggggacggc tctcctggca ggcacccagc catctcaccc      300
tgcagctgga ccctgtgagc ctcaaccaca gcggggcgta cgtgtgctgg gcggccgtag      360
agattcctga gttggaggag gctgagggca acataacaag gctctttgtg gacccagatg      420
accccacaca gaacagaaac cggatcgcaa gcttcccagg attcctcttc gtgctgctgg      480
gggtgggaag catgggtgtg gctgcgatcg tgtggggtgc ctggttctgg ggccgccgca      540
gctgccagca aagggactca gtaacagcc  caggaaatgc attctacagc aacgtcctat      600
accggccccg gggggcccca agaagagtg  aggactgctc tggagagggg aaggaccaga      660
ggggccagag catttattca acctccttcc cgcaaccggc cccccgccag ccgcacctgg      720
cgtcaagacc ctgccccagc ccgagaccct gccccagccc caggcccggc caccccgtct      780
ctatggtcag ggtctctcct agaccaagcc ccacccagca gccgaggcca aaagggttcc      840
ccaaagtggg agaggagtga gagatcccag gagacctcaa caggacccca cccataggta      900
cacacaaaaa aggggggatc gaggccgac  acggtggctc acgcctgtaa tcccagcagt      960
ttgggaagcc gaggcgggtg gaacacttga ggtcagggggt ttgagaccag cctggcttga    1020
acctgggagg cggaggttgc agtgagccga gattgcgcca ctgcactcca gcctgggcga    1080
cagagtgaga ctccgtctca aaaaaaacaa aaagcaggag gattgggagc ctgtcagccc    1140
catcctgaga ccccgtcctc atttctgtaa tgatggatct cgctcccact ttcccccaag    1200
aacctaataa aggcttgtga agaaaaaaaa aaaaaaa                              1237
```

<210> SEQ ID NO 51
<211> LENGTH: 1397
<212> TYPE: DNA
<213> ORGANISM: Homo sapiens
<220> FEATURE:
<221> NAME/KEY: SITE
<222> LOCATION: (1383)
<223> OTHER INFORMATION: n equals a,t,g, or c
<221> NAME/KEY: SITE
<222> LOCATION: (1396)
<223> OTHER INFORMATION: n equals a,t,g, or c

<400> SEQUENCE: 51

```
ggtccctagg agttgagcag gaacaggcat ctgtggttta cggcgacctg gctctccgcr       60
ggccacgtgg gtggtgaggg cacacgagtg ggaagcggca ccgacgtgtt tctccccgac      120
cgtggctttg ccaaagactt ttaatagcat tttttaagtg caaaacgtct aggtaaaaat      180
ctttatcatc agtgaccaaa ttagaatgta tttaatatag taggtggttt aagaactgtt      240
ttaacgtaag acaaactgat agcaacattc tgttgtttta aggaagtgg  gtccgtgaca      300 ttctgcagct agtccactac tccaaggtaa ctatcgactt ggtttcagtg aatctatttt      360
gtttttaact acagtgattt attagctcag tatctagaaa ttacgtatat tttgtgctac      420
tgtcatcgat gtgtaaactc tgtttttatt tgtatttatg cacttggttc ccatttggag      480
cctctggtct tttctgggat aagtggtgtc tgccagaca  tctcccggtt gtcagtggtc      540
aggagcagct gagctctagt ctgccagctg ctctgctctt tctgggaagg aggtggcgcc      600
cgcccctcag ggtgtctcca gggctcagct tccggggtgg tagagctggg gagccccagg      660
ggtgggggga cagctgggag atggaggtgg cacctgctcc cctagatcag tactggctct      720
gaggacaggt gagcagtggg aagaccaaag aatggctggc agcgctgcca rggttggaaa      780
tgggggcaag atcctggggc tgtgtgccct ggggcctccc tcacctgtct tggtggccat      840
```

```
ggcctcaggg atggctccta ggtggctgag gcacagcagt ggctggaagg tgccccgtgg    900
aggctgaggt ggaggcgcgc ccagcagctc ccccctgtgg ccatggcggg cacgggscgt    960
aggagctggc tggcggccgg ctctgcatgt tcttgttgcc tgtcgtctgt aactctagtg   1020
ttcgacattc gccgtgatac agtggtgtca cgacgtgtgt aactgtggtc agcagacctt   1080
gttccgcgtg gacgcctcaa gtggattaat ttctggaagc ctcaatctgt atgtttgagt   1140
atttacatga gaatgttatt tgaatggaat tttcttaacc cagaaggtag tatttataat   1200
catttacttg tagcgaactg tttaaagtta acacttgttt aaatttttt acactatagc    1260 atttatgcaa tggtttacag aattcatgga gttattttta tcagtatggg aattaattaa   1320
aaccttgaat cttaaaaaaa aaaaaaaaag gcggccgct ctagaggatc caagcttacg    1380
tangcgtgca tgcgana                                                  1397

<210> SEQ ID NO 52
<211> LENGTH: 2271
<212> TYPE: DNA
<213> ORGANISM: Homo sapiens

<400> SEQUENCE: 52
cggcacgagc ggcacgagta tcggagggct ttggaccatg aggaggaggc cctgtcatcg     60
ggcagtgtgc aagaggcaga agccatgtta gatgagcctc aggaacaagc ggagggctcc    120
ctgactgtgt acgtgatatc tgaacactcc tcacttcttc cccaggacat gatgagctac    180
attgggccca gaggacagc agtggtgcgg gggataatgc accgggaggc ctttaacatc     240
attggccgcc gcatagtcca ggtggcccag gccatgtctt tgactgagga tgtgcttgct    300
gctgctctgg ctgaccacct tccagaggac aagtggagcg ctgagaagag gcggcctctc    360
aagtccagct ggggctatga gatcaccttc agtttactca acccagaccc caagtcccat    420
gatgtctact gggacattga gggggctgtc cggcgctatg tgcaaccttt cctgaatgcc    480
ctcggtgccg ctggcaactt ctctgtggac tctcagattc tttactatgc aatgttgggg    540
gtgaatcccc gctttgactc agcttcctcc agctactatt tggacatgca cagcctcccc    600
catgtcatca acccagtgga gtcccggctg ggatccagtg ctgcctcctt gtaccctgtg    660
ctcaactttc tactctacgt gcctgagctt gcacactcac cgctgtacat tcaggacaag    720
gatggcgctc cagtggccac caatgccttc catagtcccc gctggggtgg cattatggta    780
tataatgttg actccaaaac ctataatgcc tcagtgctgc cagtgagagt cgaggtggac    840
atggtgcgag tgatggaggt gttcctggca cagttgcggt tgctctttgg gattgctcag    900
ccccagctgc ctccaaaatg cctgctttca gggcctacga gtgaagggct aatgacctgg    960
gagctagacc ggctgctctg ggctcggtca gtggagaacc tggccacagc caccaccacc   1020
cttacctccc tggcgcagct tctgggcaag atcagcaaca ttgtcattaa ggacgacgtg   1080
gcatctgagg tgtacaaggc tgtagctgcc gtccagaagt cggcagaaga gttggcgtct   1140
gggcacctgg catctgcctt tgtcgccagc caggaagctg tgacatcctc tgagcttgcc   1200
ttctttgacc cgtcactcct ccacctcctt tatttccctg atgaccagaa gtttgccatc   1260
tacatcccac tcttcctgcc tatggctgtg cccatcctcc tgtccctggt caagatcttc   1320
ctggagaccc gcaagtcctg gagaaagcct gagaagacag actgagcagg gcagcacctc   1380
cataggaagc cttcctttct ggccaaggtg ggcggtgtta gattgtgagg cacgtacatg   1440
gggcctgccg gaatgactta aatatttgtc tccagtctcc actgttggct ctccagcaac   1500
caaagtacaa cactccaaga tgggttcatc ttttcttcct ttcccattca cctggctcaa   1560
```

```
tcctcctcca ccaccagggg cctcaaaagg cacatcatcc gggtctcctt atcttgtttg   1620
ataaggctgc tgcctgtctc cctctgtggc aaggactgtt tgttcttttg ccccatttct   1680
caacatagca cacttgtgca ctgagaggag ggagcattat gggaaagtcc ctgccttcca   1740
cacctctctc tagtccctgt gggacagccc tagcccctgc tgtcatgaag gggccaggca   1800
ttggtcacct gtgggacctt ctccctcact cccctccctc ctagttggct ttgtctgtca   1860
ggtgcagtct ggcgggagtc caggaggcag cagctcagga catggtgctg tgtgtgtgtg   1920
tgtgtgtgtg tgtgtgtgtg tgtgtgtgtc agaggttcca gaaagttcca gatttggaat   1980
caaacagtcc tgaattcaaa tccttgtttt tgcacttatt gtctggagag ctttggataa   2040
ggtattgaat ctctctgagc ctcagttttt catttgttca aatggcactg atgatgtctc   2100
ccttacaaga tggttgtgag gagtaaatgt gatcagcatg taaagtgtct ggcgtgtagt   2160
aggctcttaa taaacactgg ctgaatatga attggaatga tacaaaaaaa aaaaaaaaaa   2220
actcgagggg gggcccggta cccaattcgc cctatagtga gtcgtattac a           2271
```

<210> SEQ ID NO 53
<211> LENGTH: 2769
<212> TYPE: DNA
<213> ORGANISM: Homo sapiens

<400> SEQUENCE: 53

```
ctgccaccgc cgctccccccc ctcccgctgc cctcgggccg ggctgggtcg agctgcgatg     60
ccctcggact tcatctcatt gctcagcgcg gacctagacc tggaatcgcc caagtccctc    120
tactcgcgag attctctgaa gttacaccca tcacagaatt ttcatagagc tggactattg    180
gaaggtcagc aaagtaccat tttaaagcat attgtgttag tatgcaaagg ctttctctga    240
aatggagttt aaatgggaaa gtatgaaact ttgcaaactc acacaatgta gttttctcct    300
aaagagtctg atccttcttt tagagcagct gaatgtttca atgggttttg ttgctgcgtt    360
tgatgtgctt gttggctgtt ctatctgctt tgagaaacat tgaaaaaaaa atcattttaa    420
attatgtgtt gagtgttcta ctttagaatt ccagaccttc attttagctt tttatacaca    480
aaatagaatg tgaaaaggcc caaacattaa catgaatata aaagagtgac accaaacaca    540
taattagttt gaaaattcag aatttagaac atttatatgc tgagcatttc aaaatatgtt    600
aattatttat tgcaaaagca ttgatgccat tgttattgca ttatacttaa gggtaaggaa    660
agccaagtaa tagcgatgat gattgagcta tgcttagaag aaagggtttt agaaagttct    720
ggaaatgtta atagagtctg tagattagtt taaacagctt acacttactt tagaaaactt    780
ttggctttgt gtgtgtgtgt gttttaacat tttaagacat aaaatagtct tgtgttttttg   840 tagattttga agtgatttca catatatcat ctttaaatct ttataatttt ggaattggac    900
agcaaaggta ctaatttccc cattgtagag aagagaaact aaggctgaaa ttaagaaacc    960
aaaaaaaaaa aaaagtccca cagtagaaga ataatactt tctgcgtttc agttagtgct   1020
ctttatgcaa agcggccacc gtgaaataca catgtaacca gtaacaaaca ttttatggtc   1080
tactttaaaa aggccctaaa tatttaagtt tgacttgaga agattttttgc ctcccttgga   1140 ggtagtccgg gatagtgggg ggcaagtggg ttttgtagtt gagcttaaat ttggatacca   1200
acttagctcc ttattagttc tgtgacttcg ggcaagtgat tttacctctc taaactttaa   1260
tattcttcct gttaaaatgt agctgtctct taaatttagt gagctaatgt gtattaaatt   1320
gcctagcata gcgtctagct taataaatgt tagtttttc ctttagtatc agctaaattt   1380
```

```
ttttaacagt ataatttaga gcatataaaa tgttctcaaa taaataattg gttaaatttg      1440
ttttgtacgt gtaagaagcc catagatata cattagtatg aaaatcaaat attttaaaa       1500 ctacaatttg aagtgagaaa ttttagcag tgtttcttag tgaagcagat ttctggtttt        1560
tattcatatt caatttgtga ccatgttgta gagacatatt tgtctgtaca aacccatctc      1620
atttcctgga caacaaacca tagagtgtca taatcataga gatgatcagg gaggagaaag      1680
acatgaagaa aaaatgagt gttaattatt taagcaaata ttttttagtga gctgatggaa      1740 atacagacaa ccatttagca tgtttattta catgtttatg cctaaatact ttcgttaatt      1800
tttcatttta gttaaggga ttctcattta aagtaaggct acccttttag aaattatata       1860
taaaatataa catgtataag tatcaattct gtcatgccct ttaaaatgtt ttgagacagg      1920
gtgtcttaaa aaagttgttt gcttctgtaa tgaagtgtct aatctgtgcc acctcattgc      1980
tatttctttt ttattattga catttttaaag aatacataaa agtagagaga ataaaataag    2040
ccccatatac ccatcaccac agtttaacca gtatctaatc ttgcttcttt tatcccttct      2100
tctctctcaa gctggattat tttaaaacaa atatcaaaca tcagatcact tcatacataa      2160
gtatttctgt attacagtga ctttcttata ttaattattg atataaattta attgttaata    2220 taattattgt attaattttt aattactctg tatagtttat aaactatttc ttggaatatt     2280
ctagtttatt tcagcaaagt ctcttgtgac tctcctgccc tcttttcaag acagagtgct    2340
gcaggaggct accgcttcta gtatatagta tatcctataa cctatgttga aattgtaggc    2400
catgctgcta gattggagtt catattgttg ctctgacatt tacttgtatg gccttagcct    2460
aataatttaa tcttttttgc ttcaattttc tcatctttaa acgggagcaa taatagtgcc    2520
tcatcctagg tttttgtgaa gattatttga ggcaaattcg tgtaaagcat ttaatttagc    2580
acatgctaag tgctcagtaa atgttagcta aagttaaaaa attttttaaaa cctaaatgct    2640 agctgtagag tgtttactgt gtgccaagaa ctttacaaat aagaactcct gaggtgggca    2700
tatcacttgc ggtcaggagt ttgagaccag cctggcttac atggtgaaac cccatctcta    2760
ctaaaaaaa                                                             2769
```

<210> SEQ ID NO 54
<211> LENGTH: 1389
<212> TYPE: DNA
<213> ORGANISM: Homo sapiens

<400> SEQUENCE: 54

```
ctgcaggatt cggcacgagg atctgttgac cacagatgta agaatttatt tctggagcct      60
caattctaat ccattgctct acatgtgcac tggtttcctg gggctgccac agcagaatac     120
cacagacttg ggggcttaaa caacaaagtg attcctcaca gttctggagg ctccaagtct    180
gagatcaagt agtcggcatg tttggttcct cctgaggctt ctctccttgg cctgcagatg    240
accacgttct cactgtgttc tcagctggcc cttctctgtg catgtacatc cctggtgtct    300
cttcctcctt tgttgactac taaggatacc agtcctgttg gaccagagcc ccactgtaaa    360
ggcctcattt taacttaatc cacttaaata acttatttcc acacacagta agtctgaggt    420
tgagtctttt gaattctggg ggagacactg cagcccatca cgtatgttga cgtgtgccac    480
cgccacactg cctggttact gcagagtgtt agtaagtttt gaaattagaa agtataagtg    540
ctccagttct gttatttttc aggattatta gggctattct gggtcccttc catctcccata    600 tgaatttgag aatcagcttg tttattcctg ctaaaattta gttgggattt tttttttttt     660
gagatggagc ctggctgtgt caccaggctg gtgtgcagtg gtgcaatctc gcctcactgc    720
```

```
aacctccacc tcccgggttc aagtgattct cctgcctcag cctcctgagt agctgggact        780
acatgcgcac gccaccacac tcagctaatt tttgtatttt tagtagagac ggggtttcac        840
catgttggcc aggatggtct tgatctcttg acctcgtgat ccgcccacct tggcctccca        900
aagtgctggg attacaggca tgagccaccg cgcctggcct cagttgggat tttcacaggg        960
ctcgttttga gtctgcagat caatttgggt agtactgaca tcttaaaatt aagtctaccg       1020
atccacataa gtgggatgct agttaatatg gacaagtgaa tttattactc ctccaaaaaa       1080
ctattttcac aaactttata tcaacatgag aaatcatgtt gtatctttct acctggaggg       1140
agcaagaaag tcaggtggtg tgccttttgt acatgggcaa cccaatttct tatctagact       1200
ttcttttgct cgcctggaaa aaaaaaaaaa tgaggtattg caaaaatgtg ataattgctt       1260
tccttagtat gaaaaactgt taaaatgagt aaagcctgtg ctcaactaga attctcacat       1320
ttccgttttg atgtatccgc atttcacctc gtgccgaatt cgatatcaag cttatcgata       1380
ccgtcgacc                                                               1389
```

<210> SEQ ID NO 55
<211> LENGTH: 748
<212> TYPE: DNA
<213> ORGANISM: Homo sapiens
<220> FEATURE:
<221> NAME/KEY: SITE
<222> LOCATION: (15)
<223> OTHER INFORMATION: n equals a,t,g, or c
<221> NAME/KEY: SITE
<222> LOCATION: (17)
<223> OTHER INFORMATION: n equals a,t,g, or c
<221> NAME/KEY: SITE
<222> LOCATION: (29)
<223> OTHER INFORMATION: n equals a,t,g, or c
<221> NAME/KEY: SITE
<222> LOCATION: (32)
<223> OTHER INFORMATION: n equals a,t,g, or c
<221> NAME/KEY: SITE
<222> LOCATION: (646)
<223> OTHER INFORMATION: n equals a,t,g, or c
<221> NAME/KEY: SITE
<222> LOCATION: (741)
<223> OTHER INFORMATION: n equals a,t,g, or c

<400> SEQUENCE: 55

```
ggtgcggccg tttanantag ggatccccng gntgcaggaa ttcggcacga gcttattgka         60
tgtgctmcag tgacaggcat ctgggacttt tccaatctga agctgttagg aacaccacca        120
ccatgaatat tcttgtatgt gttttctggc tctggggtgg agttgctggg tcatggggca        180
ggcacatttt cattttact tcagtaaaaa atgtcyagkg ggccagccac tgtgcctggc        240
ccaratgact tcttcacaag gagacacata ctgtgtgtat cagtcaggat ccaaccagga       300
gacaaaccac acagtaattt aaacagcgat tgtttaatat acagaattgt taactatgat       360
aggggatttg agtaagagga actggttact aagaaataaa gagaatgcta acgaatgtag       420
aaatagactg ggcacaatgg ctcacacctg taatcccagc actttgggag gcaaggcagg       480
tggatcacga ggtcaagaga tcgagaccat cctggccaac atggtgaaac cccgtcccta       540
ctacaaaaag tagctgggcg tggtggcgtg tgcctgtagt cccagctact caaggaggct       600
gaggcaggag aatagtttga acccaggagg cagaggttgc ggtganccga gatcttgcca       660
ctgcactcca gcctgggtga cagagagaga ctccatctca aaaaaaaaaa aaaaaaaaa       720 actcgagggg gggcccggta nccaattc                                          748
```

```
<210> SEQ ID NO 56
<211> LENGTH: 4202
<212> TYPE: DNA
<213> ORGANISM: Homo sapiens
<220> FEATURE:
<221> NAME/KEY: SITE
<222> LOCATION: (57)
<223> OTHER INFORMATION: n equals a,t,g, or c
<221> NAME/KEY: SITE
<222> LOCATION: (58)
<223> OTHER INFORMATION: n equals a,t,g, or c
<221> NAME/KEY: SITE
<222> LOCATION: (61)
<223> OTHER INFORMATION: n equals a,t,g, or c
<221> NAME/KEY: SITE
<222> LOCATION: (4137)
<223> OTHER INFORMATION: n equals a,t,g, or c

<400> SEQUENCE: 56
accagctcaa agattcatga gtttcatcga gtcactgtga gtggagccca tgctggnntg      60
ntgccctctg tgtctgtgca tgcgcgtgtg tgtgtgggcg tgtgtgcatt gctgggccag     120
cttgaaggga aggcccgtca tgtccctgca ctctgttttg caagatgcca accccagtt     180
ctgatgggc tccaacagcc aggctgtggt cctttgacgt tcctcacctg ttgccaacct     240
atcccgtagt gaactgaaac cccaatgaag acagaactgt gcctgggag atgcaatgag     300
gtgagggctg aactcatcct tttatatttc ttttcaagat tggatcagag ctcatctcca     360
tccagtcttg tttctatgaa ggcttcaatc tgtttccatg caaatttgct aatcagagcc     420
cagagctgct gggtccctca tctccctcat ctattataga ttgacttaca gcagggagag     480
aatctcttta gctcattcct aatggggttg ggatcacaat atggtctggt ccaatctgca     540
tcttgttgtg tcccaagacc ctatctcctc cccaacattc ttattgcctt tggctcccag     600
taaggaacga attgggggcc agggaggaga acagggggga tcaagaaggg aaacccaatt     660
cccccttga aagtgggttc tttgaactat gtgtttgggg gaagttcctc tggatactaa     720
tttgaattta tacctcat gttttggggg tttgacgtat atatatat atatatat     780
atgcatatat atttcataat atttggaagg tttttgatgc tagaaaaatg gaaacaagag     840
aaccttcaaa aatggtactt agatgggaac tggaggccaa tctttcataa agccagcccc     900
atagctgctt gctgttaggc ctccagccat tttgacattg gggtggatag tcgattcacc     960
tgcctgtcag tcgattcacc tgcctgtcac ccagttctgt ggatgtgctg gtgctgagcc    1020
tttgctctct ttccaaatgg ttacagggat gttgatcagc tccaccagag ggagctctga    1080
tgggaggaat tgctctgcca tccttgtccc tgtgtctcct gtcggcaggc agccattgta    1140
tctcaccagc agaccaggag actggtccca aggttactgc accacagggc aatttcctgc    1200
catagttagg aaggaaacac ctgaactaaa tggaagagac atccctgcgg tgtttaatat    1260
cacacccatg cccttttgtca ggttaccatg tacagagatt acttggagag cctcatgccg    1320
tctctacctt cgcacactgg tcaagtatct gctgagcttc ttggccgcaa ggatgcagaa    1380
ataggctgag ggtccatggg aagaaagaca caatgaggca gtaggaggtg gggaagaaaa    1440
gaagacagac tttcaaaatg gaattaggca ctggggagag atcagtttcc ccacatcagg    1500
gagaagaagg tataggtggg gaaggggggtg gccaggagca aaggaagaa gactcaagat    1560
ggaaagggag ccgctgtgcc tgtggcaata ccacttggag aggtcgactt cataccttca    1620
agccttttcc cctgggcttt tgattgtgtc tgtgcccct ttcttgtcct ctctgcagat    1680
gcccagtagg ggctacctca tcctcgtgct gttcttgtgt ggctttctgg gcagtaggga    1740
tcttgaattt cctttctaac actgtgcccg gcaaggcggg gagcattcct ctgccctttg    1800
```

```
tcttgtgcca acctggaaag gtgcagtcta gatttcagtg agaaccctgc cagctgagcc    1860
ctgtgcatct actaccttga cacagagtgt tttcccacta gaagctctgc tctgctctcc    1920
tggcccaagt aggggattcc atgccttccc tttcatggtc ttagcaccag cagcctagtt    1980
tctcccttcc agagtctcca gggatgacaa attggattgg agacaaacct cgtcagatgc    2040
tcatcccta aaaggttaat tgtgtatttg tggctgcgtg tgcctttgtg ttttcattct    2100
cttcccattt ttgtacattt tggtcttctc tgtggtttta tacttggtca aaagtactcg    2160
tcttggtatt gcactgttgt gtgcatgaga aaactggggg aaggctcact ggtacaagaa    2220
aggaccctg accctttcc ttctctgtgg tccccggcat tagattgggg gttctgggag      2280
aggcaggtga atgtcctaag tgaattgttc tgtttgtaac tggaatgttt ttgaagtctt    2340
tggtgttgct ccgtgaaagg acatcgccac ctggtgctca tgaggtgtct ttgcagaaca    2400
ataaatggca aatgaacaac camaaaattg ttacycttgt tggccttctg ctgtttgtag    2460
attagtgcac ctatctgtga gggatttggg ttacctccct gagtctgtaa gcaaccacaa    2520
gccctgccac tgggtggggg aagtccctcc ccaaccactt aaaaacaaat tttcccacat    2580
attaccccac cccacacatt tgaccctggc tagactttgt ttgcctaaag aacagacca    2640
cattgctggg aaaatgagta agtgaacgtg tgggagaaaa acacttttag aatcacgaat    2700
attcactttt aaaggtctct ttgcctggct gcaatatagt gtgtgtttaa attatttaca    2760
ggctgttgtt tctcaaataa atgtttaata ttaatcattc ccaaactgac aagaacacaa    2820
aaataaaatg caaatacaga gccagctttg tcacccaaat ctgtgtctat ttctgatagt    2880
ccatggaatg tggttttctt ggaagccagg gttggtctcc ccacagaccc caggctaagg    2940
tcaccagtta ggaacccagg acttggaagg cagagctgtg agctcttcca tcagggatct    3000
gactccgcaa aacgacttga tgaatgcaat tggcaaactc ccatgttcgg acttcatatg    3060
catgagccgt tggacagagg gtttcttagt atatacttta atgcatgttt atgtgcaatc    3120
ttgttagtgg gtatacaagt ttgtgaagaa cttctcattt caataggcag ttaatgtaat    3180
gcattaaaag cctgggaatt tggggctata ttttttcctt ctgactcaat aatcttcaaa    3240
gaattcatag gaaagtcagt acttgcagac aagtggttag cttggctaaa atgtacaaaa    3300
cacccagaac ccacaaaaca ctcagaggtt taggagaatg ttttaatgct taagaggcag    3360
gatcaagtga agaggttaca gaaatcagtg tctctggctg ggcagtcaag agagcgggct    3420
caaattctgt gactcacttc tctgtgtctc ggttggaaat gaatgggtat cctggttccc    3480
accttcccac acgctgtgat acttcaaact cctgggtga agggcctctt ctcagcccaa    3540
gatcttgatt gtgaacatta acaaagagaa cagtcatcct ccacagaaga taactcatta    3600
atgacatttg attcagtgaa taaatatatc atttaaaaaa atattgtagg gggatcatga    3660
aagtagtgga ggtaattaca atcaggagag attggtatta aaattgagca aagtcccaac    3720
tctcaccaga tgacaattat gcatcctgct agatgcccca gggctgtcag cctggaactg    3780
aaataaagt gttataagtg gtgctggatg ccttttttcag ttcatttgaa aacatggatt    3840
tgatcatgtc agctcccttt ctgctggaaa aaaagtagt ttgcataatt ggtgttaact    3900
actctgtttt gattctacag agtaagtaat actcaaatgt ggtcttactt taacttcttg    3960
cctttgttac ccccagaacc atgcagacat tgaaatgtgg tgtgcgtgtg tgtgtgtgtg    4020
tgtgtgtgtg tgtgtgttca tataacagga ggacaggaaa ggtaaggacc cagaacaatg    4080
aagacttatt gaaatgtggg gggggtgtgt gtgtgtgtgt gttcatagaa caggagnaca    4140
```

```
ggaaaggtaa tgaccatcca tggaagatga agggggtagta cttagccgga cgcgtgggtc    4200
ga                                                                     4202
```

<210> SEQ ID NO 57
<211> LENGTH: 854
<212> TYPE: DNA
<213> ORGANISM: Homo sapiens
<220> FEATURE:
<221> NAME/KEY: SITE
<222> LOCATION: (831)
<223> OTHER INFORMATION: n equals a,t,g, or c
<221> NAME/KEY: SITE
<222> LOCATION: (839)
<223> OTHER INFORMATION: n equals a,t,g, or c
<221> NAME/KEY: SITE
<222> LOCATION: (844)
<223> OTHER INFORMATION: n equals a,t,g, or c
<221> NAME/KEY: SITE
<222> LOCATION: (851)
<223> OTHER INFORMATION: n equals a,t,g, or c

<400> SEQUENCE: 57

```
cgaaattact cctcactaaa gttgaacaaa agctggagct cgcgcgcctg caggtcgaca     60
ctagtggatc caaagaattc ggcacgagcg ggatcccggc aaaatgcaga ttccccaaaa    120
tttttgtaaa tacagatgac acttatgaag agctccattt aatcgtttat aaggtaacaa    180
ctgttttcct tccagcgtta atgattgtgc tgaagtggat cttcttgca tgtgtacacg     240 agtgcatgtg caaacctctt aaatgtttct tggaaaagat attggaagtt ctgattatgg    300
taaaactcaa aatgggtgtt cttccagcgt aataagttta ttttcagctc cttttaaaca    360
gttctgttat tagtgaaaga ggaactgttt aagattgtga tttataaacg tgtgaagtct    420
cacgtgctct caaaccaaag gctgtcagag gttggtgctg cctgttctcg aaatggctct    480
ggatgggggc cgtagccacg tgtctgtgca tatgctgctt ttgctctgat tttaaagctg    540
taggcttgct aattccataa ggatcgtatt ttgkttctgt caggacatgg tcttgtaagg    600
atatgtactc aggttgtgtt tctaattaaa ggcagttttt gattcaagaa agaagacgga    660
gcatgtgcac gtgtttctcc tctttcctgc ctgaggctgt ggagaagttt tcatttataa    720
aggctcagaa atgatgccgt ggggggamcag gaaggagcgg agaactagtc tcgagagtac    780
ttctagagcg gccgcgggcc catcgatttt ccacccgggt ggggtaccag ntaagtgtng    840
aagnattccc ntta                                                      854
```

<210> SEQ ID NO 58
<211> LENGTH: 1455
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<221> NAME/KEY: SITE
<222> LOCATION: (39)
<223> OTHER INFORMATION: n equals a,t,g, or c
<221> NAME/KEY: SITE
<222> LOCATION: (40)
<223> OTHER INFORMATION: n equals a,t,g, or c

<400> SEQUENCE: 58

```
ggcanagctg ggatggggtc agcacccaga agccagccnn ctctgacagc ttcctctttg     60
gccaagccct gcctctgtac agcctcgagt ggacagccag agggcacgag ggagcccaga    120
gcccaagatg gagccccagc tggggcctga ggctgccgcc ctccgccctg ctggctggc     180
```

```
cctgctgctg tgggtctcag ccctgagctg ttcttttctcc ttgccagctt cttcccttttc    240 ttctctggtg ccccaagtca gaaccagcta caattttgga aggactttcc tcggtcttga    300
taaatgcaat gcctgcatcg ggacatctat ttgcaagaag ttctttaaag aagaaataag    360
atctgacaac tggctggctt cccaccttgg actgcctccc gattccttgc tttcttatcc    420
tgcaaattac tcagatgatt ccaaaatctg gcgccctgtg gagatcttta gactggtcag    480
caaatatcaa aacgagatct cagacaggaa atctgtgcc tctgcatcag ccccaaagac    540
ctgcagcatt gagcgtgtcc tgcggaaaac agagaggttc cagaaatggc tgcaggccaa    600
gcgcctcacg ccggacctgg tgcaggactg tcaccagggc cagagagaac taaagttcct    660
gtgtatgctg agataacacc agtgaaaaag cctggcatgg agcccagcac tgagaacttc    720
cagaaagtgt tagccttctc ccaactgtgt tataccaacc acattttcaa atagtaatca    780
ttaaagaggc ttctgcatca aaccttcaca tgcagctccc atgccacctc cagaattcac    840
caacacacag gcccaccagc aacaggtacc tttgcacaat atttttttgat gacaatccaa    900 agccccggct ctttcccacc acactgtggt cccctagatg gggctgttgc tgagcccacc    960
ccaatcccag atgtgatccc ccctgtgatc tacttcctgg caagattcct ccagtcctgg   1020
acaggtcttc cctatgagat agaacctgat aaggagctag gcaattctg acaacattac   1080 caaaggccca cataacttct aaattttggt ctggtctgaa ggaaaacctg ttcttgccct   1140
agtgatggat gaactctctt atctctggct tctagaggga aaaaaagca tacctctttt   1200 acttttttaag tacctccatc agagtcatga aatcacctgt caagactatc tatcttttat   1260
gtttccattc tggtaagaac tctttaaatg aggacactgc tgattgctgg tgatgttttt   1320
tgagcaaaca ctcgggggta tggatgaaag ccaatcgcag gtcaaatgac tccttgggga   1380
agctacttct cctctattca gatttcacta aaatcttcca agatgaaagc aaaaaaaaaa   1440
aaaaaaaaaa aaaaa                                                    1455

<210> SEQ ID NO 59
<211> LENGTH: 593
<212> TYPE: DNA
<213> ORGANISM: Homo sapiens

<400> SEQUENCE: 59
ccacgcttcc ggagctctta cttctccagc aacgctcttc agtacataat aagcttaact     60
gataaacaga atatttagaa aggtgagact tgggcttacc attgggttta aatcataggg    120
acctagggcg agggttcagg gcttctctgg agcagatatt gtcaagttca tggccttagg    180
tagcatgtat ctggtcttaa ctctgattgt agcaaaagtt ctgagaggag ctgagccctg    240
ttgtggccca ttaaagaaca gggtcctcag gccctgcccg cttcctgtcc actgccccct    300
ccccatcccc agcccagccg agggaatccc gtgggttgct tacctaccta taaggtggtt    360
tataagctgc tgtcctggcc actgcattca aattccaatg tgtacttcat agtgtaaaaa    420
tttatattat tgtgaggttt tttgtctttt ttttttttt tttttttttg gtatattgct    480
gtatctactt taacttccag aaataaacgt tatataggaa ccgacaaaaa aaaaaaaaa    540 aaaaaaaaa aaaaaaaaa aaaaaaaaa aaaaaaaaa aaaaaaaaa aaa               593

<210> SEQ ID NO 60
<211> LENGTH: 496
<212> TYPE: DNA
<213> ORGANISM: Homo sapiens

<400> SEQUENCE: 60
```

```
aattcggctt tcgagcggcc gcccgggcag gtcctgcttt ttgcttataa ttgacaacat      60
gtgcaaaaat accaaatttg tgtcctgtgc agtatgaaga attcagtgaa tattcattaa     120
tgtattagct tgttttgctc tctgttcata tatggctcta ttcttagaaa tataatttga     180
atgtgatctt tcaatagtct gaatatttta caaattatag ctatgtcttg tgaaaataac     240
ctcaaaaaga aaaatacgac tctgttgtct tacttgatat ttcttgccct agtaatgtac     300
ttgacattta tgttcctaag cagtgtaagt accagtagaa tttctctgtc aaactcaatg     360
atcatttagt acttttgtct tctcccatgt gcttgaagga aaaataaagt gtcactaccg     420
tatttcttgt tttcatcaaa aaataaaaat aatttaaaaa aaaaaaaaaa aaaaaaaaa      480 aarrgggsgg cccccc                                                     496

<210> SEQ ID NO 61
<211> LENGTH: 1292
<212> TYPE: DNA
<213> ORGANISM: Homo sapiens
<220> FEATURE:
<221> NAME/KEY: SITE
<222> LOCATION: (71)
<223> OTHER INFORMATION: n equals a,t,g, or c
<221> NAME/KEY: SITE
<222> LOCATION: (697)
<223> OTHER INFORMATION: n equals a,t,g, or c
<221> NAME/KEY: SITE
<222> LOCATION: (1280)
<223> OTHER INFORMATION: n equals a,t,g, or c
<221> NAME/KEY: SITE
<222> LOCATION: (1287)
<223> OTHER INFORMATION: n equals a,t,g, or c
<221> NAME/KEY: SITE
<222> LOCATION: (1291)
<223> OTHER INFORMATION: n equals a,t,g, or c

<400> SEQUENCE: 61
aaacctcttc tataggtaaa gctggtacgc ctgcaggtac cggtccggaa ttcccgggtc      60
gacccacgcg nccggaaaga ggaaacatag aggtgccaaa ggaacaaaga cataatgatg     120
tcatccaagc caacaagcca tgctgaagta atgaaaacca tacccaaccc ttacccacca     180
agcagcttta tggctcctgg atttcaacag cctctgggtt caatcaactt agaaaaccaa     240
gctcagggtg ctcagcgtgc tcagccctac ggcatcacat ctccgggaat ctttgctagc     300
agtcaaccgg gtcaaggaaa tatacaaatg ataaatccaa gtgtgggaac agcagtaatg     360
aactttaaag aagaagcaaa ggcactaggg gtgatccaga tcatggttgg attgatgcac     420
attggttttg gaattgtttt gtgtttaata tccttctctt ttagagaagt attaggtttt     480
gcctctactg ctgktattgg tggatacccg ttctggggtg gcctttcttt tattatctct     540
ggctctctct ctgtgtcagc atccaaggag cttttcccgtt gtctggtgaa aggcagcctg     600
ggaatgaaca ttggtaggtc tatccttggcc ttcattggag tgattctgct gctggtggat     660
atgtgcatca atggggtarc tggccaagac tactggnccg tgctttctgg aaaaggcatt     720
tcagccacgc tgatgatctt ctccytcttg gagttcttcg tagcttgtgc cacagcccat     780
tttgccaacc aagcaaacac cacaaccaat atgtctgtcc tggttattcc aaatatgtat     840
gaaagcaacc ctgkgacacc agcgtcttct tcagctcctc ccagatgcaa caactactca     900
gctaatgccc ctaaaagaaa aagggggtatc agtctaatct catggagaaa aactacttgc     960
aaaaacttct taagaagatg tctttttattg tctacaatga tttctagtct ttaaaaactg    1020
tgtttgagat ttgttttttag gttggtcgct aatgatggct gtatctccct tcactgtctc    1080
```

-continued ttcctacatt accactacta catgctggca aaggtgaagg atcagaggac tgaaaaatga  1140
ttctgcaact ctcttaaagt tagaaatgtt tctgttcata ttacttttc cttaataaaa  1200 tgtcattaga aacaaaaaaa aaaaaaaaaa aaaaaaaaaa aaaaagggc ggccgctcta  1260 gaggatccaa gcttacgtan gcgtgcntgc na  1292

<210> SEQ ID NO 62
<211> LENGTH: 398
<212> TYPE: DNA
<213> ORGANISM: Homo sapiens

<400> SEQUENCE: 62 ccccctggc ccccccatta atgccatggt ttgggaggag cckgatcccc tgaaccccat   60
atttaacctc tactgcccms ggaaatgccc tacattattt ttccctaatt ggaagtataa  120
ttagagtgat gttggtaggg tagaaaaaga gggagtcact tgatgctttc aggttaatca  180
gagctatggg tgctacaggc ttgtctttct aagtgacata ttcttatcta attctcagat  240
caggttttga aagmtwtggg ggtctttta gattttaatc cctactttct ttatggtaca  300
aatatgtaca aagaaaaag gtcttatatt cttttacaca aatttataaa taaattttga  360
actccttctg tttaaaaaaa aaaaaaaaaa aaaaaaa  398

<210> SEQ ID NO 63
<211> LENGTH: 1202
<212> TYPE: DNA
<213> ORGANISM: Homo sapiens
<220> FEATURE:
<221> NAME/KEY: SITE
<222> LOCATION: (282)
<223> OTHER INFORMATION: n equals a,t,g, or c
<221> NAME/KEY: SITE
<222> LOCATION: (596)
<223> OTHER INFORMATION: n equals a,t,g, or c
<221> NAME/KEY: SITE
<222> LOCATION: (607)
<223> OTHER INFORMATION: n equals a,t,g, or c
<221> NAME/KEY: SITE
<222> LOCATION: (1200)
<223> OTHER INFORMATION: n equals a,t,g, or c

<400> SEQUENCE: 63
gaattcggca cgagattaag ttgtgcactt taattgggtg aattgtacat gtragttata   60
tatctractg tagttgtwat taaaaaacaa caggaggcca tgtgggctgc taggagtagc  120
aatgtctgty cccagccagc aggtagagac cagggctgga cagagkagta tgggctgtgc  180
tgcagattat ttgtggtacc caactgttgc ataaaacagg gtgtgatctc ttgcattgct  240
atgcatgagt ggattcccag taattgtgc caggctgcct gnatgatgtg tggcttgtgc  300
tttggatcgt aatgcttacc tatgctactt aagttacata ccctgtggcc tttgtggcca  360
ggactgtggg ctactacctg kagtgattcg ttaggggaaa ggacccacag cctgtgcagg  420
aggaaaaaag catctctgag tacagggtgg atgagctgga tgagctgccg ggcaagagcc  480
acgcacaccc agtggtgag tcttaaggat aaggtggaat ttgccccata gctgtcctgg  540
acagaaactg cccagagaag aatgaatgga ggacataggg ctctgtggtc ccaccnttt  600 ttgggganacc tgtgactggt cctgttacca tgtcaactta gccccaaacc catctctgat  660
tgacttggtt gcttattttg gcacattctt gctccacaca gccacataca tactggctgc  720
tcctcsaagg ccaggcagat gcagcagctg tgggccasc aaagargaar gtcctggaar  780
gttctggcct gaacgctgca tctgttgtgt gacagccaca actgctcagg cttccttgtc  840

| | |
|---|---|
| tgtgggtgca ctgtggggag gagtgttatg ataagaacat tggctctcag tcttccctgg | 900 |
| ggagaagttt ggcctcacgt gggatttggg cgttgccttt aggaaggctc tctgcatgtc | 960 |
| tagttccagt tgtactggg aagaattaaa aaagtctgcc agcttcttta gtttgtcctg | 1020 |
| tcttttgtga tgattctttc tgagatcccc tcctatcagc tcaggagtgg gattttctgg | 1080 |
| agaaggaaag tgttttcct gttcctcact gctcaccttg gggcattcag gaacatgggc | 1140 |
| ctgatgaatt tgcttgaagg cagtctgtaa tcccatcact ttgggagcca agaggcggn | 1200 |
| ca | 1202 |

<210> SEQ ID NO 64
<211> LENGTH: 1517
<212> TYPE: DNA
<213> ORGANISM: Homo sapiens

<400> SEQUENCE: 64

| | |
|---|---|
| gattacgcca actcgaattt aaccctcact aaagggaaca aaagctggag ctccaccgcg | 60 |
| gtggcggccg ctctagaact agtggatccc ccgggctgca ggaattcggc acgagggagc | 120 |
| ccagagccca agatggagcc ccagctgggg cctgaggctg ccgccctccg ccctggctgg | 180 |
| ctggccctgc tgctgtgggt ctcagccctg agctgttctt tctccttgcc agcttcttcc | 240 |
| ctttcttctc tggtgcccca agtcagaacc agctacaatt ttggaaggac tttcctcggt | 300 |
| cttgataaat gcaatgcctg catcgggaca tctatttgca agaagttctt taagaaaga | 360 |
| aataagatct gacaactggc tggcttccca ccttgggact gcctcccgat tcccttgctt | 420 |
| tcttatcctg gcaaattact caggatgatt ccaaaatctg gcgccctgtg gagatcttta | 480 |
| gactggtcag caaatatcaa aacgagatct cagacaggaa aatctgtgcc tctgcatcag | 540 |
| ccccaaagac ctgcagcatt gagcgtgtcc tgcggaaaac agagaggttc cagaaatggc | 600 |
| tgcaggccaa gcgcctcacg ccggacctgg tgcaggactg tcaccagggc cagagagaac | 660 |
| taaagttcct gtgtatgctg gagataacac cagtgaaaaa gccttggcat ggagccccag | 720 |
| cactgagaac ttccagaaag tgttagcctt ctcccaactg tgttatacca accacatttt | 780 |
| caaatagtaa tcattaaaga ggcttctgca tcaaaccttc acatgcagct cccatgccac | 840 |
| cctccagaat tcaccaacac acaggcccac cagcaacagg cttaccttt gcacaatatt | 900 |
| ttttgatgac aatccaaagc cccggctctt tcccaccaca ctgtggtccc ctagatgggg | 960 |
| ctgttgctga gcccacccca atcccagatg tgatcccct gtgatctact ctgggccaa | 1020 |
| gattctccag tctggacagg tcttcccta tgagatagaa cctgataagg agctagggca | 1080 |
| attctgacaa cattaccaaa ggcccacata acttctaaat tttggtctgg tctgaaggaa | 1140 |
| aacctgttct tgccctagtg atggatgaac tctcttatct ctggcttcta gagggaaaaa | 1200 |
| aaagcatacc tcttttactt tttaagtacc tccatcagag tcatgaaatc acctgtcaag | 1260 |
| actatctatc ttttatgttt ccattctggt aagaactctt taaatgagga cactgctgat | 1320 |
| tgctggtgat gtttttgag caaacactcg ggggtatgga tgaaagccaa tcgcaggtca | 1380 |
| aatgactcct tggggaagct acttctcctc tattcagatt tcactaaaat cttccaagat | 1440 |
| gaaagcaaaa aaaaaaaaaa aaaaaaaaaa actcgagggg gggcccgtac ccaattcgcc | 1500 |
| ctatagtgag tcgtatt | 1517 |

<210> SEQ ID NO 65
<211> LENGTH: 526
<212> TYPE: DNA
<213> ORGANISM: Homo sapiens
<220> FEATURE:
<221> NAME/KEY: SITE
<222> LOCATION: (66)
<223> OTHER INFORMATION: n equals a,t,g, or c
<221> NAME/KEY: SITE
<222> LOCATION: (106)
<223> OTHER INFORMATION: n equals a,t,g, or c
<221> NAME/KEY: SITE
<222> LOCATION: (484)
<223> OTHER INFORMATION: n equals a,t,g, or c

<400> SEQUENCE: 65

```
ctctgacagc ttcctctttg gccaagccct gcctctgtac agcctcgagt ggacagccag      60
aggtcnagac tggagcccag agcccaagat ggagcccag ctgggncctg aggctgccgc     120
cctccgccct ggctggctgg ccctgctgct gtgggtctca gccctgagct gttctttctc     180
cttgccagct tcttcccttt cttctctggt gccccaagtc agaaccagct acaattttgg     240
aaggactttc ctcggtcttg ataaatgcaa tgcctgcatc gggacatcta tttgcaagaa     300
gttcttttaaa gaagaaataa gatctgacaa ctggctggct tcccaccttg ggactgcctc    360
ccgattccct ttgstttctt atccttgcaa attactccar atgattycca aaatctggsg     420
sccttgtgga ratctttttaa ctggtcagca awtwtcaaac gaaatctcca aacaggaaat    480
cttntgcctc ctgcatccac ccccaaagaa cttgcacatt gacgtt                    526
```

<210> SEQ ID NO 66
<211> LENGTH: 664
<212> TYPE: DNA
<213> ORGANISM: Homo sapiens
<220> FEATURE:
<221> NAME/KEY: SITE
<222> LOCATION: (31)
<223> OTHER INFORMATION: n equals a,t,g, or c
<221> NAME/KEY: SITE
<222> LOCATION: (63)
<223> OTHER INFORMATION: n equals a,t,g, or c

<400> SEQUENCE: 66

```
caggctctca atacggactc actcataggg naaagctggt acgcctgcag gtaccggtcc      60
ggnaattccc gggtcgaccc acgcgtcgcr gagctcttac ttctccagca acrctcttca     120
gtacataata agcttaactg ataaacagaa tatttagaaa ggtgagactt gggcttacca     180
ttgggtttaa atcataggga cctagggcga gggttcaggg cttctctgga gcagatattg     240
tcaagttcat ggcctaggt agcatgtatc tggtcttaac tctgattgta gcaaaagttc     300
tgagaggagc tgagccctgt tgtggcccat aaagaacag ggtcctcagg ccctgcccgc      360
ttcctgtcca ctgcccccctc cccatcccca gcccagccga gggaatcccg tgggttgctt    420
acctacctat aaggtggttt ataagctgct gtcctggcca ctgcattcaa attccaatgt     480
gtacttcata gtgtaaaaat ttatattatt gtgaggtttt ttgtcttttt ttttttttt     540
tttttggta tattgctgta tctactttaa cttccagaaa taaacgttat atrggaaaaa      600
aaaaaaaaa aaaaaaaaa aaaaaaaaa aaaaaaaaa aaaaaaaaa aaaaaaaaa           660
aaaa                                                                 664
```

<210> SEQ ID NO 67
<211> LENGTH: 156
<212> TYPE: PRT
<213> ORGANISM: Homo sapiens
<220> FEATURE:
<221> NAME/KEY: SITE
<222> LOCATION: (156)
<223> OTHER INFORMATION: Xaa equals stop translation -continued

```
<400> SEQUENCE: 67

Met Arg Leu Trp Lys Ala Val Val Thr Leu Ala Phe Met Ser Val
 1               5                  10                  15

Asp Ile Cys Val Thr Thr Ala Ile Tyr Val Phe Ser His Leu Asp Arg
                20                  25                  30

Ser Leu Leu Glu Asp Ile Arg His Phe Asn Ile Phe Asp Ser Val Leu
             35                  40                  45

Asp Leu Trp Ala Ala Cys Leu Tyr Arg Ser Cys Leu Leu Gly Ser
         50                  55                  60

His His Trp Cys Gly Gln Glu Gln Cys Ala Gly Ala Pro Ala Ala
 65                  70                  75                  80

Gly Leu Val Ala Gly His His Pro Arg Val Pro Leu Arg Gly His Leu
                 85                  90                  95

Cys His Gly Glu Ala Ala Leu Leu Arg Gly Ala Gln Ala His Pro
                100                 105                 110

Gly Pro Leu Val Leu Gly Pro Val Arg Val Asp Val His Phe Thr Arg
                115                 120                 125

Arg Ile Leu Pro Ala Leu Val Ala Val His Arg Ala Ala Arg His
                130                 135                 140

Pro Gly Pro Gly Ala Arg Gly Gly His Arg Gly Xaa
145                 150                 155

<210> SEQ ID NO 68
<211> LENGTH: 70
<212> TYPE: PRT
<213> ORGANISM: Homo sapiens
<220> FEATURE:
<221> NAME/KEY: SITE
<222> LOCATION: (70)
<223> OTHER INFORMATION: Xaa equals stop translation

<400> SEQUENCE: 68

Met Ala Ala Arg His Leu Pro Gly Phe His Thr Tyr Thr Asn Leu Leu
 1               5                  10                  15

Phe Leu Leu Leu Pro Ser Leu Leu Met Gly Tyr Ser Glu Ser Pro Pro
                20                  25                  30

Pro Ile Thr Asp Ser Trp Ala Pro Phe Ile Ser Leu Thr His His Val
             35                  40                  45

Leu Ser Gln Ser Gln Ser Pro Leu Ser Ser Asn Cys Trp Ile Cys Leu
         50                  55                  60

Ser Thr His Thr Gln Xaa
 65                  70

<210> SEQ ID NO 69
<211> LENGTH: 502
<212> TYPE: PRT
<213> ORGANISM: Homo sapiens
<220> FEATURE:
<221> NAME/KEY: SITE
<222> LOCATION: (502)
<223> OTHER INFORMATION: Xaa equals stop translation

<400> SEQUENCE: 69

Met Trp Lys Leu Trp Arg Ala Glu Glu Gly Ala Ala Leu Gly Gly
 1               5                  10                  15

Ala Leu Phe Leu Leu Leu Phe Ala Leu Gly Val Arg Gln Leu Leu Lys
                20                  25                  30

Gln Arg Arg Pro Met Gly Phe Pro Pro Gly Pro Pro Gly Leu Pro Phe
```

```
              35                  40                  45
Ile Gly Asn Ile Tyr Ser Leu Ala Ala Ser Ser Glu Leu Pro His Val
             50                  55                  60

Tyr Met Arg Lys Gln Ser Gln Val Tyr Gly Ile Phe Ser Leu Asp
 65                  70                  75                  80

Leu Gly Gly Ile Ser Thr Val Val Leu Asn Gly Tyr Asp Val Lys
                 85                  90                  95

Glu Cys Leu Val His Gln Ser Glu Ile Phe Ala Asp Arg Pro Cys Leu
                100                 105                 110

Pro Leu Phe Met Lys Met Thr Lys Met Gly Gly Leu Leu Asn Ser Arg
                115                 120                 125

Tyr Gly Arg Gly Trp Val Asp His Arg Arg Leu Ala Val Asn Ser Phe
130                 135                 140

Arg Tyr Phe Gly Tyr Gly Gln Lys Ser Phe Glu Ser Lys Ile Leu Glu
145                 150                 155                 160

Glu Thr Lys Phe Phe Asn Asp Ala Ile Glu Thr Tyr Lys Gly Arg Pro
                165                 170                 175

Phe Asp Phe Lys Gln Leu Ile Thr Asn Ala Val Ser Asn Ile Thr Asn
                180                 185                 190

Leu Ile Ile Phe Gly Glu Arg Phe Thr Tyr Glu Asp Thr Asp Phe Gln
                195                 200                 205

His Met Ile Glu Leu Phe Ser Glu Asn Val Glu Leu Ala Ala Ser Ala
                210                 215                 220

Ser Val Phe Leu Tyr Asn Ala Phe Pro Trp Ile Gly Ile Leu Pro Phe
225                 230                 235                 240

Gly Lys His Gln Gln Leu Phe Arg Asn Ala Ala Val Val Tyr Asp Phe
                245                 250                 255

Leu Ser Arg Leu Ile Glu Lys Ala Ser Val Asn Arg Lys Pro Gln Leu
                260                 265                 270

Pro Gln His Phe Val Asp Ala Tyr Leu Asp Glu Met Asp Gln Gly Lys
                275                 280                 285

Asn Asp Pro Ser Ser Thr Phe Ser Lys Glu Asn Leu Ile Phe Ser Val
290                 295                 300

Gly Glu Leu Ile Ile Ala Gly Thr Glu Thr Thr Thr Asn Val Leu Arg
305                 310                 315                 320

Trp Ala Ile Leu Phe Met Ala Leu Tyr Pro Asn Ile Gln Gly Gln Val
                325                 330                 335

Gln Lys Glu Ile Asp Leu Ile Met Gly Pro Asn Gly Lys Pro Ser Trp
                340                 345                 350

Asp Asp Lys Cys Lys Met Pro Tyr Thr Glu Ala Val Leu His Glu Val
                355                 360                 365

Leu Arg Phe Cys Asn Ile Val Pro Leu Gly Ile Phe His Ala Thr Ser
370                 375                 380

Glu Asp Ala Val Val Arg Gly Tyr Ser Ile Pro Lys Gly Thr Thr Val
385                 390                 395                 400

Ile Thr Asn Leu Tyr Ser Val His Phe Asp Glu Lys Tyr Trp Arg Asp
                405                 410                 415

Pro Glu Val Phe His Pro Glu Arg Phe Leu Asp Ser Ser Gly Tyr Phe
                420                 425                 430

Ala Lys Lys Glu Ala Leu Val Pro Phe Ser Leu Gly Arg Arg His Cys
                435                 440                 445

Leu Gly Glu His Leu Ala Arg Met Glu Met Phe Leu Phe Phe Thr Ala
450                 455                 460
```

```
Leu Leu Gln Arg Phe His Leu His Phe Pro His Glu Leu Val Pro Asp
465                 470                 475                 480

Leu Lys Pro Arg Leu Gly Met Thr Leu Gln Pro Gln Pro Tyr Leu Ile
            485                 490                 495

Cys Ala Glu Arg Arg Xaa
            500
```

<210> SEQ ID NO 70
<211> LENGTH: 189
<212> TYPE: PRT
<213> ORGANISM: Homo sapiens
<220> FEATURE:
<221> NAME/KEY: SITE
<222> LOCATION: (85)
<223> OTHER INFORMATION: Xaa equals any of the naturally occurring
      L-amino acids
<221> NAME/KEY: SITE
<222> LOCATION: (104)
<223> OTHER INFORMATION: Xaa equals any of the naturally occurring
      L-amino acids
<221> NAME/KEY: SITE
<222> LOCATION: (164)
<223> OTHER INFORMATION: Xaa equals any of the naturally occurring
      L-amino acids
<221> NAME/KEY: SITE
<222> LOCATION: (189)
<223> OTHER INFORMATION: Xaa equals stop translation

<400> SEQUENCE: 70

```
Met Arg Pro Ala Phe Ala Leu Cys Leu Leu Trp Gln Ala Leu Trp Pro
1               5                   10                  15

Gly Pro Gly Gly Gly Glu His Pro Thr Ala Asp Arg Ala Gly Cys Ser
                20                  25                  30

Ala Ser Gly Ala Cys Tyr Ser Leu His His Ala Thr Met Lys Arg Gln
            35                  40                  45

Ala Ala Glu Glu Ala Cys Ile Leu Arg Gly Gly Ala Leu Ser Thr Val
        50                  55                  60

Arg Ala Gly Ala Glu Leu Arg Ala Val Leu Ala Leu Leu Arg Ala Gly
65                  70                  75                  80

Pro Gly Pro Gly Xaa Gly Ser Lys Asp Leu Leu Phe Trp Val Ala Leu
                85                  90                  95

Glu Arg Arg Arg Ser His Cys Xaa Leu Glu Asn Glu Pro Leu Arg Gly
                100                 105                 110

Phe Ser Trp Leu Ser Ser Asp Pro Gly Gly Leu Glu Ser Asp Thr Leu
            115                 120                 125

Gln Trp Val Glu Glu Pro Gln Arg Ser Cys Thr Ala Arg Arg Trp Val
130                 135                 140

Leu Pro Gly His Arg Trp Gly Arg Ala Arg Ser Trp Lys Glu Met Arg
145                 150                 155                 160

Cys His Leu Xaa Ala Asn Ala Thr Cys Ala Ser Thr Ser Leu Arg Ser
                165                 170                 175

Cys Val Leu Arg Arg Ala Pro Gly Pro Pro Leu Thr Xaa
            180                 185
```

<210> SEQ ID NO 71
<211> LENGTH: 486
<212> TYPE: PRT
<213> ORGANISM: Homo sapiens

<400> SEQUENCE: 71

```
Met Gln Pro Ser Gly Leu Glu Gly Pro Gly Thr Phe Gly Arg Trp Pro
```

-continued

```
  1                   5                  10                  15
Leu Leu Ser Leu Leu Leu Leu Leu Leu Leu Gln Pro Val Thr Cys
             20                  25                  30

Ala Tyr Thr Thr Pro Gly Pro Arg Ala Leu Thr Thr Leu Gly Ala
             35                  40                  45

Pro Arg Ala His Thr Met Pro Gly Thr Tyr Ala Pro Ser Thr Thr Leu
     50                  55                  60

Ser Ser Pro Ser Thr Gln Gly Leu Gln Glu Gln Ala Arg Ala Leu Met
 65                  70                  75                  80

Arg Asp Phe Pro Leu Val Asp Gly His Asn Asp Leu Pro Leu Val Leu
             85                  90                  95

Arg Gln Val Tyr Gln Lys Gly Leu Gln Asp Val Asn Leu Arg Asn Phe
            100                 105                 110

Ser Tyr Gly Gln Thr Ser Leu Asp Arg Leu Arg Asp Gly Leu Val Gly
            115                 120                 125

Ala Gln Phe Trp Ser Ala Tyr Val Pro Cys Gln Thr Gln Asp Arg Asp
    130                 135                 140

Ala Leu Arg Leu Thr Leu Glu Gln Ile Asp Leu Ile Arg Arg Met Cys
145                 150                 155                 160

Ala Ser Tyr Ser Glu Leu Glu Leu Val Thr Ser Ala Lys Ala Leu Asn
            165                 170                 175

Asp Thr Gln Lys Leu Ala Cys Leu Ile Gly Val Glu Gly His Ser
            180                 185                 190

Leu Asp Asn Ser Leu Ser Ile Leu Arg Thr Phe Tyr Met Leu Gly Val
            195                 200                 205

Arg Tyr Leu Thr Leu Thr His Thr Cys Asn Thr Pro Trp Ala Glu Ser
    210                 215                 220

Ser Ala Lys Gly Val His Ser Phe Tyr Asn Asn Ile Ser Gly Leu Thr
225                 230                 235                 240

Asp Phe Gly Glu Lys Val Val Ala Glu Met Asn Arg Leu Gly Met Met
            245                 250                 255

Val Asp Leu Ser His Val Ser Asp Ala Val Ala Arg Arg Ala Leu Glu
            260                 265                 270

Val Ser Gln Ala Pro Val Ile Phe Ser His Ser Ala Ala Arg Gly Val
            275                 280                 285

Cys Asn Ser Ala Arg Asn Val Pro Asp Asp Ile Leu Gln Leu Leu Lys
    290                 295                 300

Lys Asn Gly Gly Val Val Met Val Ser Leu Ser Met Gly Val Ile Gln
305                 310                 315                 320

Cys Asn Pro Ser Ala Asn Val Ser Thr Val Ala Asp His Phe Asp His
            325                 330                 335

Ile Lys Ala Val Ile Gly Ser Lys Phe Ile Gly Ile Gly Gly Asp Tyr
            340                 345                 350

Asp Gly Ala Gly Lys Phe Pro Gln Gly Leu Glu Asp Val Ser Thr Tyr
    355                 360                 365

Pro Val Leu Ile Glu Glu Leu Leu Ser Arg Gly Trp Ser Glu Glu Glu
    370                 375                 380

Leu Gln Gly Val Leu Arg Gly Asn Leu Leu Arg Val Phe Arg Gln Val
385                 390                 395                 400

Glu Lys Val Gln Glu Glu Asn Lys Trp Gln Ser Pro Leu Glu Asp Lys
            405                 410                 415

Phe Pro Asp Glu Gln Leu Ser Ser Ser Cys His Ser Asp Leu Ser Arg
            420                 425                 430
```

```
Leu Arg Gln Arg Gln Ser Leu Thr Ser Gly Gln Glu Leu Thr Glu Ile
        435                 440                 445

Pro Ile His Trp Thr Ala Lys Leu Pro Ala Lys Trp Ser Val Ser Glu
    450                 455                 460

Ser Ser Pro His Met Ala Pro Val Leu Ala Val Val Ala Thr Phe Pro
465                 470                 475                 480

Val Leu Ile Leu Trp Leu
                485
```

<210> SEQ ID NO 72
<211> LENGTH: 88
<212> TYPE: PRT
<213> ORGANISM: Homo sapiens
<220> FEATURE:
<221> NAME/KEY: SITE
<222> LOCATION: (88)
<223> OTHER INFORMATION: Xaa equals stop translation

<400> SEQUENCE: 72

```
Met Val Ala Ser Gly Trp Leu Leu Ala Gln Ala Ser Phe Leu Pro
  1               5                  10                  15

Leu Ala Pro Pro Gly Ala Leu Gly Ala Gly Cys Trp Met Asp Gly Arg
                 20                  25                  30

Pro Leu Ala Pro Pro Gly Ala Leu Gly Ala Gly Cys Trp Met Gly Gly
            35                  40                  45

Arg Pro Leu Ala Pro Pro Gly Ala Leu Gly Ala Gly Cys Trp Met Gly
        50                  55                  60

Gly Arg His Gly Ala Pro Leu Leu Gly Cys Leu Cys Pro Ser Gly Leu
 65                  70                  75                  80

Cys Ser Ser Tyr Val Cys Leu Xaa
                85
```

<210> SEQ ID NO 73
<211> LENGTH: 299
<212> TYPE: PRT
<213> ORGANISM: Homo sapiens
<220> FEATURE:
<221> NAME/KEY: SITE
<222> LOCATION: (167)
<223> OTHER INFORMATION: Xaa equals any of the naturally occurring
      L-amino acids

<400> SEQUENCE: 73

```
Met Met Ser Ser Lys Pro Thr Ser His Ala Glu Val Asn Glu Thr Ile
  1               5                  10                  15

Pro Asn Pro Tyr Pro Pro Ser Ser Phe Met Ala Pro Gly Phe Gln Gln
                 20                  25                  30

Pro Leu Gly Ser Ile Asn Leu Glu Asn Gln Ala Gln Gly Ala Gln Arg
            35                  40                  45

Ala Gln Pro Tyr Gly Ile Thr Ser Pro Gly Ile Phe Ala Ser Ser Gln
        50                  55                  60

Pro Gly Gln Gly Asn Ile Gln Met Ile Asn Pro Ser Val Gly Thr Ala
 65                  70                  75                  80

Val Met Asn Phe Lys Glu Glu Ala Lys Ala Leu Gly Val Ile Gln Ile
                 85                  90                  95

Met Val Gly Leu Met His Ile Gly Phe Gly Ile Val Leu Cys Leu Ile
                100                 105                 110

Ser Phe Ser Phe Arg Glu Val Leu Gly Phe Ala Ser Thr Ala Val Ile
            115                 120                 125
```

```
Gly Gly Tyr Pro Phe Trp Gly Gly Leu Ser Phe Ile Ile Ser Gly Ser
    130                 135                 140

Leu Ser Val Ser Ala Ser Lys Glu Leu Ser Arg Cys Leu Val Lys Gly
145                 150                 155                 160

Ser Leu Gly Met Asn Ile Xaa Ser Ser Ile Leu Ala Phe Ile Gly Val
                165                 170                 175

Ile Leu Leu Leu Val Asp Met Cys Ile Asn Gly Val Ala Gly Gln Asp
                180                 185                 190

Tyr Trp Ala Val Leu Ser Gly Lys Gly Ile Ser Ala Thr Leu Met Ile
            195                 200                 205

Phe Ser Leu Leu Glu Phe Phe Val Ala Cys Ala Thr Ala His Phe Ala
210                 215                 220

Asn Gln Ala Asn Thr Thr Thr Asn Met Ser Val Leu Val Ile Pro Asn
225                 230                 235                 240

Met Tyr Glu Ser Asn Pro Val Thr Pro Ala Ser Ser Ala Pro Pro
                245                 250                 255

Arg Cys Asn Asn Tyr Ser Ala Asn Ala Pro Lys Arg Lys Arg Gly Ile
                260                 265                 270

Ser Leu Ile Ser Trp Arg Lys Thr Thr Cys Lys Asn Phe Leu Arg Arg
            275                 280                 285

Cys Leu Leu Leu Ser Thr Met Ile Ser Ser Leu
    290                 295
```

<210> SEQ ID NO 74
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 74

```
Met Ala Leu His Pro Gly Ser Ser His Leu Leu Val Ala Val Pro Val
 1               5                  10                  15

Ser Trp Phe Leu Phe Cys Ile Pro Gly Ile Ser Phe Ile Thr Leu Ser
                20                  25                  30

Trp Ser Tyr Gln Glu Ser Pro Val Ser Phe Leu Ser Val Glu Gly Xaa
            35                  40                  45
```

<210> SEQ ID NO 75
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 75

```
Met Tyr Ser Leu Phe Leu Thr Cys Ile Phe Pro Phe Thr Leu Cys His
 1               5                  10                  15

Lys Lys Ile Leu Met Val Ile His Asp Phe Thr Gly Pro Val His Val
                20                  25                  30

Phe Pro Glu Lys Thr Val Leu Glu Trp Asn Tyr Xaa
            35                  40
```

<210> SEQ ID NO 76
<211> LENGTH: 140

```
<212> TYPE: PRT
<213> ORGANISM: Homo sapiens

<400> SEQUENCE: 76

Met Cys Ala Met Tyr Leu Met Ile Lys Ala Phe Leu Pro Lys Met Leu
  1               5                  10                  15

Ala Gln Lys Ser Gly Asn Ile Ile Asn Met Ser Ser Val Ala Ser Ser
             20                  25                  30

Val Lys Gly Val Val Asn Arg Cys Val Tyr Ser Thr Thr Lys Ala Ala
         35                  40                  45

Val Ile Gly Leu Thr Lys Ser Val Ala Ala Asp Phe Ile Gln Gln Gly
     50                  55                  60

Ile Arg Cys Asn Cys Val Cys Pro Gly Thr Val Asp Thr Pro Ser Leu
 65                  70                  75                  80

Gln Glu Arg Ile Gln Ala Arg Gly Asn Pro Glu Glu Ala Arg Asn Asp
                 85                  90                  95

Phe Leu Lys Arg Gln Lys Thr Gly Arg Phe Ala Thr Ala Glu Glu Ile
            100                 105                 110

Ala Met Leu Cys Val Tyr Leu Ala Ser Asp Glu Ser Ala Tyr Val Thr
        115                 120                 125

Gly Asn Pro Val Ile Ile Asp Gly Gly Trp Ser Leu
    130                 135                 140

<210> SEQ ID NO 77
<211> LENGTH: 153
<212> TYPE: PRT
<213> ORGANISM: Homo sapiens
<220> FEATURE:
<221> NAME/KEY: SITE
<222> LOCATION: (153)
<223> OTHER INFORMATION: Xaa equals stop translation

<400> SEQUENCE: 77

Met Leu Val Val Cys Leu Leu Ala Thr Gly Phe Cys Leu Phe Arg
  1               5                  10                  15

Gly Leu Ile Ala Leu Asp Cys Pro Ser Glu Leu Cys Arg Leu Tyr Thr
             20                  25                  30

Gln Phe Gln Glu Pro Tyr Leu Lys Asp Pro Ala Ala Tyr Pro Lys Ile
         35                  40                  45

Gln Met Leu Ala Tyr Met Phe Tyr Ser Val Pro Tyr Phe Val Thr Ala
     50                  55                  60

Leu Tyr Gly Leu Val Val Pro Gly Cys Ser Trp Met Pro Asp Ile Thr
 65                  70                  75                  80

Leu Ile His Ala Gly Gly Leu Ala Gln Ala Gln Phe Ser His Ile Gly
                 85                  90                  95

Ala Ser Leu His Ala Arg Thr Ala Tyr Val Tyr Arg Val Pro Glu Glu
            100                 105                 110

Ala Lys Ile Leu Phe Leu Ala Leu Asn Ile Ala Tyr Gly Val Leu Pro
        115                 120                 125

Gln Leu Leu Ala Tyr Arg Cys Ile Tyr Lys Pro Glu Phe Phe Ile Lys
    130                 135                 140

Thr Lys Ala Glu Glu Lys Val Glu Xaa
145                 150

<210> SEQ ID NO 78
<211> LENGTH: 180
<212> TYPE: PRT
<213> ORGANISM: Homo sapiens
```

```
<220> FEATURE:
<221> NAME/KEY: SITE
<222> LOCATION: (48)
<223> OTHER INFORMATION: Xaa equals any of the naturally occurring
      L-amino acids
<221> NAME/KEY: SITE
<222> LOCATION: (180)
<223> OTHER INFORMATION: Xaa equals stop translation

<400> SEQUENCE: 78

Met Ala Ala Ser Ala Gly Ala Thr Arg Leu Leu Leu Leu Leu
 1               5                  10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Xaa
            35                  40                  45

Pro Val Ser Ser Ala Ile Pro Arg Arg Val Cys Trp Ser Leu Leu Ser
        50                  55                  60

Pro Arg Pro Thr Arg Pro Pro Gly Pro Ala Pro Cys Pro Leu Pro Ser
65                  70                  75                  80

Ala Gly Arg Gly Ala Ala Gly Leu Gly Pro Leu Ala Gln Gln Pro Val
                85                  90                  95

Ser Pro Ala Pro Ala Ser Pro Met Ala Pro Cys Ser Pro Arg Gly Phe
            100                 105                 110

Pro Pro Ala His Gly Val Glu Pro Glu Ile Leu Ala Thr Met Pro Val
        115                 120                 125

Leu Thr Ser His Pro Pro Thr Pro Ser Pro Cys Ser Leu Gly Thr Cys
130                 135                 140

Arg Leu Leu Ser Ser Leu Cys Ala Phe Val Pro Gly Gly Leu Thr Leu
145                 150                 155                 160

Leu Ser Leu Ala Gly Leu Gly Gly Pro Val Gln Ala Pro Ala Ala Pro
                165                 170                 175

Pro Ser Leu Xaa
            180

<210> SEQ ID NO 79
<211> LENGTH: 70
<212> TYPE: PRT
<213> ORGANISM: Homo sapiens
<220> FEATURE:
<221> NAME/KEY: SITE
<222> LOCATION: (70)
<223> OTHER INFORMATION: Xaa equals stop translation

<400> SEQUENCE: 79

Met Leu Met Gly Ser Ile Leu Tyr Val Leu Phe Cys Val Trp Leu Leu
 1               5                  10                  15

Gln Cys Ile Phe Glu Ile Tyr Pro His Cys Cys Val Tyr Pro Lys Cys
                20                  25                  30

Val Leu Phe His Cys Gln Ile Met Phe Cys Tyr Met Asn Ile Leu Gln
            35                  40                  45

Asn Ile Cys Leu Phe Ile Tyr Trp Trp Ile Phe Ala Phe Val Pro Val
        50                  55                  60

Trp Gly Tyr Tyr Glu Xaa
65                  70

<210> SEQ ID NO 80
<211> LENGTH: 191
<212> TYPE: PRT
<213> ORGANISM: Homo sapiens
```

```
<220> FEATURE:
<221> NAME/KEY: SITE
<222> LOCATION: (191)
<223> OTHER INFORMATION: Xaa equals stop translation

<400> SEQUENCE: 80
```

Met Arg Ala Cys Pro Trp Ala Gln Val Pro Leu Tyr Leu Leu Leu Asp
 1               5                  10                  15

Gly His Leu Ala Val Ser Gln Ala Gly Val Met Ala Gly Val Ser Gly
                20                  25                  30

Gly Arg Gly Gly Arg Arg Leu Arg Gly Pro Ile Thr Ser Arg Val Ile
            35                  40                  45

Thr Ser Cys Gln Gln Pro Gly Val Gly Val Trp Val Ser Leu Arg Pro
    50                  55                  60

Glu Leu Leu Asn Leu Glu Ser Leu Gly Val Ala Ala Lys Gly Val Tyr
65                  70                  75                  80

Asp Lys His Val Ser Leu Asp Ile Ser Gly Glu Arg Ser Gly Ala Leu
                85                  90                  95

Val Thr Phe Ser Lys Gly Cys Trp Ala Ser Glu Gln Ser Pro Pro Met
            100                 105                 110

Ser Gln Pro Leu Gln Gly Pro Ser Leu Ser Leu His Pro Arg Pro Ser
        115                 120                 125

Ala Ala Leu Val Met Ser Arg Arg Lys Val Leu Gly Cys Ala Gln Ser
    130                 135                 140

Gln Glu Ser Lys Ile Cys Gln Lys Ala Pro Gly Lys Ser Arg Arg
145                 150                 155                 160

Ser Leu Gly Trp Pro Pro Gly Cys Gly Ala Ala Arg Ala Lys Thr Val
                165                 170                 175

Asn Thr Ala Leu Gln Leu Ser Glu Pro Gln Phe Ser Asn Leu Xaa
            180                 185                 190

```
<210> SEQ ID NO 81
<211> LENGTH: 166
<212> TYPE: PRT
<213> ORGANISM: Homo sapiens
<220> FEATURE:
<221> NAME/KEY: SITE
<222> LOCATION: (127)
<223> OTHER INFORMATION: Xaa equals any of the naturally occurring
      L-amino acids
<221> NAME/KEY: SITE
<222> LOCATION: (166)
<223> OTHER INFORMATION: Xaa equals stop translation

<400> SEQUENCE: 81
```

Met Cys Leu Ser Leu Leu Ala Ala Leu Ala Cys Ser Ala Gly Asp Thr
 1               5                  10                  15

Trp Ala Ser Glu Val Gly Pro Val Leu Ser Lys Ser Ser Pro Arg Leu
                20                  25                  30

Ile Thr Thr Trp Glu Lys Val Pro Val Gly Thr Asn Gly Gly Val Thr
            35                  40                  45

Val Val Gly Leu Val Ser Leu Leu Gly Gly Thr Phe Val Gly Ile
        50                  55                  60

Ala Tyr Phe Leu Thr Gln Leu Ile Phe Val Asn Asp Leu Asp Ile Ser
65                  70                  75                  80

Ala Pro Gln Trp Pro Ile Ile Ala Phe Gly Gly Leu Ala Gly Leu Leu
                85                  90                  95

Gly Ser Ile Val Asp Ser Tyr Leu Gly Ala Thr Met Gln Tyr Thr Gly
            100                 105                 110

Leu Asp Glu Ser Thr Gly Met Val Val Asn Ser Pro Thr Asn Xaa Ala
            115                 120                 125

Arg His Ile Ala Gly Lys Pro Ile Leu Asp Asn Asn Ala Val Asn Leu
        130                 135                 140

Phe Ser Ser Val Leu Ile Ala Leu Leu Pro Thr Ala Ala Trp Gly
145                 150                 155                 160

Phe Trp Pro Arg Gly Xaa
                165

<210> SEQ ID NO 82
<211> LENGTH: 42
<212> TYPE: PRT
<213> ORGANISM: Homo sapiens
<220> FEATURE:
<221> NAME/KEY: SITE
<222> LOCATION: (42)
<223> OTHER INFORMATION: Xaa equals stop translation

<400> SEQUENCE: 82

Met Cys Gly Leu Val Ile Leu Trp Pro Cys Ile Met Thr Leu Phe Ser
1               5                   10                  15

Ser Leu Ser Thr Gly Asp Val Leu Leu Pro Cys Lys Ile Leu Val Gly
            20                  25                  30

Leu Arg Val Phe Ile Gly Ala Arg Val Xaa
        35                  40

<210> SEQ ID NO 83
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 83

Met Cys Phe Pro Ala Cys Leu Cys Ser Pro Leu Thr Cys Leu Leu Ser
1               5                   10                  15

Val Trp Lys Pro Gly Leu Ala His Ala Val Val His Cys Met Leu Glu
            20                  25                  30

Pro Val Glu Phe Ala Arg Val Val Gln Tyr Glu Ala Gly His Val Leu
        35                  40                  45

Xaa

<210> SEQ ID NO 84
<211> LENGTH: 57
<212> TYPE: PRT
<213> ORGANISM: Homo sapiens
<220> FEATURE:
<221> NAME/KEY: SITE
<222> LOCATION: (57)
<223> OTHER INFORMATION: Xaa equals stop translation

<400> SEQUENCE: 84

Met Leu Ile Ala Lys Leu Pro Val Leu Glu Ser Ile Cys Phe Phe Met
1               5                   10                  15

Leu Phe Leu Asn Pro Leu Val Ile Leu Ser Leu Asn Asn Ala Leu
            20                  25                  30

Pro Leu Val Phe His Pro His Ser Glu Phe Leu Glu Asp His Asn Arg
        35                  40                  45

Gly Asp Thr Leu Pro Ser Ile Val Xaa

<210> SEQ ID NO 85
<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 85

Met Leu Val Ala Thr Ala Val Cys Cys Tyr Leu Phe Trp Leu Ile Ala
 1               5                  10                  15

Ile Leu Ala Gln Leu Asn Pro Leu Phe Gly Pro Gln Leu Lys Asn Glu
            20                  25                  30

Thr Ile Trp Tyr Val Arg Phe Leu Trp Glu Xaa
        35                  40

<210> SEQ ID NO 86
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 86

Met Leu Leu Leu Trp Ala Phe Ser Gly Val Cys Ala Val Pro Ala Arg
 1               5                  10                  15

Ala Thr Pro Val Pro Ser Ser Phe Cys Pro Gln Gly Pro Ser Leu Cys
            20                  25                  30

Pro Lys Gln Pro Ala Ser Leu Ala Xaa
        35                  40

<210> SEQ ID NO 87
<211> LENGTH: 74
<212> TYPE: PRT
<213> ORGANISM: Homo sapiens
<220> FEATURE:
<221> NAME/KEY: SITE
<222> LOCATION: (74)
<223> OTHER INFORMATION: Xaa equals stop translation

<400> SEQUENCE: 87

Met His Ala Tyr Ala Cys Val Cys Ala Cys Met Leu Val Cys Val Cys
 1               5                  10                  15

Val Cys Val Cys Arg Ala Leu Val Ile Pro Thr Glu Gln Arg His Arg
            20                  25                  30

Arg Val Ala His Gly Arg Thr Ser Asp Ser Thr Leu Pro Cys Thr Val
        35                  40                  45

Lys Ile Trp Pro Ser Glu Arg Gly Asp Gly Arg Gly Glu Arg Gly Glu
    50                  55                  60

Arg Arg Arg Gly Thr Asp Trp Arg Gly Xaa
65                  70

<210> SEQ ID NO 88
<211> LENGTH: 47
<212> TYPE: PRT
<213> ORGANISM: Homo sapiens
<220> FEATURE:
<221> NAME/KEY: SITE
<222> LOCATION: (34)

```
<223> OTHER INFORMATION: Xaa equals any of the naturally occurring
      L-amino acids
<221> NAME/KEY: SITE
<222> LOCATION: (47)
<223> OTHER INFORMATION: Xaa equals stop translation

<400> SEQUENCE: 88

Met His His Pro Asn Leu Cys Leu His Phe His Ala Ala Phe Ser Leu
  1               5                  10                  15

Cys Val His Gly Cys Leu Cys Val Gln Phe Phe Pro Phe Tyr Lys Asp
             20                  25                  30

Thr Xaa His Ile Gly Leu Glu Pro Thr Leu Met Thr Ser Ser Xaa
         35                  40                  45

<210> SEQ ID NO 89
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 89

Met Leu Phe Leu Asn Val Ile Leu Phe Ser Thr Val Phe Thr Leu
  1               5                  10                  15

Ile Ser Thr Ala His Thr Leu Asp Arg Ala Val Arg Ser Asp Trp Leu
             20                  25                  30

Leu Leu Val Leu Ile Tyr Ala Cys Leu Glu Glu Leu Ile Pro Glu Leu
         35                  40                  45

Ile Phe Asn Leu Tyr Cys Gln Gly Asn Ala Thr Leu Phe Phe Xaa
     50                  55                  60

<210> SEQ ID NO 90
<211> LENGTH: 70
<212> TYPE: PRT
<213> ORGANISM: Homo sapiens
<220> FEATURE:
<221> NAME/KEY: SITE
<222> LOCATION: (20)
<223> OTHER INFORMATION: Xaa equals any of the naturally occurring
      L-amino acids
<221> NAME/KEY: SITE
<222> LOCATION: (70)
<223> OTHER INFORMATION: Xaa equals stop translation

<400> SEQUENCE: 90

Met Leu Leu Lys Leu His Thr Leu Trp Pro Leu Trp Pro Gly Leu Trp
  1               5                  10                  15

Ala Thr Thr Xaa Ser Asp Ser Leu Gly Glu Arg Thr His Ser Leu Cys
             20                  25                  30

Arg Arg Lys Lys Ala Ser Leu Ser Thr Gly Trp Met Ser Trp Met Ser
         35                  40                  45

Cys Arg Ala Arg Ala Thr His Thr Gln Val Val Ser Leu Lys Asp Lys
     50                  55                  60

Val Glu Phe Ala Pro Xaa
 65                  70

<210> SEQ ID NO 91
<211> LENGTH: 57
<212> TYPE: PRT
<213> ORGANISM: Homo sapiens
<220> FEATURE:
<221> NAME/KEY: SITE
```

```
<222> LOCATION: (57)
<223> OTHER INFORMATION: Xaa equals stop translation

<400> SEQUENCE: 91

Met Lys Glu Ser Arg Lys Met Leu Trp Val Phe Lys Met Leu Phe Phe
 1               5                  10                  15

Lys Ile Val Leu Trp Val Asn Leu Leu Ser Ala Ala Leu Ser Cys Ile
            20                  25                  30

Gln Lys Gln Met Leu Gly Ile Ala Pro Gln Lys Cys Val Pro Lys Leu
        35                  40                  45

Cys Phe Gln Leu Tyr Ile Met Arg Xaa
    50                  55

<210> SEQ ID NO 92
<211> LENGTH: 68
<212> TYPE: PRT
<213> ORGANISM: Homo sapiens
<220> FEATURE:
<221> NAME/KEY: SITE
<222> LOCATION: (68)
<223> OTHER INFORMATION: Xaa equals stop translation

<400> SEQUENCE: 92

Met Tyr Phe Leu Leu Ser Val Thr Ser Glu Ser Val Trp Arg Ser Trp
 1               5                  10                  15

Thr Leu Thr Phe His Ser Phe Ala Ile Leu Ser Leu Arg Cys Trp Thr
            20                  25                  30

Ser Leu Leu Leu Leu Ile Pro Leu Thr Ser Cys Asn Phe Ser Ser Pro
        35                  40                  45

Ser Trp Arg Met Thr Ala Ser Gln Val Pro Ser Lys Arg Lys Ala Ser
    50                  55                  60

Met Thr Leu Xaa
 65

<210> SEQ ID NO 93
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 93

Met Lys Gly Trp Pro Val Phe Leu Leu Val Gln Ala Val Thr Phe Leu
 1               5                  10                  15

Ser Val Ala Gln Ser Gly Ala Met Ala Cys Ala Ala Ser Gly Val Val
            20                  25                  30

Tyr Ser Val Asp Val Pro Ala Cys Ser Ser Arg Ser Xaa
        35                  40                  45

<210> SEQ ID NO 94
<211> LENGTH: 55
<212> TYPE: PRT
<213> ORGANISM: Homo sapiens
<220> FEATURE:
<221> NAME/KEY: SITE
<222> LOCATION: (55)
<223> OTHER INFORMATION: Xaa equals stop translation

<400> SEQUENCE: 94

Met Val Leu Ser Pro Trp Ala Cys Leu Phe Val Val Phe Phe Pro Tyr
 1               5                  10                  15
```

```
Ile Gln Ser Ser Leu Arg Ser Asp Lys His Leu Gln Leu Ser Asn Ile
            20                  25                  30

Leu Pro Thr Pro Ser His His Ile His Leu Pro Ala Ser Ile Cys Ile
        35                  40                  45

Gln Leu Arg Ala Gly Asn Xaa
     50                  55

<210> SEQ ID NO 95
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 95

Met Cys Glu Tyr Val Leu Leu Tyr Ile Val Leu Leu Cys Asn Arg
 1               5                  10                  15

Ser Tyr Ala Val Phe Thr Gln Cys Val Leu Arg Ser Ser Pro Ile Asp
            20                  25                  30

Ser Ser Arg Asn Ala Val Leu Leu Xaa
        35                  40

<210> SEQ ID NO 96
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 96

Met Thr Thr Pro Gly Leu Leu Ile Leu Phe Leu Ala His Val Cys Leu
 1               5                  10                  15

Val Asn His Gln Gln Ala Ala Glu Pro Gly Trp Lys Gln His Cys Cys
            20                  25                  30

Asn Trp Glu Gly His Arg Val Leu Xaa
        35                  40

<210> SEQ ID NO 97
<211> LENGTH: 50
<212> TYPE: PRT
<213> ORGANISM: Homo sapiens
<220> FEATURE:
<221> NAME/KEY: SITE
<222> LOCATION: (14)
<223> OTHER INFORMATION: Xaa equals any of the naturally occurring
      L-amino acids
<221> NAME/KEY: SITE
<222> LOCATION: (50)
<223> OTHER INFORMATION: Xaa equals stop translation

<400> SEQUENCE: 97

Met Leu Cys His Val Tyr Leu Leu Val Gly His Ala Xaa Phe Ser
 1               5                  10                  15

Val Gly Leu Met Gly Gln Arg Lys Leu Arg Cys Ser Ile Asn Ser Ala
            20                  25                  30

Leu Arg Ser Ala Val Ser Ser Ala Trp Asn Ser Ser Ile Cys Phe Asn
        35                  40                  45

Ser Xaa
    50
```

<210> SEQ ID NO 98
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

<400> SEQUENCE: 98

Met Ser Glu Trp Cys Gln Pro Asp Gln Ile Leu Leu Gln Phe Pro Val
1               5                   10                  15

Leu Ala Thr Met Ser Val Ala Phe Leu Ile Gln Arg Cys Phe Cys Phe
            20                  25                  30

Trp Trp Phe Val Leu Asn Ala Phe Ser Ile Pro Ser Gly Thr Glu Lys
        35                  40                  45

Lys Arg Ile Val Phe Lys Lys Trp Leu Xaa
    50                  55

<210> SEQ ID NO 99
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 99

Met Lys Val Val Val Met Val Val Ile Leu Val Val Val Thr Leu
1               5                   10                  15

Val Val Val Val Met Val Val Ile Leu Val Met Val Val Met Val Val
            20                  25                  30

Ala Leu Val Thr Leu Thr Trp Gly Pro Val Ala Val Thr Val Asp Ala
        35                  40                  45

Gly Ser Trp Xaa
    50

<210> SEQ ID NO 100
<211> LENGTH: 45
<212> TYPE: PRT
<213> ORGANISM: Homo sapiens
<220> FEATURE:
<221> NAME/KEY: SITE
<222> LOCATION: (45)
<223> OTHER INFORMATION: Xaa equals stop translation

<400> SEQUENCE: 100

Met Pro His Phe Leu Arg Trp Leu Leu Thr Thr Phe Arg Ile Arg Ala
1               5                   10                  15

Ser Cys Gly Ser Thr Pro Cys Trp Ser Pro Ser His Leu Gly Cys Leu
            20                  25                  30

Gln Pro Ala Leu Pro Arg Asp Leu Ser His Leu Glu Xaa
        35                  40                  45

<210> SEQ ID NO 101
<211> LENGTH: 58
<212> TYPE: PRT
<213> ORGANISM: Homo sapiens
<220> FEATURE:
<221> NAME/KEY: SITE
<222> LOCATION: (58)
<223> OTHER INFORMATION: Xaa equals stop translation

```
<400> SEQUENCE: 101

Met Ser Thr Lys Ile Leu Gln Phe Leu Phe Ser Ser Cys Cys Trp Val
1               5                   10                  15

Pro Pro Met Leu Phe Leu Phe Lys Asn Thr Lys Cys Arg Thr Ser Leu
            20                  25                  30

Leu Tyr Cys Phe Tyr Phe Ile Leu Leu Thr Cys Ser Leu Ser Glu Tyr
        35                  40                  45

Asp Ser Leu Leu Ser Ser Lys Val Phe Xaa
    50                  55

<210> SEQ ID NO 102
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals stop translation

<400> SEQUENCE: 102

Met Phe Trp Phe Trp Phe Leu Leu Ser Leu Ser Phe Gln Gln Val Glu
1               5                   10                  15

Gln Gln Gln Val Phe Gln Cys Ile Cys Cys Thr Arg Thr Lys Tyr Lys
            20                  25                  30

Ser Val Trp His Gln Lys Ser Lys Xaa
        35                  40

<210> SEQ ID NO 103
<211> LENGTH: 143
<212> TYPE: PRT
<213> ORGANISM: Homo sapiens
<220> FEATURE:
<221> NAME/KEY: SITE
<222> LOCATION: (104)
<223> OTHER INFORMATION: Xaa equals any of the naturally occurring
      L-amino acids
<221> NAME/KEY: SITE
<222> LOCATION: (105)
<223> OTHER INFORMATION: Xaa equals any of the naturally occurring
      L-amino acids
<221> NAME/KEY: SITE
<222> LOCATION: (115)
<223> OTHER INFORMATION: Xaa equals any of the naturally occurring
      L-amino acids
<221> NAME/KEY: SITE
<222> LOCATION: (143)
<223> OTHER INFORMATION: Xaa equals stop translation

<400> SEQUENCE: 103

Met Thr Leu Ile Glu Val Leu Val Ser Val Leu Ile Leu Ala Val Gly
1               5                   10                  15

Leu Leu Arg Ala Ala Val Ile Gln Leu Asn Ala Leu Lys Tyr Thr Asp
            20                  25                  30

Ser Ser Arg Met Thr Ser Gln Ala Ser Phe Ile Ala Tyr Asp Met Leu
        35                  40                  45

Asp Arg Ile Arg Ala Asn Ser Gly Ala Asp Tyr Ser Trp Gly Gln Gly
    50                  55                  60

Glu Arg Ala Pro Ser Thr Thr Ser Val Ala Ser Val Arg Asp Leu Asp
65                  70                  75                  80

Leu His Asp Phe Glu Ala Asn Ile Val Gly Phe Ala Gly Glu Ser Ala
                85                  90                  95

Lys Gly Ser Val Ala Val Asn Xaa Xaa Glu Val Thr Ile Ser Ile Ser
```

```
               100                 105                 110
Trp Asp Xaa Ser Arg Gly Ala Asn Ala Gln Gly Thr Arg Glu Thr Phe
            115                 120                 125
Thr Leu Thr Ser Arg Val Ala Val Asp Pro Arg Val Leu Pro Xaa
        130                 135                 140
```

<210> SEQ ID NO 104
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 104

```
Met Ala Phe Phe Phe Ala Leu Phe Val Ile Phe Phe Val Ile Val Val
 1               5                  10                  15

Gln Met Glu Ser His Ser Gly Leu Gly Lys Lys Ser Lys Ile Leu Ser
                20                  25                  30

Gly Gly Gln Gly Glu Glu Val Tyr Phe Leu Asp Xaa
            35                  40
```

<210> SEQ ID NO 105
<211> LENGTH: 63
<212> TYPE: PRT
<213> ORGANISM: Homo sapiens
<220> FEATURE:
<221> NAME/KEY: SITE
<222> LOCATION: (63)
<223> OTHER INFORMATION: Xaa equals stop translation

<400> SEQUENCE: 105

```
Met Tyr Phe Tyr Leu Ala Val Lys Pro Pro Leu Leu Trp Ala Arg Pro
 1               5                  10                  15

Gln Val Ser Cys Arg Leu Ser Val Ser Leu Ala Trp Ser Tyr His Leu
                20                  25                  30

His Leu Trp Ala Leu Phe Leu Phe Ser Ile Leu Leu Gln Cys Arg Ala
            35                  40                  45

Arg Phe Leu Leu Leu Val Leu Ser Gln Thr Gln Asp Leu Xaa
        50                  55                  60
```

<210> SEQ ID NO 106
<211> LENGTH: 283
<212> TYPE: PRT
<213> ORGANISM: Homo sapiens
<220> FEATURE:
<221> NAME/KEY: SITE
<222> LOCATION: (283)
<223> OTHER INFORMATION: Xaa equals stop translation

<400> SEQUENCE: 106

```
Met Gly Ser Pro Gly Met Val Leu Gly Leu Leu Val Gln Ile Trp Ala
 1               5                  10                  15

Leu Gln Glu Ala Ser Ser Leu Ser Val Gln Gln Gly Pro Asn Leu Leu
                20                  25                  30

Gln Val Arg Gln Gly Ser Gln Ala Thr Leu Val Cys Gln Val Asp Gln
            35                  40                  45

Ala Thr Ala Trp Glu Arg Leu Arg Val Lys Trp Thr Lys Asp Gly Ala
        50                  55                  60

Ile Leu Cys Gln Pro Tyr Ile Thr Asn Gly Ser Leu Ser Leu Gly Val
65                  70                  75                  80
```

-continued

```
Cys Gly Pro Gln Gly Arg Leu Ser Trp Gln Ala Pro Ser His Leu Thr
                 85                  90                  95
Leu Gln Leu Asp Pro Val Ser Leu Asn His Ser Gly Ala Tyr Val Cys
            100                 105                 110
Trp Ala Val Glu Ile Pro Glu Leu Glu Glu Ala Glu Gly Asn Ile
        115                 120                 125
Thr Arg Leu Phe Val Asp Pro Asp Pro Thr Gln Asn Arg Asn Arg
    130                 135                 140
Ile Ala Ser Phe Pro Gly Phe Leu Phe Val Leu Leu Gly Val Gly Ser
145                 150                 155                 160
Met Gly Val Ala Ala Ile Val Trp Gly Ala Trp Phe Trp Gly Arg Arg
                165                 170                 175
Ser Cys Gln Gln Arg Asp Ser Gly Asn Ser Pro Gly Asn Ala Phe Tyr
                180                 185                 190
Ser Asn Val Leu Tyr Arg Pro Arg Gly Ala Pro Lys Lys Ser Glu Asp
            195                 200                 205
Cys Ser Gly Glu Gly Lys Asp Gln Arg Gly Gln Ser Ile Tyr Ser Thr
    210                 215                 220
Ser Phe Pro Gln Pro Ala Pro Arg Gln Pro His Leu Ala Ser Arg Pro
225                 230                 235                 240
Cys Pro Ser Pro Arg Pro Cys Pro Ser Pro Arg Pro Gly His Pro Val
                245                 250                 255
Ser Met Val Arg Val Ser Pro Arg Pro Ser Pro Thr Gln Gln Pro Arg
                260                 265                 270
Pro Lys Gly Phe Pro Lys Val Gly Glu Glu Xaa
            275                 280
```

<210> SEQ ID NO 107
<211> LENGTH: 98
<212> TYPE: PRT
<213> ORGANISM: Homo sapiens
<220> FEATURE:
<221> NAME/KEY: SITE
<222> LOCATION: (98)
<223> OTHER INFORMATION: Xaa equals stop translation

<400> SEQUENCE: 107

```
Met Cys Lys Leu Cys Phe Tyr Leu Tyr Leu Cys Thr Trp Phe Pro Phe
  1               5                  10                  15
Gly Ala Ser Gly Leu Phe Trp Asp Lys Trp Cys Leu Pro Arg His Leu
             20                  25                  30
Pro Val Val Ser Gly Gln Glu Gln Leu Ser Ser Ser Leu Pro Ala Ala
         35                  40                  45
Leu Leu Phe Leu Gly Arg Arg Trp Arg Pro Pro Leu Arg Val Ser Pro
 50                  55                  60
Gly Leu Ser Phe Arg Gly Gly Arg Ala Gly Glu Pro Gln Gly Trp Gly
 65                  70                  75                  80
Asp Ser Trp Glu Met Glu Val Ala Pro Ala Pro Leu Asp Gln Tyr Trp
                85                  90                  95
Leu Xaa
```

<210> SEQ ID NO 108
<211> LENGTH: 62
<212> TYPE: PRT
<213> ORGANISM: Homo sapiens
<220> FEATURE:
<221> NAME/KEY: SITE

```
<222> LOCATION: (62)
<223> OTHER INFORMATION: Xaa equals stop translation

<400> SEQUENCE: 108

Met Cys Leu Leu Leu Trp Leu Thr Thr Phe Gln Arg Thr Ser Gly
1               5                   10                  15

Ala Leu Arg Arg Gly Gly Leu Ser Ser Pro Ala Trp Ala Met Arg Ser
            20                  25                  30

Pro Ser Val Tyr Ser Thr Gln Thr Pro Ser Pro Met Met Ser Thr Gly
        35                  40                  45

Thr Leu Arg Gly Leu Ser Gly Ala Met Cys Asn Leu Ser Xaa
        50                  55                  60

<210> SEQ ID NO 109
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 109

Met Lys Leu Cys Lys Leu Thr Gln Cys Ser Phe Leu Leu Lys Ser Leu
1               5                   10                  15

Ile Leu Leu Leu Glu Gln Leu Asn Val Ser Met Gly Phe Val Ala Ala
            20                  25                  30

Phe Asp Val Leu Val Gly Cys Ser Ile Cys Phe Glu Lys His Xaa
        35                  40                  45

<210> SEQ ID NO 110
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 110

Met Thr Thr Phe Ser Leu Cys Ser Gln Leu Ala Leu Leu Cys Ala Cys
1               5                   10                  15

Thr Ser Leu Val Ser Leu Pro Pro Phe Val Asp Tyr Lys Asp Thr Ser
            20                  25                  30

Pro Val Gly Pro Glu Pro His Cys Lys Gly Leu Ile Leu Thr Xaa
        35                  40                  45

<210> SEQ ID NO 111
<211> LENGTH: 42
<212> TYPE: PRT
<213> ORGANISM: Homo sapiens
<220> FEATURE:
<221> NAME/KEY: SITE
<222> LOCATION: (32)
<223> OTHER INFORMATION: Xaa equals any of the naturally occurring
      L-amino acids
<221> NAME/KEY: SITE
<222> LOCATION: (33)
<223> OTHER INFORMATION: Xaa equals any of the naturally occurring
      L-amino acids
<221> NAME/KEY: SITE
<222> LOCATION: (41)
<223> OTHER INFORMATION: Xaa equals any of the naturally occurring
      L-amino acids
<221> NAME/KEY: SITE
<222> LOCATION: (42)
```

```
<223> OTHER INFORMATION: Xaa equals stop translation

<400> SEQUENCE: 111

Met Asn Ile Leu Val Cys Val Phe Trp Leu Trp Gly Val Ala Gly
 1               5                  10                  15

Ser Trp Gly Arg His Ile Phe Ile Phe Thr Ser Val Lys Asn Val Xaa
                20                  25                  30

Xaa Ala Ser His Cys Ala Trp Pro Xaa Xaa
            35                  40

<210> SEQ ID NO 112
<211> LENGTH: 41
<212> TYPE: PRT
<213> ORGANISM: Homo sapiens

<400> SEQUENCE: 112

Met Gly Gly Ile Ala Leu Pro Ser Leu Ser Leu Cys Leu Leu Ser Ala
 1               5                  10                  15

Gly Ser His Cys Ile Ser Pro Ala Asp Gln Glu Thr Gly Pro Lys Val
                20                  25                  30

Thr Ala Pro Gln Gly Asn Phe Leu Pro
            35                  40

<210> SEQ ID NO 113
<211> LENGTH: 44
<212> TYPE: PRT
<213> ORGANISM: Homo sapiens
<220> FEATURE:
<221> NAME/KEY: SITE
<222> LOCATION: (44)
<223> OTHER INFORMATION: Xaa equals stop translation

<400> SEQUENCE: 113

Met Ile Val Leu Lys Trp Ile Phe Leu Ala Cys Val His Glu Cys Met
 1               5                  10                  15

Cys Lys Pro Leu Lys Cys Phe Leu Glu Lys Ile Leu Glu Val Leu Ile
                20                  25                  30

Met Val Lys Leu Lys Met Gly Val Leu Pro Ala Xaa
            35                  40

<210> SEQ ID NO 114
<211> LENGTH: 182
<212> TYPE: PRT
<213> ORGANISM: Homo sapiens

<400> SEQUENCE: 114

Met Glu Pro Gln Leu Gly Pro Glu Ala Ala Ala Leu Arg Pro Gly Trp
 1               5                  10                  15

Leu Ala Leu Leu Leu Trp Val Ser Ala Leu Ser Cys Ser Phe Ser Leu
                20                  25                  30

Pro Ala Ser Ser Leu Ser Ser Leu Val Pro Gln Val Arg Thr Ser Tyr
            35                  40                  45

Asn Phe Gly Arg Thr Phe Leu Gly Leu Asp Lys Cys Asn Ala Cys Ile
    50                  55                  60

Gly Thr Ser Ile Cys Lys Lys Phe Phe Lys Glu Ile Arg Ser Asp
65                  70                  75                  80

Asn Trp Leu Ala Ser His Leu Gly Leu Pro Pro Asp Ser Leu Leu Ser
                85                  90                  95

Tyr Pro Ala Asn Tyr Ser Asp Asp Ser Lys Ile Trp Arg Pro Val Glu
            100                 105                 110
```

```
Ile Phe Arg Leu Val Ser Lys Tyr Gln Asn Glu Ile Ser Asp Arg Lys
            115                 120                 125

Ile Cys Ala Ser Ala Ser Ala Pro Lys Thr Cys Ser Ile Glu Arg Val
        130                 135                 140

Leu Arg Lys Thr Glu Arg Phe Gln Lys Trp Leu Gln Ala Lys Arg Leu
145                 150                 155                 160

Thr Pro Asp Leu Val Gln Asp Cys His Gln Gly Arg Glu Leu Lys
                165                 170                 175

Phe Leu Cys Met Leu Arg
            180

<210> SEQ ID NO 115
<211> LENGTH: 81
<212> TYPE: PRT
<213> ORGANISM: Homo sapiens
<220> FEATURE:
<221> NAME/KEY: SITE
<222> LOCATION: (81)
<223> OTHER INFORMATION: Xaa equals stop translation

<400> SEQUENCE: 115

Met Ala Leu Gly Ser Met Tyr Leu Val Leu Thr Leu Ile Val Ala Lys
1               5                   10                  15

Val Leu Arg Gly Ala Glu Pro Cys Cys Gly Pro Leu Lys Asn Arg Val
            20                  25                  30

Leu Arg Pro Cys Pro Leu Pro Val His Cys Pro Leu Pro Ile Pro Ser
        35                  40                  45

Pro Ala Glu Gly Ile Pro Trp Val Ala Tyr Leu Pro Ile Arg Trp Phe
    50                  55                  60

Ile Ser Cys Cys Pro Gly His Cys Ile Gln Ile Pro Met Cys Thr Ser
65                  70                  75                  80

Xaa

<210> SEQ ID NO 116
<211> LENGTH: 49
<212> TYPE: PRT
<213> ORGANISM: Homo sapiens
<220> FEATURE:
<221> NAME/KEY: SITE
<222> LOCATION: (49)
<223> OTHER INFORMATION: Xaa equals stop translation

<400> SEQUENCE: 116

Met Ser Cys Glu Asn Asn Leu Lys Lys Lys Asn Thr Thr Leu Leu Ser
1               5                   10                  15

Tyr Leu Ile Phe Leu Ala Leu Val Met Tyr Leu Thr Phe Met Phe Leu
            20                  25                  30

Ser Ser Val Ser Thr Ser Arg Ile Ser Leu Ser Asn Ser Met Ile Ile
        35                  40                  45

Xaa

<210> SEQ ID NO 117
<211> LENGTH: 204
<212> TYPE: PRT
<213> ORGANISM: Homo sapiens
<220> FEATURE:
<221> NAME/KEY: SITE
<222> LOCATION: (31)
<223> OTHER INFORMATION: Xaa equals any of the naturally occurring
      L-amino acids
<221> NAME/KEY: SITE
```

```
<222> LOCATION: (93)
<223> OTHER INFORMATION: Xaa equals any of the naturally occurring
      L-amino acids
<221> NAME/KEY: SITE
<222> LOCATION: (99)
<223> OTHER INFORMATION: Xaa equals any of the naturally occurring
      L-amino acids
<221> NAME/KEY: SITE
<222> LOCATION: (115)
<223> OTHER INFORMATION: Xaa equals any of the naturally occurring
      L-amino acids
<221> NAME/KEY: SITE
<222> LOCATION: (151)
<223> OTHER INFORMATION: Xaa equals any of the naturally occurring
      L-amino acids
<221> NAME/KEY: SITE
<222> LOCATION: (204)
<223> OTHER INFORMATION: Xaa equals stop translation

<400> SEQUENCE: 117

Met Val Gly Leu Met His Ile Gly Phe Gly Ile Val Leu Cys Leu Ile
 1               5                  10                  15

Ser Phe Ser Phe Arg Glu Val Leu Gly Phe Ala Ser Thr Ala Xaa Ile
            20                  25                  30

Gly Gly Tyr Pro Phe Trp Gly Gly Leu Ser Phe Ile Ile Ser Gly Ser
        35                  40                  45

Leu Ser Val Ser Ala Ser Lys Glu Leu Ser Arg Cys Leu Val Lys Gly
 50                  55                  60

Ser Leu Gly Met Asn Ile Gly Arg Ser Ile Leu Ala Phe Ile Gly Val
 65                  70                  75                  80

Ile Leu Leu Leu Val Asp Met Cys Ile Asn Gly Val Xaa Gly Gln Asp
                85                  90                  95

Tyr Trp Xaa Val Leu Ser Gly Lys Gly Ile Ser Ala Thr Leu Met Ile
            100                 105                 110

Phe Ser Xaa Leu Glu Phe Phe Val Ala Cys Ala Thr Ala His Phe Ala
            115                 120                 125

Asn Gln Ala Asn Thr Thr Thr Asn Met Ser Val Leu Val Ile Pro Asn
130                 135                 140

Met Tyr Glu Ser Asn Pro Xaa Thr Pro Ala Ser Ser Ser Ala Pro Pro
145                 150                 155                 160

Arg Cys Asn Asn Tyr Ser Ala Asn Ala Pro Lys Arg Lys Arg Gly Ile
                165                 170                 175

Ser Leu Ile Ser Trp Arg Lys Thr Thr Cys Lys Asn Phe Leu Arg Arg
            180                 185                 190

Cys Leu Leu Leu Ser Thr Met Ile Ser Ser Leu Xaa
            195                 200

<210> SEQ ID NO 118
<211> LENGTH: 19
<212> TYPE: PRT
<213> ORGANISM: Homo sapiens
<220> FEATURE:
<221> NAME/KEY: SITE
<222> LOCATION: (19)
<223> OTHER INFORMATION: Xaa equals stop translation

<400> SEQUENCE: 118

Ser Leu Asp Ala Phe Arg Leu Ile Arg Ala Met Gly Ala Thr Gly Leu
 1               5                  10                  15

Ser Phe Xaa

<210> SEQ ID NO 119
```

```
<211> LENGTH: 13
<212> TYPE: PRT
<213> ORGANISM: Homo sapiens
<220> FEATURE:
<221> NAME/KEY: SITE
<222> LOCATION: (13)
<223> OTHER INFORMATION: Xaa equals stop translation

<400> SEQUENCE: 119

Leu Val Leu Trp Ile Val Met Leu Thr Tyr Ala Thr Xaa
 1               5                  10

<210> SEQ ID NO 120
<211> LENGTH: 80
<212> TYPE: PRT
<213> ORGANISM: Homo sapiens
<220> FEATURE:
<221> NAME/KEY: SITE
<222> LOCATION: (80)
<223> OTHER INFORMATION: Xaa equals stop translation

<400> SEQUENCE: 120

Met Glu Pro Gln Leu Gly Pro Glu Ala Ala Leu Arg Pro Gly Trp
 1               5                  10                  15
Leu Ala Leu Leu Leu Trp Val Ser Ala Leu Ser Cys Ser Phe Ser Leu
                20                  25                  30
Pro Ala Ser Ser Leu Ser Ser Leu Val Pro Gln Val Arg Thr Ser Tyr
            35                  40                  45
Asn Phe Gly Arg Thr Phe Leu Gly Leu Asp Lys Cys Asn Ala Cys Ile
     50                  55                  60
Gly Thr Ser Ile Cys Lys Lys Phe Phe Lys Glu Arg Asn Lys Ile Xaa
 65                  70                  75                  80

<210> SEQ ID NO 121
<211> LENGTH: 146
<212> TYPE: PRT
<213> ORGANISM: Homo sapiens
<220> FEATURE:
<221> NAME/KEY: SITE
<222> LOCATION: (96)
<223> OTHER INFORMATION: Xaa equals any of the naturally occurring
      L-amino acids
<221> NAME/KEY: SITE
<222> LOCATION: (107)
<223> OTHER INFORMATION: Xaa equals any of the naturally occurring
      L-amino acids
<221> NAME/KEY: SITE
<222> LOCATION: (111)
<223> OTHER INFORMATION: Xaa equals any of the naturally occurring
      L-amino acids
<221> NAME/KEY: SITE
<222> LOCATION: (115)
<223> OTHER INFORMATION: Xaa equals any of the naturally occurring
      L-amino acids
<221> NAME/KEY: SITE
<222> LOCATION: (122)
<223> OTHER INFORMATION: Xaa equals any of the naturally occurring
      L-amino acids
<221> NAME/KEY: SITE
<222> LOCATION: (132)
<223> OTHER INFORMATION: Xaa equals any of the naturally occurring
      L-amino acids

<400> SEQUENCE: 121

Met Glu Pro Gln Leu Gly Pro Glu Ala Ala Leu Arg Pro Gly Trp
 1               5                  10                  15

Leu Ala Leu Leu Leu Trp Val Ser Ala Leu Ser Cys Ser Phe Ser Leu
                20                  25                  30

Pro Ala Ser Ser Leu Ser Ser Leu Val Pro Gln Val Arg Thr Ser Tyr
            35                  40                  45

Asn Phe Gly Arg Thr Phe Leu Gly Leu Asp Lys Cys Asn Ala Cys Ile
```

```
            50                  55                  60
Gly Thr Ser Ile Cys Lys Lys Phe Lys Glu Glu Ile Arg Ser Asp
 65                  70                  75                  80

Asn Trp Leu Ala Ser His Leu Gly Thr Ala Ser Arg Phe Pro Leu Xaa
                 85                  90                  95

Ser Tyr Pro Cys Lys Leu Leu Gln Met Ile Xaa Lys Ile Trp Xaa Pro
                100                 105                 110

Cys Gly Xaa Leu Leu Thr Gly Gln Gln Xaa Ser Asn Glu Ile Ser Lys
            115                 120                 125

Gln Glu Ile Xaa Cys Leu Leu His Pro Pro Lys Asn Leu His Ile
130                 135                 140

Asp Val
145

<210> SEQ ID NO 122
<211> LENGTH: 81
<212> TYPE: PRT
<213> ORGANISM: Homo sapiens
<220> FEATURE:
<221> NAME/KEY: SITE
<222> LOCATION: (81)
<223> OTHER INFORMATION: Xaa equals stop translation

<400> SEQUENCE: 122

Met Ala Leu Gly Ser Met Tyr Leu Val Leu Thr Leu Ile Val Ala Lys
  1               5                  10                  15

Val Leu Arg Gly Ala Glu Pro Cys Cys Gly Pro Leu Lys Asn Arg Val
                 20                  25                  30

Leu Arg Pro Cys Pro Leu Pro Val His Cys Pro Leu Pro Ile Pro Ser
             35                  40                  45

Pro Ala Glu Gly Ile Pro Trp Val Ala Tyr Leu Pro Ile Arg Trp Phe
         50                  55                  60

Ile Ser Cys Cys Pro Gly His Cys Ile Gln Ile Pro Met Cys Thr Ser
 65                  70                  75                  80

Xaa

<210> SEQ ID NO 123
<211> LENGTH: 337
<212> TYPE: PRT
<213> ORGANISM: Homo sapiens

<400> SEQUENCE: 123

Glu Pro His Arg Gly Pro His Leu Pro Pro Asp Leu Gly His His His
  1               5                  10                  15

Gly Gln Arg Pro Gly Leu Gln Asn Ile Asn Val Phe Leu Arg Asn Thr
                 20                  25                  30

Val Lys Val Thr Gly Val Val Val Phe Met Phe Ser Leu Ser Trp Gln
             35                  40                  45

Leu Ser Leu Val Thr Phe Met Gly Phe Pro Ile Ile Met Met Val Ser
         50                  55                  60

Asn Ile Tyr Gly Lys Tyr Tyr Lys Arg Leu Ser Lys Glu Val Gln Asn
 65                  70                  75                  80

Ala Leu Ala Arg Ala Ser Asn Thr Ala Glu Glu Thr Ile Ser Ala Met
                 85                  90                  95

Lys Thr Val Arg Ser Phe Ala Asn Glu Glu Glu Glu Ala Glu Val Tyr
            100                 105                 110

Leu Arg Lys Leu Gln Gln Val Tyr Lys Leu Asn Arg Lys Glu Ala Ala
```

```
              115                 120                 125
Ala Tyr Met Tyr Val Trp Gly Ser Gly Leu Thr Leu Val Val
    130                 135                 140

Gln Val Ser Ile Leu Tyr Tyr Gly Gly His Leu Val Ile Ser Gly Gln
145                 150                 155                 160

Met Thr Ser Gly Asn Leu Ile Ala Phe Ile Ile Tyr Glu Phe Val Leu
                165                 170                 175

Gly Asp Cys Met Glu Asn Val Ser Phe Ser Leu Ser Pro Gly Lys Val
            180                 185                 190

Thr Ala Leu Val Gly Pro Ser Gly Ser Gly Lys Ser Cys Val Asn
        195                 200                 205

Ile Leu Glu Asn Phe Tyr Pro Leu Glu Gly Gly Arg Val Leu Leu Asp
    210                 215                 220

Gly Lys Pro Ile Ser Ala Tyr Asp His Lys Tyr Leu His Arg Val Ile
225                 230                 235                 240

Ser Leu Val Ser Gln Glu Pro Val Leu Phe Ala Arg Ser Ile Thr Asp
                245                 250                 255

Asn Ile Ser Tyr Gly Leu Pro Thr Val Pro Phe Glu Met Val Val Glu
            260                 265                 270

Ala Ala Gln Lys Ala Asn Ala His Gly Phe Ile Met Glu Leu Gln Asp
        275                 280                 285

Gly Tyr Ser Thr Glu Thr Gly Glu Lys Gly Ala Gln Leu Ser Gly Gly
    290                 295                 300

Gln Lys Gln Arg Val Ala Trp Pro Gly Leu Trp Cys Gly Thr Pro Gln
305                 310                 315                 320

Ser Ser Ser Trp Met Lys Pro Pro Ala Leu Trp Met Pro Arg Ala Ser
                325                 330                 335

Ile

<210> SEQ ID NO 124
<211> LENGTH: 315
<212> TYPE: PRT
<213> ORGANISM: Homo sapiens

<400> SEQUENCE: 124

Met Ser Ser Ala Thr Trp Thr Ala Ala Ser Trp Arg Thr Ser Ala Thr
1               5                   10                  15

Ser Thr Ser Leu Thr Arg Cys Trp Ile Ser Gly Gln Pro Ala Cys Thr
            20                  25                  30

Ala Ala Ala Cys Cys Trp Gly Ala Thr Ile Gly Val Ala Lys Asn Ser
        35                  40                  45

Ala Leu Gly Pro Arg Arg Leu Arg Ala Ser Trp Leu Val Ile Thr Leu
    50                  55                  60

Val Cys Leu Phe Val Gly Ile Tyr Ala Met Val Lys Leu Leu Leu Phe
65                  70                  75                  80

Ser Glu Val Arg Arg Pro Ile Arg Asp Pro Trp Phe Trp Ala Leu Phe
                85                  90                  95

Val Trp Thr Tyr Ile Ser Leu Gly Ala Ser Phe Leu Leu Trp Trp Leu
            100                 105                 110

Leu Ser Thr Val Arg Pro Gly Thr Gln Ala Leu Glu Pro Gly Ala Ala
        115                 120                 125

Thr Glu Ala Glu Gly Phe Pro Gly Ser Gly Arg Pro Pro Glu Gln
    130                 135                 140

Ala Ser Gly Ala Thr Leu Gln Lys Leu Leu Ser Tyr Thr Lys Pro Asp
```

```
145                 150                 155                 160
Val Ala Phe Leu Val Ala Ala Ser Phe Phe Leu Ile Val Ala Ala Leu
                165                 170                 175

Gly Glu Thr Phe Leu Pro Tyr Tyr Thr Gly Arg Ala Ile Asp Gly Ile
            180                 185                 190

Val Ile Gln Lys Ser Met Asp Gln Phe Ser Thr Ala Val Val Ile Val
        195                 200                 205

Cys Leu Leu Ala Ile Gly Ser Ser Phe Ala Ala Gly Ile Arg Gly Gly
    210                 215                 220

Ile Phe Thr Leu Ile Phe Ala Arg Leu Asn Ile Arg Leu Arg Asn Cys
225                 230                 235                 240

Leu Phe Arg Ser Leu Val Ser Gln Glu Thr Ser Phe Phe Asp Glu Asn
                245                 250                 255

Arg Thr Gly Asp Leu Ile Ser Arg Leu Thr Ser Asp Thr Thr Met Val
            260                 265                 270

Ser Asp Leu Val Ser Arg Thr Ser Met Ser Ser Cys Gly Thr Gln Ser
        275                 280                 285

Arg Ser Arg Ala Trp Trp Ser Ser Cys Ser Ala Ser His Gly Ser Ser
    290                 295                 300

Pro Trp Ser Pro Ser Trp Ala Ser Pro Ser Ser
305                 310                 315
```

<210> SEQ ID NO 125
<211> LENGTH: 167
<212> TYPE: PRT
<213> ORGANISM: Homo sapiens

<400> SEQUENCE: 125

```
His Leu Leu Arg Pro Ala His Cys Ala Phe Arg Asp Gly Gly Gly Gly
  1               5                  10                  15

Arg Thr Glu Gly Gln Cys Pro Arg Leu His His Gly Thr Pro Gly Arg
             20                  25                  30

Leu Gln His Arg Asp Arg Gly Glu Gly Arg Pro Ala Val Arg Trp Pro
         35                  40                  45

Glu Ala Ala Gly Gly Met Ala Arg Ala Leu Val Arg Asn Pro Pro Val
    50                  55                  60

Leu Ile Leu Asp Glu Ala Thr Ser Ala Leu Asp Ala Glu Ser Glu Tyr
65                  70                  75                  80

Leu Ile Gln Gln Ala Ile His Gly Asn Leu Gln Lys His Thr Val Leu
                85                  90                  95

Ile Ile Ala His Arg Leu Ser Thr Val Glu His Ala His Leu Ile Val
            100                 105                 110

Val Leu Asp Lys Gly Arg Val Val Gln Gln Gly Thr His Gln Gln Leu
        115                 120                 125

Leu Ala Gln Gly Gly Leu Tyr Ala Lys Leu Val Gln Arg Gln Met Leu
    130                 135                 140

Gly Leu Gln Pro Ala Ala Asp Phe Thr Ala Gly His Asn Glu Pro Val
145                 150                 155                 160

Ala Asn Gly Ser His Lys Ala
                165
```

<210> SEQ ID NO 126
<211> LENGTH: 227
<212> TYPE: PRT
<213> ORGANISM: Homo sapiens
<220> FEATURE:

```
<221> NAME/KEY: SITE
<222> LOCATION: (71)
<223> OTHER INFORMATION: Xaa equals any of the naturally occurring
      L-amino acids

<400> SEQUENCE: 126
```

Arg Leu Thr Lys Thr Ile Ser Phe Ser Leu Gln Asn Gln Thr Ala Phe
 1               5                  10                  15

Ile Asn Ser Leu Ala Lys Thr Pro Tyr Gln Ala Leu Thr Gly Ala Ala
                20                  25                  30

Leu Ala Gly Ser Tyr Pro Ile Trp Glu Asn Glu Asn Thr Leu Ser Trp
            35                  40                  45

Tyr Leu Pro Ser Pro Thr Thr Leu Leu Ser Pro Pro Val Leu Phe Cys
    50                  55                  60

Val Ile Gln Leu Ile Phe Xaa Leu Pro Ala Asn Trp Ser Gly Thr Cys
65                  70                  75                  80

Thr Leu Val Phe Gln Ala Pro Thr Ile Asn Ile Leu Pro Pro Asn Gln
                85                  90                  95

Thr Ile Leu Ile Ser Val Glu Ala Ser Ile Ser Ser Pro Ile Arg
                100                 105                 110

Asn Lys Trp Ala Leu His Leu Ile Thr Leu Leu Thr Gly Leu Gly Ile
            115                 120                 125

Thr Ala Ala Leu Gly Thr Gly Ile Ala Gly Ile Thr Thr Ser Ile Thr
    130                 135                 140

Ser Tyr Gln Thr Leu Phe Thr Thr Leu Ser Asn Thr Val Glu Asp Met
145                 150                 155                 160

His Thr Ser Ile Thr Ser Leu Gln Arg Gln Leu Asp Phe Leu Val Gly
                165                 170                 175

Val Ile Leu Gln Asn Trp Arg Val Leu Asp Leu Leu Thr Thr Glu Lys
            180                 185                 190

Gly Gly Thr Cys Ile Tyr Leu Gln Glu Glu Cys Cys Phe Cys Val Asn
    195                 200                 205

Glu Ser Gly Ile Val His Ile Ala Val Arg Arg Leu His Asp Arg Ala
210                 215                 220

Ala Glu Leu
225

```
<210> SEQ ID NO 127
<211> LENGTH: 29
<212> TYPE: PRT
<213> ORGANISM: Homo sapiens

<400> SEQUENCE: 127
```

Tyr Pro Ile Trp Glu Asn Glu Asn Thr Leu Ser Trp Tyr Leu Pro Ser
 1               5                  10                  15

Pro Thr Thr Leu Leu Ser Pro Pro Val Leu Phe Cys Val
                20                  25

```
<210> SEQ ID NO 128
<211> LENGTH: 27
<212> TYPE: PRT
<213> ORGANISM: Homo sapiens

<400> SEQUENCE: 128
```

Arg Val Leu Asp Leu Leu Thr Thr Glu Lys Gly Gly Thr Cys Ile Tyr
 1               5                  10                  15

Leu Gln Glu Glu Cys Cys Phe Cys Val Asn Glu
                20                  25

```
<210> SEQ ID NO 129
<211> LENGTH: 10
<212> TYPE: PRT
<213> ORGANISM: Homo sapiens

<400> SEQUENCE: 129

Phe Ser Leu Gly Arg Arg His Cys Leu Gly
 1               5                  10

<210> SEQ ID NO 130
<211> LENGTH: 123
<212> TYPE: PRT
<213> ORGANISM: Homo sapiens
<220> FEATURE:
<221> NAME/KEY: SITE
<222> LOCATION: (64)
<223> OTHER INFORMATION: Xaa equals any of the naturally occurring
      L-amino acids
<221> NAME/KEY: SITE
<222> LOCATION: (83)
<223> OTHER INFORMATION: Xaa equals any of the naturally occurring
      L-amino acids

<400> SEQUENCE: 130

Glu His Pro Thr Ala Asp Arg Ala Gly Cys Ser Ala Ser Gly Ala Cys
 1               5                  10                  15

Tyr Ser Leu His His Ala Thr Met Lys Arg Gln Ala Ala Glu Glu Ala
                20                  25                  30

Cys Ile Leu Arg Gly Gly Ala Leu Ser Thr Val Arg Ala Gly Ala Glu
            35                  40                  45

Leu Arg Ala Val Leu Ala Leu Leu Arg Ala Gly Pro Gly Pro Gly Xaa
        50                  55                  60

Gly Ser Lys Asp Leu Leu Phe Trp Val Ala Leu Glu Arg Arg Arg Ser
 65                  70                  75                  80

His Cys Xaa Leu Glu Asn Glu Pro Leu Arg Gly Phe Ser Trp Leu Ser
                85                  90                  95

Ser Asp Pro Gly Gly Leu Glu Ser Asp Thr Leu Gln Trp Val Glu Glu
                100                 105                 110

Pro Gln Arg Ser Cys Thr Ala Arg Arg Trp Val
            115                 120

<210> SEQ ID NO 131
<211> LENGTH: 344
<212> TYPE: PRT
<213> ORGANISM: Homo sapiens
<220> FEATURE:
<221> NAME/KEY: SITE
<222> LOCATION: (19)
<223> OTHER INFORMATION: Xaa equals any of the naturally occurring
      L-amino acids

<400> SEQUENCE: 131

Ser Arg Pro Pro Val Gly Ser Ser Pro Gln Leu Glu Gly Asp Ala Met
 1               5                  10                  15

Pro Pro Xaa Arg Gln Arg Tyr Leu Cys Lys Tyr Gln Phe Glu Val Leu
                20                  25                  30

Cys Pro Ala Pro Arg Pro Gly Ala Ala Ser Asn Leu Ser Tyr Arg Ala
            35                  40                  45

Pro Phe Gln Leu His Ser Ala Ala Leu Asp Phe Ser Pro Pro Gly Thr
        50                  55                  60

Glu Val Ser Ala Leu Cys Arg Gly Gln Leu Pro Ile Ser Val Thr Cys
```

```
              65                  70                  75                  80
Ile Ala Asp Glu Ile Gly Ala Arg Trp Asp Lys Leu Ser Gly Asp Val
                         85                  90                  95
Leu Cys Pro Cys Pro Gly Arg Tyr Leu Arg Ala Gly Lys Cys Ala Glu
            100                 105                 110
Leu Pro Asn Cys Leu Asp Asp Leu Gly Gly Phe Ala Cys Glu Cys Ala
            115                 120                 125
Thr Gly Phe Glu Leu Gly Lys Asp Gly Arg Ser Cys Val Thr Ser Gly
            130                 135                 140
Glu Gly Gln Pro Thr Leu Gly Gly Thr Gly Val Pro Thr Arg Arg Pro
145                 150                 155                 160
Pro Ala Thr Ala Thr Ser Pro Val Pro Gln Arg Thr Trp Pro Ile Arg
                165                 170                 175
Val Asp Glu Lys Leu Gly Glu Thr Pro Leu Val Pro Glu Gln Asp Asn
            180                 185                 190
Ser Val Thr Ser Ile Pro Glu Ile Pro Arg Trp Gly Ser Gln Ser Thr
            195                 200                 205
Met Ser Thr Leu Gln Met Ser Leu Gln Ala Glu Ser Lys Ala Thr Ile
    210                 215                 220
Thr Pro Ser Gly Ser Val Ile Ser Lys Phe Asn Ser Thr Thr Ser Ser
225                 230                 235                 240
Ala Thr Pro Gln Ala Phe Asp Ser Ser Ala Val Val Phe Ile Phe
                245                 250                 255
Val Ser Thr Ala Val Val Leu Val Ile Leu Thr Met Thr Val Leu
            260                 265                 270
Gly Leu Val Lys Leu Cys Phe His Glu Ser Pro Ser Ser Gln Pro Arg
            275                 280                 285
Lys Glu Ser Met Gly Pro Pro Gly Trp Arg Val Ile Leu Lys Pro Ala
    290                 295                 300
Ala Leu Gly Ser Ser Ser Ala His Cys Thr Asn Asn Gly Val Lys Val
305                 310                 315                 320
Gly Asp Cys Asp Leu Arg Asp Arg Ala Glu Gly Ala Leu Leu Ala Glu
                325                 330                 335
Ser Pro Leu Gly Ser Ser Asp Ala
            340

<210> SEQ ID NO 132
<211> LENGTH: 7
<212> TYPE: PRT
<213> ORGANISM: Homo sapiens

<400> SEQUENCE: 132

Arg Tyr Leu Thr Leu Thr His
 1               5

<210> SEQ ID NO 133
<211> LENGTH: 6
<212> TYPE: PRT
<213> ORGANISM: Homo sapiens

<400> SEQUENCE: 133

Cys Asn Thr Pro Trp Ala
 1               5

<210> SEQ ID NO 134
<211> LENGTH: 8
<212> TYPE: PRT
```

<213> ORGANISM: Homo sapiens

<400> SEQUENCE: 134

Ala Pro Val Ile Phe Ser His Ser
 1               5

<210> SEQ ID NO 135
<211> LENGTH: 6
<212> TYPE: PRT
<213> ORGANISM: Homo sapiens

<400> SEQUENCE: 135

Arg Asn Val Pro Asp Asp
 1               5

<210> SEQ ID NO 136
<211> LENGTH: 6
<212> TYPE: PRT
<213> ORGANISM: Homo sapiens

<400> SEQUENCE: 136

Gly Leu Glu Asp Val Ser
 1               5

<210> SEQ ID NO 137
<211> LENGTH: 23
<212> TYPE: PRT
<213> ORGANISM: Homo sapiens

<400> SEQUENCE: 137

Val Glu Gly Gly His Ser Leu Asp Asn Ser Leu Ser Ile Leu Arg Thr
 1               5                  10                  15

Phe Tyr Met Leu Gly Val Arg
                20

<210> SEQ ID NO 138
<211> LENGTH: 6
<212> TYPE: PRT
<213> ORGANISM: Homo sapiens

<400> SEQUENCE: 138

Val Glu Gly Gly His Ser
 1               5

<210> SEQ ID NO 139
<211> LENGTH: 190
<212> TYPE: PRT
<213> ORGANISM: Homo sapiens

<400> SEQUENCE: 139

Thr Trp Leu Arg Leu Gly Ser Ser Gln Ile Trp Leu Gly Thr Ala Pro
 1               5                  10                  15

Arg Gly Pro Arg Ile His Pro Glu Gln Ala Gly Leu Ala Gly Ala Pro
                20                  25                  30

Val Lys Ser Thr Ser Ser Glu Glu Ser Gln Pro Gly Gly Gln Cys Gln
                35                  40                  45

Ser Ser Gly Gly Ala Gln Thr Leu Pro Ser Leu Arg Ala Ala Pro Val
         50                  55                  60

Ala Ala Leu Gly Ser Leu Ser Ser Tyr Pro Asp Ser Cys Pro Arg Ala
 65                  70                  75                  80

Thr Thr Pro Glu Leu Cys Pro Gly Ala Pro Thr Leu His Leu Ala Asp
                85                  90                  95

```
Ser Ile Ser Gly Pro Val Ser Pro Gly Ser Leu Gly Pro Asp
            100                 105                 110

Ala Trp Thr Leu Cys Ala Lys His His Gln Ala Lys Gly Met Thr Leu
            115                 120                 125

Gly Thr Pro Lys Val Leu Arg Leu Gln Pro Val Ser Pro Cys Trp Gly
            130                 135                 140

Pro Lys Ser Trp Arg Val Pro Gly Pro Phe Gln Pro Gly Arg Arg Arg
145                 150                 155                 160

Gly Glu Ser Arg Gln Gln Gly Arg Gly Lys Arg Ser Ala Arg Ser
            165                 170                 175

Ala Gln Ser Pro Thr Gly Pro Glu Ser Ala Ala Trp Pro Cys
            180                 185                 190

<210> SEQ ID NO 140
<211> LENGTH: 129
<212> TYPE: PRT
<213> ORGANISM: Homo sapiens

<400> SEQUENCE: 140

Thr Val Ala Thr Ala Cys Val Trp Ala Ala Cys Thr Gly Cys Trp Ala
1               5                   10                  15

Arg Pro Pro Val Pro Thr Trp Ala Gly Cys Ala Ala Arg Cys Ala Ala
            20                  25                  30

Glu Asp Ala Arg Ala Gly Val Gly Asp Leu Pro Ala Thr Gly Gly Ala
        35                  40                  45

Ala Thr Gly Arg Arg Ala Leu Thr Pro Ala Pro Arg Gly Pro Cys
    50                  55                  60

Ile Leu Ser Pro Gln Pro Trp Ala Leu Gly Leu Pro Gly Ala Pro Leu
65                  70                  75                  80

Pro Ala Ala Leu Pro Gly Arg Ala Arg Gly Arg Pro Gly Leu Pro Ala
                85                  90                  95

Leu Pro Ala Leu Ser Thr Leu Pro Gly Cys Pro Ala Leu Asp Pro Ala
            100                 105                 110

Gly Ala Gly Thr Leu Cys Pro Pro Gly Ala Ala Glu Pro Ala Gly
            115                 120                 125

Pro

<210> SEQ ID NO 141
<211> LENGTH: 90
<212> TYPE: PRT
<213> ORGANISM: Homo sapiens

<400> SEQUENCE: 141

Arg Ser Gly Gln Pro Gly Glu Gly Ser Met Leu Arg Lys Phe Ser Leu
1               5                   10                  15

Gln Arg Leu Leu Ser Pro Leu Asp Gln Ala Gln Thr Arg Trp Gly Leu
            20                  25                  30

Ala Leu Ala Cys Val Ala Gly Asp Lys Gly Pro Pro Arg Pro Trp Asn
        35                  40                  45

Ile Ser Ser Ala Pro Ala His Pro His Val Thr Thr Pro Gly Met Glu
    50                  55                  60

Thr Ser Gly Gly Pro Ala Arg Asp Gly Gly Leu Ile Leu Glu Arg Glu
65                  70                  75                  80

Ala Ala Phe Asn Lys Pro Ala Pro Gly Glu
                85                  90
```

-continued

```
<210> SEQ ID NO 142
<211> LENGTH: 307
<212> TYPE: PRT
<213> ORGANISM: Homo sapiens
<220> FEATURE:
<221> NAME/KEY: SITE
<222> LOCATION: (135)
<223> OTHER INFORMATION: Xaa equals any of the naturally occurring
      L-amino acids
<221> NAME/KEY: SITE
<222> LOCATION: (197)
<223> OTHER INFORMATION: Xaa equals any of the naturally occurring
      L-amino acids
<221> NAME/KEY: SITE
<222> LOCATION: (203)
<223> OTHER INFORMATION: Xaa equals any of the naturally occurring
      L-amino acids
<221> NAME/KEY: SITE
<222> LOCATION: (219)
<223> OTHER INFORMATION: Xaa equals any of the naturally occurring
      L-amino acids
<221> NAME/KEY: SITE
<222> LOCATION: (255)
<223> OTHER INFORMATION: Xaa equals any of the naturally occurring
      L-amino acids

<400> SEQUENCE: 142

Arg Cys Gln Arg Asn Lys Asp Ile Met Met Ser Ser Lys Pro Thr Ser
 1               5                  10                  15

His Ala Glu Val Asn Glu Thr Ile Pro Asn Pro Tyr Pro Pro Ser Ser
                20                  25                  30

Phe Met Ala Pro Gly Phe Gln Gln Pro Leu Gly Ser Ile Asn Leu Glu
            35                  40                  45

Asn Gln Ala Gln Gly Ala Gln Arg Ala Gln Pro Tyr Gly Ile Thr Ser
        50                  55                  60

Pro Gly Ile Phe Ala Ser Ser Gln Pro Gly Gln Gly Asn Ile Gln Met
 65                  70                  75                  80

Ile Asn Pro Ser Val Gly Thr Ala Val Met Asn Phe Lys Glu Glu Ala
                85                  90                  95

Lys Ala Leu Gly Val Ile Gln Ile Met Val Gly Leu Met His Ile Gly
                100                 105                 110

Phe Gly Ile Val Leu Cys Leu Ile Ser Phe Ser Phe Arg Glu Val Leu
            115                 120                 125

Gly Phe Ala Ser Thr Ala Xaa Ile Gly Gly Tyr Pro Phe Trp Gly Gly
        130                 135                 140

Leu Ser Phe Ile Ile Ser Gly Ser Leu Ser Val Ser Ala Ser Lys Glu
145                 150                 155                 160

Leu Ser Arg Cys Leu Val Lys Gly Ser Leu Gly Met Asn Ile Gly Arg
                165                 170                 175

Ser Ile Leu Ala Phe Ile Gly Val Ile Leu Leu Leu Val Asp Met Cys
            180                 185                 190

Ile Asn Gly Val Xaa Gly Gln Asp Tyr Trp Xaa Val Leu Ser Gly Lys
        195                 200                 205

Gly Ile Ser Ala Thr Leu Met Ile Phe Ser Xaa Leu Glu Phe Phe Val
    210                 215                 220

Ala Cys Ala Thr Ala His Phe Ala Asn Gln Ala Asn Thr Thr Thr Asn
225                 230                 235                 240

Met Ser Val Leu Val Ile Pro Asn Met Tyr Glu Ser Asn Pro Xaa Thr
                245                 250                 255

Pro Ala Ser Ser Ser Ala Pro Pro Arg Cys Asn Asn Tyr Ser Ala Asn
            260                 265                 270
```

Ala Pro Lys Arg Lys Arg Gly Ile Ser Leu Ile Ser Trp Arg Lys Thr
            275                 280                 285

Thr Cys Lys Asn Phe Leu Arg Arg Cys Leu Leu Leu Ser Thr Met Ile
            290                 295                 300

Ser Ser Leu
305

<210> SEQ ID NO 143
<211> LENGTH: 246
<212> TYPE: PRT
<213> ORGANISM: Homo sapiens

<400> SEQUENCE: 143

Met Gly Arg Leu Asp Gly Lys Val Ile Ile Leu Thr Ala Ala Ala Gln
 1               5                  10                  15

Gly Ile Gly Gln Ala Ala Ala Leu Ala Phe Ala Arg Glu Gly Ala Lys
             20                  25                  30

Val Ile Ala Thr Asp Ile Asn Glu Ser Lys Leu Gln Glu Leu Glu Lys
         35                  40                  45

Tyr Pro Gly Ile Gln Thr Arg Val Leu Asp Val Thr Lys Lys Lys Gln
     50                  55                  60

Ile Asp Gln Phe Ala Asn Glu Val Glu Arg Leu Asp Val Leu Phe Asn
 65                  70                  75                  80

Val Ala Gly Phe Val His His Gly Thr Val Leu Asp Cys Glu Lys
                 85                  90                  95

Asp Trp Asp Phe Ser Met Asn Leu Asn Val Arg Asn Val Met Tyr Leu
                100                 105                 110

Met Ile Lys Ala Phe Leu Pro Lys Met Leu Ala Gln Lys Ser Gly Asn
            115                 120                 125

Ile Ile Asn Met Ser Ser Val Ala Ser Val Lys Gly Val Val Asn
        130                 135                 140

Arg Cys Val Tyr Ser Thr Thr Lys Ala Ala Val Ile Gly Leu Thr Lys
145                 150                 155                 160

Ser Val Ala Ala Asp Phe Ile Gln Gln Gly Ile Arg Cys Asn Cys Val
                165                 170                 175

Cys Pro Gly Thr Val Asp Thr Pro Ser Leu Gln Glu Arg Ile Gln Ala
            180                 185                 190

Arg Gly Asn Pro Glu Glu Ala Arg Asn Asp Phe Leu Lys Arg Gln Lys
        195                 200                 205

Thr Gly Arg Phe Ala Thr Ala Glu Glu Ile Ala Met Leu Cys Val Tyr
    210                 215                 220

Leu Ala Ser Asp Glu Ser Ala Tyr Val Thr Gly Asn Pro Val Ile Ile
225                 230                 235                 240

Asp Gly Gly Trp Ser Leu
                245

<210> SEQ ID NO 144
<211> LENGTH: 234
<212> TYPE: PRT
<213> ORGANISM: Homo sapiens

<400> SEQUENCE: 144

Gly Thr Ile Gly Leu Tyr Trp Val Gly Ser Ile Ile Met Ser Val Val
 1               5                  10                  15

Val Phe Val Pro Gly Asn Ile Val Gly Lys Tyr Gly Thr Arg Ile Cys
             20                  25                  30

-continued

```
Pro Ala Phe Phe Leu Ser Ile Pro Tyr Thr Cys Leu Pro Val Trp Ala
            35                  40                  45

Gly Phe Arg Ile Tyr Asn Gln Pro Ser Glu Asn Tyr Asn Tyr Pro Ser
 50                  55                  60

Lys Val Ile Gln Glu Ala Gln Ala Lys Asp Leu Leu Arg Arg Pro Phe
 65                  70                  75                  80

Asp Leu Met Leu Val Val Cys Leu Leu Leu Ala Thr Gly Phe Cys Leu
                 85                  90                  95

Phe Arg Gly Leu Ile Ala Leu Asp Cys Pro Ser Glu Leu Cys Arg Leu
                100                 105                 110

Tyr Thr Gln Phe Gln Glu Pro Tyr Leu Lys Asp Pro Ala Ala Tyr Pro
            115                 120                 125

Lys Ile Gln Met Leu Ala Tyr Met Phe Tyr Ser Val Pro Tyr Phe Val
130                 135                 140

Thr Ala Leu Tyr Gly Leu Val Val Pro Gly Cys Ser Trp Met Pro Asp
145                 150                 155                 160

Ile Thr Leu Ile His Ala Gly Gly Leu Ala Gln Ala Gln Phe Ser His
                165                 170                 175

Ile Gly Ala Ser Leu His Ala Arg Thr Ala Tyr Val Tyr Arg Val Pro
                180                 185                 190

Glu Glu Ala Lys Ile Leu Phe Leu Ala Leu Asn Ile Ala Tyr Gly Val
            195                 200                 205

Leu Pro Gln Leu Leu Ala Tyr Arg Cys Ile Tyr Lys Pro Glu Phe Phe
        210                 215                 220

Ile Lys Thr Lys Ala Glu Glu Lys Val Glu
225                 230

<210> SEQ ID NO 145
<211> LENGTH: 238
<212> TYPE: PRT
<213> ORGANISM: Homo sapiens
<220> FEATURE:
<221> NAME/KEY: SITE
<222> LOCATION: (184)
<223> OTHER INFORMATION: Xaa equals any of the naturally occurring
      L-amino acids

<400> SEQUENCE: 145

Met Ser Asn His Asp Pro Arg Gly Cys Thr Arg Arg Ala Gln Lys
 1               5                  10                  15

Pro Leu Ala Ile Gln Pro Arg Leu Phe His Ala Ser Ala Pro Asp Glu
                 20                  25                  30

Gly Thr Gln Gly Thr Leu Lys Gly Thr Gln Lys Gly Gly Cys Ile Leu
            35                  40                  45

Val Gln Cys Gln Ser Glu Gly Gly Ala Ala Gly Ala Trp Thr Gly Pro
 50                  55                  60

Pro Ser Pro Ala Arg Asp Arg Val Arg Pro Pro Gly Thr Lys Ala
 65                  70                  75                  80

Gln Arg Leu Glu Arg Arg Arg His Val Pro Arg Leu His Gly Leu Gly
                 85                  90                  95

Val Gly Gly Cys Glu Val Arg Thr Gly Ile Val Ala Arg Ile Ser Gly
                100                 105                 110

Ser Thr Pro Trp Ala Gly Gly Lys Pro Leu Gly Leu His Gly Ala Met
            115                 120                 125

Gly Glu Ala Gly Ala Gly Asp Thr Gly Cys Cys Ala Lys Gly Pro Ser
130                 135                 140
```

```
Pro Ala Ala Pro Leu Pro Ala Glu Gly Arg Gly Gln Gly Ala Gly Pro
145                 150                 155                 160

Gly Gly Leu Val Gly Arg Gly Glu Arg Arg Asp Gln Gln Thr Leu Leu
            165                 170                 175

Gly Met Ala Glu Asp Thr Gly Xaa Ser Pro Ser Arg Pro Ser Ala Pro
        180                 185                 190

Ala Pro Arg Ala Pro Val Pro Ala Arg Gln Pro Leu Pro Arg Ala Arg
        195                 200                 205

Leu Gly Ala Ala Thr Ala Ile Ser Lys Ser Arg Ser Ser Arg Val Ala
    210                 215                 220

Pro Ala Leu Ala Ala Ala Ile Ser Ala Ser Ser His Gln Arg
225                 230                 235
```

<210> SEQ ID NO 146
<211> LENGTH: 207
<212> TYPE: PRT
<213> ORGANISM: Homo sapiens
<220> FEATURE:
<221> NAME/KEY: SITE
<222> LOCATION: (3)
<223> OTHER INFORMATION: Xaa equals any of the naturally occurring L-amino acids
<221> NAME/KEY: SITE
<222> LOCATION: (5)
<223> OTHER INFORMATION: Xaa equals any of the naturally occurring L-amino acids
<221> NAME/KEY: SITE
<222> LOCATION: (9)
<223> OTHER INFORMATION: Xaa equals any of the naturally occurring L-amino acids
<221> NAME/KEY: SITE
<222> LOCATION: (30)
<223> OTHER INFORMATION: Xaa equals any of the naturally occurring L-amino acids
<221> NAME/KEY: SITE
<222> LOCATION: (169)
<223> OTHER INFORMATION: Xaa equals any of the naturally occurring L-amino acids

<400> SEQUENCE: 146

```
Ser Thr Xaa Thr Xaa Thr Ile Gly Xaa Ala Gly Thr Pro Ala Gly Thr
1               5                   10                  15

Gly Pro Glu Phe Pro Gly Arg Pro Thr Arg Pro Gly Glu Xaa Pro Val
            20                  25                  30

Asp Phe Ser Lys Gln Tyr Ser Ala Ser Trp Met Cys Leu Ser Leu Leu
        35                  40                  45

Ala Ala Leu Ala Cys Ser Ala Gly Asp Thr Trp Ala Ser Glu Val Gly
    50                  55                  60

Pro Val Leu Ser Lys Ser Ser Pro Arg Leu Ile Thr Thr Trp Glu Lys
65                  70                  75                  80

Val Pro Val Gly Thr Asn Gly Val Thr Val Val Gly Leu Val Ser
            85                  90                  95

Ser Leu Leu Gly Gly Thr Phe Val Gly Ile Ala Tyr Phe Leu Thr Gln
            100                 105                 110

Leu Ile Phe Val Asn Asp Leu Asp Ile Ser Ala Pro Gln Trp Pro Ile
        115                 120                 125

Ile Ala Phe Gly Gly Leu Ala Gly Leu Leu Gly Ser Ile Val Asp Ser
        130                 135                 140

Tyr Leu Gly Ala Thr Met Gln Tyr Thr Gly Leu Asp Glu Ser Thr Gly
145                 150                 155                 160

Met Val Val Asn Ser Pro Thr Asn Xaa Ala Arg His Ile Ala Gly Lys
```

```
                    165                 170                 175
Pro Ile Leu Asp Asn Asn Ala Val Asn Leu Phe Ser Ser Val Leu Ile
                180                 185                 190
Ala Leu Leu Leu Pro Thr Ala Ala Trp Gly Phe Trp Pro Arg Gly
            195                 200                 205

<210> SEQ ID NO 147
<211> LENGTH: 116
<212> TYPE: PRT
<213> ORGANISM: Homo sapiens

<400> SEQUENCE: 147

Met Ser Gln Arg Ala Gly Arg Arg Pro Gly Gly Trp Asn Pro Ser Leu
  1               5                  10                  15
Ser Val Val Glu Val Cys Arg Gly Cys Arg Gly Thr Gly Pro Leu Pro
                 20                  25                  30
Trp Gly Ala Ser Leu Phe Pro Cys Ser Ala Ser Pro Leu Phe Pro Leu
             35                  40                  45
Pro Leu Asn Arg Arg Gly Asp Val His Gly Thr Leu Gly Gly Arg Met
         50                  55                  60
Leu Asn Arg Val Glu Cys Arg Asp Gly Val Ala Ala Trp Leu Cys
 65                  70                  75                  80
Leu His Asp Ala Ala Ile Arg Gly Ala Val Gly Arg Cys Pro Met
                 85                  90                  95
Trp Thr Gln Pro Thr His Trp Val Leu Leu Cys Trp Ala Leu His
                100                 105                 110
Phe Tyr Cys Arg
        115

<210> SEQ ID NO 148
<211> LENGTH: 81
<212> TYPE: PRT
<213> ORGANISM: Homo sapiens

<400> SEQUENCE: 148

Met Thr Ala His Ser Phe Ala Leu Pro Val Ile Ile Phe Thr Thr Phe
  1               5                  10                  15
Trp Gly Leu Val Gly Ile Ala Gly Pro Trp Phe Val Pro Lys Gly Pro
                 20                  25                  30
Asn Arg Gly Val Ile Ile Thr Met Leu Val Ala Thr Ala Val Cys Cys
             35                  40                  45
Tyr Leu Phe Trp Leu Ile Ala Ile Leu Ala Gln Leu Asn Pro Leu Phe
         50                  55                  60
Gly Pro Gln Leu Lys Asn Glu Thr Ile Trp Tyr Val Arg Phe Leu Trp
 65                  70                  75                  80
Glu

<210> SEQ ID NO 149
<211> LENGTH: 110
<212> TYPE: PRT
<213> ORGANISM: Homo sapiens

<400> SEQUENCE: 149

Ala Gln Arg Ala Ala Arg Leu Gly Thr Arg Ala Pro Ala Ala Pro Ala
  1               5                  10                  15
Ala Arg Pro Cys Ile Leu Pro Gly His Pro Ala Pro Gly His Asp Gly
                 20                  25                  30
```

```
Ala Leu Ile Arg Pro Gly His His Leu His His Val Leu Gly Pro
            35                  40                  45

Arg Arg His Arg Gly Pro Trp Phe Val Pro Lys Gly Pro Asn Arg Gly
 50                  55                  60

Val Ile Ile Thr Met Leu Val Ala Thr Ala Val Cys Cys Tyr Leu Phe
 65                  70                  75                  80

Trp Leu Ile Ala Ile Leu Ala Gln Leu Asn Pro Leu Phe Gly Pro Gln
                 85                  90                  95

Leu Lys Asn Glu Thr Ile Trp Tyr Val Arg Phe Leu Trp Glu
            100                 105                 110
```

<210> SEQ ID NO 150
<211> LENGTH: 135
<212> TYPE: PRT
<213> ORGANISM: Homo sapiens

<400> SEQUENCE: 150

```
Met Thr Leu Glu Glu His Arg Asp Arg Pro Arg Leu Gly Met Cys Met
 1               5                  10                  15

Cys Val Cys Ala Cys Val Tyr Ala Cys Met Leu Met His Val Cys Val
            20                  25                  30

His Ala Cys Leu Cys Val Cys Val Cys Val Cys Val Glu Pro Trp Ser
            35                  40                  45

Ser Arg Gln Ser Lys Asp Thr Gly Gly Trp His Met Glu Glu Gln Val
 50                  55                  60

Thr Pro Pro Ser Leu Ala Gln Leu Lys Ser Gly Gln Val Arg Gly Glu
 65                  70                  75                  80

Met Gly Glu Gly Arg Gly Glu Lys Gly Glu Glu Ala Leu Thr Gly Gly
                 85                  90                  95

Ala Glu Ala Leu Ser Leu Leu Gly Arg Arg Ser Pro Ser Thr Pro Leu
            100                 105                 110

Phe Leu Asp Arg Glu Asp Lys Gln Ala Lys Asp Ala Arg Asn Leu Ser
            115                 120                 125

Ser Thr Val Ala Pro Asp Phe
            130                 135
```

<210> SEQ ID NO 151
<211> LENGTH: 82
<212> TYPE: PRT
<213> ORGANISM: Homo sapiens

<400> SEQUENCE: 151

```
His Glu Lys Ile Leu Thr Pro Ile Trp Pro Ser Ser Thr Asp Leu Glu
 1               5                  10                  15

Lys Pro His Glu Met Leu Phe Leu Asn Val Ile Leu Phe Ser Leu Thr
            20                  25                  30

Val Phe Thr Leu Ile Ser Thr Ala His Thr Leu Asp Arg Ala Val Arg
            35                  40                  45

Ser Asp Trp Leu Leu Val Leu Ile Tyr Ala Cys Leu Glu Glu Leu
 50                  55                  60

Ile Pro Glu Leu Ile Phe Asn Leu Tyr Cys Gln Gly Asn Ala Thr Leu
 65                  70                  75                  80

Phe Phe
```

<210> SEQ ID NO 152
<211> LENGTH: 71
<212> TYPE: PRT

<213> ORGANISM: Homo sapiens

<400> SEQUENCE: 152

```
Pro Ala Asn Lys Ala Gly Ala Ile Glu Ala Gly Ile Gly Ile Ser
 1               5                  10                  15

Leu Met Val Leu Ser Pro Trp Ala Cys Leu Phe Val Val Phe Phe Pro
                20                  25                  30

Tyr Ile Gln Ser Ser Leu Arg Ser Asp Lys His Leu Gln Leu Ser Asn
                35                  40                  45

Ile Leu Pro Thr Pro Ser His His Ile His Leu Pro Ala Ser Ile Cys
        50                  55                  60

Ile Gln Leu Arg Ala Gly Asn
 65                 70
```

<210> SEQ ID NO 153
<211> LENGTH: 75
<212> TYPE: PRT
<213> ORGANISM: Homo sapiens

<400> SEQUENCE: 153

```
Ala Gly Ser Pro Ala Gly Thr Gly Pro Glu Phe Pro Gly Arg Pro Thr
 1               5                  10                  15

Arg Pro Ile Ser Thr His Val Phe Glu Tyr Glu Cys Ile Cys Lys Ile
                20                  25                  30

Pro Arg Phe Met Cys Glu Tyr Val Leu Leu Leu Tyr Ile Val Leu Leu
                35                  40                  45

Cys Asn Arg Ser Tyr Ala Val Phe Thr Gln Cys Val Leu Arg Ser Ser
        50                  55                  60

Pro Ile Asp Ser Ser Arg Asn Ala Val Leu Leu
 65                 70                  75
```

<210> SEQ ID NO 154
<211> LENGTH: 483
<212> TYPE: PRT
<213> ORGANISM: Homo sapiens
<220> FEATURE:
<221> NAME/KEY: SITE
<222> LOCATION: (194)
<223> OTHER INFORMATION: Xaa equals any of the naturally occurring
      L-amino acids
<221> NAME/KEY: SITE
<222> LOCATION: (205)
<223> OTHER INFORMATION: Xaa equals any of the naturally occurring
      L-amino acids

<400> SEQUENCE: 154

```
Met Pro Ser Gly Met Ser Ala Ala Val Pro Ile Ser Gly Leu Leu Asp
 1               5                  10                  15

Leu Ser His Asn Ser Ile Ser Gln Glu Ser Ala Leu Tyr Leu Leu Glu
                20                  25                  30

Thr Leu Pro Ser Cys Pro Arg Val Arg Glu Ala Ser Val Asn Leu Gly
                35                  40                  45

Ser Glu Gln Ser Phe Arg Ile His Phe Ser Arg Glu Asp Gln Ala Gly
        50                  55                  60

Lys Thr Leu Arg Leu Ser Glu Cys Ser Phe Arg Pro Glu His Val Ser
 65                 70                  75                  80

Arg Leu Ala Thr Gly Leu Ser Lys Ser Leu Gln Leu Thr Glu Leu Thr
                85                  90                  95

Leu Thr Gln Cys Cys Leu Gly Gln Lys Gln Leu Ala Ile Leu Leu Ser
                100                 105                 110
```

Leu Val Gly Arg Pro Ala Gly Leu Phe Ser Leu Arg Val Gln Glu Pro
            115                 120                 125

Trp Ala Asp Arg Ala Arg Val Leu Ser Leu Leu Glu Val Cys Ala Gln
    130                 135                 140

Ala Ser Gly Ser Val Thr Glu Ile Ser Ile Ser Glu Thr Gln Gln Gln
145                 150                 155                 160

Leu Cys Val Gln Leu Glu Phe Pro Arg Gln Glu Asn Pro Glu Ala
                165                 170                 175

Val Ala Leu Arg Leu Ala His Cys Asp Leu Gly Ala His His Ser Leu
            180                 185                 190

Leu Xaa Gly Gln Leu Met Glu Thr Cys Ala Arg Leu Xaa Gln Leu Ser
        195                 200                 205

Leu Ser Gln Val Asn Leu Cys Glu Asp Asp Ala Ser Ser Leu Leu
    210                 215                 220

Leu Gln Ser Leu Leu Leu Ser Leu Ser Glu Leu Lys Thr Phe Arg Leu
225                 230                 235                 240

Thr Ser Ser Cys Val Ser Thr Glu Gly Leu Ala His Leu Ala Ser Gly
                245                 250                 255

Leu Gly His Cys His His Leu Glu Glu Leu Asp Leu Ser Asn Asn Gln
            260                 265                 270

Phe Asp Glu Glu Gly Thr Lys Ala Leu Met Arg Ala Leu Glu Gly Lys
        275                 280                 285

Trp Met Leu Lys Arg Leu Asp Leu Ser His Leu Leu Asn Ser Ser
    290                 295                 300

Thr Leu Ala Leu Leu Thr His Arg Leu Ser Gln Met Thr Cys Leu Gln
305                 310                 315                 320

Ser Leu Arg Leu Asn Arg Asn Ser Ile Gly Asp Val Gly Cys His
                325                 330                 335

Leu Ser Glu Ala Leu Arg Ala Ala Thr Ser Leu Glu Glu Leu Asp Leu
            340                 345                 350

Ser His Asn Gln Ile Gly Asp Ala Gly Val Gln His Leu Ala Thr Ile
        355                 360                 365

Leu Pro Gly Leu Pro Glu Leu Arg Lys Ile Asp Leu Ser Gly Asn Ser
370                 375                 380

Ile Ser Ser Ala Gly Gly Val Gln Leu Ala Glu Ser Leu Val Leu Cys
385                 390                 395                 400

Arg Arg Leu Glu Glu Leu Met Leu Gly Cys Asn Ala Leu Gly Asp Pro
                405                 410                 415

Thr Ala Leu Gly Leu Ala Gln Glu Leu Pro Gln His Leu Arg Val Leu
            420                 425                 430

His Leu Pro Phe Ser His Leu Gly Pro Gly Ala Leu Ser Leu Ala
        435                 440                 445

Arg Pro Trp Met Asp Pro Pro Ile Trp Lys Arg Ser Ala Trp Arg Lys
    450                 455                 460

Thr Thr Trp Leu Glu Gly Ser Val Ser Val Trp Ser Ser Arg Cys
465                 470                 475                 480

Ser Asp Arg

<210> SEQ ID NO 155
<211> LENGTH: 221
<212> TYPE: PRT
<213> ORGANISM: Homo sapiens

<400> SEQUENCE: 155

His Gln Leu Ser Arg Gly Ser Ala Val Gly Arg Val Ser Arg Ser Leu
1               5                   10                  15

Gln Ala Pro Gly Gly Val Asp Ala Trp Leu Gln Cys Pro Gly Gly Ser
            20                  25                  30

His Ser Pro Gly Ala Gly Ser Gly Ala Ala Pro Ala Pro Glu Gly Pro
        35                  40                  45

Thr Pro Thr Ile Gln Pro Ser Gly Pro Arg Trp Gly Pro Glu Pro Gly
    50                  55                  60

Gln Ala Leu Asp Gly Ser Pro His Leu Glu Glu Ile Ser Leu Ala Glu
65                  70                  75                  80

Asn Asn Leu Ala Gly Gly Val Leu Arg Phe Cys Met Glu Leu Pro Leu
                85                  90                  95

Leu Arg Gln Ile Asp Leu Val Ser Cys Lys Ile Asp Asn Gln Thr Ala
            100                 105                 110

Lys Leu Leu Thr Ser Ser Phe Thr Ser Cys Pro Ala Leu Glu Val Ile
            115                 120                 125

Leu Leu Ser Trp Asn Leu Leu Gly Asp Glu Ala Ala Glu Leu Ala
        130                 135                 140

Gln Val Leu Pro Gln Met Gly Arg Leu Lys Arg Val Asp Leu Glu Lys
145                 150                 155                 160

Asn Gln Ile Thr Ala Leu Gly Ala Trp Leu Leu Ala Glu Gly Leu Ala
                165                 170                 175

Gln Gly Ser Ser Ile Gln Val Ile Arg Leu Trp Asn Asn Pro Ile Pro
            180                 185                 190

Cys Asp Met Ala Gln His Leu Lys Ser Gln Glu Pro Arg Leu Asp Phe
            195                 200                 205

Ala Phe Phe Asp Asn Gln Pro Gln Ala Pro Trp Gly Thr
            210                 215                 220

<210> SEQ ID NO 156
<211> LENGTH: 89
<212> TYPE: PRT
<213> ORGANISM: Homo sapiens

<400> SEQUENCE: 156

Glu Lys Leu Phe Cys Phe Glu Met Leu Leu Ile Cys Lys Phe Ser Pro
1               5                   10                  15

Asn Ser Val Pro Pro Glu Thr Cys Ala Ile Leu Asn Gln Gly Leu Met
            20                  25                  30

Asp Leu Gly Leu Cys Arg Met Cys Leu Gly Asn Asn Met Phe Ala Gly
        35                  40                  45

Ser Met Leu Gly Lys Ser His Arg His Ser Pro Phe Ser Ile Asn Gln
    50                  55                  60

Arg His Asn Ala Leu Arg Lys Ala Ala Gly Thr Pro Ala Gln Lys Ser
65                  70                  75                  80

Leu Gly Ile Val Gln Val Ser Pro Asn
                85

<210> SEQ ID NO 157
<211> LENGTH: 58
<212> TYPE: PRT
<213> ORGANISM: Homo sapiens

<400> SEQUENCE: 157

Gly Cys Ala Gly Cys Ala Leu Val Thr Ile Cys Leu Gln Ala Val Cys
1               5                   10                  15

-continued

Leu Val Lys Ala Ile Ala Ile Leu His Ser Arg Leu Thr Arg Asp Thr
            20                  25                  30

Met His Cys Gly Arg Pro Gln Gly Pro Leu Pro Arg Lys Ala Trp Val
        35                  40                  45

Leu Ser Arg Phe Pro Pro Thr Glu Thr Ala
    50                  55

<210> SEQ ID NO 158
<211> LENGTH: 48
<212> TYPE: PRT
<213> ORGANISM: Homo sapiens

<400> SEQUENCE: 158

Pro Glu Thr Gln Cys Thr Ala Glu Gly Arg Arg Asp Pro Cys Pro Glu
1               5                   10                  15

Lys Pro Gly Tyr Cys Pro Gly Phe Pro Gln Leu Arg Gln Pro Glu Ile
            20                  25                  30

Trp Pro Arg Gly Lys Gly Lys Thr Leu His Pro Pro Ala Arg His Met
        35                  40                  45

<210> SEQ ID NO 159
<211> LENGTH: 8
<212> TYPE: PRT
<213> ORGANISM: Homo sapiens

<400> SEQUENCE: 159

Ser Glu Ile Gly Glu Asn Arg Pro
1               5

<210> SEQ ID NO 160
<211> LENGTH: 8
<212> TYPE: PRT
<213> ORGANISM: Homo sapiens

<400> SEQUENCE: 160

His Asp Thr Asp Ser Phe Ala His
1               5

<210> SEQ ID NO 161
<211> LENGTH: 7
<212> TYPE: PRT
<213> ORGANISM: Homo sapiens

<400> SEQUENCE: 161

Ala Leu Arg Lys Ala Ala Gly
1               5

<210> SEQ ID NO 162
<211> LENGTH: 148
<212> TYPE: PRT
<213> ORGANISM: Homo sapiens

<400> SEQUENCE: 162

Met Arg Gly Pro Val Cys Gly Phe Ser Leu Val Glu Met Leu Leu Ala
1               5                   10                  15

Leu Ala Leu Gly Leu Met Leu Ile Leu Gly Val Thr Gln Ile Ala Leu
            20                  25                  30

Ser Ser Arg Thr Thr Tyr Ala Ser Gln Ser Ala Ala Ser Leu Leu Gln
        35                  40                  45

Asp Asp Ala Arg Phe Ala Leu Gly Lys Leu Ile Gln Glu Ile Arg Gln
    50                  55                  60

```
Ala Gly Met Phe Gly Cys Leu Ser Ala Ala Ser Ile Ser Asn Ala Pro
 65                  70                  75                  80

Ala Gly Phe Asp Arg Pro Ile Gly Trp Ser Thr Thr Gly Ser Ser Arg
                 85                  90                  95

Ser Leu Thr Leu Val Thr Ala Asp Val Gly Glu Gly Gly Ser Lys Pro
            100                 105                 110

Asp Trp Thr Val Leu Ser Asp Cys Thr Gly Ser Ala His Ala Tyr Val
            115                 120                 125

Gly Ser Pro Pro Ala Ala Asn Ala Arg Ala Asn Pro Leu Pro Thr Cys
    130                 135                 140

Ala Lys Leu Thr
145

<210> SEQ ID NO 163
<211> LENGTH: 137
<212> TYPE: PRT
<213> ORGANISM: Homo sapiens

<400> SEQUENCE: 163

Met Gly Tyr Tyr Leu Ser Arg Ser Arg Gln Ala Gly Met Val Leu Leu
  1               5                  10                  15

Ile Ser Leu Val Phe Leu Leu Leu Ala Leu Leu Gly Val Ser Ser
                 20                  25                  30

Met Gln Gly Ala Ile Ser Gln Glu Lys Ile Thr Gly Ser Leu Arg Gln
             35                  40                  45

Arg Asn Gln Ser Phe Gln Gln Ala Glu Ser Gly Leu Arg Leu Gly Glu
 50                  55                  60

Ser Leu Val Gln Ala Ser Gly Phe Ala Leu Arg Pro Cys His Ser Thr
 65                  70                  75                  80

Ala Ala Cys Ala Pro Pro Ala Glu Ser Val Ser Val Val Gly Pro Gly
                 85                  90                  95

Thr Asn Pro Val Ser Thr Val Thr Trp Ile Gly Met Lys Asp Gly Val
            100                 105                 110

Tyr Gly Ile Gln Asn Leu Gly Pro Gly Thr Gly Leu Val Asn Ser Arg
            115                 120                 125

Gln Arg Pro Arg Pro Arg Ser Ile Ala
    130                 135

<210> SEQ ID NO 164
<211> LENGTH: 209
<212> TYPE: PRT
<213> ORGANISM: Homo sapiens

<400> SEQUENCE: 164

Glu Asn Glu Ser Thr Lys Glu Pro Ser Leu Leu Gln Tyr Leu Cys Val
  1               5                  10                  15

Gln Ser Pro Ala Gly Leu Asn Gly Phe Asn Val Leu Leu Ser Gly Ser
                 20                  25                  30

Gln Thr Pro Pro Thr Val Gly Pro Ser Ser Gly Gln Leu Pro Ser Phe
             35                  40                  45

Ser Val Pro Cys Met Val Leu Pro Ser Pro Leu Gly Pro Phe Pro
 50                  55                  60

Val Leu Tyr Ser Pro Ala Met Pro Gly Pro Val Ser Ser Thr Leu Gly
 65                  70                  75                  80

Ala Leu Pro Asn Thr Gly Pro Val Asn Phe Ser Leu Pro Gly Leu Gly
                 85                  90                  95
```

```
Ser Ile Ala Gln Leu Leu Val Gly Pro Thr Ala Val Val Asn Pro Lys
            100                 105                 110

Ser Ser Thr Leu Pro Ser Ala Asp Pro Gln Leu Gln Ser Gln Pro Ser
            115                 120                 125

Leu Asn Leu Ser Pro Val Met Ser Arg Ser His Ser Val Val Gln Gln
        130                 135                 140

Pro Glu Ser Pro Val Tyr Val Gly His Pro Val Ser Val Val Lys Leu
145                 150                 155                 160

His Gln Ser Pro Val Pro Val Thr Pro Lys Ser Ile Gln Arg Thr His
                165                 170                 175

Arg Glu Thr Phe Phe Lys Thr Pro Gly Ser Leu Gly Asp Pro Val Leu
            180                 185                 190

Lys Arg Arg Glu Arg Asn Asn His Glu Thr Pro Ala Arg Pro Arg Gly
        195                 200                 205

Asp

<210> SEQ ID NO 165
<211> LENGTH: 454
<212> TYPE: PRT
<213> ORGANISM: Homo sapiens

<400> SEQUENCE: 165

Arg His Glu Arg His Glu Tyr Arg Arg Ala Leu Asp His Glu Glu Glu
1               5                   10                  15

Ala Leu Ser Ser Gly Ser Val Gln Glu Ala Glu Ala Met Leu Asp Glu
            20                  25                  30

Pro Gln Glu Gln Ala Glu Gly Ser Leu Thr Val Tyr Val Ile Ser Glu
        35                  40                  45

His Ser Ser Leu Leu Pro Gln Asp Met Met Ser Tyr Ile Gly Pro Lys
    50                  55                  60

Arg Thr Ala Val Val Arg Gly Ile Met His Arg Glu Ala Phe Asn Ile
65                  70                  75                  80

Ile Gly Arg Arg Ile Val Gln Val Ala Gln Ala Met Ser Leu Thr Glu
                85                  90                  95

Asp Val Leu Ala Ala Ala Leu Ala Asp His Leu Pro Glu Asp Lys Trp
            100                 105                 110

Ser Ala Glu Lys Arg Arg Pro Leu Lys Ser Ser Leu Gly Tyr Glu Ile
        115                 120                 125

Thr Phe Ser Leu Leu Asn Pro Asp Pro Lys Ser His Asp Val Tyr Trp
    130                 135                 140

Asp Ile Glu Gly Ala Val Arg Arg Tyr Val Gln Pro Phe Leu Asn Ala
145                 150                 155                 160

Leu Gly Ala Ala Gly Asn Phe Ser Val Asp Ser Gln Ile Leu Tyr Tyr
                165                 170                 175

Ala Met Leu Gly Val Asn Pro Arg Phe Asp Ser Ala Ser Ser Ser Tyr
            180                 185                 190

Tyr Leu Asp Met His Ser Leu Pro His Val Ile Asn Pro Val Glu Ser
        195                 200                 205

Arg Leu Gly Ser Ser Ala Ala Ser Leu Tyr Pro Val Leu Asn Phe Leu
    210                 215                 220

Leu Tyr Val Pro Glu Leu Ala His Ser Pro Leu Tyr Ile Gln Asp Lys
225                 230                 235                 240

Asp Gly Ala Pro Val Ala Thr Asn Ala Phe His Ser Pro Arg Trp Gly
                245                 250                 255
```

-continued

```
Gly Ile Met Val Tyr Asn Val Asp Ser Lys Thr Tyr Asn Ala Ser Val
            260                 265                 270

Leu Pro Val Arg Val Glu Val Asp Met Val Arg Val Met Glu Val Phe
            275                 280                 285

Leu Ala Gln Leu Arg Leu Leu Phe Gly Ile Ala Gln Pro Gln Leu Pro
            290                 295                 300

Pro Lys Cys Leu Leu Ser Gly Pro Thr Ser Glu Gly Leu Met Thr Trp
305                 310                 315                 320

Glu Leu Asp Arg Leu Leu Trp Ala Arg Ser Val Glu Asn Leu Ala Thr
                325                 330                 335

Ala Thr Thr Thr Leu Thr Ser Leu Ala Gln Leu Leu Gly Lys Ile Ser
            340                 345                 350

Asn Ile Val Ile Lys Asp Asp Val Ala Ser Glu Val Tyr Lys Ala Val
            355                 360                 365

Ala Ala Val Gln Lys Ser Ala Glu Glu Leu Ala Ser Gly His Leu Ala
            370                 375                 380

Ser Ala Phe Val Ala Ser Gln Glu Ala Val Thr Ser Ser Glu Leu Ala
385                 390                 395                 400

Phe Phe Asp Pro Ser Leu Leu His Leu Leu Tyr Phe Pro Asp Asp Gln
                405                 410                 415

Lys Phe Ala Ile Tyr Ile Pro Leu Phe Leu Pro Met Ala Val Pro Ile
            420                 425                 430

Leu Leu Ser Leu Val Lys Ile Phe Leu Glu Thr Arg Lys Ser Trp Arg
            435                 440                 445

Lys Pro Glu Lys Thr Asp
        450

<210> SEQ ID NO 166
<211> LENGTH: 66
<212> TYPE: PRT
<213> ORGANISM: Homo sapiens

<400> SEQUENCE: 166

Lys Leu Leu Leu Thr Lys Val Glu Gln Lys Leu Glu Leu Ala Arg Leu
  1               5                  10                  15

Gln Val Asp Thr Ser Gly Ser Lys Glu Phe Gly Thr Ser Gly Ile Pro
            20                  25                  30

Ala Lys Cys Arg Phe Pro Lys Ile Phe Val Asn Thr Asp Asp Thr Tyr
        35                  40                  45

Glu Glu Leu His Leu Ile Val Tyr Lys Val Thr Thr Val Phe Leu Pro
    50                  55                  60

Ala Leu
 65

<210> SEQ ID NO 167
<211> LENGTH: 79
<212> TYPE: PRT
<213> ORGANISM: Homo sapiens

<400> SEQUENCE: 167

Met Glu Pro Gln Leu Gly Pro Glu Ala Ala Leu Arg Pro Gly Trp
  1               5                  10                  15

Leu Ala Leu Leu Leu Trp Val Ser Ala Leu Ser Cys Ser Phe Ser Leu
            20                  25                  30

Pro Ala Ser Ser Leu Ser Ser Leu Val Pro Gln Val Arg Thr Ser Tyr
        35                  40                  45
```

```
Asn Phe Gly Arg Thr Phe Leu Gly Leu Asp Lys Cys Asn Ala Cys Ile
         50                  55                  60

Gly Thr Ser Ile Cys Lys Lys Phe Phe Lys Glu Arg Asn Lys Ile
 65                  70                  75
```

<210> SEQ ID NO 168
<211> LENGTH: 209
<212> TYPE: PRT
<213> ORGANISM: Homo sapiens

<400> SEQUENCE: 168

```
Gln Leu Pro Leu Trp Pro Ser Pro Ala Ser Val Gln Pro Arg Val Asp
 1               5                  10                  15

Ser Gln Arg Ala Arg Gly Ser Pro Glu Pro Lys Met Glu Pro Gln Leu
             20                  25                  30

Gly Pro Glu Ala Ala Ala Leu Arg Pro Gly Trp Leu Ala Leu Leu Leu
         35                  40                  45

Trp Val Ser Ala Leu Ser Cys Ser Phe Ser Leu Pro Ala Ser Ser Leu
 50                  55                  60

Ser Ser Leu Val Pro Gln Val Arg Thr Ser Tyr Asn Phe Gly Arg Thr
 65                  70                  75                  80

Phe Leu Gly Leu Asp Lys Cys Asn Ala Cys Ile Gly Thr Ser Ile Cys
                 85                  90                  95

Lys Lys Phe Phe Lys Glu Glu Ile Arg Ser Asp Asn Trp Leu Ala Ser
                100                 105                 110

His Leu Gly Leu Pro Pro Asp Ser Leu Leu Ser Tyr Pro Ala Asn Tyr
            115                 120                 125

Ser Asp Asp Ser Lys Ile Trp Arg Pro Val Glu Ile Phe Arg Leu Val
130                 135                 140

Ser Lys Tyr Gln Asn Glu Ile Ser Asp Arg Lys Ile Cys Ala Ser Ala
145                 150                 155                 160

Ser Ala Pro Lys Thr Cys Ser Ile Glu Arg Val Leu Arg Lys Thr Glu
                165                 170                 175

Arg Phe Gln Lys Trp Leu Gln Ala Lys Arg Leu Thr Pro Asp Leu Val
            180                 185                 190

Gln Asp Cys His Gln Gly Gln Arg Glu Leu Lys Phe Leu Cys Met Leu
        195                 200                 205

Arg
```

<210> SEQ ID NO 169
<211> LENGTH: 146
<212> TYPE: PRT
<213> ORGANISM: Homo sapiens
<220> FEATURE:
<221> NAME/KEY: SITE
<222> LOCATION: (96)
<223> OTHER INFORMATION: Xaa equals any of the naturally occurring L-amino acids
<221> NAME/KEY: SITE
<222> LOCATION: (107)
<223> OTHER INFORMATION: Xaa equals any of the naturally occurring L-amino acids
<221> NAME/KEY: SITE
<222> LOCATION: (111)
<223> OTHER INFORMATION: Xaa equals any of the naturally occurring L-amino acids
<221> NAME/KEY: SITE
<222> LOCATION: (115)
<223> OTHER INFORMATION: Xaa equals any of the naturally occurring L-amino acids
<221> NAME/KEY: SITE

```
<222> LOCATION: (122)
<223> OTHER INFORMATION: Xaa equals any of the naturally occurring
      L-amino acids
<221> NAME/KEY: SITE
<222> LOCATION: (132)
<223> OTHER INFORMATION: Xaa equals any of the naturally occurring
      L-amino acids

<400> SEQUENCE: 169

Met Glu Pro Gln Leu Gly Pro Glu Ala Ala Ala Leu Arg Pro Gly Trp
 1               5                  10                  15

Leu Ala Leu Leu Leu Trp Val Ser Ala Leu Ser Cys Ser Phe Ser Leu
             20                  25                  30

Pro Ala Ser Ser Leu Ser Ser Leu Val Pro Gln Val Arg Thr Ser Tyr
         35                  40                  45

Asn Phe Gly Arg Thr Phe Leu Gly Leu Asp Lys Cys Asn Ala Cys Ile
     50                  55                  60

Gly Thr Ser Ile Cys Lys Lys Phe Phe Lys Glu Ile Arg Ser Asp
 65                  70                  75                  80

Asn Trp Leu Ala Ser His Leu Gly Thr Ala Ser Arg Phe Pro Leu Xaa
                 85                  90                  95

Ser Tyr Pro Cys Lys Leu Leu Gln Met Ile Xaa Lys Ile Trp Xaa Pro
            100                 105                 110

Cys Gly Xaa Leu Leu Thr Gly Gln Gln Xaa Ser Asn Glu Ile Ser Lys
        115                 120                 125

Gln Glu Ile Xaa Cys Leu Leu His Pro Pro Lys Asn Leu His Ile
    130                 135                 140

Asp Val
145

<210> SEQ ID NO 170
<211> LENGTH: 97
<212> TYPE: PRT
<213> ORGANISM: Homo sapiens

<400> SEQUENCE: 170

Gly Pro Arg Ala Arg Val Gln Gly Phe Ser Gly Ala Asp Ile Val Lys
 1               5                  10                  15

Phe Met Ala Leu Gly Ser Met Tyr Leu Val Leu Thr Leu Ile Val Ala
             20                  25                  30

Lys Val Leu Arg Gly Ala Glu Pro Cys Cys Gly Pro Leu Lys Asn Arg
         35                  40                  45

Val Leu Arg Pro Cys Pro Leu Pro Val His Cys Pro Leu Pro Ile Pro
     50                  55                  60

Ser Pro Ala Glu Gly Ile Pro Trp Val Ala Tyr Leu Pro Ile Arg Trp
 65                  70                  75                  80

Phe Ile Ser Cys Cys Pro Gly His Cys Ile Gln Ile Pro Met Cys Thr
                 85                  90                  95

Ser
```

49 HUMAN SECRETED PROTEINS

This application is a continuation application of U.S. application Ser. No. 09/739,254, filed Dec. 19, 2000, now abandoned which is a continuation of Ser. No. 09/511,554 filed Feb. 23, 2000, now abandoned which is a continuation-in-part of, and claims benefit under 35 U.S.C. §120 of copending International patent application Serial No. PCT/US99/19330, filed Aug. 24, 1999, and published in the English language, which is hereby incorporated by reference, which claims benefit under 35 U.S.C. §119(e) based on U.S. Provisional Application Nos. 60/097,917 filed Aug. 25, 1998 and 60/098,634 filed Aug. 31, 1998.

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical diseases, disorders, and/or conditions by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting diseases, disorders, and/or conditions related to the polypeptides and polynucleotides, and therapeutic methods for treating such diseases, disorders, and/or conditions. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a generic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M $NaH_2PO_4$; 0.02M EDTA, pH 7.4), 0.5% SDS, 30% formamide, 100 ug/mil salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention
Features of Protein Encoded by Gene No: 1

The translation product of this gene shares sequence homology with the TAP2 of Rattus norvegicus (See, e.g., Genbank Accession No.gi|407479) AAD15830; all references available through this accession are hereby incorporated by reference herein.) which is thought to be important in antigen presentation in T-cells. As such, the protein product of this gene may be useful for a variety of diagnostic tests for various immune system dysfunctions, and for intervention of the antigen presentation process (e.g., to enhance the immune response to vaccines and diminish the immune response associated with autoimmune disease). The major histocompatibility complex (Mhc) regions of mice, rats, and humans all contain a pair of related genes, TAP1 and TAP2, which encode members of a large superfamily of proteins of similar structure and function. A functional TAP1/TAP2 heterodimer is probably required for efficient presentation of antigens to CD8(+) T cells. This heterodimer resides in the membrane of the endoplasmic reticulum, and transports peptides from the cytoplasm into the endoplasmic reticulum lumen for binding to Mhc class I molecules.

The translation product of this gene also shares sequence homology with the transport-associated proteins and ATP-binding proteins (see, e.g., Genbank accesssion numbers CAB05918 (z83328.1) and AAB95060 (AF040659.1); all references available through these accessions are hereby incorporated by reference herein.)

Preferred polypeptides of the invention comprise the following amino acid sequence:

EPHRGPHLPPDLGHHHGQRPGLQNINVFLRNTVKVTGVVVFMFSLSWQLSLV    (SEQ ID NO: 123)

TFMGFPIIMMVSNIYGKYYKRLSKEVQNALARASNTAEETISAMKTVRSFAN

EEEEAEVYLRKLQQVYKLNRKEAAAYMYYVWGSGLTLLVVQVSILYYGGH

LVISGQMTSGNLIAFIIYEFVLGDCMENVSFSLSPGKVTALVGPSGSGKSSCVN

ILENFYPLEGGRVLLDGKPISAYDHKYLHRVISLVSQEPVLFARSITDNISYGLP

TVPFEMVVEAAQKANAHGFIMELQDGYSTETGEKGAQLSGGQKQRVAWPG

LWCGTPQSSSWMKPPALWMPRASI,

MSSATWTAASWRTSATSTSLTRCWISGQPACTAAACCWGATIGVAKNSALG    (SEQ ID NO: 124)

PRRLRASWLVITLVCLFVGIYAMVKLLLFSEVRRPIRDPWFWALFVWTYISLG

ASFLLWWLLSTVRPGTQALEPGAATEAEGFPGSGRPPPQASGATLQKLLSYT

KPDVAFLVAASFFLIVAALGETFLPYYTGRAIDGIVIQKSMDQFSTAVVIVCLL

AIGSSFAAGIRGGIFTLIFARLNIRLRNCLFRSLVSQETSFFDENRTGDLISRLTS

DTTMVSDLVSRTSMSSCGTQSRSRAWWSSCSASHGSSPWSPSWASPSS, or

HLLRPAHCAFRDGGGGRTEGQCPRLHHGTPGRLQHRDRGEGRPAVRWPEAA    (SEQ ID NO: 125)

GGMARALVRNPPVLILDEATSALDAESEYLIQQAIHGNLQKHTVLIIAHRLST

VEHAHLIVVLDKGRVVQQGTHQQLLAQGGLYAKLVQRQMLGLQPAADFTA

GHNEPVANGSHKA.

Polynucleotides encoding these polypeptides are also encompassed by the invention.

The gene encoding the disclosed cDNA is believed to reside on chromosome 12. Accordingly, polynucleotides related to this invention are useful as a marker in linkage analysis for chromosome 12.

This gene is expressed primarily in brain and testes, and to a lesser extent in amniotic cells, merkel cells and fetal tissue.

Therefore, polynucleotides and polypeptides of the invention are useful as reagents for differential identification of the tissue(s) or cell type(s) present in a biological sample and for diagnosis of diseases and conditions which include, but are not limited to, neural, reproductive, or immune disorders, particularly immunodeficiency, infection, lymphomas, auto-immunities, cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, neural, reproductive, developmental, differentiating, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 67 as residues: His-65 to Cys-73, His-144 to Gly-152. Polynucleotides encoding said polypeptides are also provided.

The major histocompatibility complex (Mhc) regions of mice, rats, and humans all contain a pair of related genes, TAP1 and TAP2, which encode members of a large superfamily of proteins of similar structure and function. A functional TAP1/TAP2 heterodimer is probably required for efficient presentation of antigens to CD8(+) T cells. Furmermore, the tissue distribution in merkel cells and homology to TAP indicates that polynucleotides and polypeptides corresponding to this gene are useful for the diagnosis and treatment of conditions in which antigen presentation is at issue, such as general microbial infection, auto-immunity, inflammation or cancer. Alternatively, expression within brain tissue indicates that polynucleotides and polypeptides corresponding to this gene are useful for the detection/treatment of neurodegenerative disease states, behavioural disorders, or inflamatory conditions such as Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3275 of SEQ ID NO:11, b is an integer of 15 to 3289, where both a and b correspond to the positions of nucleotide residues shown in SEQ ID NO:11, and where b is greater than or equal to a+14.

Features of Protein Encoded by Gene No: 2

The translation product of this gene shares sequence homology with a human retrovirus related env glycoprotein (for examples, see Genbank Accession No. AAD34324 and AAD14546; all references available through this accession are hereby incorporated herein by reference; for example Lindeskog, M., et al. Virology 258 (2), 441–450 (1999) and Blond, J. L., et al., J. Virol. 73 (2), 1175–1185 (1999)). This similarity indicates that the human protein described herein is cell surface protein.

Preferred polypeptides of the invention comprise the following amino acid sequence:

```
RLTKTISFSLQNQTAFINSLAKTPYQALTGAALAGSYPIWENENTLSWYLPSPT    (SEQ ID NO: 126)

TLLSPPVLFCVIQLIFXLPANWSGTCTLVFQAPTINILPPNQTILISVEASISSSPIR

NKWALHLITLLTGLGITAALGTGIAGITTSITSYQTLFTTLSNTVEDMHTSITSL

QRQLDFLVGVILQNWRVLDLLTTEKGGTCIYLQEECCFCVNESGIVHIAVRRL

HDRAAEL,

YPIWENENTLSWYLPSPTTLLSPPVLFCV,                            (SEQ ID NO: 127)

or,

RVLDLLTTEKGGTCIYLQEECCFCVNE.                              (SEQ ID NO: 128)
```

Polynucleotides encoding these polypeptides are also provided.

Further, the gene encoding the disclosed cDNA is believed to reside on the X chromosome. Accordingly, polynucleotides related to this invention are useful as a marker in linkage analysis for the X chromosome.

This gene is expressed primarily in human prostate cancer (stage C fraction), subtracted kidney cortex, adult brain and breast, and to a lesser extent in a variety of normal and transformed tissue types.

Therefore, polynucleotides and polypeptides of the invention are useful as reagents for differential identification of the tissue(s) or cell type(s) present in a biological sample and for diagnosis of diseases and conditions which include, but are not limited to, anti-viral therapies, including cancer and other proliferative diseases and/or disorders. Similarly, polypeptides and antibodies directed to these polypeptides are useful in providing immunological probes for differential identification of the tissue(s) or cell type(s). For a number of disorders of the above tissues or cells, particularly of the prostate, kidney, brain and breast, expression of this gene at significantly higher or lower levels may be routinely detected in certain tissues or cell types (e.g., reproductive, neural, endocrine, and cancerous and wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 68 as residues: Ser-28 to Ser-37, Ser-50 to Ser-58. Polynucleotides encoding said polypeptides are also provided.

The tissue distribution in various transformed tissues, combined with its similarity to retroviral env proteins indicates that the protein product is useful for the detection, diagnosis, and treatment of a variety of cancers and other proliferative disorders. This gene may show utility in gene therapy applications in viral prophylaxis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2328 of SEQ ID NO:12, b is an integer of 15 to 2342, where both a and b correspond to the positions of nucleotide residues shown in SEQ ID NO:12, and where b is greater than or equal to a+14.

Features of Protein Encoded by Gene No: 3

The translation product of this gene shares sequence homology with Cytochrome P450 monooxygenase which is thought to be important in NADPH-dependent oxidation of a number of cellular substrates (See Genbank Accession Nos. gi|1185452, gb|AAC50370.1, and gb|AAB87635.1, in addition to Geneseq Accession No. R72378; all information and references available through these accessions are hereby incorporated herein by reference). The polypeptide of this gene has been determined to have a transmembrane domain at about amino acid position 11–27 of the amino acid sequence referenced in Table 1 for this gene. Moreover, a cytoplasmic tail encompassing amino acids 28 to 501 of this protein has also been determined. Based upon these characteristics, it is believed that the protein product of this gene shares structural features to type Ib membrane proteins. Included in this invention as a preferred domain is the cytochrome P450 cysteine heme-iron ligand signature domain, which was identified using the ProSite analysis tool (Swiss Institute of Bioinformatics). Cytochrome P450's [1, 2, 3] are a group of enzymes involved in the oxidative metabolism of a high number of natural compounds (such as steroids, fatty acids, prostaglandins, leukotrienes, etc) as well as drugs, carcinogens and mutagens. Based on sequence similarities, P450's have been classified into about forty different families [4,5]. P450's are proteins of 400 to 530 amino acids; the only exception is Bacillus BM-3 (CYP102) which is a protein of 1048 residues that contains a N-terminal P450 domain followed by a reductase domain. P450's are heme proteins. A conserved cysteine residue in the C-terminal part of P450's is involved in binding the heme iron in the fifth coordination site. From a region around this residue, we developed a ten residue signature specific to P450's. The concensus pattern is as follows: [FW]-[SGNH]-x-[GD]-x-[RHPT]-x-C-[LIVMFAP]-[GAD] [C is the heme iron ligand].

Preferred polypeptides of the invention comprise the following amino acid sequence: FSLGRRHCLG (SEQ ID NO: 129). Polynucleotides encoding these polypeptides are also provided. Further preferred are polypeptides comprising the cytochrome P450 cysteine heme-iron ligand signature domain of the sequence referenced in Table 1 for this gene, and at least 5, 10, 15, 20, 25, 30, 50, or 75 additional contiguous amino acid residues of this referenced sequence. The additional contiguous amino acid residues may be N-terminal or C-terminal to the cytochrome P450 cysteine heme-iron ligand signature domain. Alternatively, the additional contiguous amino acid residues may be both N-terminal and C-terminal to the cytochrome P450 cysteine heme-iron ligand signature domain, wherein the total N- and C-terminal continuous amino acid residues equal the specified number. The above preferred polypeptide domain is characteristic of a signature specific to cytochrome P450 cysteine heme-iron proteins. Based on the sequence similarity, the translation product of this gene is expected to share at least some biological activities with cytochrome P450 cysteine heme-iron proteins. Such activities are known in the art, some of which are described elsewhere herein. The following references were reference above and are hereby incorporated by reference herein: [1] Nebert D. W., Gonzalez F. J. Annu. Rev. Biochem. 56:945–993(1987). [2] Coon M. J., Ding X., Pemecky S. J., Vaz A. D. N. FASEB J. 6:669–673(1992). [3] Guengerich F. P. J. Biol. Chem. 266:10019–10022(1991).[4] Nelson D. R., Kamataki T., Waxman D. J., Guengerich F. P., Estrabrook R. W., Feyereisen R., Gonzalez F. J., Coon M. J., Gunsalus I. C., Gotoh O., Okuda K., Nebert D. W. DNA Cell Biol. 12:1–51(1993).[5] Degtyarenko K. N., Archakov A. I. FEBS Lett. 332:1–8 (1993).

When tested against Jurket T-cells and U937 cell lines, supernatants removed from cells containing this gene activated the GAS (gamma activation site) promoter element. Thus, it is likely that this gene activates T-cells and myeloid cells through the Jaks-STAT signal transduction pathway. GAS is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the GAS element, can be used to indicate proteins involved in the proliferation and differentiation of cells.

The gene encoding the disclosed cDNA is believed to reside on chromosome 11. Accordingly, polynucleotides related to this invention are useful as a marker in linkage analysis for chromosome 11.

This gene is expressed primarily in fetal liver spleen, and to a lesser extent in lung, LNCAP prostate cell line, control synovial fibroblasts, human testes tumor, and Hodgkin's lymphoma.

Therefore, polynucleotides and polypeptides of the invention are useful as reagents for differential identification of the tissue(s) or cell type(s) present in a biological sample and for diagnosis of diseases and conditions which include, but are not limited to, hepatic or developmental diseases and/or disorders, particularly cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the liver, spleen, lung, prostate, testes, and lymphatic system, expression of this gene at significantly higher or lower levels may be routinely detected in certain tissues or cell types (e.g., liver, spleen, developmental, reproductive, and cancerous and wounded tissues) or bodily fluids (e.g., lymph, bile, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 69 as residues: Leu-30 to Gly-38, Arg-67 to Val-72, Ser-127 to Trp-133, Gly-148 to Phe-154, Thr-171 to Phe-177, Thr-201 to Asp-206, Ser-265 to Pro-273, Glu-283 to Lys-297, Pro-346 to Lys-357, Phe-409 to Glu-418, Glu-423 to Ser-428, Leu-443 to Cys-448. Polynucleotides encoding said polypeptides are also provided.

The tissue distribution in fetal liver and homology to cytochrome P450 monooxygenase indicates indicates that polynucleotides and polypeptides corresponding to this gene are useful for the detection and treatment of liver disorders and cancers (e.g., hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma. The secreted protein can also be used to determine biological activity, to raise antibodies, as tissue markers, to isolate cognate ligands or receptors, to identify agents that modulate their interactions and as nutritional supplements. It may also have a very wide range of biological acitivities. Representative uses are described in the "Chemotaxis" and "Binding Activity" sections below, in Examples 11, 12, 13, 14, 15, 16, 18, 19, and 20, and elsewhere herein. Briefly, the protein may possess the following activities: cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1652 of SEQ ID NO:13, b is an integer of 15 to 1666, where both a and b correspond to the positions of nucleotide residues shown in SEQ ID NO:13, and where b is greater than or equal to a+14.

Features of Protein Encoded by Gene No: 4

The translation product of this gene shares sequence homology with C1qR(P), the human C1q/MBL/SPA receptor that mediates enhanced phagocytosis in vitro (see, e.g., Genbank Accesion number AAB53110.1 (U94333.1); all references available through this accession are hereby incorporated by reference herein. Also see, Immunity 1997 February; 6(2):119–129). Preferred polypeptides encoded by this gene comprise one or more of the following amino acid sequences:

```
EHPTADRAGCSASGACYSLHHATMKRQAAEEACILRGGALSTVRAGAELRA         (SEQ ID NO: 130)

VLALLRAGPGPGXGSKDLLFWVALERRRSHCXLENEPLRGFSWLSSDPGGLE

SDTLQWVEEPQRSCTARRWV, and/or

SRPPVGSSPQLEGDAMPPXRQRYLCKYQFEVLCPAPRPGAASNLSYRAPFQL         (SEQ ID NO: 131)

HSAALDFSPPGTEVSALCRGQLPISVTCIADEIGARWDKLSGDVLCPCPGRYL

HSAALDFSPPGTEVSALCRGQLPISVTCIADEIGARWDKLSGDVLCPCPGRYL

RAGKCAELPNCLDDLGGFACECATGFELGKDGRSCVTSGEGQPTLGGTGVPT

RRPPATATSPVPQRTWPIRVDEKLGETPLVPEQDNSVTSIPEIPRWGSQSTMST

LQMSLQAESKATITPSGSVISKFNSTTSSATPQAFDSSSAVVFIFVSTAVVVLVI

LTMTVLGLVKLCFHESPSSQPRKESMGPPGWRVILKPAALGSSSAHCTNNGV

KVGDCDLRDRAEGALLAESPLGSSDA.
```

Polynucleotides encoding such polypeptides are also provided.

This gene is believed to reside on chromosome 14. Therefore, polynucleotides and polypeptides related to this gene are useful in linkage analysis as markers for chromosome 14.

This gene is expressed primarily in chondrosarcoma, smooth muscle tissue, bone marrow, chondrosarcoma, fetal tissue (e.g., heart) and to a lesser extent in ovarian cancer, adult pulmonary tissues, and brain.

Therefore, polynucleotides and polypeptides of the invention are useful as reagents for differential identification of the tissue(s) or cell type(s) present in a biological sample and for diagnosis of diseases and conditions which include, but are not limited to, chondrosarcoma, immune disorders, ovarian cancer, respiratory and gastrointestinal disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 70 as residues: Pro-18 to Gly-30. Polynucleotides encoding said polypeptides are also provided.

The tissue distribution in bone marrow and homology to C1qR(P) indicates that polynucleotides and polypeptides corresponding to this gene are useful for diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells indicates this protein may play a role in the regulation of cellular division, and may show utility in the diagnosis, treatment, and/or prevention of developmental diseases and disorders, including cancer (e.g., ovarian, chondrosarcoma), and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Alternatively, the protein is useful in the detection, treatment, and/or prevention of vascular conditions, which include, but are not limited to, microvascular disease, vascular leak syndrome, aneurysm, stroke, atherosclerosis, arteriosclerosis, or embolism. For example, this gene product may represent a soluble factor produced by smooth muscle that regulates the innervation of organs or regulates the survival of neighboring neurons. Likewise, it is involved in controlling the digestive process, and such actions as peristalsis. Similarly, it is involved in controlling the vasculature in areas where smooth muscle surrounds the endothelium of blood vessels. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2013 of SEQ ID NO:14, b is an integer of 15 to 2027, where both a and b correspond to the positions of nucleotide residues shown in SEQ ID NO:14, and where b is greater than or equal to a+14.

Features of Protein Encoded by Gene No: 5

The translation product of this gene shares sequence homology with human renal dipeptidase, which is a glycosyl-phosphatidylinositol-anchored ectoenzyme thought to be important in the metabolism of dihydro peptide bonds (See Genbank Accession No.bbs|148378; dbj|BAA02433.1; gb|AAB59410.1; dbj|BAA02431.1; and Geneseq Accession Nos. W29665 and R30823; all information and references available through these accessions are hereby incorporated herein by reference). Included in this invention as a preferred domain is the renal dipeptidase active site domain, which was identified using the ProSite analysis tool (Swiss Institute of Bioinformatics). Renal dipeptidase (rDP) ($EC_{3.4.13.19}$), also known as microsomal dipeptidase, is a zinc-dependent metalloenzyme which hydrolyzes a wide range of dipeptides. It is involved in renal metabolism of glutathione and its conjugates. It is a homodimeric disulfide-linked glycoprotein attached to the renal brush border microvilli membrane by a GPI-anchor. A glutamate residue has recently been shown [1] to be important for the catalytic activity of rDP. RDP seems to be evolutionary related to hypothetical proteins in the PQQ biosynthesis operons of *Acinetobacter calcoaceticus* and *Klebsiella pneumoniae*. The concensus pattern is as follows: [LIVM]-E-G-[GA]-x(2)-[LIVMF]-x(6)-L-x(3)-Y-x(2)-G-[LIVM]-R [E is the active site residue].

Preferred polypeptides of the invention comprise the following amino acid sequence: VEGGHSLDNSLSILRT-FYMLGVR (SEQ ID NO: 137). Polynucleotides encoding these polypeptides are also provided. Further preferred are polypeptides comprising the renal dipeptidase active site domain of the sequence referenced in Table for this gene, and at least 5, 10, 15, 20, 25, 30, 50, or 75 additional contiguous amino acid residues of this referenced sequence. The additional contiguous amino acid residues may be N-terminal or C-terminal to the renal dipeptidase active site domain. Alternatively, the additional contiguous amino acid residues may be both N-terminal and C-terminal to the renal dipeptidase active site domain, wherein the total N- and C-terminal contiguous amino acid residues equal the specified number. The above preferred polypeptide domain is characteristic of a signature specific to renal dipeptidase proteins. Based on the sequence similarity, the translation product of this gene is expected to share at least some biological activities with renal dipeptidase proteins. Such activities are known in the art, some of which are described elsewhere herein. The following references were referenced above and are hereby incorporated herein by reference: [1] Adachi H., Katayama T., Nakazato H., Tsujimoto M. Biochim. Biophys. Acta 1163:42–48(1993) and [2] Rawlings N. D., Barrett A. J. Meth. Enzymol. 248:183–228(1995). The polypeptide of this gene has been determined to have two transmembrane domains at about amino acid position 17–33 and 470–486 of the amino acid sequence referenced in Table 1 for this gene. Based upon these characteristics, it is believed that the protein product of this gene shares structural features to type IIIb membrane proteins.

When tested against Jurket T-cell cell lines, supernatants removed from cells containing this gene activated the GAS (gamma activation site) and NF-kB (Nuclear Factor kB) pathway. Thus, it is likely that this gene activates T-cells through the Jaks-STAT signal transduction pathway and may be involved in the activation of apoptosis. GAS is a promoter element found upstream in many genes which are involved in the Jaks-STAT pathway. The Jaks-STAT pathway is a large, signal transduction pathway involved in the differentiation and proliferation of cells. Therefore, activation of the Jaks-STATs pathway, reflected by the binding of the GAS element, can be used to indicate proteins involved in the proliferation and differentiation of cells. Similarly, NF-kB is a transcription factor activated by a wide variety of agents, leading to cell activation, differentiation, or apoptosis. Reporter constructs utilizing the NF-KB promoter element are used to screen supernatants for such activity.

Preferred polypeptides of the invention comprise the following amino acid sequence: RYLTLTH (SEQ ID NO: 132), CNTPWA (SEQ ID NO: 133), APVIFSHS (SEQ ID NO: 134), RNVPDD (SEQ ID NO: 135), GLEDVS (SEQ ID NO: 136), or VEGGHS (SEQ ID NO: 138). Polynucleotides encoding these polypeptides are also encompassed by the invention.

The gene encoding the disclosed cDNA is believed to reside on chromosome 16. Accordingly, polynucleotides related to this invention are useful as a marker in linkage analysis for chromosome 16.

This gene is expressed primarily in infant brain, and to a lesser extent, in primary dendritic cells, L428 cells, melanocytes, keratinocytes, eosinophils, ovarian tumor, thymus stromal cells, treated bone marrow, and Hodgkins lymphoma, and (to a lesser extent) in a variety of other normal and transformed cell types.

Therefore, polynucleotides and polypeptides of the invention are useful as reagents for differential identification of the tissue(s) or cell type(s) present in a biological sample and for diagnosis of diseases and conditions which include, but are not limited to, renal, urogenital, or neural disorders, particularly neurodegenerative and/or developmental disorders of the brain, including cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the immune and neurological systems, expression of this gene at significantly higher or lower levels may be routinely detected in certain tissues or cell types (e.g., immune, neural, renal, urogenital, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 71 as residues: Thr-36 to Arg-41, Pro-55 to Pro-60, Pro-67 to Leu-72, Asn-111 to Ser-118, Cys-138 to Asp-144, Asn-290 to Pro-296, Gly-350 to Phe-358, Gly-379 to Glu-384, Gln-399 to Cys-426, Ser-428 to Ser-438. Polynucleotides encoding said polypeptides are also provided.

The tissue distribution combined with its homology to the human renal dipeptidase indicates that this gene or gene product could be used in the treatment and/or detection of kidney diseases including renal failure, nephritis, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Representative uses are described here and elsewhere herein.

Alternatively, the tissue distribution in brain indicates that polynucleotides and polypeptides corresponding to this gene are useful for the detection/treatment of neurodegenerative disease states and behavioural disorders such as Alzheimer's Disease, Parkinson's Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Moreover, expression within embryonic tissue and other cellular sources marked by proliferating cells combined with the detected GAS and NF-KB biological activity indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2320 of SEQ ID NO:15, b is an integer of 15 to 2334, where both a and b correspond to the positions of nucleotide residues shown in SEQ ID NO:15, and where b is greater than or equal to a+14.

Features of Protein Encoded by Gene No: 6

Preferred polypeptides of the invention comprise the following amino acid sequence:

| | |
|---|---|
| TWLRLGSSQIWLGTAPRGPRIHPEQAGLAGAPVKSTSSEESQPGGQCQ | (SEQ ID NO: 139) |
| SSGGAQTLPSLRAAPVAALGSLSSYPDSCPRATTPELCPGAPTLHLADSISGPV | |
| SPPGSSLGPDAWTLCAKHHQAKGMTLGTPKVLRLQPVSPCWGPKSWRVPGP | |
| FQPGRRRGESRQQGRGKRRSARSAQSPTGPESAAWPC, | |
| TVATACVWAACTGCWARPPVPTWAGCAARCAAEDARAGVGDLPATGGAA | (SEQ ID NO: 140) |
| TGRRALTPAPPRGPCILSPQPWALGLPGAPLPAALPGRARGRPGLPALPALSTL | |
| PGCPALDPAGAGTLCPPPGAAEPAGP, | |
| or | |
| RSGQPEGSMLRKFSLQRLLSPLDQAQTRWGLALACVAGDKGPPRPWNISSA | (SEQ ID NO: 141) |
| PAHPHVTTGMETSGGPARDGGLILEREAAFNKPAPGE. | |

Polynucleotides encoding these polypeptides are also encompassed by the invention.

This gene is expressed primarily in immune cells (e.g., eosinophils, T-cells, and macrophage), leukemic and lymphoid cells, rectum, colon, and tonsils.

Therefore, polynucleotides and polypeptides of the invention are useful as reagents for differential identification of the tissue(s) or cell type(s) present in a biological sample and for diagnosis of diseases and conditions which include, but are not limited to, inflammatory disorders, particularly immunodeficiency, tumor necrosis, infection, lymphomas, auto-immunities, breast cancer, disorders of the colon and rectum, metastasis, inflammation, anemias (leukemia) and other hematopoeitic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product is involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Additionally, expression of this gene product in a variety of immune cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersentivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types.

The tissue distribution in kidney indicates the protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2594 of SEQ ID NO:16, b is an integer of 15 to 2608, where both a and b correspond to the positions of nucleotide residues shown in SEQ ID NO:16, and where b is greater than or equal to a+14.

Features of Protein Encoded by Gene No: 7

The translation product of this gene shares sequence homology with the human IgE receptor which is thought to be important in immune regulation, particularly in immune cell aggregation (See Genbank Accession No gi|337418; all references available through this accession are hereby incorporated herein by reference). Moreover, the protein is believed to share structural features to the TM4SF superfamily of proteins. The polypeptide of this gene has been determined to have two transmembrane domains at about amino acid position 73–89 and 106–122 of the amino acid sequence referenced in Table 1 for this gene. Based upon these characteristics, it is believed that the protein product of this gene shares structural features to type IIIa membrane proteins. Based on the sequence similarity, the translation product of this gene is expected to share at least some biological activities with human IgE receptor proteins. Such activities are known in the art, some of which are described elsewhere herein.

In another embodiment, polypeptides comprising the amino acid sequence of the open reading frame upstream of the predicted signal peptide are contemplated by the present invention. Specifically, polypeptides of the invention comprise the following amino acid sequence:

```
RCQRNKDIMMSSKPTSHAEVNETIPNPYPPSSFMAPGFQQPLGSINLENQAQG        (SEQ ID NO: 142)

AQRAQPYGITSPGIFASSQPGQGNIQMINPSVGTAVMNFKEEAKALGVIQIMV

GLMHIGFGIVLCLISFSFREVLGFASTAXIGGYFWGGLSFIISGSLSVSASKELS

RCLVKGSLGMNIGRSILAFIGVILLLVDMCINGVXGQDYWXVLSGKGISATL

MIFSXLEFFVACATAHFANQANTTTNMSVLVIPNMYESNPXTPASSSAPPRCN

NYSANAPKRKRGISLISWRKTTCKNFLRRCLLLSTMISSL.
```

Polynucleotides encoding these polypeptides are also provided.

This gene is expressed primarily in colon.

Therefore, polynucleotides and polypeptides of the invention are useful as reagents for differential identification of the tissue(s) or cell type(s) present in a biological sample and for diagnosis of diseases and conditions which include, but are not limited to, immune disorders and disorders of the digestive tract. Similarly, polypeptides and antibodies directed to these polypeptides are useful in providing immunological probes for differential identification of the tissue(s) or cell type(s). For a number of disorders of the above tissues or cells, particularly of the immune and digestive system, expression of this gene at significantly higher or lower levels may be routinely detected in certain tissues or cell types (e.g., immune, hematopoietic, gastrointesinal, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 73 as residues: Met-2 to Ser-8, Glu-14 to Ser-23, Leu-39 to Gly-53. Polynucleotides encoding said polypeptides are also provided.

The tissue distribution and homology to the human IgE receptor indicates that that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Expression of this gene product in colon indicates a role in the regulation of the proliferation; survival; differentiation; and/or activation of proliferative mechanisms in the digestive tract. This gene product may be involved in the regulation of cytokine production, antigen presentation, or other processes that may also suggest a usefulness in the treatment of cancer (e.g., by boosting immune responses). Since the gene has homology to a gene of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1277 of SEQ ID NO:17, b is an integer of 15 to 1291, where both a and b correspond to the positions of nucleotide residues shown in SEQ ID NO:17, and where b is greater than or equal to a+14.

Features of Protein Encoded by Gene No: 8

This gene is expressed primarily in T-cells and lymph node.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly immuodeficiencies or inflammatory disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells and lymph node indicates that polynucleotides and polypeptides corresponding to this gene are useful for the diagnosis and treatment of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3115 of SEQ ID NO:18, b is an integer of 15 to 3129, where both a and b correspond to the positions of nucleotide residues shown in SEQ ID NO:18, and where b is greater than or equal to a+14.

Features of Protein Encoded by Gene No: 9

The gene encoding the disclosed cDNA is believed to reside on chromosome 2. Accordingly, polynucleotides related to this invention are useful as a marker in linkage analysis for chromosome 2.

This gene is expressed primarily in immune and haemopoietic cells, particularly messangial cells.

Therefore, polynucleotides and polypeptides of the invention are useful as reagents for differential identification of the tissue(s) or cell type(s) present in a biological sample and for diagnosis of diseases and conditions which include, but are not limited to, immune or haemopoietic diseases. Similarly, polypeptides and antibodies directed to these polypeptides are useful in providing immunological probes for differential identification of the tissue(s) or cell type(s). For a number of disorders of the above tissues or cells, particularly of the immune and haemopoitic systems, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells and hemopoeitic cells indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3615 of SEQ ID NO:19, b is an integer of 15 to 3629, where both a and b correspond to the positions of nucleotide residues shown in SEQ ID NO:19, and where b is greater than or equal to a+14.

Features of Protein Encoded by Gene No: 10

The translation product of this gene shares sequence homology with various dehydrogenase and oxidoreductase polypeptides and appears to belong in the alcohol dehydrogenase Irybitol dehydrogenase family (see, e.g., Genbank accession number AAD36790.1 (AE001811.1) and CAA68181 (X99908.1); all references available through this accession are hereby incorporated by reference herein.) Preferred polypeptides encoded by this gene comprise the following amino acid sequence:

```
MGRLDGKVIILTAAAQGIGQAAALAFAREGAKVIATDINESKLQELEKYPGIQ      (SEQ ID NO: 143)

TRVLDVTKKKQIDQFANEVERLDVLFNVAGFVHHGTVLDCEEKDWDFSMNL

NVRNVMYLMIKAFLPKMLAQKSGNIINMSSVASSVKGVVNRCVYSTTKAAV

IGLTKSVAADFIQQGIRCNCVCPGTVDTPSLQERIQARGNPEEARNDFLKRQK

TGRFATAEEIAMLCVYLASDESAYVTGNPVIIDGGWSL.
```

Also provided are fragments thereof having dehydrogenase activity and polypeptides comprising at least 30 residues of the foregoing amino acid sequence. Polynucleotides encoding such polypeptides are also provided.

This gene is expressed primarily in fetal tissue (e.g., liver, spleen, lung), gall bladder, heart, bone marrow and to a lesser extent in smooth muscle, and parathyroid tumor.

Therefore, polynucleotides and polypeptides of the invention are useful as reagents for differential identification of the tissue(s) or cell type(s) present in a biological sample and for diagnosis of diseases and conditions which include, but are not limited to, immune, cardiovascular and developmental disorders. Similarly, polypeptides and antibodies directed to these polypeptides are useful in providing immunological probes for differential identification of the tissue(s) or cell type(s). For a number of disorders of the above tissues or cells, particularly of the immune and fetal systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 76 as residues: Pro-78 to Gln-85, Arg-87 to Arg-94, Asp-96 to Gly-104. Polynucleotides encoding said polypeptides are also provided.

The tissue distribution in bone marrow indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1130 of SEQ ID NO:20, b is an integer of 15 to 1144, where both a and b correspond to the positions of nucleotide residues shown in SEQ ID NO:20, and where b is greater than or equal to a+14.

Features of Protein Encoded by Gene No: 11

The polypeptide of this gene has been determined to have a transmembrane domain at about amino acid position 115–131 of the amino acid sequence referenced in Table 1 for this gene. Moreover, a cytoplasmic tail encompassing amino acids 132 to 152 of this protein has also been determined. Based upon these characteristics, it is believed that the protein product of this gene shares structural features to type Ia membrane proteins.

In another embodiment, polypeptides comprising the amino acid sequence of the open reading frame upstream of the predicted signal peptide are contemplated by the present invention. Specifically, polypeptides of the invention comprise the following amino acid sequence:

```
GTIGLLYWVGSIIMSVVVFVPGNIVGKYGTRICPAFFLSIPYTCLPVWAGFRIYN     (SEQ ID NO: 144)

QPSENYNYPSKVIQEAQAKDLLRRPFDLMLVVCLLLATGFCLFRGLIALDCPS

ELCRLYTQFQEPYLKDPAAYPKIQMLAYMFYSVPYFVTALYGLVVPGCSWM

PDITLIHAGGLAAQFSHIGASLHARTAYVYRVPEEAKILFLALNIAYGVLP

QLLAYRCIYKPEFFIKTAKAEEKVE.
```

Polynucleotides encoding these polypeptides are also provided.

This gene is expressed primarily in osteoclastoma, and to a lesser extent, in other human tissues.

Therefore, polynucleotides and polypeptides of the invention are useful as reagents for differential identification of the tissue(s) or cell type(s) present in a biological sample and for diagnosis of diseases and conditions which include, but are not limited to, skeletal diseases and/or disorders, particularly osteoclastoma and osteoporosis. Similarly, polypeptides and antibodies directed to these polypeptides are useful in providing immunological probes for differential identification of the tissue(s) or cell type(s). For a number of disorders of the above tissues or cells, particularly of the skeletal system, expression of this gene at significantly higher or lower levels may be routinely detected in certain tissues or cell types (e.g., skeletal, immune, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 77 as residues: Thr-32 to Lys-40, Lys-146 to Glu-152. Polynucleotides encoding said polypeptides are also provided.

The tissue distribution in osteoclastoma indicates a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). Representative uses are described here and elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1429 of SEQ ID NO:21, b is an integer of 15 to 1443, where both a and b correspond to the positions of nucleotide residues shown in SEQ ID NO:21, and where b is greater than or equal to a+14.

Features of Protein Encoded by Gene No: 12

The polypeptide of this gene has been determined to have transmembrane domains at about amino acid position 1–23 and 149–167 of the amino acid sequence referenced in Table 1 for this gene. Based upon these characteristics, it is believed that the protein product of this gene shares structural features to type IIIb membrane proteins.

Preferred polypeptides of the invention comprise the following amino acid sequence:

MSNHDPRGCTRRRAQKPLAIQPRLFHASAPDEGTQKGGCILVQCQ (SEQ ID NO: 145)

SEGGAAGAWTGPPSPARDRRVRPPGTKAQRLERRRHVPRLHGLGVGGCEVR

TGIVARISGSTPWAGGKPLGLHGAMGEAGAGDTGCCAKGPSPAAPLPAEGRG

QGAGPGGLVGRGERRDQQTLLGMAEDTGXPSRPSAPAPRAPVPARQPLPRA

RLGAATAISKSRSSRVAPALAAAISASSHQR.

Polynucleotides encoding these polypeptides are also encompassed by the invention.

This gene is expressed primarily in neutrophils, haemopoietic cells, tymus tumor, osteosarcoma, synovial sarcoma, B-cell lymphoma, dendritic cells, pineal gland, brain, prostate and to a lesser extent in other tissues, including cancers.

Therefore, polynucleotides and polypeptides of the invention are useful as reagents for differential identification of the tissue(s) or cell type(s) present in a biological sample and for diagnosis of diseases and conditions which include, but are not limited to, immune and haemopoietic disorders, particularly neutropenia or neutrophilia, and cancers. Similarly, polypeptides and antibodies directed to these polypeptides are useful in providing immunological probes for differential identification of the tissue(s) or cell type(s). For a number of disorders of the above tissues or cells, particularly of the immune and haemopoietic systems, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 78 as residues: Ser-23 to Ala-32, Gly-40 to Glu-47. Polynucleotides encoding said polypeptides are also provided.

The tissue distribution in immune cells (e.g., neutrophils) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Expression of this gene product in tonsils also indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses).

The tissue distribution in pineal gland and brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The tissue distribution in thymus tumor, B-cell lymphoma, osteosarcoma, and synovial sarcoma indicates polynucleotides and polypeptides corresponding to this gene are useful for the diagnosis and treatment of these and related diseases.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1039 of SEQ ID NO:22, b is an integer of 15 to 1053, where both a and b correspond to the positions of nucleotide residues shown in SEQ ID NO:22, and where b is greater than or equal to a+14.

Features of Protein Encoded by Gene No: 13

The translation product of this gene shares sequence homology with lymphoblastic leukemia antigen, which is thought to be important in cancers including leukemia. The polypeptide of this gene has been determined to have a transmembrane domain at about amino acid position 46–62 of the amino acid sequence referenced in Table 1 for this gene. Moreover, a cytoplasmic tail encompassing amino acids 63 to 69 of this protein has also been determined. Based upon these characteristics, it is believed that the protein product of this gene shares structural features to type Ia membrane proteins.

This gene is expressed primarily in lung, and infant adrenal gland.

Therefore, polynucleotides and polypeptides of the invention are useful as reagents for differential identification of the tissue(s) or cell type(s) present in a biological sample and for diagnosis of diseases and conditions which include, but are not limited to, disorders of the pulmonary and endocrine system, including cancers and developmental diseases and/or disorders. Similarly, polypeptides and antibodies directed to these polypeptides are useful in providing immunological probes for differential identification of the tissue(s) or cell type(s). For a number of disorders of the above tissues or cells, particularly of the pulmonary and endocrine systems, expression of this gene at significantly higher or lower levels may be routinely detected in certain tissues or cell types (e.g., pulmonary, endocrine, developmental, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adrenal gland indicates that polynucleotides and polypeptides corresponding to this gene are useful for the detection, treatment, and/or prevention of various endocrine disorders and cancers. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Similarly, expression within fetal tissues and other cellular sources marked by proliferating cells, combined with the homology to the human lymphoblastic leukaemia antigen, indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 727 of SEQ ID NO:23, b is an integer of 15 to 741, where both a and b correspond to the positions of nucleotide residues shown in SEQ ID NO:23, and where b is greater than or equal to a+14.

Features of Protein Encoded by Gene No: 14

This gene is expressed primarily in human tonsils.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic diseases and/or disorders, particularly leukemia and cancers. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 80 as residues: Gly-33 to Arg-40, Ser-106 to Met-112, Ala-154 to Gly-163. Polynucleotides encoding said polypeptides are also provided.

The tissue distribution in tonsils indicates that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Expression of this gene product indicates a role in the regulation of the proliferation; survival; differentiation; and/ or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory conditions such as inflammatory bowel disease, sepsis, acne, and psoriasis.and tissues. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 932 of SEQ ID NO:24, b is an integer of 15 to 946, where both a and b correspond to the positions of nucleotide residues shown in SEQ ID NO:24, and where b is greater than or equal to a+14.

Features of Protein Encoded by Gene No: 15

The polypeptide of this gene has been determined to have two transmembrane domains at about amino acid position 49–65 and 141–157 of the amino acid sequence referenced in Table 1 for this gene. Based upon these characteristics, it is believed that the protein product of this gene shares structural features to type IIIa membrane proteins.

In another embodiment, polypeptides comprising the amino acid sequence of the open reading frame upstream of the predicted signal pep tide are contemplated by the present invention. Specifically, polypeptides of the invention comprise the following amino acid sequence:

```
STXTXTIGXAGTPAGTGPEFPGRPTRPGEXPVDFSKQYSASWMCLSLLAALA        (SEQ ID NO: 146)

CSAGDTWASEVGPVLSKSSPRLITTWEKVPVGTNGGVTVVGLVSSLLGGTFV

GIAYFLTQLIFVNDLDISAPQWPIIAFGGLAGLLGSIVDSYLGATMQYTGLDES

TGMVVNSPTNXARHIAGKPILDNNAVNLFSSVLIALLLPTAAWGFWPRG.
```

Polynucleotides encoding these polypeptides are also provided.

This gene is expressed primarily in colon, brain, and to a lesser extent, in epiglottis.

Therefore, polynucleotides and polypeptides of the invention are useful as reagents for differential identification of the tissue(s) or cell type(s) present in a biological sample and for diagnosis of diseases and conditions which include, but are not limited to, diseases and/or disorders of the central nervous system and gastrointestinal or digestive tract. Similarly, polypeptides and antibodies directed to these polypeptides are useful in providing immunological probes for differential identification of the tissue(s) or cell type(s). For a number of disorders of the above tissues or cells, particularly of the digestive and central nervous system, expression of this gene at significantly higher or lower levels may be routinely detected in certain tissues or cell types (e.g., gastrointesinal, neural, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for the detection/treatment of neurodegenerative disease states and behavioural disorders. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntingtons Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. The protein product of this gene may also be useful for the detection, treatment, or prevention of a variety of gastrointestinal and digestive tract disorders, particularly proliferative disorders, such as ulcers and cancers. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 817 of SEQ ID NO:25, b is an integer of 15 to 831, where both a and b correspond to the positions of nucleotide residues shown in SEQ ID NO:25, and where b is greater than or equal to a+14.

Features of Protein Encoded by Gene No: 16

The polypeptide of this gene has been determined to have a transmembrane domain at about amino acid position 21–39 of the amino acid sequence referenced in Table 1 for this gene. Moreover, a cytoplasmic tail encompassing amino acids 4041 of this protein has also been determined. Based upon these characteristics, it is believed that the protein product of this gene shares structural features to type Ia membrane proteins. Preferred polypeptides comprise the following amino acid sequence:

and tonsillular neoplasms. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, saliva, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for the diagnosis and treatment of a variety of immune system disorders. Expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersentivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence data-

MSQRAGRRPGGWNPSLSVVEVCRGCRGTGPLPWGASLFPCSASPLFPLPLNR     (SEQ ID NO: 147)

RGDVHGTLGGRMLNRVECRDGVAAAWLCLHDAAAIRGAVGRCPMWTQPT

HWVLLLCWALHFYCR

Also preferred are the polynucleotides encoding these polypeptides.

This gene is expressed primarily in tonsils.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly tonsilitis bases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1280 of SEQ ID NO:26, b is an integer of 15 to 1294, where both a and b correspond to the positions of nucleotide residues shown in SEQ ID NO:26, and where b is greater than or equal to a+14.

Features of Protein Encoded by Gene No: 17

The gene encoding the disclosed cDNA is believed to reside on chromosome 9. Accordingly, polynucleotides related to this invention are useful as a marker in linkage analysis for chromosome 9.

This gene is expressed primarily in fetal tissue (e.g., bone, liver, spleen), smooth muscle, chondrosarcoma, osteoblasts, osteosarcoma, and placenta.

Therefore, polynucleotides and polypeptides of the invention are useful as reagents for differential identification of the tissue(s) or cell type(s) present in a biological sample and for diagnosis of diseases and conditions which include, but are not limited to, disorders of developing and growing organs and tissues, bone disease, osteosarcoma, and other cancers. Similarly, polypeptides and antibodies directed to these polypeptides are useful in providing immunological probes for differential identification of the tissue(s) or cell type(s). For a number of disorders of the above tissues or cells, particularly of the fetal and developing systems, expression of this gene at significantly higher or lower levels may be routinely detected in certain tissues or cell types (e.g., fetal tissue, bone, cancerous and wounded tissues) or bodily fluids (e.g., lymph, serum, plasma, urine, bone marrow, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in osteosarcoma, osteoblasts, and chondrosarcoma indicates polynucleotides and polypeptides corresponding to this gene are useful for the detection, treatment, and/or prevention of bone disease and diseases of the skeletal system. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1642 of SEQ ID NO:27, b is an integer of 15 to 1656, where both a and b correspond to the positions of nucleotide residues shown in SEQ ID NO:27, and where b is greater than or equal to a+14.

Features of Protein Encoded by Gene No: 18

This gene is expressed primarily in liver, fetal liver, and to a lesser extent in bone marrow stromal cells.

Therefore, polynucleotides and polypeptides of the invention are useful as reagents for differential identification of the tissue(s) or cell type(s) present in a biological sample and for diagnosis of diseases and conditions which include, but are not limited to, hepatic dysfunction, immune disorders, and disease of the hemopoietic system. Similarly, polypeptides and antibodies directed to these polypeptides are useful in providing immunological probes for differential identification of the tissue(s) or cell type(s). For a number of disorders of the above tissues or cells, particularly of the liver and immune system, expression of this gene at significantly higher or lower levels may be routinely detected in certain tissues or cell types (e.g., immune, liver, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 84 as residues: Glu-44 to Asp-50. Polynucleotides encoding said polypeptides are also provided.

The tissue distribution in liver and fetal liver indicates that polynucleotides and polypeptides corresponding to this gene are useful for the detection and treatment of liver disorders and cancers (e.g., hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma.

The tissue distribution in bone marrow indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1336 of SEQ ID NO:28, b is an integer of 15 to 1350, where both a and b correspond to the positions of nucleotide residues shown in SEQ ID NO:28, and where b is greater than or equal to a+14.

Features of Protein Encoded by Gene No: 19

The translation product of this gene shares sequence homology with vacuolar proton-ATPase subunit M9.2 (see, e.g., Genbank accession numbers CAA75571 (Y15286.1); all references available through this accession are hereby incorporated by reference herein.). Preferred polypeptide encoded by this gene comprise the following amino acid sequence:

This gene is expressed primarily in infant brain, pancreas islet cell tumor, ovary tumors, immune cells (e.g., T-cells), normal cerebellum, endometrial tumor tissues and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, neurodevelopmental disorders, endocrine system disorders, disorders of the immune system, and ovarian cancer. Similarly, polypeptides and antibodies directed to these polypeptides are useful in providing immunological probes for differential identification of the tissue(s) or cell type(s). For a number of disorders of the above tissues or cells, particularly of the central nervous system, ovaries, immune system, expression of this gene at significantly higher or lower levels may be routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and homology to vacuolar proton-ATPase subunit M9.2 indicates that polynucleotides and polypeptides corresponding to this gene are useful for diagnosis and treatment of neurodevelopmental disorders. The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating-diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransrnission, learning, cognition, homeostasis, or neuronal differentiation or survival.

The tissue distribution in immune cells (e.g., T-cells) indicates polynucleotides and polypeptides corresponding to

MTAHSFALPVIIFTTFWGLVGIAGPWFVPKGPNRGVIITMLVATAVCCYLFWL    (SEQ ID NO: 148)

IAILAQLNPLFGPQLKNETIWYVRFLWE and

AQRAARLGTRAPAAPAARPCILPGHPAPGHDGALIRPPGHHLHHVLGPRRHR    (SEQ ID NO: 149)

GPWFVPKGPNRGVIITML

VATAVCCYLFWLIAILAQLNPLFGPQLKNETIWYVRFLWE

Polynucleotides encoding such polypeptides are also provided.

this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The tissue distribution in endocrine tissues such as the pancreas indicates polynucleotides and polypeptides corresponding to this gene are useful for the detection, treatment, and/or prevention of various endocrine disorders and cancers. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1752 of SEQ ID NO:29, b is an integer of 15 to 1766, where both a and b correspond to the positions of nucleotide residues shown in SEQ ID NO:29, and where b is greater than or equal to a+14.
Features of Protein Encoded by Gene No: 20

This gene is expressed primarily in placenta, induced endothelial cells, immune cells (e.g, T-cells, B-cells, leukocytes), brain, fetal tissue, epididiymus, lung, lung cancer, thyroid tumor and to a lesser extent in many other tissues.

Therefore, polynucleotides and polypeptides of the invention are useful as reagents for differential identification of the tissue(s) or cell type(s) present in a biological sample and for diagnosis of diseases and conditions which include, but are not limited to, fetal developmental disorders, immune disorders, cancer of the lungs, thyroid, and cancer, in general. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in immune cells (e.g., T-cells, B-cells, and leukocytes) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

The tissue distribution in endothelial cells indicates that polynucleotides and polypeptides corresponding to this gene are useful for the diagnosis and/or treatment of disorders involving the vasculature. Elevated expression of this gene product by endothelial cells indicates that it may play vital roles in the regulation of endothelial cell function; secretion; proliferation; or angiogenesis. Alternately, this may represent a gene product expressed by the endothelium and transported to distant sites of action on a variety of target organs. Expression of this gene product by hematopoietic cells also indicates involvement in the proliferation; survival; activation; or differentiation of all blood cell lineages. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2776 of SEQ ID NO:30, b is an integer of 15 to 2790, where both a and b correspond to the positions of nucleotide residues shown in SEQ ID NO:30, and where b is greater than or equal to a+14.

Features of Protein Encoded by Gene No: 21

The polypeptide of this gene has been determined to have a transmembrane domain at about amino acid position 1–29 of the amino acid sequence referenced in Table 1 for this gene. Based upon these characteristics, it is believed that the protein product of this gene shares structural features to type Ib membrane proteins. Preferred polypeptides comprise the following amino acid sequence:

```
MTLEEHRDRPRLGMCMCVCACVYACMLMHVCVHACLCVCVCVCVEPWSS        (SEQ ID NO: 150)

R QSKDTGGWHMEEQVTPPSLAQLKSGQVRGEMGEGRGEKGEEALTGGAEA

LSLLGRRSPSTPLFLDREDKQ AKDARNLSSTVAPDF
```

Also preferred are the polynucleotides encoding these polypeptides.

This gene is expressed primarily in tonsils and activated monocytes and to a lesser extent in activated neutrophils and anergic T-cells.

Therefore, polynucleotides and polypeptides of the invention are useful as reagents for differential identification of the tissue(s) or cell type(s) present in a biological sample and for diagnosis of diseases and conditions which include, but are not limited to, immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 87 as residues: Thr-27 to Arg-33, Gly-37 to Ser-42, Pro-52 to Arg-72. Polynucleotides encoding said polypeptides are also provided.

The tissue distribution in immunne cells (e.g., T-cells, neutrophils) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Expression of this gene product in tonsils indicates a role in the regulation of the proliferation; survival; differentiation; and/or activation of potentially all hematopoietic cell lineages, including blood stem cells. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1403 of SEQ ID NO:31, b is an integer of 15 to 1417, where both a and b correspond to the positions of nucleotide residues shown in SEQ ID NO:31, and where b is greater than or equal to a+14.

Features of Protein Encoded by Gene No: 22

The gene encoding the disclosed cDNA is believed to reside on chromosome 1. Accordingly, polynucleotides related to this invention are useful as a marker in linkage analysis for chromosome 1.

This gene is expressed primarily in CD34 positive cells (Cord Blood) and resting T-cells and to a lesser extent in anergic T-cells and neutrophils.

Therefore, polynucleotides and polypeptides of the invention are useful as reagents for differential identification of the tissue(s) or cell type(s) present in a biological sample and for diagnosis of diseases and conditions which include, but are not limited to, immune disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells (e.g., T-cells, neutrophils) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1892 of SEQ ID NO:32, b is an integer of 15 to 1906, where both a and b correspond to the positions of nucleotide residues shown in SEQ ID NO:32, and where b is greater than or equal to a+14.

Features of Protein Encoded by Gene No: 23

The polypeptide of this gene has been determined to have a transmembrane domain at about amino acid position 33–49 of the amino acid sequence referenced in Table 1 for this gene. Moreover, a cytoplasmic tail encompassing amino acids 50 to 62 of this protein has also been determined. Based upon these characteristics, it is believed that the protein product of this gene shares structural features to type Ia membrane proteins.

In another embodiment, polypeptides comprising the amino acid sequence of the open reading frame upstream of the predicted signal peptide are contemplated by the present invention. Specifically, polypeptides of the invention comprise the following amino acid sequence:

HEKILTPIWPSSTDLEKPHEMLFLNVILFSLTVFTLISTAHTLDRAVRSDWLLL (SEQ ID NO: 151)

VLIYACLEELIPELIF NLYCQGNATLFF.

Polynucleotides encoding these polypeptides are also provided.

This gene is expressed primarily in activated T cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic diseases and/or disorders, particularly inflammatory conditions or immunodeficiencies such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 529 of SEQ ID NO:33, b is an integer of 15 to 543, where both a and b correspond to the positions of nucleotide residues shown in SEQ ID NO:33, and where b is greater than or equal to a+14.

Features of Protein Encoded by Gene No: 24

This gene is expressed primarily in activated T-cells.

Therefore, polynucleotides and polypeptides of the invention are useful as reagents for differential identification of the tissue(s) or cell type(s) present in a biological sample and for diagnosis of diseases and conditions which include, but are not limited to, immune or hematopoietic diseases and/or disorders, particularly inflammatory or immundeficiency disorders, such as AIDS. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Expression of this gene product in indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1438 of SEQ ID NO:34, b is an integer of 15 to 1452, where both a and b correspond to the positions of nucleotide residues shown in SEQ ID NO:34, and where b is greater than or equal to a+14.

Features of Protein Encoded by Gene No: 25

This gene is expressed primarily in multiple schlerosis tissue, immune cells (e.g., T-cells and dendritic cells), brain, uterus, ovary, stomach, placenta, and fetal tissue.

Therefore, polynucleotides and polypeptides of the invention are useful as reagents for differential identification of the tissue(s) or cell type(s) present in a biological sample and for diagnosis of diseases and conditions which include, but are not limited to, multiple sclerosis, disorders of the fetus and female reproductive system, immune disorders, particularly immunodeficiency, tumor necrosis, infection, lymphomas, auto-immunities, cancer, metastasis, wound healing, inflammation, anemias (leukemia) and other hematopoeitic disorders, in addition to developmental or proliferative disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, developmental, reproductive system, differentiating, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 91 as residues: Met-1 to Lys-6. Polynucleotides encoding said polypeptides are also provided.

The tissue distribution in immune cells (e.g., T-cells, dendritic cells) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

The tissue distribution in female reproductive organs indicates that polynucleotides and polypeptides corresponding to this gene are useful for treating female infertility and cancers including but not limited to ovaries and uterus. The protein product is likely involved in preparation of the endometrium of implantation and could be administered either topically or orally. Alternatively, this gene could be transfected in gene-replacement treatments into the cells of the endometrium and the protein products could be produced. Similarly, these treatments could be performed during artificial insemination for the purpose of increasing the likelyhood of implantation and development of a healthy embryo. In both cases this gene or its gene product could be administered at later stages of pregnancy to promote heathy development of the endometrium.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2894 of SEQ ID NO:35, b is an integer of 15 to 2908, where both a and b correspond to the positions of nucleotide residues shown in SEQ ID NO:35, and where b is greater than or equal to a+14.

Features of Protein Encoded by Gene No: 26

The gene encoding the disclosed cDNA is believed to reside on chromosome 20. Accordingly, polynucleotides related to this invention are useful as a marker in linkage analysis for chromosome 20.

This gene is expressed primarily in fetal and developing tissues, tumors of male and female reproductive tissue (e.g., ovary and testes), and immune cells (e.g., T-cells).

Therefore, polynucleotides and polypeptides of the invention are useful as reagents for differential identification of the tissue(s) or cell type(s) present in a biological sample and for diagnosis of diseases and conditions which include, but are not limited to, developmental and growth disorders, disorders of the immune system, disorders and cancers of ovaries and testes. Similarly, polypeptides and antibodies directed to these polypeptides are useful in providing immunological probes for differential identification of the tissue(s) or cell type(s). For a number of disorders of the above tissues or cells, particularly of the fetal, reproductive, or developing systems, expression of this gene at significantly higher or lower levels may be routinely detected in certain tissues or cell types (e.g., developing, differentiating, reproductive, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 92 as residues: Val-57 to Ala-63. Polynucleotides encoding said polypeptides are also provided.

The tissue distribution in immune cells (e.g., T-cells) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The tissue distribution in ovaries and testes indicates polynucleotides and polypeptides corresponding to this gene are useful for the diagnosis and treatment of diseases of the reproductive organs, including but not limited to ovarian and testicular cancer. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 939 of SEQ ID NO:36, b is an integer of 15 to 953, where both a and b correspond to the positions of nucleotide residues shown in SEQ ID NO:36, and where b is greater than or equal to a+14.

Features of Protein Encoded by Gene No: 27

This gene is expressed primarily in T-cells.

Therefore, polynucleotides and polypeptides of the invention are useful as reagents for differential identification of the tissue(s) or cell type(s) present in a biological sample and for diagnosis of diseases and conditions which include, but are not limited to, immune and haemopoietic disorders, particularly immunodeficiencies, such as AIDS, or inflammatory disorders. Similarly, polypeptides and antibodies directed to these polypeptides are useful in providing immunological probes for differential identification of the tissue(s) or cell type(s). For a number of disorders of the above tissues or cells, particularly of the immune and haemopoietic system, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cells indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3850 of SEQ ID NO:37, b is an integer of 15 to 3864, where both a and b correspond to the positions of nucleotide residues shown in SEQ ID NO:37, and where b is greater than or equal to a+14.

Features of Protein Encoded by Gene No: 28

In another embodiment, polypeptides comprising the amino acid sequence of the open reading frame upstream of the predicted signal peptide are contemplated by the present invention. Specifically, polypeptides of the invention comprise the following amino acid sequence:

PANKAGAAIEAGIGISLMVLSPWACLFVVFFPYIQSSLRSDKHLQLSNILPTPS (SEQ ID NO: 152)

HHI HLPASICIQLRAGN.

Polynucleotides encoding these polypeptides are also provided.

This gene is expressed primarily in brain (early stage human brain and cerebellum) and immune cells (activated neutrophils, activated T-cells, neutrophils and dendritic cells) and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, neural or immune diseases and/or disorders, particularly inflammatory disorders, in addition to cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the brain or the immune system, expression of this gene at significantly higher or lower levels may be routinely detected in certain tissues or cell types (e.g., immune, hematopoietic, neural, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for the detection/treatment of neurodegenerative disease states and behavioural disorders. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system.

Alternatively, the tissue distribution indicates that polynucleotides and polypeptides corresponding to this gene are useful for the diagnosis and treatment of a variety of immune system disorders. Expression of this gene product in a variety of hematopoietic derived cells (T-cells, neutrophils, etc.) indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immune deficiency diseases such as AIDS, leukemia, rheumatoid arthritis, inflammatory bowel disease, sepsis, acne, and psoriasis, and tissues. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1397 of SEQ ID NO:38, b is an integer of 15 to 1411, where both a and b correspond to the positions of nucleotide residues shown in SEQ ID NO:38, and where b is greater than or equal to a+14.

Features of Protein Encoded by Gene No: 29

When tested against Jurket T-cell cell lines, supernatants removed from cells containing this gene activated the NF-kB (Nuclear Factor kB) promoter element. Thus, it is likely that this gene activates T-cells. NF-kB is a transcription factor activated by a wide variety of agents, leading to cell activation, differentiation, or apoptosis. Reporter constructs utilizing the NF-kB promoter element are used to screen supernatants for such activity. The polypeptide of this gene has been determined to have a transmembrane domain at about amino acid position 5–21 of the amino acid sequence referenced in Table 1 for this gene. Moreover, a cytoplasmic tail encompassing amino acids 22 to 40 of this protein has also been determined. Based upon these characteristics, it is believed that the protein product of this gene shares structural features to type Ib membrane proteins.

In another embodiment, polypeptides comprising the amino acid sequence of the open reading frame upstream of the predicted signal peptide are contemplated by the present invention. Specifically, polypeptides of the invention comprise the following amino acid sequence:

AGSPAGTGPEFPGRPTRPISTHVFEYECICKIPRFMCEYVLLLYIVLLCNRSYA (SEQ ID NO: 153)

VFTQCVLRSSPIDSSRNAVLL.

Polynucleotides encoding these polypeptides are also provided.

This gene is expressed primarily in colon, synovium, chondrosarcoma and to a lesser extent in dendritic cells.

Therefore, polynucleotides and polypeptides of the invention are useful as reagents for differential identification of the tissue(s) or cell type(s) present in a biological sample and for diagnosis of diseases and conditions which include, but are not limited to, immune, gastrointestinal, or skeletal diseases and/or disorders, particularly cancers. Similarly, polypeptides and antibodies directed to these polypeptides are useful in providing immunological probes for differential identification of the tissue(s) or cell type(s). For a number of disorders of the above tissues or cells, particularly of the immune and digestive systems, expression of this gene at significantly higher or lower levels may be routinely detected in certain tissues or cell types (e.g., lymph, skeletal, gastrointestinal, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution of this gene product in synovium would suggest a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familial osteoarthritis, Atelosteogenesis type II, metaphyseal chondrodysplasia type Schmid). The secreted protein can also be used to determine biological activity, to raise antibodies, as tissue markers, to isolate cognate ligands or receptors, to identify agents that modulate their interactions and as nutritional supplements. It may also have a very wide range of biological acitivities, particularly NFk-B activation. Representative uses are described in the "Chemotaxis" and "Binding Activity" sections below, in Examples 11, 12, 13, 14, 15, 16, 18, 19, and 20, and elsewhere herein. Briefly, the protein may possess the following activities: cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1168 of SEQ ID NO:39, b is an integer of 15 to 1182, where both a and b correspond to the positions of nucleotide residues shown in SEQ ID NO:39, and where b is greater than or equal to a+14.

Features of Protein Encoded by Gene No: 30

The gene encoding the disclosed cDNA is believed to reside on chromosome 11. Accordingly, polynucleotides related to this invention are useful as a marker in linkage analysis for chromosome 11.

This gene is expressed primarily in immune cells (e.g., activated T-cells), testes, fetal, spleen, and to a lesser extent in colon tumor, teratocarcinoma cells, brain and number of other tissues and cell types.

Therefore, polynucleotides and polypeptides of the invention are useful as reagents for differential identification of the tissue(s) or cell type(s) present in a biological sample and for diagnosis of diseases and conditions which include, but are not limited to, immune disorders related to T-cell dysfunction, such as immunodefeciencies or inflammatory conditions, in addition to neural, or reproductive disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, neural, reproductive, and cancerous and wounded tissues) or bodily fluids (e.g., seminal fluid, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 96 as residues: Pro-25 to Arg-38. Polynucleotides encoding said polypeptides are also provided.

The tissue distribution in activated T-cells and spleen indicates that polynucleotides and polypeptides corresponding to this gene are useful for the diagnosis and treatment of immune related disorders and diseases, including hypersentivities, such as T-cell mediated cytotoxicity; immune reactions to transplanted organs and tissues, such as host-versus-graft and graft-versus-host diseases; immunodeficiency diseases, such as acquired immunodeficiency syndrome, autoimmunity, such as autoimmune infertility, lense tissue injury, demyelination, systemic lupus erythematosis, drug induced hemolytic anemia, rheumatoid arthritis, Sjogren's disease, scleroderma; infections, and other inflammatory diseases and complications.

Additionally, the tissue distribution in T-cells and spleen indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. In addition, the secreted protein can be used to determine biological activity, to raise antibodies, as tissue markers, to isolate cognate ligands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, periodontal disease, neurological diseases stroke, fibrosis); inhibition or stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2443 of SEQ ID NO:40, b is an integer of 15 to 2457, where both a and b correspond to the positions of nucleotide residues shown in SEQ ID NO:40, and where b is greater than or equal to a+14.

Features of Protein Encoded by Gene No: 31

The translation product of this gene shares sequence homology with epidermal growth factor which is thought to be important in the growth and proliferation of epidermal cells, fibroblasts and a variety of other cell types and tissues.

The gene encoding the disclosed cDNA is believed to reside on chromosome 16. Accordingly, polynucleotides related to this invention are useful as a marker in linkage analysis for chromosome 16.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly autoimmunities or connective tissue diseases. Similarly, polypeptides and antibodies directed to these polypeptides are useful in providing immunological probes for differential identification of the tissue(s) or cell type(s). For a number of disorders of the above tissues or cells, particularly of the immune and connective tissue systems, expression of this gene at significantly higher or lower levels may be routinely detected in certain tissues or cell types (e.g., immune, hematopoietic, epithelial, endothelial, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene are useful for for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 1833 of SEQ ID NO:41, b is an integer of 15 to 1847, where both a and b correspond to the positions of nucleotide residues shown in SEQ ID NO:41, and where b is greater than or equal to a+14.

Features of Protein Encoded by Gene No: 32

When tested against Reh cell lines, supernatants removed from cells containing this gene activated the GAS (gamma activating sequence) promoter element. Thus, it is likely that this gene activates myeloid cells, and to a lesser extent, other cells and tissue cell types, through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in kidneys, tonsils and dendritic cells.

Therefore, polynucleotides and polypeptides of the invention are useful as reagents for differential identification of the tissue(s) or cell type(s) present in a biological sample and for diagnosis of diseases and conditions which include, but are not limited to, renal disorders and neoplasms, tonsilitis and immune disorders, particularly infections. Similarly, polypeptides and antibodies directed to these polypeptides are useful in providing immunological probes for differential identification of the tissue(s) or cell type(s). For a number of disorders of the above tissues or cells, particularly of the renal and immune systems, expression of this gene at significantly higher or lower levels may be routinely detected in certain tissues or cell types (e.g., renal, urogenital, immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in kidney indicates that polynucleotides and polypeptides corresponding to this gene are useful for the treatment and diagnosis of renal conditions such as acute renal failure, kidney fibrosis and kidney tubule regeneration and neoplasms. Conditioned media, generated from the transient expression of this gene in CHO cells has been shown to activate a IFNg-reponsive element (GAS) in a B cell line (Reh). The same conditioned media had no effect on T-cell (Jurkat) and pro-monocyte (U937) derived cell lines, suggesting that the protein product of this gene may exhibit IFNg-like activity in a (B)cell-specific manner. This experimental data in conjunction with expression on dendritic cells indicates that polynucleotides and polypeptides corresponding to this gene are useful for the diagnosis and treatment of immune disorders including: leukemias, lymphomas, auto-immunities, immunodeficiencies (e.g., AIDS), immuno-supressive conditions (transplantation) and hematopoeitic disorders. In addition this gene product may be applicable in conditions of general microbial infection, inflammation or cancer. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ D NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a-b, where a is any integer between 1 to 2583 of SEQ ID NO:42, b is an integer of 15 to 2597, where both a and b correspond to the positions of nucleotide residues shown in SEQ ID NO:42, and where b is greater than or equal to a+14.

Features of Protein Encoded by Gene No: 33

The translation product of this gene was shown to have homology to the classic MHC transactivator CIITA of Mus musculus (See, e.g., Genbank Accession No gi|1870520 and AAB48859.1; all references available through this accession are hereby incorporated by reference herein.), which is thought to regulate MHC class II gene expression in B lymphocytes via direct interaction with the MHC class II-specific transcription factors. Furthermore, the CIITA protein is thought to play an indirect role in reducing tumorigenicity and inducing long-term tumor immunity.

Preferred polypeptides of the invention comprise the following amino acid sequence:

```
MPSGNSAAVOUSGKKDKSGBSUSQESAKTKKETKOSCORVREASVBKGSEQSF    (SEQ ID NO: 154)

RIHFSREDQAGKTLRLSECSFRPEHVSRLATGLSKSLQTELTLTQCCLGQKQL

AILLSLVGRPAGLFSLRVQEPWADRARVLSLLEVCAQASGSVTEISISETQQQL

CVQLEFPRQEENPEAVALRLAHCDLGAHHSLLXGQLMETCARLXQLSLSQV

NLCEDDDASSLLLQSLLLSLSELKTFRLTSSCVSTEGLAHLASGLGHCHHLEEL

DLSNNQFDEEGTKALMRALEGKWMLKRLDLSHLLLNSSTLALLTHRLSQMT

CLQSLRLNRNSIGDVGCCHLSEALRAATSLEELDLSHNQIGDAGVQHLATILP

GLPELRKIDLSGNSISSAGGVQLAESLVLCRRLEELMLGCNALGDPTALGLAQ

ELPQHLRVLHLPFSHLGPGGALSLARPWMDPPIWKRSAWRKTTWLEGSCVS

VWSSRCSDR, or

HQLSRGSAVGRVSRSLQAPGGVDAWLQCPGGSHSPGAGSGAAPAPEGPTPTI    (SEQ ID NO: 155)

QPSGPRWGPEPGQALDGSPHLEEISLENNLAGGVLRFCMELPLLRQIDLVSC

KISNQTAKLLTSSFTSCPALEVILLSWNLLGDEAAAELAQVLPQMGRLKRVD

LEKNQITALGAWLLAEGLAQGSSIQVIRLWNNPIPCDMAQHLKSQEPRLDFAF

FDNQPQAPWGT.
```

Polynucleotides encoding these polypeptides are also encompassed by the invention.

The gene encoding the disclosed cDNA is believed to reside on chromosome 16. Accordingly, polynucleotides related to this invention are useful as a marker in linkage analysis for chromosome 16.

The polypeptide of this gene has been determined to have transmembrane domains at about amino acid positions 1–47 and 24–47 of the amino acid sequence referenced in Table 1 for this gene. Based upon these characteristics, it is believed that the protein product of this gene shares structural features to type IIIa membrane proteins.

This gene is expressed primarily in immune cells (e.g., eosinophils, T-cells, dendritic) and other cell types of hematopoeitic origin and to a lesser extent in ovary tumor and heart.

Therefore, polynucleotides and polypeptides of the invention are useful as reagents for differential identification of the tissue(s) or cell type(s) present in a biological sample and for diagnosis of diseases and conditions which include, but are not limited to, immune disorders, particularly immunodeficiency, tumor necrosis, infection, lymphomas, auto-immunities, cancer, metastasis, inflammation, anemias (leukemia) and other hematopoeitic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells (T-cells, dendritic, and eosinophils) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3102 of SEQ ID NO:43, b is an integer of 15 to 3116, where both a and b correspond to the positions of nucleotide residues shown in SEQ ID NO:43, and where b is greater than or equal to a+14.

Features of Protein Encoded by Gene No: 34

Polynucleotides of the invention do not comprise the nucleic acid sequence shown as Genbank accession no.gb|Z85986|HS 108K11, which is hereby incorporated herein by reference.

The gene encoding the disclosed cDNA is believed to reside on chromosome 6. Accordingly, polynucleotides related to this invention are useful as a marker in linkage analysis for chromosome 6.

This gene is expressed primarily in smooth muscle and cells of hematopoeitic origin.

Therefore, polynucleotides and polypeptides of the invention are useful as reagents for differential identification of the tissue(s) or cell type(s) present in a biological sample and for diagnosis of diseases and conditions which include, but are not limited to, vascular disorders, particularly heart disease, vasculitis, atherosclerosis, in addition to immune disorders, such as immunodeficiency, auto-immunities, cancer, metastasis, anemias (leukemia) and other hematopoeitic disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, endothelial, muscle, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue expression in hematopoeitic tissues indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. In addition, the expression in smooth muscle might indicates that polynucleotides and polypeptides corresponding to this gene are useful for the treatment and diagnosis of cardiovasular and disorders such as atherosclerosis, restenosis, stoke, angina, thrombosis hypertension, inflammation and vascular wound healing. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3446 of SEQ ID NO:44, b is an integer of 15 to 3460, where both a and b correspond to the positions of nucleotide residues shown in SEQ ID NO:44, and where b is greater than or equal to a+14.

Features of Protein Encoded by Gene No: 35

The gene encoding the disclosed cDNA is believed to reside on chromosome 17. Accordingly, polynucleotides related to this invention are useful as a marker in linkage analysis for chromosome 17.

The translation product of this gene was shown to have homology to the human cytochrome c-like polypeptide from lung adenocarcinoma A549 (See Genbank Accession No.bbs|175350) which is thought to be involved in metabolic processes, specific to tumors or transformed cells.

Preferred polypeptides of the invention comprise the following amino acid sequence:

```
EKLFCFEMLLICKFSPNSVPPETCAILNQGLMDLGLCRMCLGNNMFAGSMLG      (SEQ ID NO: 156)
KSHRHSPFSINQRHNALRKAAGTPAQKSLGIVQVSPN,

GCAGCALVTICLQAVCLVKAIAILHSRLTRDTMHCGRPQGPLPRKAWVLSRF     (SEQ ID NO: 157)
PPTETA,

PETQCTAEGRRDPCPEKPGYCPGFPQLRQPEIWPRGKGKTLHPPARHM,        (SEQ ID NO: 158)

SEIGENRP,                                                (SEQ ID NO: 159)

HDTDSFAH,                                                (SEQ ID NO: 160)

ALRKAAG.                                                 (SEQ ID NO: 161)
```

Polynucleotides encoding these polypeptides are also encompassed by the invention. Polynucleotides of the invention do not comprise the nucleic acid sequence shown as Genbank accession no.gb|AC0047061AC004706, which is hereby incorporated herein by reference.

This gene is expressed primarily in fetal tissue, lung, melanocyte, retina, brain, T-cell lymphoma, and to a lesser extent, in other tissues and cell types.

Therefore, polynucleotides and polypeptides of the invention are useful as reagents for differential identification of the tissue(s) or cell type(s) present in a biological sample and for diagnosis of diseases and conditions which include, but are not limited to, immune, hepatic, pulmonary, developmental, or growth disorders. Similarly, polypeptides and antibodies directed to these polypeptides are useful in providing immunological probes for differential identification of the tissue(s) or cell type(s). For a number of disorders of the above tissues or cells, particularly of the immune and pulmonary systems, expression of this gene at significantly higher or lower levels may be routinely detected in certain tissues or cell types (e.g., immune, pulmonary, hematopoietic, developing, differentiating, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in T-cell lymphoma indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2608 of SEQ ID NO:45, b is an integer of 15 to 2622, where both a and b correspond to the positions of nucleotide residues shown in SEQ ID NO:45, and where b is greater than or equal to a+14.

Features of Protein Encoded by Gene No: 36

The translation product of this gene was shown to have homology to the human protein kinase C substrate 80K-H (See Genbank Accession No. P14314), which is may be important in the regulation of various signal transduction pathways. Polynucleotides of the invention do not comprise the nucleic acid sequence shown as Genbank accession no. gb|G21007|G21007, which is hereby incorporated herein by reference. Additionally, this gene shares sequence homology with a recently described rat neuronal immediate early gene (IEG) cDNA gene R055 (see, e.g., Genseq Accession number Z28293, which is hereby incorporated herein by reference.). An IEG is a gene whose expression is rapidly increased immediately following a stimulus e.g., neuronal stimulation. Such neuronal IEGs have been found to encode a variety of proteins, including transcription factors, cytoskeletal proteins, growth factors and metabolic enzymes, as well as proteins involved in signal transduction. The identification of neuronal IEGs and the proteins they encode may provide important information about the function of neurons in, for example, learning, memory, synaptic transmission, tolerance and neuronal plasticity. Based on the sequence similarity, the translation product of this gene is expected to share at least some biological activities with IEG gene products. Such activities are known in the art, some of which are described elsewhere herein.

This gene is expressed primarily in breast and prostate cancer, retina, ovary, parathyroid tumor, fetal tissue and to a lesser extent in ovary.

Therefore, polynucleotides and polypeptides of the invention are useful as reagents for differential identification of the tissue(s) or cell type(s) present in a biological sample and for diagnosis of diseases and conditions which include, but are not limited to, reproductive, endocrine, or ocular disorders, particular breast or other cancers. Similarly, polypeptides and antibodies directed to these polypeptides are useful in providing immunological probes for differential identification of the tissue(s) or cell type(s). For a number of disorders of the above tissues or cells, particularly of the reproductive and endocrine systems, expression of this gene at significantly higher or lower levels may be routinely detected in certain tissues or cell types (e.g., reproductive, endocrine, differentiating, and cancerous and wounded tissues) or bodily fluids (e.g., lymph, breast milk, aquaeous humor, vitreous humor, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 102 as residues: Gln-14 to Val-20, Arg-28 to Trp-35. Polynucleotides encoding said polypeptides are also provided.

The tissue distribution in breast cancer cell lines, combined with the homology to a PKC substrate indicates that polynucleotides and polypeptides corresponding to this gene are useful for the study, diagnosis, treatment, and/or prevention of a variety of tumors, particularly of the breast or other neoplasms.

Alternatively, the tissue distribution in ovary and parathyroid tumors indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes. Protein, as well as, antibodies directed against the protein may show utility as a tumor marker and/or immunotherapy targets for the above listed tissues. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The tissue distribution in immune cells (e.g., germinal B-cells) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The tissue distribution in parathyroid tumor, prostate cancer and breast cancer tissue indicates polynucleotides and polypeptides corresponding to this gene are useful for the diagnosis and treatment these and related disorders.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1970 of SEQ ID NO:46, b is an integer of 15 to 1984, where both a and b correspond to the positions of nucleotide residues shown in SEQ ID NO:46, and where b is greater than or equal to a+14.

Features of Protein Encoded by Gene No: 37

Preferred polypeptides of the invention comprise the following amino acid sequence:

MRGPVCGFSLVEMLLALALGLMLILGVTQIALSRTTYASQSAASLLQDDAR (SEQ ID NO: 162)

FALGKLIQEIRQAGMFGCLSAASISNAPAGFDRPIGWSTTGSSRSLTLVTADVG

EGGSKPDWTVLSDCTGSPPAANARANPLPTCAKLT, or

MGYYLSRSRQAGMVLLISLVFLLLLALLGVSSMQGAISQEKITGSLRQRNQSF (SEQ ID NO: 163)

QQAESGLRLGESLVQASGFALRPCHSTAACAPPAESVSVVGPGTNPVSTVTWI

GMKDGVYGIQNLGPGTGLVNSRQRPRPRSIA.

Polynucleotides encoding these polypeptides are also encompassed by the invention.

This gene is expressed primarily in cord blood, ovary, tumors of the parathyroid, testes, and pancreas, and to a lesser extent in fetal tissue, retina, brain, colon, endometrial stromal, HL-60 cells, and many other tissues.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, or developmental disorders, cancer of the ovaries and endocrine system. Similarly, polypeptides and antibodies directed to these polypeptides are useful in providing immunological probes for differential identification of the tissue(s) or cell type(s). For a number of disorders of the above tissues or cells, particularly of the hemopoietic and immune systems, expression of this gene at significantly higher or lower levels may be routinely detected in certain tissues or cell types (e.g., immune, hematopoietic, reproductive, developmental, endocrine, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 103 as residues: Lys-29 to Ser-38, Ser-55 to Trp-61, Gln-63 to Ser-69. Polynucleotides encoding said polypeptides are also provided.

The tissue distribution in endocrine tissues indicates that polynucleotides and polypeptides corresponding to this gene are useful for the detection, treatment, and/or prevention of various endocrine disorders and cancers, particularly Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothallamus, and testes.

The tissue distribution in immune cells (e.g., neutrophils and T-cells) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1973 of SEQ ID NO:47, b is an integer of 15 to 1987, where both a and b correspond to the positions of nucleotide residues shown in SEQ ID NO:47, and where b is greater than or equal to a+14.

Features of Protein Encoded by Gene No: 38

The polypeptide of this gene has been determined to have a transmembrane domain at about amino acid position 1–24 of the amino acid sequence referenced in Table 1 for this gene. Based upon these characteristics, it is believed that the protein product of this gene shares structural features to type Ib membrane proteins.

This gene is expressed primarily in activated monocytes, dendritic cells, and cancerous ovary.

Therefore, polynucleotides and polypeptides of the invention are useful as reagents for differential identification of the tissue(s) or cell type(s) present in a biological sample and for diagnosis of diseases and conditions which include, but are not limited to, ovarian cancer, immune or hematopoietic disorders, particularly immunodeficiencies or inflammatory disordes. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in monocytes and dendritic cells indicates that polynucleotides and polypeptides corresponding to this gene are useful for the treatment and diagnosis of hematopoetic related disorders such as anemia, pancytopenia, leukopenia, thrombocytopenia or leukemia since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc.

cumbersome. Accordingly, preferably excluded from the present invention are one or more polynucleotides comprising a nucleotide sequence described by the general formula of a–b, where a is any integer between 1 to 2099 of SEQ ID NO:48, b is an integer of 15 to 2113, where both a and b correspond to the positions of nucleotide residues shown in SEQ ID NO:48, and where b is greater than or equal to a+14.

Features of Protein Encoded by Gene No: 39

The polypeptide of this gene has been determined to have a transmembrane domain at about amino acid position 36–57 of the amino acid sequence referenced in Table 1 for this gene. Based upon these characteristics, it is believed that the protein product of this gene shares structural features to type II membrane proteins. Preferred polypeptides encoded by this gene comprise the following amino acid sequence:

ENESTKEPSLLQYLCVQSPAGLNGFNVLLSGSQTPPTVGPSSGQLPSFSVPCM    (SEQ ID NO: 164)

VLPSPPLGPEFVLYSPAMPGPVSSTLGALPNTGPVNFSLPGLGSIAQLLVGPTA

VVNPKSSTLPSADPQLQSQPSLNLSPVMSRSHSVVQQPESPVYVGHPVSVVKL

HQSPVPVTPKSIQRTHRETFFKTPGSLGDPVLKRRERNNHETPARPRGD.

The tissue distribution in dendritic cells indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. The tissue distribution in ovarian cancer tissue indicates that polynucleotides and polypeptides corresponding to this gene are useful for the treatment and diagnosis of ovarian, as well as, other cancers.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence is Polynucleotides encoding such polypeptides are also provided.

This gene is expressed primarily in 8 week-old embryo, stromal cells, fetal lung, testes, and colon.

Therefore, polynucleotides and polypeptides of the invention are useful as reagents for differential identification of the tissue(s) or cell type(s) present in a biological sample and for diagnosis of diseases and conditions which include, but are not limited to, reproductive and immune defects, cancer, T-cell lymphoma, and developmental disorders. Similarly, polypeptides and antibodies directed to these polypeptides are useful in providing immunological probes for differential identification of the tissue(s) or cell type(s). For a number of disorders of the above tissues or cells, particularly of the pulmonary and immune systems, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T-cell lymphoma indicates that polynucleotides and polypeptides corresponding to this gene are useful for study and treatment of developmental and pulmonary defects and neoplasms of blood, reproductive and other organs.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

The tissue distribution in testes tissue indicates that polynucleotides and polypeptides corresponding to this gene are useful for the diagnosis and/or treatment of male reproductive and endocrine disorders. It may also prove to be valuable in the diagnosis and treatment of testicular cancer, as well as cancers of other tissues where expression has been observed. The expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3451 of SEQ ID NO:49, b is an integer of 15 to 3465, where both a and b correspond to the positions of nucleotide residues shown in SEQ ID NO:49, and where b is greater than or equal to a+14.

Features of Protein Encoded by Gene No: 40

The polypeptide of this gene has been determined to have a transmembrane domain at about amino acid position 145–171 of the amino acid sequence referenced in Table 1 for this gene. Moreover, a cytoplasmic tail encompassing amino acids 168–282 of this protein has also been determined. Based upon these characteristics, it is believed that the protein product of this gene shares structural features to type Ia membrane proteins.

This gene is expressed primarily in T helper cells, breast cancer, kidney, fetal tissue and to a lesser extent in thymus and cells from some other hemopoietic and endocrine sources.

Therefore, polynucleotides and polypeptides of the invention are useful as reagents for differential identification of the tissue(s) or cell type(s) present in a biological sample and for diagnosis of diseases and conditions which include, but are not limited to, immune and inflammatory conditions, cancer. Similarly, polypeptides and antibodies directed to these polypeptides are useful in providing immunological probes for differential identification of the tissue(s) or cell type(s). For a number of disorders of the above tissues or cells, particularly of the hemopoietic and lymphoid systems, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 106 as residues: Pro-135 to Ile-145, Trp-173 to Gly-188, Pro-199 to Gln-219, Ser-225 to Ala-237, Pro-240 to Gly-253, Ser-262 to Gly-275. Polynucleotides encoding said polypeptides are also provided.

The tissue distribution in breast cancer tissue indicates that polynucleotides and polypeptides corresponding to this gene are useful for diagnosis and treatment of neoplasms of breast and other organs.

The tissue distribution in immune cells (e.g., T-helper cells) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

The tissue distribution in kidney indicates the protein product of this gene could be used in the treatment and/or detection of kidney diseases including renal failure, nephritis, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1223 of SEQ ID NO:50, b is an integer of 15 to 1237, where both a and b correspond to the positions of nucleotide residues shown in SEQ ID NO:50, and where b is greater than or equal to a+14.

Features of Protein Encoded by Gene No: 41

The gene encoding the disclosed cDNA is believed to reside on chromosome 16. Accordingly, polynucleotides related to this invention are useful as a marker in linkage analysis for chromosome 16.

This gene is expressed primarily in adipose tissue, brain, Hodgkin's lymphoma, and to a lesser extent in fetal tissue colon tumor, synovium, salivary gland, immune cells (e.g., neutrophils), and other tissues.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders, immune, or metabolic disorders, particularly diseases or disorders of adipose tissue or Hodgkin's lymphoma. Similarly, polypeptides and antibodies directed to these polypeptides are useful in providing immunological probes for differential identification of the tissue(s) or cell type(s). For a number of disorders of the above tissues or cells, particularly of the adipose tissues and immune system, expression of this gene at significantly higher or lower levels may be routinely detected in certain tissues or cell types (e.g., immune, adipose, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 107 as residues: Arg-54 to Leu-60, Ala-73 to Gly-78. Polynucleotides encoding said polypeptides are also provided.

The tissue distribution in adipose tissue indicates that polynucleotides and polypeptides corresponding to this gene are useful for diagnosis and treatment of obesity, or other metabolic disorders, such as Tay-Sachs disease, phenylkenonuria, galactosemia, hyperlipidemias, porphyrias, and Hurler's syndrome, in addition to various immune disorders and neoplasia.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in immune cells (e.g., neutrophils) indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. In addition, the expression of this gene product in synovium would suggest a role in the detection and treatment of disorders and conditions afflicting the skeletal system, in particular osteoporosis, bone cancer, connective tissue disorders (e.g., arthritis, trauma, tendonitis, chrondomalacia and inflammation). The protein is also useful in the diagnosis or treatment of various autoimmune disorders (i.e., rheumatoid arthritis, lupus, scleroderma, and dermatomyositis), dwarfism, spinal deformation, joint abnormalities, and chondrodysplasias (i.e. spondyloepiphyseal dysplasia congenita, familial osteoarthritis, Atelosteogenesis type II, metaphyseal chondrodysplasia type Schmid, etc.). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1383 of SEQ ID NO:51, b is an integer of 15 to 1397, where both a and b correspond to the positions of nucleotide residues shown in SEQ ID NO:51, and where b is greater than or equal to a+14.

Features of Protein Encoded by Gene No: 42

Polynucleotides of the invention do not comprise the nucleic acid sequence shown as Genbank accession no.gb|G15452|G|5452, which is hereby incorporated herein by reference.

Preferred polypeptides of the invention comprise the following amino acid sequence:

```
RHERHEYRRALDHEEEALSSGSVQEAEAMLDEPQEQAEGSLTVYVISEHSSLL    (SEQ ID NO: 165)

PQDMMSYIGPKRTAVVRGIMHREAFNIIGRRIVQVAQAMSLTEDVLAAALAD

HLPEDKWSAEKRRPLKSSLGYEITFSLLNPDPKSHDVYWDIEGAVRRYVQPFL

NALGAAGNFSVDSQILYYAMLGVNPRFDSASSSYYLDMHSLPHVINPVESRL

GSSAASLYPVLNFLLYVPELAHSPLYIQDKDGAPVATNAFHSPRWGGIMVYN

VDSKTYNASVLPVRVEVDMVRVMEVFLAQLRLLFGIAQPQLPPKCLLSGPTS

EGLMTWELDRLLWARSVENLATATTTLTSLAQLLGKISNIVIKDDVASEVYK

AVAAVQKSAEELASGHLASAFVASQEAVTSSELAFFDPSLLHLLYFPDDQKF

AI YIPLFLPMAVPILLSLVKIFLETRKSWRKPEKTD.
```

Polynucleotides encoding these polypeptides are also encompassed by the invention.

This gene is expressed primarily in immune and haemopoietic cells, tumors of the ovaries, endometrium, and parathyroid.

Therefore, polynucleotides and polypeptides of the invention are useful as reagents for differential identification of the tissue(s) or cell type(s) present in a biological sample and for diagnosis of diseases and conditions which include, but are not limited to, immune or haemopoietic disorders, particularly cancers, ovarian cancer, cancers of the endocrine system and endometrium, and disorders of the retina. Similarly, polypeptides and antibodies directed to these polypeptides are useful in providing immunological probes for differential identification of the tissue(s) or cell type(s). For a number of disorders of the above tissues or cells, particularly of the haemopoietic system, expression of this gene at significantly higher or lower levels may be routinely detected in certain tissues or cell types (e.g., immune, haemopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 108 as residues: Phe-11 to Gly-16, Pro-33 to Ser-42. Polynucleotides encoding said polypeptides are also provided.

The tissue distribution in T-cells and bone marrow indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g., by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2257 of SEQ ID NO:52, b is an integer of 15 to 2271, where both a and b correspond to the positions of nucleotide residues shown in SEQ ID NO:52, and where b is greater than or equal to a+14.

Features of Protein Encoded by Gene No: 43

The gene encoding the disclosed cDNA is believed to reside on chromosome 19. Accordingly, polynucleotides related to this invention are useful as a marker in linkage analysis for chromosome 19. The polypeptide of this gene has been determined to have a transmembrane domain at about amino acid position 2544 of the amino acid sequence referenced in Table 1 for this gene. Based upon these characteristics, it is believed that the protein product of this gene shares structural features to type Ia membrane proteins.

This gene is expressed primarily in infant brain, fetal heart, uterine cancer, colon, metastatic melanoma, spleen, liver, thymus and other cancers.

Therefore, polynucleotides and polypeptides of the invention are useful as reagents for differential identification of the tissue(s) or cell type(s) present in a biological sample and for diagnosis of diseases and conditions which include, but are not limited to, disorders of developing tissues, haemopoietic or immune system, cardiovascular or musculoskeletal, or neural tissues, uterine cancer and metastatic melanoma. Similarly, polypeptides and antibodies directed to these polypeptides are useful in providing immunological probes for differential identification of the tissue(s) or cell type(s). For a number of disorders of the above tissues or cells, particularly of the immune system and developing systems, expression of this gene at significantly higher or lower levels may be routinely detected in certain tissues or cell types (e.g., neural, muscle, immune, hematopoietic, hepatic, developing, differentiating, and cancerous and wounded tissues) or bodily fluids (e.g., lymph, bile, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain indicates that polynucleotides and polypeptides corresponding to this gene are useful for the detection/treatment of neurodegenerative disease states, behavioural disorders, or inflamatory conditions such as Alzheimer's Disease, Parkinson's Disease, Huntingtons Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered bahaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Alternatively, expression within embryonic tissue and other cellular sources marked by proliferating cells indicates that this protein may play a role in the regulation of cellular division, and may show utility in the diagnosis and treatment of cancer and other proliferative disorders. Similarly, embryonic development also involves decisions involving cell differentiation and/or apoptosis in pattern formation. Thus this protein may also be involved in apoptosis or tissue differentiation and could again be useful in cancer therapy. The secreted protein can also be used to determine biological activity, to raise antibodies, as tissue markers, to isolate cognate ligands or receptors, to identify agents that modulate their interactions and as nutritional supplements. It may also have a very wide range of biological acitivities. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of hematopoiesis (e.g., for treating anaemia or as adjunct to chemotherapy); stimulation or growth of bone, cartilage, tendons, ligaments and/or nerves (e.g., for treating wounds, stimulation of follicle stimulating hormone (for control of fertility); chemotactic and chemokinetic activities (e.g., for treating infections, tumors); hemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative diseases; for regulation of metabolism, and behaviour. Also contemplated is the use of the corresponding nucleic acid in gene therapy procedures.

The tissue distribution in uterine cancer and metastatic melanoma indicates that polynucleotides and polypeptides corresponding to this gene are useful for the detection/treatment of these cancers.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2755 of SEQ ID NO:53, b is an integer of 15 to 2769, where both a and b correspond to the positions of nucleotide residues shown in SEQ ID NO:53, and where b is greater than or equal to a+14.

Features of Protein Encoded by Gene No: 44

This gene shares sequence homology with Serglycin (see GenSeq accession number Q44278; all references available through this accession are hereby incorporated by reference herein.) Serglycin is involved in the regulation of haematopoietic cell function and development.

This gene is expressed primarily in brain frontal cortex.

Therefore, polynucleotides and polypeptides of the invention are useful as reagents for differential identification of the tissue(s) or cell type(s) present in a biological sample and for diagnosis of diseases and conditions which include, but are not limited to, neurological and cognitive conditions. Similarly, polypeptides and antibodies directed to these polypeptides are useful in providing immunological probes for differential identification of the tissue(s) or cell type(s). For a number of disorders of the above tissues or cells, particularly of the central nervous system (CNS), expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 110 as residues: Tyr-28 to Cys-40. Polynucleotides encoding said polypeptides are also provided.

The tissue distribution indicates that polynucleotides and polypeptides corresponding to this gene are useful for study and treatment of central nervous system disorders, esp. schizophrenia, neurodegenerative and memory disorders.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1375 of SEQ ID NO:54, b is an integer of 15 to 1389, where both a and b correspond to the positions of nucleotide residues shown in SEQ ID NO:54, and where b is greater than or equal to a+14.

Features of Protein Encoded by Gene No: 45

This gene is expressed primarily in human stomach.

Therefore, polynucleotides and polypeptides of the invention are useful as reagents for differential identification of the tissue(s) or cell type(s) present in a biological sample and for diagnosis of diseases and conditions which include, but are not limited to, gastrointestinal disorders, particularly gastritis, stomach ulcers, and stomach cancer. Similarly, polypeptides and antibodies directed to these polypeptides are useful in providing immunological probes for differential identification of the tissue(s) or cell type(s). For a number of disorders of the above tissues or cells, particularly of the gastrointestinal system, expression of this gene at significantly higher or lower levels may be routinely detected in certain tissues or cell types (e.g., gastrointesinal, endothelial, and cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in stomach cells and tissues indicates that polynucleotides and polypeptides corresponding to this gene are useful for treating or diagnosing disease involving the stomach such as inflammation, ulceration or cancers. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 734 of SEQ ID NO:55, b is an integer of 15 to 748, where both a and b correspond to the positions of nucleotide residues shown in SEQ ID NO:55, and where b is greater than or equal to a+14.

Features of Protein Encoded by Gene No: 46

The gene encoding the disclosed cDNA is believed to reside on chromosome 11. Accordingly, polynucleotides related to this invention are useful as a marker in linkage analysis for chromosome 11.

This gene is expressed primarily in brain and fetal liver, and to a lesser extent, in other cell types.

Therefore, polynucleotides and polypeptides of the invention are useful as reagents for differential identification of the tissue(s) or cell type(s) present in a biological sample and for diagnosis of diseases and conditions which include, but are not limited to, developmental, neurological, behavioral, hepatic or immune diseases and/or disorders. Similarly, polypeptides and antibodies directed to these polypeptides are useful in providing immunological probes for differential identification of the tissue(s) or cell type(s). For a number of disorders of the above tissues or cells, particularly of the immune or nervous systems, expression of this gene at significantly higher or lower levels may be routinely detected in certain tissues or cell types (e.g., hepatic, immune, hematopoietic, neural, and cancerous and wounded tissues) or bodily fluids (e.g., lymph, bile, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 112 as residues: Ala-24 to Lys-31. Polynucleotides encoding said polypeptides are also provided.

The tissue distribution of this gene predominantly in fetal liver indicates that the gene could be important for the treatment or detection of immune or hematopoietic disorders including arthritis, asthma, immunodeficiency diseases and leukemia. Representative uses are described in the "Regeneration" and "Hyperproliferative Disorders" sections below, in Example 11, 15, and 18, and elsewhere herein. Briefly, the uses include, but are not limited to the detection, treatment, and/or prevention of neurodegenerative disease states and behavioural disorders such as Alzheimer's Disease, Parkinson's Disease, Huntington's Disease, schizophrenia, mania, dementia, paranoia, obsessive compulsive disorder and panic disorder. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 4188 of SEQ ID NO:56, b is an integer of 15 to 4202, where both a and b correspond to the positions of nucleotide residues shown in SEQ ID NO:56, and where b is greater than or equal to a+14.

Features of Protein Encoded by Gene No: 47

Preferred polypeptides of the invention comprise the following amino acid sequence:

KLLLTKVEQKLELARLQVDTSGSKEFGTSGIPAKCRFPKIFVNTDDTYEELHLI    (SEQ ID NO: 166)
VYKVTTVFLPAL.

Polynucleotides encoding these polypeptides are also encompassed by the invention.

This gene is expressed primarily in brain and lymph node of breast cancer.

Therefore, polynucleotides and polypeptides of the invention are useful as reagents for differential identification of the tissue(s) or cell type(s) present in a biological sample and for diagnosis of diseases and conditions which include, but are not limited to, breast cancer and neural disorders, particular neurodegenerative, neurological, or psycholigical disorders. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene are useful for diagnosis and treatment of neurological and psychological disorders, including but not limited to: trauma, congenital malformations, spinal cord injuries, ischemia and infarction, aneurysms, hemorrhages, toxic neuropathies induced by neurotoxins, inflammatory diseases such as meningitis and encephalitis, demyelinating diseases, neurodegenrative diseases such as Parkinson's disease, Huntington's disease, Alzheimer's disease, peripheral neuropathies, multiple sclerosis, neoplasia of neuroectodermal origin, etc. In addition, the secreted protein can be used to determine biological activity, to raise antibodies, as tissue markers, to isolate cognate ligands or receptors, to identify agents that modulate their interactions and as nutritional supplements. It may also have a very wide range of biological activities although no evidence for any is provided in the specification. Typical of these are cytokine, cell proliferation/differentiation modulating activity or induction of other cytokines; immunostimulating/immunosuppressant activities (e.g., for treating human immunodeficiency virus infection, cancer, autoimmune diseases and allergy); regulation of haematopoiesis (e.g., for treating anaemia or as adjunct to chemotherapy); stimulation of growth of bone, cartilage, tendons, ligaments and/or nerves (e.g., for treating wounds, periodontal disease, neurological diseases stroke, fibrosis); inhibition or stimulation of follicle stimulating hormone (for control of fertility); chemotactic and chemokinetic activities (e.g., for treating infections, tumours); haemostatic or thrombolytic activity (e.g., for treating haemophilia, cardiac infarction etc.); anti-inflammatory activity (e.g., for treating septic shock, Crohn's disease); as antimicrobials; for treating psoriasis or other hyperproliferative disease; for regulation of metabolism, behaviour, and many others. Also contemplated is the use of the corresponding nucleic acid in gene therapy procedures.

The tissue distribution in cancerous breast tissue indicates polynucleotides and polypeptides corresponding to this gene are useful for the detection, treatment, and/or prevention of breast cancer, and cancer in general. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 840 of SEQ ID NO:57, b is an integer of 15 to 854, where both a and b correspond to the positions of nucleotide residues shown in SEQ ID NO:57, and where b is greater than or equal to a+14.

Features of Protein Encoded by Gene No: 48

A preferred polypeptide fragment of the invention comprises the following amino acid sequence:

MEPQLGPEAAALRPGWLALLLWVSALSCSFSLPASSLSSLVPQVRTSYNFGRT (SEQ ID NO: 167)
FLGLDKCNACIGTSICKKFFKERNKI.

Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence:

QLPLWPSPASVQPRVDSQRARGSPEPKMEPQLGPEAAALRPGWLALLLWVS (SEQ ID NO: 168)
ALSCSFSLPASSLSSLVPQVRTSYNFGRTFLGLDKCNACIGTSICKKFFKEEIRS
DNWLASHLGLPPDSLLSYPANYSDDSKIWRPVEIFRLVSKYQNEISDRKICAS
ASAPKTCSIERVLRKTERFQKWLQAKRLTPDLVQDC HQCQRELKFLCMLR.

Polynucleotides encoding these polypeptides are also provided.

A preferred polypeptide variant of the invention comprises the following amino acid sequence:

MEPQLGPEAAALRPGWLALLLWVSALSCSFSLPASSLSSLVPQVRTSYNFGRT (SEQ ID NO: 169)

FLGLDKCNACIGTSICKKFFKEEIRSDNWLASHLGTASRFPLXSYPCKLLQMIX

KIWXPCGXLLTGQQXSNEISKQEIXCLLHPPPKNLHIDV.

Polynucleotides encoding these polypeptides are also provided.

This gene is expressed primarily in endothelial cells, and to a lesser extent, in the adult pulmonary system.

Therefore, polynucleotides and polypeptides of the invention are useful as reagents for differential identification of the tissue(s) or cell type(s) present in a biological sample and for diagnosis of diseases and conditions which include, but are not limited to, vascular and pulmonary diseases and/or disorders, particularly atherosclerosis, and microvascular disease. Similarly, polypeptides and antibodies directed to these polypeptides are useful in providing immunological probes for differential identification of the tissue(s) or cell type(s). For a number of disorders of the above tissues or cells, particularly of the pulmonary and vascular systems, expression of this gene at significantly higher or lower levels may be routinely detected in certain tissues or cell types (e.g., endothelial, pulmonary, cardiovascular, and cancerous and wounded tissues) or bodily fluids (e.g., lymph, pulmonary surfactant, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 114 as residues: Arg-45 to Gly-51, Glu-75 to Asn-81, Ala-99 to Ile-107, Lys-119 to Asp-126, Leu-145 to Gln-152. Polynucleotides encoding said polypeptides are also provided.

The tissue distribution of this gene in the pulmonary system, and in particular endothelial cells, indicates that it could play a role in the treatment/detection of lung lymphoma or sarcoma formation, pulmonary edema and embolism, bronchitis and cystic fibrosis. Expression in endothelial cells suggest a role in the treatment and/or detection of vascular disorders including vasculitis, cardiovascular disorders such as myocardial infarction, myocarditis, ischemia and stroke. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1441 of SEQ ID NO:58, b is an integer of 15 to 1455, where both a and b correspond to the positions of nucleotide residues shown in SEQ ID NO:58, and where b is greater than or equal to a+14.

Features of Protein Encoded by Gene No: 49

In another embodiment, polypeptides comprising the amino acid sequence of the open reading frame upstream of the predicted signal peptide are contemplated by the present invention. Specifically, polypeptides of the invention comprise the following amino acid sequence:

GPRARVQGFSGADIVKFMALGSMYLVLTLIVAKVLRGAEPCCGPLKNRVLRP (SEQ ID NO: 170)

CPLPVHCPLPIPSPAEGIPWVAYLPIRWFISCCPGHCIQIPMCTS.

Polynucleotides encoding these polypeptides are also provided.

This gene is expressed primarily in kidney, and to a lesser extent, in a wide variety of human tissues.

Therefore, polynucleotides and polypeptides of the invention are useful as reagents for differential identification of the tissue(s) or cell type(s) present in a biological sample and for diagnosis of diseases and conditions which include, but are not limited to, renal or urogenital diseases and/or disorders, particularly kidney cancer or nephritis. Similarly, polypeptides and antibodies directed to these polypeptides are useful in providing immunological probes for differential identification of the tissue(s) or cell type(s). For a number of disorders of the above tissues or cells, particularly of the urological or renal system, expression of this gene at significantly higher or lower levels may be routinely detected in certain tissues or cell types (e.g., renal, urogenital, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in kidney indicates that this gene or gene product could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilms Tumor Disease, and congenital kidney abnormalities such as horseshoe kidney, polycystic kidney, and Falconi's syndrome. Representative uses are described here and elsewhere herein. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 579 of SEQ ID NO:59, b is an integer of 15 to 593, where both a and b correspond to the positions of nucleotide residues shown in SEQ ID NO:59, and where b is greater than or equal to a+14.

TABLE 1

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HKGCN17 | 203105 08/13/98 | pSport1 | 11 | 3289 | 1 | 3289 | 218 | 218 | 67 | 1 | 23 | 24 | 155 |
| 2 | HETAD68 | 203081 07/30/98 | Uni-ZAP XR | 12 | 2342 | 1 | 2342 | 84 | 84 | 68 | 1 | 32 | 33 | 69 |
| 3 | HPIAT78 | 203081 07/30/98 | Uni-ZAP XR | 13 | 1666 | 1 | 1666 | 30 | 30 | 69 | 1 | 29 | 30 | 501 |
| 4 | HMWGY65 | 203105 08/13/98 | Uni-ZAP XR | 14 | 2027 | 1 | 1976 | 42 | 42 | 70 | 1 | 21 | 22 | 188 |
| 5 | HDTAB58 | 203081 07/30/98 | pCMVSport 2.0 | 15 | 2334 | 1874 | 2334 | 133 | 133 | 71 | 1 | 33 | 34 | 486 |
| 5 | HDTAB58 | 203081 07/30/98 | pCMVSport 2.0 | 60 | 496 | 159 | 496 | 223 | 223 | 116 | 1 | 37 | 38 | 48 |
| 6 | HEOMQ62 | 203105 08/13/98 | pSport1 | 16 | 2608 | 1 | 2608 | 130 | 130 | 72 | 1 | 24 | 25 | 87 |
| 7 | HWLJQ88 | 203081 07/30/98 | pSport1 | 17 | 1291 | 1 | 1291 | 114 | 114 | 73 | 1 | 30 | 31 | 299 |
| 7 | HWLJQ88 | 203081 07/30/98 | pSport1 | 61 | 1292 | 1 | 1292 | 403 | 403 | 117 | 1 | 25 | 26 | 203 |
| 8 | HMICP03 | 203105 08/13/98 | Uni-ZAP XR | 18 | 3129 | 1 | 3129 | 86 | 86 | 74 | 1 | 34 | 35 | 47 |
| 9 | HAJAB01 | 203105 08/13/98 | pCMVSport 3.0 | 19 | 3629 | 1 | 3629 | 147 | 147 | 75 | 1 | 15 | 16 | 43 |
| 10 | HE2AT09 | 203105 08/13/98 | Uni-ZAP XR | 20 | 1144 | 437 | 1144 | 435 | 435 | 76 | 1 | 17 | 18 | 140 |
| 11 | HSDJA15 | 203081 07/30/98 | Uni-ZAP XR | 21 | 1443 | 1 | 1443 | 247 | 247 | 77 | 1 | 20 | 21 | 152 |
| 12 | HAMGW29 | 203105 08/13/98 | pCMVSport 3.0 | 22 | 1053 | 12 | 1053 | 25 | 25 | 78 | 1 | 27 | 28 | 179 |
| 13 | HAPSR85 | 203081 07/30/98 | Uni-ZAP XR | 23 | 741 | 1 | 741 | 428 | 428 | 79 | 1 | 21 | 22 | 69 |
| 14 | HTOHD42 | 203081 07/30/98 | Uni-ZAP XR | 24 | 946 | 1 | 946 | 155 | 155 | 80 | 1 | 24 | 25 | 190 |
| 15 | HWLIH65 | 203081 07/30/98 | pSport1 | 25 | 831 | 1 | 831 | 129 | 129 | 81 | 1 | 18 | 19 | 165 |
| 16 | HTOJA73 | 203105 08/13/98 | Uni-ZAP XR | 26 | 1294 | 1 | 1294 | 100 | 100 | 82 | 1 | 21 | 22 | 41 |
| 17 | HPMGJ45 | 203105 08/13/98 | Uni-ZAP XR | 27 | 1656 | 1 | 1656 | 119 | 119 | 83 | 1 | 25 | 26 | 48 |
| 18 | HFVIC62 | 203105 08/13/98 | pBluescript | 28 | 1350 | 1 | 1350 | 114 | 114 | 84 | 1 | 31 | 32 | 56 |
| 19 | HHENW77 | 203105 08/13/98 | pCMVSport 3.0 | 29 | 1766 | 1 | 1714 | 205 | 205 | 85 | 1 | 19 | 20 | 42 |
| 20 | HMSIV91 | 203105 08/13/98 | Uni-ZAP XR | 30 | 2790 | 1 | 2790 | 95 | 95 | 86 | 1 | 19 | 20 | 40 |
| 21 | HMSKC04 | 203105 08/13/98 | Uni-ZAP XR | 31 | 1417 | 1 | 1417 | 133 | 133 | 87 | 1 | 22 | 23 | 73 |
| 22 | HSAZG33 | 203105 08/13/98 | Uni-ZAP XR | 32 | 1906 | 1 | 1906 | 122 | 122 | 88 | 1 | 23 | 24 | 46 |
| 23 | HTEBC92 | 203081 07/30/98 | Uni-ZAP XR | 33 | 543 | 1 | 543 | 63 | 63 | 89 | 1 | 22 | 23 | 62 |
| 23 | HTEBC92 | 209215 08/21/97 | Uni-ZAP XR | 62 | 398 | 241 | 398 | | 156 | 118 | 1 | 13 | 14 | 18 |
| 24 | HTXEL29 | 203081 07/30/98 | Uni-ZAP XR | 34 | 1452 | 1 | 1452 | 322 | 322 | 90 | 1 | 25 | 26 | 69 |
| 24 | HTXEL29 | 209090 06/05/97 | Uni-ZAP XR | 63 | 1202 | 1 | 1202 | | 294 | 119 | 1 | | | 12 |
| 25 | HDPAW44 | 203105 08/13/98 | pCMVSport 3.0 | 35 | 2908 | 1 | 2908 | 40 | 40 | 91 | 1 | 30 | 31 | 56 |
| 26 | HMACS20 | 203105 08/13/98 | Uni-ZAP XR | 36 | 953 | 1 | 953 | 227 | 227 | 92 | 1 | 43 | 44 | 67 |
| 27 | HAJAY88 | 203105 08/13/98 | pCMVSport 3.0 | 37 | 3864 | 1 | 3864 | 201 | 201 | 93 | 1 | 25 | 26 | 44 |
| 28 | HBOEG69 | 203081 07/30/98 | pSport1 | 38 | 1411 | 1 | 1411 | 302 | 302 | 94 | 1 | 19 | 20 | 54 |

TABLE 1-continued

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 29 | HWLEQ37 | 203081 07/30/98 | pSport1 | 39 | 1182 | 1 | 1182 | 110 | 110 | 95 | 1 | 19 | 20 | 40 |
| 30 | HE9CS37 | 203105 08/13/98 | Uni-ZAP XR | 40 | 2457 | 65 | 2454 | 183 | 183 | 96 | 1 | 22 | 23 | 40 |
| 31 | HNGEI34 | 203105 08/13/98 | Uni-ZAP XR | 41 | 1847 | 1 | 1847 | 70 | 70 | 97 | 1 | 18 | 19 | 49 |
| 32 | HTOAT76 | 203105 08/13/98 | Uni-ZAP XR | 42 | 2597 | 1 | 2597 | 100 | 100 | 98 | 1 | 41 | 42 | 57 |
| 33 | HDPVH60 | 203105 08/13/98 | pCMVSport 3.0 | 43 | 3116 | 1 | 3100 | 8 | 8 | 99 | 1 | 45 | 46 | 51 |
| 34 | HLYCR65 | 203105 08/13/98 | pSport1 | 44 | 3460 | 1 | 3460 | 28 | 28 | 100 | 1 | 19 | 20 | 44 |
| 35 | HARAY91 | 203105 08/13/98 | pBluescript SK- | 45 | 2622 | 1 | 2622 | 214 | 214 | 101 | 1 | 46 | 47 | 57 |
| 36 | HCHNT03 | 203105 08/13/98 | pSport1 | 46 | 1984 | 133 | 1984 | 228 | 228 | 102 | 1 | 17 | 18 | 40 |
| 37 | HCUBW95 | 203105 08/13/98 | ZAP Express | 47 | 1987 | 1 | 1987 | 131 | 131 | 103 | 1 | 20 | 21 | 142 |
| 38 | HDPLV95 | 203105 08/13/98 | pCMVSport 3.0 | 48 | 2113 | 1 | 2113 | 12 | 12 | 104 | 1 | 18 | 19 | 43 |
| 39 | HEMGB12 | 203105 08/13/98 | Uni-ZAP XR | 49 | 3465 | 1 | 3438 | 78 | 78 | 105 | 1 | 48 | 49 | 62 |
| 40 | HHENP27 | 203105 08/13/98 | pCMVSport 3.0 | 50 | 1237 | 1 | 1237 | 12 | 12 | 106 | 1 | 22 | 23 | 282 |
| 41 | HSPBF70 | 203105 08/13/98 | pSport1 | 51 | 1397 | 288 | 1397 | 429 | 429 | 107 | 1 | 19 | 20 | 97 |
| 42 | HTXKB57 | 203105 08/13/98 | Uni-ZAP XR | 52 | 2271 | 1 | 2271 | 290 | 290 | 108 | 1 | 16 | 17 | 61 |
| 43 | HUKAA55 | 203105 08/13/98 | Lambda ZAP II | 53 | 2769 | 129 | 2769 | 263 | 263 | 109 | 1 | 32 | 33 | 46 |
| 44 | HFXGT58 | 203105 08/13/98 | Lambda ZAP II | 54 | 1389 | 12 | 1389 | 238 | 238 | 110 | 1 | 28 | 29 | 46 |
| 45 | HROAS46 | 203081 07/30/98 | Uni-ZAP XR | 55 | 748 | 1 | 748 | 123 | 123 | 111 | 1 | 19 | 20 | 41 |
| 46 | HUSFF19 | 203081 07/30/98 | pBluescript | 56 | 4202 | 863 | 2447 | 1080 | 1080 | 112 | 1 | 20 | 21 | 41 |
| 47 | HBWBX21 | 203105 08/13/98 | ZAP Express | 57 | 854 | 1 | 854 | 201 | 201 | 113 | 1 | 17 | 18 | 43 |
| 48 | HUVDJ43 | 203081 07/30/98 | Uni-ZAP XR | 58 | 1455 | 103 | 1455 | 128 | 128 | 114 | 1 | 31 | 32 | 182 |
| 48 | HUVDJ43 | 203081 07/30/98 | Uni-ZAP XR | 64 | 1517 | 1 | 1517 | 133 | 133 | 120 | 1 | 31 | 32 | 79 |
| 48 | HUVDJ43 | 203027 06/26/97 | Uni-ZAP XR | 65 | 526 | 69 | 526 | 89 | 89 | 121 | 1 | 31 | 32 | 146 |
| 49 | HTLCU49 | 203081 07/30/98 | Uni-ZAP XR | 59 | 593 | 1 | 593 | 170 | 170 | 115 | 1 | 20 | 21 | 80 |
| 49 | HTLCU49 | 203027 06/26/97 | Uni-ZAP XR | 66 | 664 | 1 | 664 | 249 | 249 | 122 | 1 | 20 | 21 | 80 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:3140 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X, and/or a cDNA contained in ATCC deposit Z. The present invention also provides a polypeptide comprising, or alternatively, consisting of, the polypeptide sequence of SEQ ID NO:Y and/or a polypeptide encoded by the cDNA contained in ATCC deposit Z. Polynucleotides encoding a polypeptide comprising, or alternatively consisting of the polypeptide sequence of SEQ ID NO:Y and/or a polypeptide sequence encoded by the cDNA contained in ATCC deposit Z are also encompassed by the invention.

Signal Sequences

The present invention also encompasses mature forms of the polypeptide having the polypeptide sequence of SEQ ID NO:Y and/or the polypeptide sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. According to the signal hypothesis, proteins secreted by mammalian cells have a signal or secretary leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as desribed below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in a deposited clone.

The present invention also encompasses variants of the polypeptide sequence disclosed in SEQ ID NO:Y and/or encoded by a deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nucleotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix= Unitary, k-tuple=4, Mismatch Penalty=1, Joining Penalty= 30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table 1 (SEQ ID NO:Y) or to the amino acid sequence encoded by cDNA contained in a deposited clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a "functional activity" is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

For example, in one embodiment where one is assaying for the ability to bind or compete with full-length polypeptide of the invention for binding to an antibody of the polypeptide of the invention, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand for a polypeptide of the invention identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of binding of a polypeptide of the invention to its substrates (signal transduction) can be assayed.

In addition, assays described herein (see Examples) and otherwise known in the art may routinely be applied to measure the ability of polypeptides of the invention and fragments, variants derivatives and analogs thereof to elicit related biological activity related to that of the polypeptide of the invention (either in vitro or in vivo). Other methods will be known to the skilled artisan and are within the scope of the invention.

Epitopes and Antibodies

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC deposit No. Z or encoded by a polynucleotide that hybridizes to the complement of the sequence of SEQ ID NO:X or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666(1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA-segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $1 \times 10^{-4}$ M, $5 \times 10^{-5}$ M, $10^{-5}$ M, $5 \times 10^{-6}$ M, $10^{-6}$ M, $5 \times 10^{-7}$ M $10^7$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15) :3209–3214 (1998); Yoon et al., J. Immunol. 160(7) :3170–3179 (1998); Prat et al., J. Cell. Sci. 111(Pt2) :237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety.

Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92101047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5)

:155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (ANIC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:73749 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion-assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5) :155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem.

262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S 1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., NY, and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NABH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337).

The chemical moieties for derivatization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative diseases, disorders, and/or conditions are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRCPress, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.
Uses of the Polypeptides Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.
Gene Therapy Methods Another aspect of the present invention is to gene therapy methods for treatingor preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the nakednucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 9419469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and $CAPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance, to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly Biological Activities The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting.

These molecules could be important in the treatment or prevention of heart attacks (infarction), strokes, or scarring.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/ or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferrably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses. 50(5):423–33 (1998), Chem Biol Interact. Apr 24;111–12:23–34 (1998), J Mol Med. 76(6):402–12 (1998), Int J Tissue React; 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a *Therapeutic*, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treator prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a mucoadhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha, alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intesting, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/ or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), *Cryptococcus neoformans*, Aspergillosis, Bacillaceae (e.g., Anthrax, Clostridium), Bacteroidaceae, Blastomycosis, Bordetella, Borrelia (e.g., *Borrelia burgdorferi*), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Kiebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerae*, Neisseriaceae (e.g., Acinetobacter, Gonorrhea, Menigococcal), *Meisseria meningitidis*, Pasteurellacea Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis, polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptidelmolecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84103564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM $MgCl_2$, 10 mM dithiothreitol (DTT) and 0.2 mM ATP) and then ligated to the EcoR1/HindIII site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature*, 372:333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.
invention, and/or (b) a ribozyme directed to the polynucleotide of the present invention Other Activities The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, bums, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in able 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

In specific embodiments of the invention, for each "Contig ID" listed in the fourth column of Table 2, preferably excluded are one or more polynucleotides comprising, or alternatively consisting of, a nucleotide sequence referenced in the fifth column of Table 2 and described by the general formula of a–b, whereas a and b are uniquely determined for the corresponding SEQ ID NO:X referred to in column 3 of Table 2. Further specific embodiments are directed to polynucleotide sequences excluding one, two, three, four, or more of the specific polynucleotide sequences referred to in the fifth column of Table 2. In no way is this listing meant to encompass all of the sequences which may be excluded by the general formula, it is just a representative example. All references available through these accessions are hereby incorporated by reference in their entirety.

TABLE 2

| Gene No. | cDNA Clone ID | NT SEQ ID NO: X | Contig ID | Public Accession Numbers |
|---|---|---|---|---|
| 1 | HKGCN17 | 11 | 798098 | None |
| 2 | HETAD68 | 12 | 793860 | R74475, H18234, H18272, H25658, H26245, N33532, N41513, N93486, W02757, W16473, W16474, W21189, W24767 |
| 3 | HPIAT78 | 13 | 790205 | T91507, T91536, R11612, T83549, T83719, R19402, AA058765, AA088847, AA099882, AA115449, AA115448, AA235247 |
| 4 | HMWGY65 | 14 | 794987 | R14788, R40100, R51562, R51653, H46612, AA004670 |
| 5 | HDTAB58 | 15 | 800678 | R13499, R18648, R20620, R41610, R41610, R78726, H10829, H10870 |
| 5 | HDTAB58 | 60 | 793685 | R44548, R44548, H42753, H98068, N24692, N32182, AA463629 |
| 10 | HE2AT09 | 20 | 710408 | T58287, T58241, R51009, H47150, H66260, H69720, H70386, H70698, H72155, H91380, N38922, N46494, N58822, N72645, N75027, N75160, N93947, N94250, W05627, W07723, W19532, W39201, W40446, W80561, N90260, AA022870, AA026818, AA026877, AA036917, AA055012, AA055436, AA057027, AA136969, AA460271, AA463838 |
| 11 | HSDJA15 | 21 | 795252 | T87220, R41971, R45396, R41971, R45396, R55771, H11649 |
| 12 | HAMGW29 | 22 | 799448 | H44706, W69343, AA085550, AA148240 |
| 19 | HHENW77 | 29 | 797475 | T74074, T77194, T87227, R39444, H43568 |
| 23 | HTEBC92 | 62 | 495967 | T78329, R70701 |
| 25 | HDPAW44 | 35 | 790193 | R27595, P27693, N39440, N48553, AA036790, AA036733, AA169377, AA186377, AA233190 |
| 28 | HBOEG69 | 38 | 793786 | R27740, R95913, H80936, W74158 |
| 30 | HE9CS37 | 40 | 797496 | R34404, R48942, H17123, H17230, H25265, H41988, H41987, N20900, AA040195, AA128254, AA256865, AA255468, AA461458, AA426036 |
| 33 | HDPVH60 | 43 | 796865 | T61473, AA005022, AA005023, AA227825, AA227999 |
| 36 | HCHNT03 | 46 | 797709 | H87265, W19728, N89985, AA459996, AA460090 |
| 41 | HSPBF70 | 51 | 793744 | R39978, R39978, AA128437, AA129952, AA136304, AA136410 |
| 46 | HUSFF19 | 56 | 797713 | T60523, T61826, T64314, T64701, T64884, T89070, T98251, R18180, R25532, R25699, R34919, R45591, R45670, R49311, R49311, R45670, R62578, R62579, R66150, R67772, H17920, H27973, H29126, H40149, H40159, H54660, H54661, H66579, H70677, H80692, H80693, H94982, W02716, W21368, W25735, W67720, W68179, W72502, W76059, AA004905, AA004999, AA009733, AA009449, AA034233, AA043665, AA043790, AA053925, AA134987, AA135085, AA220761, AA213510, AA214529 |
| 49 | HTLCU49 | 66 | 695847 | N51554, AA057753, AA458613 |

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library Plasmid | Corresponding Deposited |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into E. coli strain XL-1 Blue, also available from Stratagene. pBS comes in 4 forms SK+, SK−, KS+and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the fl origin of replication ("ori"), such that in one orientation, single stranded rescue initiated from the fl ori generates sense strand DNA and in the other, antisense.

Vectors pSport1, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into E. coli strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into E. coli strain XL-1 Blue. Vector pCR®2.1, which is available from Invitrogen, 1600 Faraday Avenue, Carlsbad, Calif. 92008, contains an ampicillin resistance gene and may be transformed into E. coli strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 3040 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7) :1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3
Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4
Chromosomal Mapping, of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5
Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilotri-acetic acid ("Ni-NTA") affinity resin column (available from QIAGEN, Inc., supra). Proteins with a 6× His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C. or frozen at −80 degree C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6
Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 7
Cloning and Expression of a Polypeptide in a Baculovirus Expression System In this example, the plasmid shuttle vector pA2 is used to insert a polynucleotide into a baculovirus to express a polypeptide. This expression vector contains the strong polyhedrin promoter of the Autographa californica nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Ca.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8
Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC$_{37152}$), pSV2dhfr (ATCC$_{37146}$), pBC12MI (ATCC$_{67109}$), pCMVSport 2.0, and pCMVSport 3.0. Mammalian host cells that could be used include, human Hela, 293, H9 and Jurkat cells, mouse NIH3T3 and C127 cells, Cos 1, Cos 7 and CVI, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five $\mu$g of the expression plasmid pC6 a pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 9
Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region:

```
GGGATCCGGAGCCCAAATCTTCTGACAAAACTCACACATGCCCACCGTGC     (SEQ ID NO: 1)

CCAGCACCTGAATTCGAGGGTGCACCGTCAGTCTTCCTCTTCCCCCCAAAA

CCCAAGGACACCCTCATGATCTCCCGGACTCCTGAGGTCACATGCGTGGT

GGTGGACGTAAGCCACGAAGACCCTGAGGTCAAGTTCAACTGGTACGTGG

ACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAAC

CACAGGTGTACACCCTGCCCCCATCCCGGGATGAGCTGACCAAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCT

CCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGTGCGACGGCCGCGACTCTAGAGGAT
```

Example 10
Production of an Antibody from a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11
Production of Secreted Protein for High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17–516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2 \times 10^5$ cells/well in 0.5 ml DMEM(Dulbecco's Modified Eagle Medium)(with 4.5 G/L glucose and L-glutamine (12-604 F Biowhittaker))/10% heat inactivated FBS(14-503 F Biowhittaker)/1× Penstrep(17-602 E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 1545 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degrees C. for 6 hours.

While cells are incubating, prepare appropriate media, either 1%BSA in DMEM with 1×penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H$_2$O; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin B$_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1x penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12
Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with L-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | GAS(elements) or ISRE |
|---|---|---|---|---|---|---|
| | tyk2 | Jak1 | Jak2 | Jak3 | | |
| IFN family | | | | | | |
| IFN-a/B | + | + | − | − | 1, 2, 3 | ISRE |
| IFN-g | | + | + | − | 1 | GAS (IRF1>Lys6 >IFP) |
| Il-10 | + | ? | ? | − | 1, 3 | |
| gp130 family | | | | | | |
| IL-6 (Pleiotrophic) | + | + | + | ? | 1, 3 | GAS (IRF1>Lys6>IFP) |
| Il-11 (Pleiotrophic) | ? | + | ? | ? | 1, 3 | |
| OnM (Pleiotrophic) | ? | + | + | ? | 1, 3 | |
| LIF (Pleiotrophic) | ? | + | + | ? | 1, 3 | |
| CNTF (Pleiotrophic) | −/+ | + | + | ? | 1, 3 | |
| G-CSF (Pleiotrophic) | ? | + | ? | ? | 1, 3 | |
| IL-12 (Pleiotrophic) | + | − | + | + | 1, 3 | |
| g-C family | | | | | | |
| IL-2 (lymphocytes) | − | + | − | + | 1, 3, 5 | GAS |

-continued

| Ligand | JAKs | | | | STATS | GAS(elements) or ISRE |
|---|---|---|---|---|---|---|
| | tyk2 | Jak1 | Jak2 | Jak3 | | |
| IL-4 (lymph/myeloid) | − | + | − | + | 6 | GAS (IRF1=IFP>>Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1>IFP>>Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS(B-CAS>IRFI=IFP>>Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector

5':GCGCCTCGAGATTTCCCCGAAATCTAGATTTCCCCGAAATGATTTCCCC (SEQ ID NO: 3)

GAAATGATTTCCCCGAAATATCTGCCATCTCAATTAG:3'

The downstream primer is complementary to the SV40 promoter and is flanked with a Hind III site:

obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

5':GCGGCAAGCTTTTTGCAAAGCCTAGGC:3' (SEQ ID NO: 4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the

5':CTCGAGATTTCCCCGAAATCTAGATTTCCCCGAAATGATTTCCCCGAAA (SEQ ID NO: 5)

TGATTTCCCCGAAATATCTGCCATCTCAATTAGTCAGCAACCATAGTCCCG

CCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCC

TCGGCCTCTGAGCTATTCCAGAAGTAGTGAGGAGGCTTTTTTGGAGGCCT

AGGCTTTTGCAAAAAGCTT:3'

GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13
High-Throughput Screening Assay for T-Cell Activity.

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1%Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degrees C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degrees C. until SEAP assays are performed according to Example 17. The plates containing the remaining treated cells are placed at 4 degrees C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14
High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2 \times 10^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degrees C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37 degrees C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15
High-Throughput Screening Assay Identifying Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                    (SEQ ID NO: 6)
    5' GCGCTCGAGGGATGACAGCGATAGAACCCCGG-3'

(SEQ ID NO: 7)
    5' GCGAAGCTTCGCGACTCCCCGGATCCGCCTC-3'
```

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08–115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16
High-Throughput Screening Assay for T-Cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 11. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:8), 18 bp of sequence complementary to the 5' end of the SV40 early promoter sequence, and is flanked with an XhoI site:

```
5':GCGGCCTCGAGGGGACTTTCCCGGGGACTTTCCGGGACTTTCCGGGAC    (SEQ ID NO: 9)
               TTTCCATCCTGCCATCTCAATTAG:3'
```

The downstream primer is complementary to the 3' end of the SV40 promoter and is flanked with a Hind III site:

5':GCGGCAAGCTTTTTGCAAAGCCTAGGC:3' (SEQ ID NO: 4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5':CTCGAGGGGACTTTCCCGGGGACTTTCCGGGGACTTTCCGGGACTTTCC (SEQ ID NO: 10)
ATCTGCCATCTCAATTAGTCAGCAACCATAGTCCCGCCCCTAACTCCGCCC
ATCCCGCCCCTAACTCCGCCCAGTTCCGCCCATTCTCCGCCCCATGGCTGA
CTAATTTTTTTTATTTATGCAGAGGCCGAGGCCGCCTCGGCCTCTGAGCTA
TTCCAGAAGTAGTGAGGAGGCTTTTTTGGAGGCCTAGGCTTTTGCAAAAA
GCTT:3'

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18
High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to $2-5 \times 10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19
High-Throughput Screening Assay Identifying Tyrosine Kinase Activity The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C. at $16,000 \times g$.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg$_{2+}$ (5 mM ATP/50 mM MgCl$_2$), then 10 ul of 5× Assay Buffer (40 mM imidazole hydrochloride, pH7.3, 40 mM beta-glycerophosphate, 1 mM EGTA, 100 mM MgCl$_2$, 5 MM MnCl$_2$, 0.5 mg/ml BSA), then 5 ul of Sodium Vanadate (1 mM), and then 5 ul of water. Mix the components gently and preincubate the reaction mix at 30 degrees C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD (0.5 u/ml)) to each well and incubate at 37 degrees C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20
High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degrees C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/mil) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21
Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22
Method of Detecting Abnormal Levels of a Polypeptide in a Biological Sample A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about lug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors.

Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLET™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/ANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent.

Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estrarnustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL11, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PDGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 24

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-ex vivo

One method of gene therapy transplants fibroblasts, which are capable of expressing a polypeptide, onto a patient.

Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27
Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC$_{18}$ plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately 1.5.$\times 10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters; a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28
Method of Treatment Using Gene Therapy—in vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5) :314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(l):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 29

Transgenic Animals.

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 30
Knock-Out Animals.

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31
Production of an Antibody
a) Hybridoma Technology

The antibodies of the present invention can be prepared by a variety of methods. (See, Current Protocols, Chapter 2.) As one example of such methods, cells expressing XXX are administered to an animal to induce the production of sera containing polyclonal antibodies. In a preferred method, a preparation of XXX protein is prepared and purified to render it substantially free of natural contaminants. Such a preparation is then introduced into an animal in order to produce polyclonal antisera of greater specific activity.

Monoclonal antibodies specific for protein XXX are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with XXX polypeptide or, more preferably, with a secreted XXX polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the XXX polypeptide.

Alternatively, additional antibodies capable of binding to XXX polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the XXX protein-specific antibody can be blocked by XXX. Such antibodies comprise anti-idiotypic antibodies to the XXX protein-specific antibody and are used to immunize an animal to induce formation of further XXX protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against XXX from a Library of scFvs

Naturally occurring V-genes isolated from human PBLs are constructed into a library of antibody fragments which contain reactivities against XXX to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×10$^8$ TU of delta gene 3 helper (M13 delta gene m, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/mil ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/mil of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 32

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In vitro Assay

Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220).

Various dilutions of each sample are placed into individual wells of a 96-well plate to which are added 105 B-cells suspended in culture medium (RPMI 1640 containing 10% FBS, $5 \times 10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In vivo Assay

BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R (B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220) dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

The studies described in this example tested activity of a polypeptide of the invention. However, one skilled in the art could easily modify the exemplified studies to test the activity of polynucleotides of the invention (e.g., gene therapy), agonists, and/or antagonists of polynucleotides or polypeptides of the invention.

Example 33

T Cell Proliferation Assay

A CD3-induced proliferation assay is performed on PBMCs and is measured by the uptake of $^3$H-thymidine. The assay is performed as follows. Ninety-six well plates are coated with 100 $\mu$l/well of mAb to CD3 (HIT3a, Pharmingen) or isotype-matched control mAb (B33.1) overnight at 4 degrees C. (1 $\mu$g/ml in 0.05M bicarbonate buffer, pH 9.5), then washed three times with PBS. PBMC are isolated by F/H gradient centrifugation from human peripheral blood and added to quadruplicate wells ($5 \times 10^4$ well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 $\mu$l of supernatant is removed and stored −20 degrees C. for measurement of IL-2 (or other cytokines) if effect on proliferation is observed. Wells are supplemented with 100 ul of medium containing 0.5 uCi of $^3$H-thymidine and cultured at 37 degrees C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

The studies described in this example tested activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

Example 34

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the Production of Cytokines.

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte Activation and/or Increased Survival.

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay.

Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 $\mu$g/ml, and then incubaed at room temperature for 5 minutes before FACScan analysis. PI uptake has been demonstrated to correlate with DNA fragmentation in this experimental paradigm.

Effect on Cytokine Release.

An important function of monocytes/macrophages is their regulatory activity on other cellular populations of the immune system through the release of cytokines after stimulation. An ELISA to measure cytokine release is performed as follows. Human monocytes are incubated at a density of $5 \times 10^5$ cells/mil with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative Burst.

Purified monocytes are plated in 96-w plate at $2-1 \times 10^5$ cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 $\mu$l 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of a polypeptide of the invention. However, one skilled in the art could easily modify the exemplified studies to test the activity of polypeptides, polynucleotides (e.g., gene therapy), agonists, and/or antagonists of the invention.

Example 35
Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or polypeptides of the invention with or without IL-1$\alpha$ for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1$\alpha$ for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36
The Effect of Polypeptides of the Invention on the Growth of Vascular Endothelial Cells On day 1, human umbilical vein endothelial cells (HUVEC) are seeded at $2-5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:Y, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37
Stimulatory Effect of Polypeptides of the Invention on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 38
Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2–3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36) :21985–21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 39
Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, Md.; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 40
Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

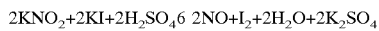

$$2KNO_2 + 2KI + 2H_2SO_4 \; 6 \; 2NO + I_2 + 2H_2O + 2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96–105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 41
Effect of Polypepides of the Invention on Cord Formation in Angiogenesis Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 42
Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 43
Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 44
Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al, *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita et al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther.* 4:749–758 (1993); Leclerc et al. *J. Clin. Invest.* 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 45
Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean +/- SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 46
Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:
  a) Ischemic skin
  b) Ischemic skin wounds
  c) Normal wounds The experimental protocol includes:
  a) Raising a 3×4 cm, single pedicle full-thickness random skin flap (myocutaneous flap over the lower back of the animal).
  b) An excisional wounding (4–6 mm in diameter) in the ischemic skin (skin-flap).

c) Topical treatment with a polypeptide of the invention of the excisional wounds (day 0, 1, 2, 3, 4 post-wounding) at the following various dosage ranges: 1 mg to 100 mg.

d) Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 47
Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) a polypeptide of the invention, in a dosage range of 20 mg–500 mg, is delivered intravenously and/or intramuscularly 3 times (perhaps more) per week for 2–3 weeks.

c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 48
Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6-0) and the thorax is closed.

b) a polypeptide of the invention, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 49
Rat Corneal Wound Healing Model

This animal model shows the effect of a polypeptide of the invention on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

The studies described in this example tested activity of a polypeptide of the invention. However, one skilled in the art could easily modify the exemplified studies to test the activity of polynucleotides (e.g., gene therapy), agonists, and/or antagonists of the invention.

Example 50
Diabetic Mouse and Glucocorticoid-Impaired Wound Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al., *Lab Invest.* 40(4):460–473 (1979); Coleman, D. L., *Diabetes* 31 (*Suppl*):1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., *J. Immunol.* 115: 476–481 (1975); Werb et al., *J. Exp. Med.* 147:1684–1694 (1978)). Glucocorticoids retard wound healing by inhibiting angiogenesis, decreasing vascular permeability (Ebert et al., *An. Intern. Med.* 37:701–705 (1952)), fibroblast proliferation, and collagen synthesis (Beck et al., *Growth Factors.* 5: 295–304 (1991); Haynes et al., *J. Clin. Invest.* 61: 703–797 (1978)) and producing a transient reduction of circulating monocytes (Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., *Growth Factors.* 5: 295–304 (1991); Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., *Proc. Natl. Acad. Sci. USA* 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm$^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

The studies described in this example tested activity of a polypeptide of the invention. However, one skilled in the art could easily modify the exemplified studies to test the activity of polynucleotides (e.g., gene therapy), agonists, and/or antagonists of the invention.

Example 51
Lymphadema Animal Model
or The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 34 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software (Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezegel, dipped into cold methylbutane, placed into labeled sample bags at −80EC until sectioning. Upon sectioning, the muscle is observed under fluorescent microscopy for lymphatics.

The studies described in this example tested activity of a polypeptide of the invention. However, one skilled in the art could easily modify the exemplified studies to test the activity of polynucleotides (e.g., gene therapy), agonists, and/or antagonists of the invention.

Example 52

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-α), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-α induced CAM expression can be examined. A modified ELISA assay which uses ECs as a solid phase absorbent is employed to measure the amount of CAM expression on TNF-α treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1 \times 10^4$ cells/well in EGM medium at 37 degree C. for 18–24 hrs or until confluent. The monolayers are subsequently washed 3 times with a serum-free solution of RPMI-1640 supplemented with 100 U/ml penicillin and 100 mg/nil streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS (with Ca++ and Mg++) is added to each well. Plates are held at 4° C. for 30 min.

Fixative is then removed from the wells and wells are washed 1× with PBS (+Ca,Mg)+0.5% BSA and drained. Do not allow the wells to dry. Add 10 µl of diluted primary antibody to the test and control wells. Anti-ICAM-l-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 µl of diluted ExtrAvidin-Alkaline Phosphotase (1:5,000 dilution) to each well and incubated at 37° C. for 30 min. Wells are washed ×3 with PBS (+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$ 0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of a polypeptide of the invention. However, one skilled in the art could easily modify the exemplified studies to test the activity of polynucleotides (e.g., gene therapy), agonists, and/or antagonists of the invention.

Example 53

Assay for the Stimulation of Bone Marrow CD34+ Cell Proliferation

This assay is based on the ability of human CD34+ to proliferate in the presence of hematopoietic growth factors and evaluates the ability of isolated polypeptides expressed in mammalian cells to stimulate proliferation of CD34+ cells.

It has been previously shown that most mature precursors will respond to only a single signal. More immature precursors require at least two signals to respond. Therefore, to test the effect of polypeptides on hematopoietic activity of a wide range of progenitor cells, the assay contains a given polypeptide in the presence or absence of other hematopoietic growth factors. Isolated cells are cultured for 5 days in the presence of Stem Cell Factor (SCF) in combination with tested sample. SCF alone has a very limited effect on the proliferation of bone marrow (BM) cells, acting in such conditions only as a "survival" factor. However, combined with any factor exhibiting stimulatory effect on these cells (e.g., IL-3), SCF will cause a synergistic effect. Therefore, if the tested polypeptide has a stimulatory effect on a hematopoietic progenitors, such activity can be easily detected. Since normal BM cells have a low level of cycling cells, it is likely that any inhibitory effect of a given polypeptide, or agonists or antagonists thereof, might not be detected. Accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+ cells are isolated using methods known in the art. The cells are thawed and resuspended in medium (QBSF 60 serum-free medium with 1% L-glutamine (500 ml) Quality Biological, Inc., Gaithersburg, Md. Cat#160-204-101). After several gentle centrifugation steps at 200×g, cells are allowed to rest for one hour. The cell count is adjusted to $2.5 \times 10^5$ cells/ml. During this time, 100 µl of sterile water is added to the peripheral wells of a 96-well plate. The cytokines that can be tested with a given polypeptide in this assay is rhSCF (R&D Systems, Minneapolis, Minn., Cat#255-SC) at 50 ng/ml alone and in combination with rhSCF and rhIL-3 (R&D Systems, Minneapolis, Minn., Cat#203-ML) at 30 ng/ml. After one hour, 10 µl of prepared cytokines, 50 µl SID (supernatants at 1:2 dilution=50 µl) and 20 µl of diluted cells are added to the media which is already present in the wells to allow for a final total volume of 100 µl. The plates are then placed in a 37° C./5% $CO_2$ incubator for five days.

Eighteen hours before the assay is harvested, 0.5 µCi/well of [3H] Thymidine is added in a 10 µl volume to each well to determine the proliferation rate. The experiment is terminated by harvesting the cells from each 96-well plate to a filtermat using the Tomtec Harvester 96. After harvesting, the filtermats are dried, trimmed and placed into OmniFilter assemblies consisting of one OmniFilter plate and one OmniFilter Tray. 60 µl Microscint is added to each well and the plate sealed with TopSeal-A press-on sealing film A bar code 15 sticker is affixed to the first plate for counting. The sealed plates is then loaded and the level of radioactivity determined via the Packard Top Count and the printed data collected for analysis. The level of radioactivity reflects the amount of cell proliferation.

The studies described in this example test the activity of a given polypeptide to stimulate bone marrow CD34+ cell proliferation. One skilled in the art could easily modify the exemplified studies to test the activity of polynucleotides (e.g., gene therapy), antibodies, agonists, and/or antagonists and fragments and variants thereof. As a nonlimiting example, potential antagonists tested in this assay would be expected to inhibit cell proliferation in the presence of cytokines and/or to increase the inhibition of cell proliferation in the presence of cytokines and a given polypeptide. In contrast, potential agonists tested in this assay would be expected to enhance cell proliferation and/or to decrease the inhibition of cell proliferation in the presence of cytokines and a given polypeptide.

The ability of a gene to stimulate the proliferation of bone marrow CD34+ cells indicates that polynucleotides and polypeptides corresponding to the gene are useful for the diagnosis and treatment of disorders affecting the immune system and hematopoiesis. Representative uses are described in the "Immune Activity" and "Infectious Disease" sections above, and elsewhere herein.

Example 54
Assay for Extracellular Matrix Enhanced Cell Response (EMECR)

The objective of the Extracellular Matrix Enhanced Cell Response (EMECR) assay is to identify gene products (e.g., isolated polypeptides) that act on the hematopoietic stem cells in the context of the extracellular matrix (ECM) induced signal.

Cells respond to the regulatory factors in the context of signal(s) received from the surrounding microenvironment. For example, fibroblasts, and endothelial and epithelial stem cells fail to replicate in the absence of signals from the ECM. Hematopoietic stem cells can undergo self-renewal in the bone marrow, but not in in vitro suspension culture. The ability of stem cells to undergo self-renewal in vitro is dependent upon their interaction with the stromal cells and the ECM protein fibronectin (fn). Adhesion of cells to fn is mediated by the $\alpha_5 . \beta_1$ and $\alpha_4 . \beta_1$ integrin receptors, which are expressed by human and mouse hematopoietic stem cells. The factor(s) which integrate with the ECM environment and responsible for stimulating stem cell self-renewal has not yet been identified. Discovery of such factors should be of great interest in gene therapy and bone marrow transplant applications Briefly, polystyrene, non tissue culture treated, 96-well plates are coated with fn fragment at a coating concentration of 0.2 µg/cm². Mouse bone marrow cells are plated (1,000 cells/well) in 0.2 ml of serum-free medium. Cells cultured in the presence of IL-3 (5 ng/ml)+SCF (50 ng,/ml) would serve as the positive control, conditions under which little self-renewal but pronounced differentiation of the stem cells is to be expected. Gene products are tested with appropriate negative controls in the presence and absence of SCF (5.0 ng/ml), where test factor supernates represent 10% of the total assay volume. The plated cells are then allowed to grow by incubating in a low oxygen environment (5% $CO_2$, 7% $O_2$, and 88% $N_2$) tissue culture incubator for 7 days. The number of proliferating cells within the wells is then quantitated by measuring thymidine incorporation into cellular DNA. Verification of the positive hits in the assay will require phenotypic characterization of the cells, which can be accomplished by scaling up of the culture system and using appropriate antibody reagents against cell surface antigens and FACScan.

One skilled in the art could easily modify the exemplified studies to test the activity of polynucleotides (e.g., gene therapy), antibodies, agonists, and/or antagonists and fragments and variants thereof.

If a particular gene product is found to be a stimulator of hematopoietic progenitors, polynucleotides and polypeptides corresponding to the gene may be useful for the diagnosis and treatment of disorders affecting the immune system and hematopoiesis. Representative uses are described in the "Immune Activity" and "Infectious Disease" sections above, and elsewhere herein. The gene product may also be useful in the expansion of stem cells and committed progenitors of various blood lineages, and in the differentiation and/or proliferation of various cell types.

Additionally, the polynucleotides and/or polypeptides of the gene of interest and/or agonists and/or antagonists thereof, may also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

Moreover, polynucleotides and polypeptides corresponding to the gene of interest may also be useful for the treatment and diagnosis of hematopoietic related disorders such as, for example, anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

Example 55
Human Dermal Fibroblast and Aortic Smooth Muscle Cell Proliferation

The polypeptide of interest is added to cultures of normal human dermal fibroblasts (NHDF) and human aortic smooth muscle cells (AoSMC) and two co-assays are performed with each sample. The first assay examines the effect of the polypeptide of interest on the proliferation of normal human dermal fibroblasts (NHDF) or aortic smooth muscle cells (AoSMC). Aberrant growth of fibroblasts or smooth muscle cells is a part of several pathological processes, including fibrosis, and restenosis. The second assay examines IL6 production by both NHDF and SMC. IL6 production is an indication of functional activation. Activated cells will have increased production of a number of cytokines and other factors, which can result in a proinflammatory or immunomodulatory outcome. Assays are run with and without co-TNFa stimulation, in order to check for costimulatory or inhibitory activity.

Briefly, on day 1, 96-well black plates are set up with 1000 cells/well (NHDF) or 2000 cells/well (AoSMC) in 100 $\mu$l culture media. NHDF culture media contains: Clonetics FB basal media, 1 mg/ml hFGF, 5 mg/ml insulin, 50 mg/ml gentamycin, 2%FBS, while AoSMC culture media contains Clonetics SM basal media, 0.5 $\mu$g/ml hEGF, 5 mg/ml insulin, 1 $\mu$g/ml hFGF, 50 mg/ml gentamycin, 50 $\mu$g/ml Amphotericin B, 5%FBS. After incubation@37° C. for at least 4–5 hours culture media is aspirated and replaced with growth arrest media. Growth arrest media for NHDF contains fibroblast basal media, 50 mg/ml gentamycin, 2% FBS, while growth arrest media for AoSMC contains SM basal media, 50 mg/ml gentamycin, 50 $\mu$l/ml Amphotericin B, 0.4% FBS. Incubate at 37C until day 2.

On day 2, serial dilutions and templates of the polypeptide of interest are designed which should always include media controls and known-protein controls. For both stimulation and inhibition experiments, proteins are diluted in growth arrest media. For inhibition experiments, TNFa is added to a final concentration of 2 ng/ml (NHDF) or 5 ng/ml (AoSMC). Then add ⅓ vol media containing controls or supernatants and incubate at 37 C/5% $CO_2$ until day 5.

Transfer 60 $\mu$l from each well to another labeled 96-well plate, cover with a plate-sealer, and store at 4C until Day 6 (for IL6 ELISA). To the remaining 100 $\mu$l in the cell culture plate, aseptically add Alamar Blue in an amount equal to 10% of the culture volume (10 $\mu$l). Return plates to incubator for 3 to 4 hours. Then measure fluorescence with excitation at 530 nm and emission at 590 nm using the CytoFluor. This yields the growth stimulation/inhibition data.

On day 5, the IL6 ELISA is performed by coating a 96 well plate with 50–100 ul/well of Anti-Human L6 Monoclonal antibody diluted in PBS, pH 7.4, incubate ON at room temperature.

On day 6, empty the plates into the sink and blot on paper towels. Prepare Assay Buffer containing PBS with 4% BSA. Block the plates with 200 $\mu$l/well of Pierce Super Block blocking buffer in PBS for 1–2 hr and then wash plates with wash buffer (PBS, 0.05% Tween-20). Blot plates on paper towels. Then add 50 $\mu$l/well of diluted Anti-Human IL-6 Monoclonal, Biotin-labeled antibody at 0.50 mg/ml. Make dilutions of IL-6 stock in media (30, 10, 3, 1, 0.3, 0 ng/ml). Add duplicate samples to top row of plate. Cover the plates and incubate for 2 hours at RT on shaker.

Wash plates with wash buffer and blot on paper towels. Dilute EU-labeled Streptavidin 1:1000 in Assay buffer, and add 100 $\mu$l/well. Cover the plate and incubate 1 h at RT. Wash plates with wash buffer. Blot on paper towels.

Add 100 $\mu$l/well of Enhancement Solution. Shake for 5 minutes. Read the plate on the Wallac DELFIA Fluorometer. Readings from triplicate samples in each assay were tabulated and averaged.

A positive result in this assay suggests AoSMC cell proliferation and that the gene product of interest may be involved in dermal fibroblast proliferation and/or smooth muscle cell proliferation. A positive result also suggests many potential uses of polypeptides, polynucleotides, agonists and/or antagonists of the gene/gene product of interest. For example, inflammation and immune responses, wound healing, and angiogenesis, as detailed throughout this specification. Particularly, polypeptides of the gene product and polynucleotides of the gene may be used in wound healing and dermal regeneration, as well as the promotion of vasculargenesis, both of the blood vessels and lymphatics. The growth of vessels can be used in the treatment of, for example, cardiovascular diseases. Additionally, antagonists of polypeptides of the gene product and polynucleotides of the gene may be useful in treating diseases, disorders, and/or conditions which involve angiogenesis by acting as an anti-vascular (e.g., anti-angiogenesis). These diseases, disorders, and/or conditions are known in the art and/or are described herein, such as, for example, malignancies, solid tumors, benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis. Moreover, antagonists of polypeptides of the gene product and polynucleotides of the gene may be useful in treating anti-hyperproliferative diseases and/or anti-inflammatory known in the art and/or described herein.

One skilled in the art could easily modify the exemplified studies to test the activity of polynucleotides (e.g., gene therapy), antibodies, agonists, and/or antagonists and fragments and variants thereof.

Example 56

Cellular Adhesion Molecule (CAM) Expression on Endothelial Cells

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Briefly, endothelial cells (e.g., Human Umbilical Vein Endothelial cells (HUVECs)) are grown in a standard 96 well plate to confluence, growth medium is removed from the cells and replaced with 100 $\mu$l of 199 Medium (10% fetal bovine serum (FBS)). Samples for testing and positive or negative controls are added to the plate in triplicate (in 10 $\mu$l volumes). Plates are then incubated at 37° C. for either 5 h (selectin and integrin expression) or 24 h (integrin expression only). Plates are aspirated to remove medium and 100 µl of 0.1% paraformaldehyde-PBS (with Ca++ and Mg++) is added to each well. Plates are held at 4° C. for 30 min. Fixative is removed from the wells and wells are washed 1× with PBS (+Ca,Mg)+0.5% BSA and drained. 10 pi of diluted primary antibody is added to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed three times with PBS (+Ca,Mg)+0.5% BSA. 20 µl of diluted ExtrAvidin-Alkaline Phosphotase (1:5,000 dilution, refered to herein as the working dilution) are added to each well and incubated at 37° C. for 30 min. Wells are washed three times with PBS (+Ca,Mg)+0.5% BSA. Dissolve 1 tablet of p-Nitrophenol Phosphate pNPP per 5 µl of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 ($10^0$) >$10^-$ $_{0.5}$>$10^{-1}$>$10^{-1.5}$0.5 µl of each dilution is added to triplicate wells and the resulting AP content in each well is 5.50 ng, 1.74 ng, 0.55 ng, 0.18 ng. 100 µl of pNNP reagent is then added to each of the standard wells. The plate is incubated at 37° C. for 4 h. A volume of 50 µl of 3M NaOH is added to all wells. The plate is read on a plate reader at 405 nm using the background subtraction option on blank wells filled with glycine buffer only. Additionally, the template is set up to indicate the concentration of AP-conjugate in each standard well [5.50 ng; 1.74 ng; 0.55 ng; 0.18 ng]. Results are indicated as amount of bound AP-conjugate in each sample.

Example 57

Alamar Blue Endothelial Cells Proliferation Assay

This assay may be used to quantitatively determine protein mediated inhibition of bFGF-induced proliferation of Bovine Lymphatic Endothelial Cells (LECs), Bovine Aortic Endothelial Cells (BAECs) or Human Microvascular Uterine Myometrial Cells (UTMECs). This assay incorporates a fluorometric growth indicator based on detection of metabolic activity. A standard Alamar Blue Proliferation Assay is prepared in EGM-2MV with 10 ng/ml of bFGF added as a source of endothelial cell stimulation. This assay may be used with a variety of endothelial cells with slight changes in growth medium and cell concentration. Dilutions of the protein batches to be tested are diluted as appropriate. Serum-free medium (GIBCO SFM) without bFGF is used as a non-stimulated control and Angiostatin or TSP-1 are included as a known inhibitory controls.

Briefly, LEC, BAECs or UTMECs are seeded in growth media at a density of 5000 to 2000 cells/well in a 96 well plate and placed at 37-C overnight. After the overnight incubation of the cells, the growth media is removed and replaced with GIBCO EC-SFM. The cells are treated with the appropriate dilutions of the protein of interest or control protein sample(s) (prepared in SFM) in triplicate wells with additional bFGF to a concentration of 10 ng/ml. Once the cells have been treated with the samples, the plate(s) is/are placed back in the 37° C. incubator for three days. After three days 10 ml of stock alamar blue (Biosource Cat#DAL1100) is added to each well and the plate(s) is/are placed back in the 37° C. incubator for four hours. The plate(s) are then read at 530 nm excitation and 590 nm emission using the CytoFluor fluorescence reader. Direct output is recorded in relative fluorescence units.

Alamar blue is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form. i.e. stimulated proliferation will produce a stronger signal and inhibited proliferation will produce a weaker signal and the total signal is proportional to the total number of cells as well as their metabolic activity. The background level of activity is observed with the starvation medium alone. This is compared to the output observed from the positive control samples (bFGF in growth medium) and protein dilutions.

Example 58

Detection of Inhibition of a Mixed Lymphocyte Reaction

This assay can be used to detect and evaluate inhibition of a Mixed Lymphocyte Reaction (MLR) by gene products (e.g., isolated polypeptides). Inhibition of a MLR may be due to a direct effect on cell proliferation and viability, modulation of costimulatory molecules on interacting cells, modulation of adhesiveness between lymphocytes and accessory cells, or modulation of cytokine production by accessory cells. Multiple cells may be targeted by these polypeptides since the peripheral blood mononuclear fraction used in this assay includes T, B and natural killer lymphocytes, as well as monocytes and dendritic cells.

Polypeptides of interest found to inhibit the MLR may find application in diseases associated with lymphocyte and monocyte activation or proliferation. These include, but are not limited to, diseases such as asthma, arthritis, diabetes, inflammatory skin conditions, psoriasis, eczema, systemic lupus erythematosus, multiple sclerosis, glomerulonephritis, inflammatory bowel disease, crohn's disease, ulcerative colitis, arteriosclerosis, cirrhosis, graft vs. host disease, host vs. graft disease, hepatitis, leukemia and lymphoma.

Briefly, PBMCs from human donors are purified by density gradient centrifugation using Lymphocyte Separation Medium (LSM®, density 1.0770 g/ml, Organon Teknika Corporation, West Chester, Pa.). PBMCs from two donors are adjusted to $2\times10^6$ cells/ml in RPMI-1640 (Life Technologies, Grand Island, N.Y.) supplemented with 10% FCS and 2 mM glutamine. PBMCs from a third donor is adjusted to $2\times10^5$ cells/ml. Fifty microliters of PBMCs from each donor is added to wells of a 96-well round bottom microtiter plate. Dilutions of test materials (50 µl) is added in triplicate to microtiter wells. Test samples (of the protein of interest) are added for final dilution of 1:4; rhuIL-2 (R&D Systems, Minneapolis, Minn., catalog number 202-IL) is added to a final concentration of 1 µg/ml; anti-CD4 mAb (R&D Systems, clone 34930.11, catalog number MAB379) is added to a final concentration of 10 µg/ml. Cells are cultured for 7–8 days at 37° C. in 5% $CO_2$, and 1 µC of [$^3$H] thymidine is added to wells for the last 16 hrs of culture. Cells are harvested and thymidine incorporation determined using a Packard TopCount. Data is expressed as the mean and standard deviation of triplicate determinations.

Samples of the protein of interest are screened in separate experiments and compared to the negative control treatment, anti-CD4 mAb, which inhibits proliferation of lymphocytes and the positive control treatment, IL-2 (either as recombinant material or supernatant), which enhances proliferation of lymphocytes.

One skilled in the art could easily modify the exemplified studies to test the activity of polynucleotides (e.g., gene therapy), antibodies, agonists, and/or antagonists and fragments and variants thereof.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 32 to 182 of SEQ ID NO:114.

2. The isolated protein of claim 1 which comprises amino acid residues 2 to 182 of SEQ ID NO:114.

3. The isolated protein of claim 1 which comprises amino acid residues 1 to 182 of SEQ ID NO:114.

4. The protein of claim 1 which further comprises a polypeptide sequence heterologous to SEQ ID NO: 114.

5. A composition comprising the protein of claim 1 and a pharmaceutically acceptable carrier.

6. An isolated protein produced by the method comprising:

(a) expressing the protein of claim 1 by a cell; and (b) recovering said protein.

7. An isolated protein comprising the amino acid sequence of the secreted portion of the polypeptide encoded by the HUVDJ43 cDNA contained in ATCC Deposit No. 203081.

8. The isolated protein of claim 7 which comprises the amino acid sequence of the complete polypeptide encoded by the HUVDJ43 cDNA contained in ATCC Deposit No. 203081, excepting the N-terminal methionine.

9. The isolated protein of claim 7 which comprises the amino acid sequence of the complete polypeptide encoded by the HUVDJ43 cDNA contained in ATCC Deposit No. 203081.

10. The protein of claim 7 which further comprises a polypeptide sequence heterologous to SEQ ID NO:114.

11. A composition comprising the protein of claim 7 and a pharmaceutically acceptable carrier.

12. An isolated protein produced by the method comprising:
(a) expressing the protein of claim 7 by a cell; and
(b) recovering said protein.

13. An isolated polypeptide having at least 90% identity to amino acid residues 32 to 182 of SEQ ID NO:114, wherein said polypeptide is expressed in lung lymphomas.

14. The isolated polypeptide of claim 13, wherein said polypeptide has at least 95% identity to amino acid residues 32 to 182 of SEQ ID NO: 114.

15. The protein of claim 13 which further comprises a polypeptide sequence heterologous to SEQ ID NO:114.

16. A composition comprising the protein of claim 13 and a pharmaceutically acceptable carrier.

17. An isolated protein produced by the method comprising:
(a) expressing the protein of claim 13 by a cell; and
(b) recovering said protein.

18. An isolated polypeptide having at least 90% identity to the secreted portion of the polypeptide encoded by the HUVDJ43 cDNA contained in ATCC Deposit No. 203081, wherein said polypeptide is expressed in Jung lymphomas.

19. The isolated polypeptide of claim 18, wherein said polypeptide has at least 95% identity to the polypeptide encoded by the HUVDJ43 cDNA contained in ATCC Deposit No. 203081.

20. The protein of claim 18 which further comprises a polypeptide sequence heterologous to SEQ ID NO:114.

21. A composition comprising the protein of claim 18 and a pharmaceutically acceptable carrier.

22. An isolated protein produced by the method comprising:
(a) expressing the protein of claim 18 by a cell; and
(b) recovering said protein.

23. An isolated polypeptide having at least 90% identity to amino acid residues 1 to 182 at SEQ ID NO:114, wherein said polypeptide is expressed in lung lymphomas.

24. The isolated polypeptide of claim 23, wherein said polypeptide has at least 95% identity to amino acid residues 1 to 182 of SEQ ID NO:114.

25. The protein of claim 23 which comprises a heterologous polypeptide sequence.

26. A composition comprising the protein of claim 23 and a pharmaceutically acceptable carrier.

27. An isolated protein produced by the method comprising:
(a) expressing the protein of claim 23 by a cell; and
(b) recovering said protein.

28. An isolated polypeptide having at least 90% identity to the complete polypeptide encoded by the HUVDJ43 cDNA contained in ATCC Deposit No. 203081, wherein said polypeptide is expressed in lung lymphomas.

29. The isolated polypeptide of claim 28, wherein said polypeptide has at least 95% identity to the complete polypeptide encoded by the HUVDJ43 cDNA contained in ATCC Deposit No. 203081.

30. The protein of claim 28 which further comprises a polypeptide sequence heterologous to SEQ ID NO:114.

31. A composition comprising the protein of claim 28 and a pharmaceutically acceptable carrier.

32. An isolated protein produced by the method comprising:
(a) expressing the protein of claim 28 by a cell; and
(b) recovering said protein.

33. An isolated protein consisting of at least 30 contiguous amino acid residues of amino acid residues 32 to 182 of SEQ ID NO:114, wherein said protein is expressed in lung lymphomas.

34. The isolated protein of claim 33 which consists of at least 50 contiguous amino acid residues of amino acid residues 30 to 182 of SEQ ID NO:114, wherein said protein is expressed in lung lymphomas.

35. The protein of claim 33 which further comprises a polypeptide sequence heterologous to SEQ ID NO:114.

36. A composition comprising the protein of claim 33 and a pharmaceutically acceptable carrier.

37. An isolated protein produced by the method comprising:
(a) expressing the protein of claim 33 by a cell; and
(b) recovering said protein.

38. An isolated protein consisting of at least 30 contiguous amino acid residues of The secreted portion of the polypeptide encoded by the HUVDJ43 cDNA contained in ATCC Deposit No. 203081, wherein said protein is expressed in lung lymphomas.

39. The isolated protein of claim 38 which consists of at least 50 contiguous amino acid residues of the secreted portion of the polypeptide encoded by the HUVDJ43 cDNA contained in ATCC Deposit No. 203081.

40. The protein of claim 38 which further comprises a polypeptide sequence heterologous to SEQ ID NO:114.

41. A composition comprising the protein of claim 38 and pharmaceutically acceptable carrier.

42. An isolated protein produced by the method comprising:
(a) expressing the protein of claim 38 by a cell; and
(b) recovering said protein.

43. An isolated protein consisting of at least 30 contiguous amino acid residues of amino acid residues 1 to 182 of SEQ ID NO:114, wherein said protein is expressed in lung lymphomas.

44. The isolated protein of claim 43 which consists of at least 50 contiguous amino acid residues of amino acid residues 1 to 182 of SEQ ID NO:114.

45. The protein of claim 43 which further comprises a polypeptide sequence heterologous to SEQ ID NO:114.

46. A composition comprising the protein of claim 43 and a pharmaceutically acceptable carrier.

47. An isolated protein produced by the method comprising:
(a) expressing the protein of claim 43 by a cell; and
(b) recovering said protein.

48. An isolated protein consisting of at least 30 contiguous amino acid residues of the complete polypeptide encoded by the HUVDJ43 cDNA contained in ATCC Deposit No. 203081, wherein said protein is expressed in lung lymphomas.

49. The isolated protein of claim 48 which consists of at least 50 contiguous amino acid residues of the complete polypeptide encoded by the HUVDJ43 cDNA contained in ATCC Deposit No. 203081.

50. The protein of claim 48 which further comprises a polypeptide sequence heterologous to SEQ ID NO:114.

51. A composition comprising the protein of claim 48 and pharmaceutically acceptable carrier.

52. An isolated protein produced by the method comprising:
   (a) expressing the protein of claim 48 by a cell; and
   (b) recovering said protein.

* * * * *

UNITED STATES PATENT AND TRADEMARK OFFICE
CERTIFICATE OF CORRECTION

PATENT NO. : 6,566,325 B2
APPLICATION NO. : 09/904615
DATED : May 20, 2003
INVENTOR(S) : Moore et al.

Page 1 of 1

It is certified that error appears in the above-identified patent and that said Letters Patent is hereby corrected as shown below:

In the Claims:

Col. 465 Line 39 in Claim 18, delete "Jung" and insert --lung--.

Col. 465 Line 53 in Claim 23, delete "at SEQ ID NO:114" and insert --of SEQ ID NO:114--.

Col. 466 Line 36 in Claim 38, delete "residues of The secreted portion" and insert --residues of the secreted portion--.

Col. 468 Line 2 in Claim 51, Insert --a-- before "pharmaceutically".

Signed and Sealed this

Fifth Day of February, 2008

JON W. DUDAS
*Director of the United States Patent and Trademark Office*